(12) United States Patent
Zipfel et al.

(10) Patent No.: US 8,735,575 B2
(45) Date of Patent: May 27, 2014

(54) PHENOXAZINE DERIVATIVES AND METHODS OF USE THEREOF

(75) Inventors: Gregory Zipfel, St. Louis, MO (US);
Byung Han, St. Louis, MO (US);
Robert Mach, St. Louis, MO (US);
Wenhau Chu, St. Louis, MO (US)

(73) Assignee: Washington University, St. Louis, MO (US)

( * ) Notice: Subject to any disclaimer, the term of this patent is extended or adjusted under 35 U.S.C. 154(b) by 149 days.

(21) Appl. No.: 13/195,344

(22) Filed: Aug. 1, 2011

(65) Prior Publication Data

US 2012/0035359 A1  Feb. 9, 2012

Related U.S. Application Data

(60) Provisional application No. 61/369,364, filed on Jul. 30, 2010.

(51) Int. Cl.
*C07D 265/38* (2006.01)

(52) U.S. Cl.
USPC .......................................... 544/102; 544/101

(58) Field of Classification Search
USPC .......................................................... 544/102
See application file for complete search history.

(56) References Cited

U.S. PATENT DOCUMENTS

| | | | |
|---|---|---|---|
| 5,304,645 A | 4/1994 | Klein et al. | |
| 6,143,492 A * | 11/2000 | Makings et al. | 435/4 |
| 7,432,372 B2 | 10/2008 | Batchelor et al. | |
| 2007/0031336 A1 | 2/2007 | Auberson et al. | |

OTHER PUBLICATIONS

Kim et al., Abeta40 inhibits amyloid deposition in vivo. J Neurosci, 2007, pp. 627-633, vol. 27, No. 3.
Kimberly et al., Silent ischemic infarcts are associated with hemorrhage burden in cerebral amyloid angiopathy. Neurology, 2009, pp. 1230-1235, vol. 72, No. 14.
Kimchi et al., Analysis of cerebral amyloid angiopathy in a transgenic mouse model of Alzheimer disease using in vivo multiphoton microscopy. J Neuropathol Exp Neurol, 2001, pp. 274-279, vol. 60, No. 3.
Klunk et al., Imaging Abeta plaques in living transgenic mice with multiphoton microscopy and methoxy-X04, a systemically administered Congo red derivative. J Neuropathol Exp Neurol, 2002, pp. 797-805, vol. 61, No. 9.
Klunk et al., Imaging brain amyloid in Alzheimer's disease with Pittsburgh Compound-B. Ann Neurol, 2004, pp. 306-319, vol. 55, No. 3.
Klunk, Biopsy support for the validity of Pittsburgh compound B positron emission tomography with a twist. Arch Neurol, 2008, pp. 1281-1283, vol. 65.
Knudsen et al., Clinical diagnosis of cerebral amyloid angiopathy: validation of the Boston criteria. Neurology, 2001, pp. 537-539, vol. 56, No. 4.
Kung et al., Binding of two potential imaging agents targeting amyloid plaques in postmortem brain tissues of patients with Alzheimer's disease. Brain Res, 2004, pp. 98-108, vol. 1025, No. 1-2.
Lebouvier et al, Cholesterol in the Senile Plaque: Often mentioned, Never Sent. Acta Neuropathol, 2009, pp. 31-34, vol. 117, No. 1.
Lee et al., Matrix metalloproteinase-9 and spontaneous hemorrhage in an animal model of cerebral amyloid angiopathy. Ann Neurol, 2003, pp. 379-382, vol. 54, No. 3.
Lee et al., Matrix metalloproteinase-9 in cerebral-amyloid-angiopathy-related hemorrhage. J Neurol Sci, 2005, pp. 249-254, vol. 229-230.
Lee, Amyloid binding ligands as Alzheimer's disease therapies. Neurobiol Aging, 2002, pp. 1039-1042, vol. 23, No. 6.
Lemaire et al., Fluorine-18-altanserin: a radioligand for the study of serotonin receptors with PET: radiolabeling and in vivo biologic behavior in rats. J Nucl Med, 1991, pp. 2266-2272, vol. 32, No. 12.
Levy et al., Mutation of the Alzheimer's disease amyloid gene in hereditary cerebral hemorrhage, Dutch type. Science, 1990, pp. 1124-1126, vol. 248, No. 4959.
Lockhart et al., Evidence for the presence of three distinct binding sites for the thioflavin T class of Alzheimer's disease PET imaging agents on beta-amyloid peptide fibrils. J Biol Chem, 2005, pp. 7677-7684, vol. 280, No. 9.
Maia et al., Clinical phenotypes of Cerebral Amyloid Angiopathy. J Neurol Sci, 2007, pp. 23-30, vol. 257, No. 1-2.
Mandybur, Cerebral amyloid angiopathy: the vascular pathology and complications. J Neuropathol Exp Neurol, 1986, pp. 79-90, vol. 45.
Mandybur, The incidence of cerebral amyloid angiopathy in Alzheimer's disease. Neurology, 1975, pp. 120-126, vol. 25, No. 2.
Mann et al. Predominant deposition of amyloid-beta 42(43) in plaques in cases of Alzheimer's disease and hereditary cerebral hemorrhage associated with mutations in the amyloid precursor protein gene. Am J Pathol, 1996, pp. 1257-1266, vol. 148, No. 4.
Mathis et al. Synthesis and evaluation of 11C-labeled 6-substituted 2-arylbenzothiazoles as amyloid imaging agents. Journal of medicinal chemistry, 2003, pp. 2740-2754, vol. 46, No. 13.
McCarron et al. Cerebral amyloid angiopathy and thrombolysis-related intracerebral haemorrhage. Lancet Neurol, 2004, pp. 484-492, vol. 3, No. 8.
McGeer et al., The inflammatory response system of brain: implications for therapy of Alzheimer and other neurodegenerative diseases. Brain Res Brain Res Rev, 1995, pp. 195-218, vol. 21, No. 2.
Mintun et al., [11C]PIB in a nondemented population: potential antecedent marker of Alzheimer disease. Neurology, 2006, pp. 446-452, vol. 67, No. 3.
Neuropathology Group, Pathological correlates of late-onset dementia in a multicentre, community-based population in England and Wales. Neuropathology Group of the Medical Research Council Cognitive Function and Ageing Study (MRC CFAS). Lancet, 2001, pp. 169-175, vol. 357, No. 9251.
Nicoll et al. Cerebral amyloid angiopathy plays a direct role in the pathogenesis of Alzheimer's disease. Pro-CAA position statement. Neurobiol Aging, 2004, pp. 589-597, vol. 25, Discussion 603-4.
Nilsberth et al., The 'Arctic' APP mutation (E693G) causes Alzheimer's disease by enhanced Abeta protofibril formation. Nat Neurosci, 2001, pp. 887-893, vol. 4, No. 9.
Nordberg, Amyloid imaging in Alzheimer's disease. Current opinion in neurology, 2007, pp. 398-402, vol. 20, No. 4.

(Continued)

*Primary Examiner* — Kahsay Habte
(74) *Attorney, Agent, or Firm* — Polsinelli PC

(57) ABSTRACT

The present invention encompasses phenoxazine derivatives and methods of use thereof.

9 Claims, 14 Drawing Sheets
(4 of 14 Drawing Sheet(s) Filed in Color)

(56) References Cited

OTHER PUBLICATIONS

Nordberg, Amyloid plaque imaging in vivo: current achievement and future prospects. European journal of nuclear medicine and molecular imaging, 2008, pp. S46-50, vol. 35, Suppl 1.

Nordberg, PET imaging of amyloid in Alzheimer's disease. Lancet Neurol, 2004, pp. 519-527, vol. 3, No. 9.

O'Donnell et al., Apolipoprotein E genotype and the risk of recurrent lobar intracerebral hemorrhage. N Engl J Med, 2000, pp. 240-245, vol. 342 No. 4.

Okazaki et al., Clinicopathologic studies of primary cerebral amyloid angiopathy. Mayo Clin Proc, 1979, pp. 22-31, vol. 54, No. 1.

Olichney et al., Association between severe cerebral amyloid angiopathy and cerebrovascular lesions in Alzheimer disease is not a spurious one attributable to apolipoprotein E4. Arch Neurol, 2000, pp. 869-874, vol. 57, No. 6.

Olichney et al., Cerebral infarction in Alzheimer's disease is associated with severe amyloid angiopathy and hypertension. Arch Neurol, 1995, pp. 702-708, vol. 52, No. 7.

Olichney et al., Relationship between severe amyloid angiopathy, apolipoprotein E genotype, and vascular lesions in Alzheimer's disease. Ann N Y Acad Sci, 2000, pp. 138-143, vol. 903.

Ono et al., 11C-labeled stilbene derivatives as Abeta-aggregate-specific PET imaging agents for Alzheimer's disease. Nuclear medicine and biology, 2003, pp. 565-571, vol. 30, No. 6.

Park et al., Nox2-derived radicals contribute to neurovascular and behavioral dysfunction in mice overexpressing the amyloid precursor protein. Proc Natl Acad Sci U S A, 2008, pp. 1347-1352, vol. 105.

Petridis et al., Outcome of cerebral amyloid angiopathic brain haemorrhage. Acta Neurochir (Wien), 2008, pp. 889-895, vol. 150, No. 9.

Pfeifer et al., Cerebral amyloid angiopathy and cognitive function: the HAAS autopsy study. Neurology, 2002, pp. 1629-1634, vol. 58, No. 11.

Premkumar et al., Apolipoprotein E-epsilon4 alleles in cerebral amyloid angiopathy and cerebrovascular pathology associated with Alzheimer's disease. Am J Pathol, 1996, pp. 2083-2095, vol. 148, No. 6.

Price et al., Kinetic modeling of amyloid binding in humans using PET imaging and Pittsburgh Compound-B. J Cereb Blood Flow Metab, 2005, pp. 1528-1547, vol. 25, No. 11.

Quik et al., Expression of D(3) receptor messenger RNA and binding sites in monkey striatum and substantia nigra after nigrostriatal degeneration: effect of levodopa treatment. Neuroscience, 2000, pp. 263-273, vol. 98, No. 2.

Racke et al., Exacerbation of cerebral amyloid angiopathy-associated microhemorrhage in amyloid precursor protein transgenic mice by immunotherapy is dependent on antibody recognition of deposited forms of amyloid beta. J Neurosci, 2005, pp. 629-636, vol. 25, No. 3.

Rensink et al., Pathogenesis of cerebral amyloid angiopathy. Brain Res Brain Res Rev, 2003, pp. 207-223, vol. 43, No. 2.

Revesz et al., Cytoskeletal pathology in familial cerebral amyloid angiopathy (British type) with non-neuritic amyloid plaque formation. Acta Neuropathol (Berl), 1999, pp. 170-176, vol. 97.

Selkoe, Alzheimer's disease: genotypes, phenotypes, and treatments. Science, 1997, pp. 630-631, vol. 275, No. 5300.

Selkoe, Alzheimer's disease: genes, proteins, and therapy. Physiol Rev, 2001, pp. 741-766, vol. 81, No. 2.

Serdons et al., Synthesis of 18F-labelled 2-(4'-fluorophenyl)-1,3-benzothiazole and evaluation as amyloid imaging agent in comparison with [11C]PIB. Bioorganic & medicinal chemistry letters, 2009, pp. 602-605, vol. 19, No. 3.

Shin et al., Age-dependent cerebrovascular dysfunction in a transgenic mouse model of cerebral amyloid angiopathy. Brain, 2007, pp. 2310-2319, vol. 130, Part 9.

Shoghi-Jadid et al., Localization of neurofibrillary tangles and beta-amyloid plaques in the brains of living patients with Alzheimer disease. Am J Geriatr Psychiatry, 2002, pp. 24-35, vol. 10, No. 1.

Sisodia, Alzheimer's disease: perspectives for the new millennium. J Clin Invest, 1999, pp. 1169-1170, vol. 104, No. 9.

Small et al., PET of brain amyloid and tau in mild cognitive impairment. N Engl J Med, 2006, pp. 2653-2663, vol. 355, No. 25.

Soffer, Cerebral amyloid angiopathy—a disease or age-related condition. Isr Med Assoc J, 2006, pp. 803-806, vol. 8, No. 11.

Stine et al., In vitro characterization of conditions for amyloid-beta peptide oligomerization and fibrillogenesis. J Biol Chem, 2003, pp. 11612-11622, vol. 278, No. 13.

Suhara et al., Neuroimaging in dementia: in vivo amyloid imaging. The Tohoku journal of experimental medicine, 2008, pp. 119-124, vol. 215, No. 2.

Thal et al., Vascular pathology in Alzheimer diseas: correlation of cerebral amyloid angiopathy and arteriosclerosis/lipohyalinosis with cognitive decline. J Neuropathol Exp Neurol, 2003, pp. 1287-1301, vol. 62, No. 12.

Tu et al., Synthesis and in Vitro and in Vivo Evaluation of (18)F-Labeled Positron Emission Tomography (PET) Ligands for Imaging the Vesicular Acetylcholine Transporter. Journal of medicinal chemistry, 2009, pp. 1358-1369, vol. 52, No. 5.

Van Nostrand et al., Pathogenic effects of D23N Iowa mutant amyloid beta -protein. J Biol Chem, 2001, pp. 32860-32866, vol. 276, No. 35.

Verhoeff et al., In-vivo imaging of Alzheimer disease beta-amyloid with [11C]SB-13 PET. Am J Geriatr Psychiatry, 2004, pp. 584-595, vol. 12.

Vermeer et al., Silent brain infarcts and the risk of dementia and cognitive decline. N Engl J Med, 2003, pp. 1215-1222, vol. 348, No. 13.

Vidal et al., Senile dementia associated with amyloid beta protein angiopathy and tau perivascular pathology but not neuritic plaques in patients homozygous for the APOE-epsilon4 allele. Acta Neuropathol (Berl), 2000, pp. 1-12, vol. 100, No. 1.

Vinters, Cerebral amyloid angiopathy. A critical review. Stroke, 1987, pp. 311-324, vol. 18, No. 2.

Wyss-Coray et al., Amyloidogenic role of cytokine TGF-beta1 in transgenic mice and in Alzheimer's disease. Nature, 1997, pp. 603-606, vol. 389, No. 6651.

Xu et al., [(3)H]4-(Dimethylamino)-N-[4-(4-(2-methoxyphenyl)piperazin-1-yl)butyl]benzamide, a selective radioligand for dopamine D(3) receptors. I. In vitro characterization. Synapse, 2009, pp. 717-728, vol. 63, No. 9.

Yamada, Cerebral amyloid angiopathy: an overview. Neuropathology, 2000, pp. 8-22, vol. 20, No. 1.

Zekry et al., Cerebral amyloid angiopathy in the elderly: vessel walls changes and relationship with dementia. Acta Neuropathol (Berl), 2003, pp. 367-373, vol. 106, No. 4.

Zhang et al., Interprotofilament interactions between Alzheimer's Abeta1-42 peptides in amyloid fibrils revealed by cryoEM. Proc Natl Acad Sci U S A, 2009, pp. 4653-4658, vol. 106, No. 12.

Zhang et al., Molecular and Cellular Mechanisms for Alzheimer's Disease: Understanding APP Metabolism. Curr Mol Med, 2007, pp. 687-696, vol. 7, No. 7.

Agdeppa et al, Binding characteristics of radiofluorinated 6-dialkylamino-2-naphthylethylidene derivatives as positron emission tomography imaging probes for beta-amyloid plaques in Alzheimer's disease, The Journal of Neurosciences, 2001, vol. 21, RC189.

Albers et al., Activity-based fluorescent reporters for monoamine oxidases in living cells. Chemical Communications, 2007, pp. 4647-4649, vol. 44.

Alonzo et al., Progression of cerebral amyloid angiopathy: accumulation of amyloid-beta40 in affected vessels., J Neuropathol Exp Neurol, 1998, vol. 57, pp. 353-359.

Archer et al., Amyloid load and cerebral atrophy in Alzheimer's diseas: an 11C-PIB positron emission tomography study, Ann Neurol, 2006, pp. 145-147, vol. 60.

Bloom et al. Cost of illness of Alzheimer's diseas: how useful are current estimates? Gerontologist, 2003, pp. 158-164 vol. 43, No. 2.

Borchelt et al. Accelerated amyloid deposition in the brains of transgenic mice coexpressing mutant presenilin 1 and amyloid precursor proteins. Neuron, 1997, pp. 939-945, vol. 19.

Borchelt et al. Familial Alzheimer's disease-linked presenilin 1 variants elevate Abeta1-42/1-40 ratio in vitro and in vivo. Neuron, 1996, pp. 1005-1013, vol. 17.

(56) References Cited

OTHER PUBLICATIONS

Cadavid et al., Cerebral beta amyloid angiopathy is a risk factor for cerebral ischemic infarction. A case control study in human brain biopsies. J Neuropathol Exp Neurol, 2000, pp. 768-773, vol. 59, No. 9.

Chao et al., Cerebral amyloid angiopathy: CT and MR imaging findings. Radiographics, 2006, pp. 1517-1531, vol. 26, No. 5.

Christie et al., Multiphoton microscopy and amyloid angiopathy. Amyloid, 2001, pp. 48-50, 8 Suppl 1.

Christie et al., Structural and functional disruption of vascular smooth muscle cells in a transgenic mouse model of amyloid angiopathy. Am J Pathol, 2001, pp. 1065-1071, vol. 158, No. 3.

Corder et al., Gene dose of apolipoprotein E type 4 allele and the risk of Alzheimer's disease in late onset families. Science, 1993, pp. 921-923 vol. 261, No. 5123.

Davis et al.. Enhanced pathologic properties of Dutch-type mutant amyloid beta-protein. Proc Natl Acad Sci U S A, 1996, pp. 2996-3000, vol. 93, No. 7.

Engler et al., Two-year follow-up of amyloid deposition in patients with Alzheimer's disease. Brain, 2006, pp. 2856-2866, vol. 129, Pt. 11.

Esiri et al., Cerebrovascular disease and threshold for dementia in the early stages of Alzheimer's disease. Lancet, 1999, pp. 919-920, vol. 354, No. 9182.

Forsberg et al., PET imaging of amyloid deposition in patients with mild cognitive impairment. Neurobiol Aging, 2008, pp. 1456-1465, vol. 29, No. 10.

Fryer et al. Human apolipoprotein E4 alters the amyloid-beta 40:42 ratio and promotes the formation of cerebral amyloid angiopathy in an amyloid precursor protein transgenic model. J Neurosci, 2005, pp. 2803-2810, vol. 25, No. 11.

Fryer et al., Apolipoprotein E markedly facilitates age-dependent cerebral amyloid angiopathy and spontaneous hemorrhage in amyloid precursor protein transgenic mice. J Neurosci, 2003, pp. 7889-7896, vol. 23, No. 21.

Fryer et al., The bad seed in Alzheimer's disease. Neuron, 2005, pp. 167-168, vol. 47, No. 2.

Games et al., Alzheimer-type neuropathology in transgenic mice overexpressing V717F beta-amyloid precursor protein. Nature, 1995, pp. 523-527, vol. 373, No. 6514.

Gao et al., Novel fluorogenic substrates for imaging beta-lactamase gene expression. Journal of the American Chemical Society, 2003, pp. 11146-11147, vol. 125, No. 37.

Glenner, Amyloidosis. Its role in Alzheimer's disease and other diseases. Ann Pathol, 1981, pp. 105-108, vol. 1.

Golde et al., Biochemical detection of Abeta isoforms: implications for pathogenesis, diagnosis, and treatment of Alzheimer's disease. Biochim Biophys Acta, 2000, pp. 172-187, vol. 1502, No. 1.

Grabowski et al., Novel amyloid precursor protein mutation in an Iowa family with dementia and severe cerebral amyloid angiopathy. Ann Neurol, 2001, pp. 697-705, vol. 49.

Greenberg et al, The clinical spectrum of cerebral amyloid angiopathy: presentations without lobar hemorrhage. Neurology, 1993, pp. 2073-2079, vol. 43, No. 3.

Greenberg et al., Amyloid angiopathy-related vascular cognitive impairment. Stroke, 2004, pp. 2616-2619, vol. 35, No. 11, Suppl 1.

Greenberg et al., Apolipoprotein E epsilon 4 and cerebral hemorrhage associated with amyloid angiopathy. Ann Neurol, 1995, pp. 254-259, vol. 38, No. 2.

Greenberg et al., Apolipoprotein E epsilon 4 is associated with the presence and earlier onset of hemorrhage in cerebral amyloid angiopathy. Stroke, 1996, pp. 1333-1337, vol. 27, No. 8.

Greenberg et al., Hemorrhage burden predicts recurrent intracerebral hemorrhage after lobar hemorrhage. Stroke, 2004, pp. 1415-1420, vol. 35, No. 6.

Greenberg, Cerebral amyloid angiopathy and dementia: two amyloids are worse than one. Neurology, 2002, pp. 1587-1588, vol. 58, No. 11.

Greenberg, Cerebral amyloid angiopathy and vessel dysfunction. Cerebrovasc Dis, 2002, pp. 42-47, vol. 13, Suppl 2.

Greenberg, Cerebral amyloid angiopathy: prospects for clinical diagnosis and treatment. Neurology, 1998, pp. 690-694, vol. 51, No. 3.

Habicht et al., Directed selection of a conformational antibody domain that prevents mature amyloid fibril formation by stabilizing Abeta protofibrils. Proc Natl Acad Sci U S A, 2007, pp. 19232-19237, vol. 104, No. 49.

Han et al., Cerebrovascular dysfunction in amyloid precursor protein transgenic mice: contribution of soluble and insoluble amyloid-beta peptide, partial restoration via gamma-secretase inhibition. J Neurosci, 2008, pp. 13542-13550, vol. 28, No. 50.

Hebert et al., Alzheimer disease in the US population: prevalence estimates using the 2000 census. Arch Neurol, 2003, pp. 1119-1122, vol. 60, No. 8.

Henriksen et al., Development and evaluation of compounds for imaging of beta-amyloid plaque by means of positron emission tomography. Eur J Nucl Med Mol Imaging, 2008, pp. S75-81, vol. 35, Suppl 1.

Herzig et al., Abeta is targeted to the vasculature in a mouse model of hereditary cerebral hemorrhage with amyloidosis. Nat Neurosci, 2004, pp. 954-960, vol. 7, No. 9.

Horsburgh et al., Marked alterations in the cellular localisation and levels of apolipoprotein E following acute subdural haematoma in rat. Brain Res, 1997, pp. 103-110, vol. 763, No. 1.

Hsiao et al. Correlative memory deficits, Abeta elevation, and amyloid plaques in transgenic mice. Science, 1996, pp. 99-102, vol. 274.

Hume et al., Quantitation of carbon-11-labeled raclopride in rat striatum using positron emission tomography. Synapse, 1992, pp. 47-54, vol. 12, No. 1.

Ishii et al., Amyloid angiopathy and lobar cerebral haemorrhage. J Neurol Neurosurg Psychiatry, 1984, pp. 1203-1210, vol. 47, No. 11.

Itoh et al., Cerebral amyloid angiopathy in the elderly: the clinicopathological features, pathogenesis, and risk factors. J Med Dent Sci, 1997, pp. 11-19, vol. 44, No. 1.

Itoh et al., Cerebral amyloid angiopathy: a significant cause of cerebellar as well as lobar cerebral hemorrhage in the elderly. J Neurol Sci, 1993, pp. 135-141, vol. 116, No. 2.

Iwatsubo et al., Full-length amyloid-beta (1-42(43)) and amino-terminally modified and truncated amyloid-beta 42 (43) deposit in diffuse plaques. Am J Pathol, 1996, pp. 1823-1830, vol. 149, No. 6.

Jankowsky et al., APP processing and amyloid deposition in mice haplo-insufficient for presenilin 1. Neurobiol Aging, 2004, pp. 885-892, vol. 25, No. 7.

Jellinger, Alzheimer disease and cerebrovascular pathology: an update. J Neural Transm, 2002, pp. 813-836, vol. 109, No. 5-6.

Johnson-Wood et al., Amyloid precursor protein processing and A beta42 deposition in a transgenic mouse model of Alzheimer disease. Proc Natl Acad Sci U S A, 1997, pp. 1550-1555, vol. 94, No. 4.

Kawarabayashi et al. (2001) Age-dependent changes in brain, CSF, and plasma amyloid (beta) protein in the Tg2576 transgenic mouse model of Alzheimer's disease. J Neurosci, 2001, pp. 372-381, vol. 21, No. 2.

Kemppainen et al., PET amyloid ligand [11C]PIB uptake is increased in mild cognitive impairment. Neurology, 2007, pp. 1603-1606, vol. 68, No. 19.

Kemppainen et al., Voxel-based analysis of PET amyloid ligand [11C]PIB uptake in Alzheimer disease. Neurology, 2006, 1576-1580, vol. 67, No. 9.

\* cited by examiner

Amyloid binding properties of phenoxazines

| Compounds | logP$_{oct}$ | K$_D$ (nM) | |
|---|---|---|---|
| | | CAA | Plaques |
| Resorufin | 0.387 | 458 | > 10,000 |
| Ethyl-resorufin | 2.206 | 247 | > 10,000 |
| Phenyl-resorufin | 2.213 | 473 | > 10,000 |
| Methoxyphenyl-resorufin | 1.907 | 186 | > 10,000 |
| Methoxy-X34 | 0.19 | 325 | 219 |

FIG. 2

Synthesis of the Click and Reverse Click analogs of resorufin (analogs 4 – 8).

Synthesis of 18F-resorufin analogs.

PHENOXAZINE DERIVATIVES AND METHODS OF USE THEREOF

CROSS REFERENCE TO RELATED APPLICATIONS

This application claims the priority of U.S. provisional application No. 61/369,364, filed Jul. 30, 2010, which is hereby incorporated by reference in its entirety.

FIELD OF THE INVENTION

The invention encompasses phenoxazine derivatives and methods of use thereof.

BACKGROUND OF THE INVENTION

Cerebral amyloid angiopathy (CAA) is almost universally noted in patients with Alzheimer's Disease (AD) (~90% of individuals) and is commonly found in non-AD elderly individuals (~30% of those >60 years of age). It is characterized by amyloid-β (Aβ) deposition in cortical cerebral arterioles. CAA is a powerful risk factor for three potentially interrelated diseases: 1) cerebral hemorrhage, 2) ischemic brain injury, and 3) dementia. Though substantial mechanistic and therapeutic progress has been made in preclinical studies (including identification of several interventions that can halt or even reverse CAA formation), progress in the clinic has been very slow. A major reason for this lack of progress has been inadequate methods for accurately diagnosing and quantifying CAA in patients. Definite diagnosis of CAA currently requires brain biopsy, which is rarely clinically indicated. "Possible" or "probable" diagnosis of CAA can be made via Magnetic Resonance Imaging (MRI) utilizing the Boston Criteria, which relies on identification of cortical hemorrhage as an indirect indicator of the presence of CAA. However, this indirect method of diagnosis has many disadvantages, some of which include: 1) it does not quantify CAA severity, 2) it cannot monitor progression of disease over time, 3) it cannot detect CAA prior to onset of cerebral hemorrhage, and 4) it will be unable to monitor response to CAA-directed therapeutics as they become available. Hence, there is a need in the art for a non-invasive compound and method for accurately and selectively diagnosing CAA in humans.

SUMMARY OF THE INVENTION

One aspect of the present invention encompasses a compound of formula (II):

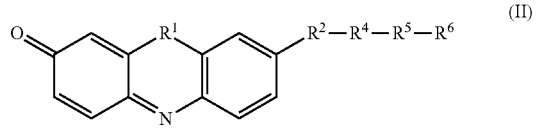

wherein:
$R^1$ is chosen from N, S, or O;
$R^2$ is chosen from N, S, or O;
$R^4$ is chosen from $(CH_2)_x$, $((CH_2)_yO)_z$, and $((CH_2)_aO(CH_2)_b)$, wherein x, y, z, a, and b are integers from 1 to 3;
$R^5$ is chosen from an aromatic ring, a cylic ring, and a heterocyclic ring; and
$R^6$ is chosen from hydrogen, a hydrocarbyl, and a substituted hydrocarbyl.

Another aspect of the present invention encompasses a compound of formula (III):

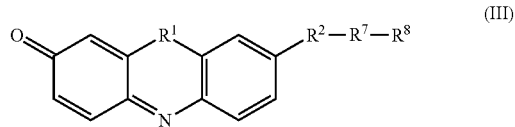

wherein:
$R^1$ is chosen from N, S, or O;
$R^2$ is chosen from N, S, or O;
$R^7$ is chosen from the group consisting of $((CH_2)_cO)_d$, and $((CH_2)_eO(CH_2)_f)$, wherein c, d, e, and f are integers from 1 to 3; and
$R^8$ is chosen from the group consisting of hydrogen, a hydrocarbyl, and a substituted hydrocarbyl.

Yet another aspect of the present invention encompasses a compound of formula (IV):

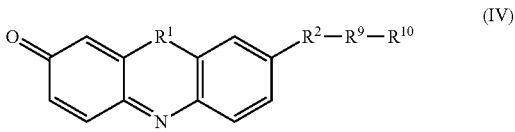

wherein:
$R^1$ is chosen from N, S, or O;
$R^2$ is chosen from N, S, or O;
$R^9$ is $(CH_2)_g$, wherein g is an integer from 1 to 10, and
$R^{10}$ is chosen from a halogen, an alkenyl group, an alkynyl group, and a substituted hydrocarbyl.

Still another aspect of the present invention encompasses a method for selectively detecting cerebral vessel amyloid deposits. The method comprises contacting a tissue sample with a compound of formula (I), and detecting the binding of the compound to the tissue, such that binding indicates the presence of cerebral vessel amyloid deposits in the tissue.

An alternative aspect of the present invention encompasses a method for diagnosing CAA in subject. The method comprises administering a compound of formula (I) to a subject, and detecting the binding of the compound in the cerebral vessels of the subject, such that if the compound is detected within the subject, then the subject is diagnosed with CAA.

An additional alternative aspect of the present invention encompasses a method for monitoring the progression of CAA over time. The method comprising administering a compound of formula (I) to a subject and detecting the compound at a first time point, and administering a compound of the invention to a subject and detecting the compound at least one additional time point, such that the different in quantity of the compound detected between the time points is an indication of the progression of CAA over time.

A further aspect of the present invention encompasses a method for monitoring the response of CAA in a subject to a therapy. The method comprises administering a compound of the invention to a subject and detecting the compound at a first time point, administering a therapy to the subject, and then administering a compound of the invention to a subject and detecting the compound at least one other time point after the therapy has been administered, such that the difference in the quantity of the compound detected between the time points is an indication of the response of CAA in the subject to the therapy.

Other aspects and iterations of the invention are described more thoroughly below.

REFERENCE TO COLOR FIGURES

The application file contains at least one photograph executed in color. Copies of this patent application publication with color photographs will be provided by the Office upon request and payment of the necessary fee.

BRIEF DESCRIPTION OF THE FIGURES

FIG. 2 depicts the amyloid binding properties of phenoxazines.

DETAILED DESCRIPTION OF THE INVENTION

Figure 1:
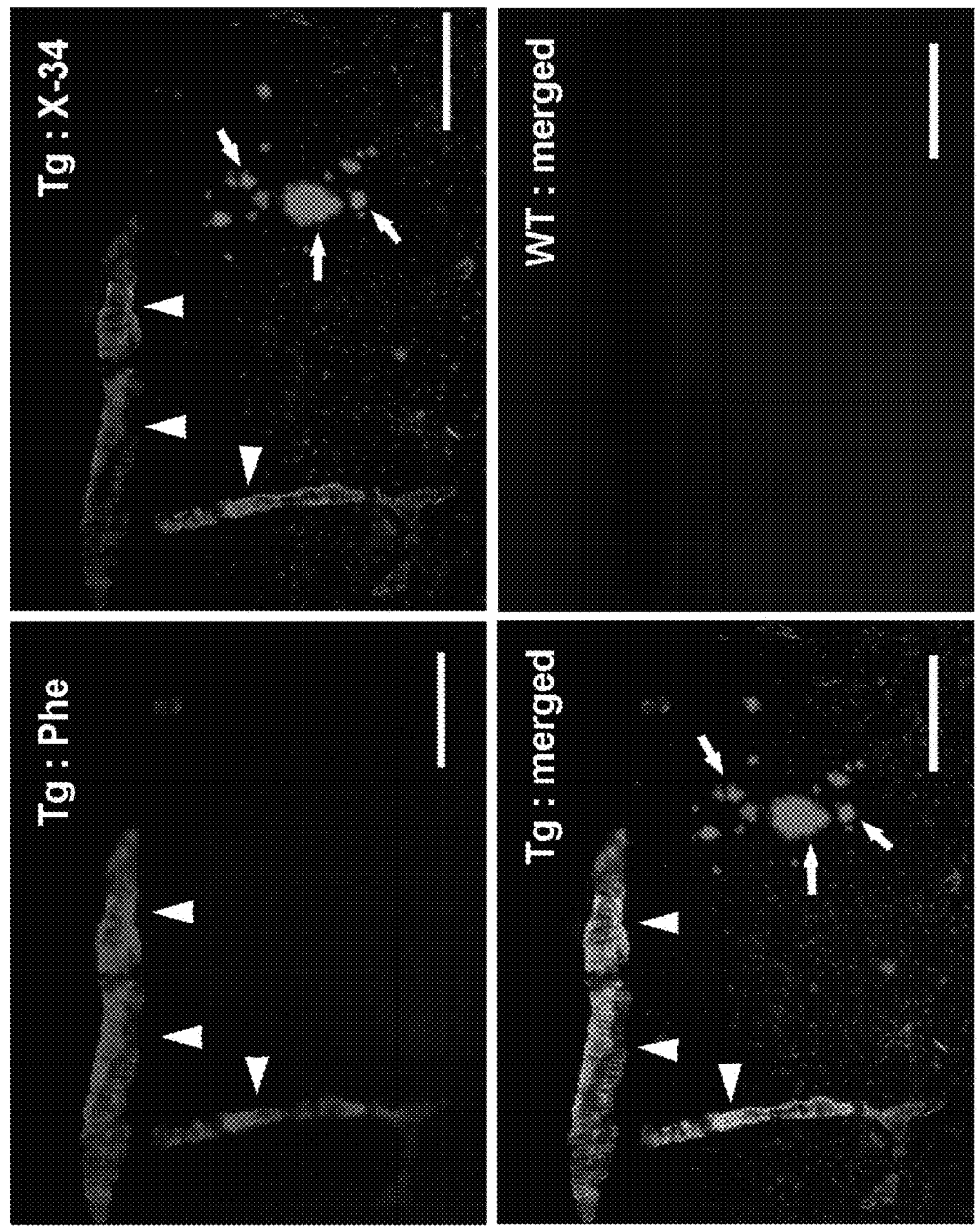
FIG. 1 depicts images showing preferential binding of the phenoxazine dye resorufin to CAA vs. neuritic plaques in Tg2576 mice. Fixed brain sections prepared from 16-month-old Tg2576 transgenic mice (Tg) or wildtype mice (WT) were co-stained with the phenoxazine dye resorufin (Phe) and methoxy-X34 (X-34). Resorufin selectively bound fibrillar amyloid-laden arterioles (arrowheads), whereas a Congo red derivative, methoxy-X34 labeled amyloid deposited in both CAA and neuritic plaques (arrows). Scale bars: 100 µm.

The present invention provides compounds of formula (I) that selectively recognize cerebral vessel amyloid deposits as opposed to parenchyma amyloid deposits. Advantageously, these compounds may be used to diagnosis cerebral amyloid angiopathy (CAA). As used herein, CAA refers to the deposition of amyloid plaques in cerebral vessels. In an exemplary embodiment, CAA refers to the deposition of amyloid plaques in leptomeningeal and cortical arterioles. Additionally, the present invention encompasses methods of using a compound described herein.

I. Compounds

One aspect of the present invention encompasses a compound that selectively recognizes cerebral vessel amyloid deposits, as opposed to parenchyma amyloid deposits. In particular, a compound of the invention may show 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 fold selectivity for cerebral vessel amyloid deposits as opposed to parenchyma amyloid deposits. Alternatively, a compound of the invention may show 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, or 200 fold selectivity for cerebral vessel amyloid deposits as opposed to parenchyma amyloid deposits. In another alternative, a compound of the invention may show greater than 200 fold selectivity for cerebral vessel amyloid deposits as opposed to parenchyma amyloid deposits.

Typically, a compound of the invention should be capable of uptake into brain or central nervous system tissue. Accordingly, a compound of the invention usually has moderate lipophilicity.

In one embodiment, the present invention encompasses a compound of formula (I):

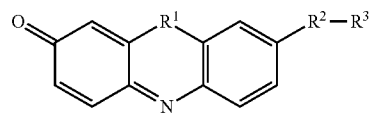

wherein:
$R^1$ is chosen from N, S, or O;
$R^2$ is chosen from N, S, or O;
$R^3$ is chosen from hydrogen, a hydrocarbyl, substituted hydrocarbyl, $R^4$-$R^5$-$R^6$, $R^7$-$R^8$, and $R^9$-$R^{10}$;
$R^4$ is chosen from $(CH_2)_x$, $((CH_2)_yO)_z$, and $((CH_2)_aO(CH_2)_b)_c$, wherein x, y, z, a, b, and c are integers from 1 to 3;
$R^5$ is chosen from an aromatic ring, a cylic ring, and a heterocyclic ring;
$R^6$ is chosen from hydrogen, a hydrocarbyl, and a substituted hydrocarbyl;
$R^7$ is chosen from the group consisting of $((CH_2)_dO)_e$, and $((CH_2)_fO(CH_2)_g)_h$, wherein d, e, f, g and h are integers from 1 to 3;
$R^8$ is chosen from the group consisting of hydrogen, a hydrocarbyl, and a substituted hydrocarbyl;
$R^9$ is $(CH_2)_j$, wherein j is an integer from 1 to 10; and
$R^{10}$ is chosen from a halogen, an alkenyl group, an alkynyl group, and a substituted hydrocarbyl.

In certain embodiments, a compound of the invention may be a compound of formula (I) wherein $R^1$ is O. In other embodiments, a compound of the invention may be a compound of formula (I) wherein $R^1$ is N. In still other embodiments, a compound of the invention may be a compound of formula (I) wherein $R^1$ is S.

In particular embodiments, a compound of the invention may be a compound listed in Table 1. Alternatively, a compound of the invention may be a compound listed in Table 5.

TABLE 1

Selected compounds from formula (I)

| Compound | R1 | R2 | R3 |
|---|---|---|---|
| I.1 | N | N | Hydrogen |
| I.2 | N | N | Hydrocarbyl |
| I.3 | N | N | Substituted hydrocarbyl |
| I.4 | N | N | $R^4$—$R^5$—$R^6$ |
| I.5 | N | N | $R^7$—$R^8$ |
| I.6 | N | N | $R^9$—$R^{10}$ |
| I.7 | N | S | Hydrogen |
| I.8 | N | S | Hydrocarbyl |
| I.9 | N | S | Substituted hydrocarbyl |
| I.10 | N | S | $R^4$—$R^5$—$R^6$ |
| I.11 | N | S | $R^7$—$R^8$ |
| I.12 | N | S | $R^9$—$R^{10}$ |
| I.13 | N | O | Hydrogen |
| I.14 | N | O | Hydrocarbyl |
| I.15 | N | O | Substituted hydrocarbyl |
| I.16 | N | O | $R^4$—$R^5$—$R^6$ |
| I.17 | N | O | $R^7$—$R^8$ |
| I.18 | N | O | $R^9$—$R^{10}$ |
| I.19 | S | N | Hydrogen |
| I.20 | S | N | Hydrocarbyl |
| I.21 | S | N | Substituted hydrocarbyl |
| I.22 | S | N | $R^4$—$R^5$—$R^6$ |
| I.23 | S | N | $R^7$—$R^8$ |
| I.24 | S | N | $R^9$—$R^{10}$ |
| I.25 | S | S | Hydrogen |
| I.26 | S | S | Hydrocarbyl |
| I.27 | S | S | Substituted hydrocarbyl |
| I.28 | S | S | $R^4$—$R^5$—$R^6$ |
| I.29 | S | S | $R^7$—$R^8$ |
| I.30 | S | S | $R^9$—$R^{10}$ |
| I.31 | S | O | Hydrogen |
| I.32 | S | O | Hydrocarbyl |
| I.33 | S | O | Substituted hydrocarbyl |
| I.34 | S | O | $R^4$—$R^5$—$R^6$ |
| I.35 | S | O | $R^7$—$R^8$ |
| I.36 | S | O | $R^9$—$R^{10}$ |
| I.37 | O | N | Hydrogen |

TABLE 1-continued

Selected compounds from formula (I)

| Compound | R1 | R2 | R3 |
|---|---|---|---|
| I.38 | O | N | Hydrocarbyl |
| I.39 | O | N | Substituted hydrocarbyl |
| I.40 | O | N | $R^4$—$R^5$—$R^6$ |
| I.41 | O | N | $R^7$—$R^8$ |
| I.42 | O | N | $R^9$—$R^{10}$ |
| I.43 | O | S | Hydrogen |
| I.44 | O | S | Hydrocarbyl |
| I.45 | O | S | Substituted hydrocarbyl |
| I.46 | O | S | $R^4$—$R^5$—$R^6$ |
| I.47 | O | S | $R^7$—$R^8$ |
| I.48 | O | S | $R^9$—$R^{10}$ |
| I.49 | O | O | Hydrogen |
| I.50 | O | O | Hydrocarbyl |
| I.51 | O | O | Substituted hydrocarbyl |
| I.52 | O | O | $R^4$—$R^5$—$R^6$ |
| I.53 | O | O | $R^7$—$R^8$ |
| I.54 | O | O | $R^9$—$R^{10}$ |

In another embodiment, the present invention encompasses a compound of formula (II):

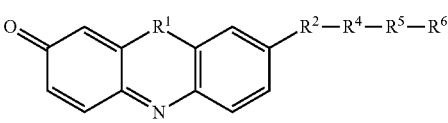

wherein:
$R^1$ is chosen from N, S, or O;
$R^2$ is chosen from N, S, or O;
$R^4$ is chosen from $(CH_2)_x$, $((CH_2)_yO)$, and $((CH_2)_aO(CH_2)_b)_c$, wherein x, y, z, a, b, and c are integers from 1 to 3;
$R^5$ is chosen from an aromatic ring, a cylic ring, and a heterocyclic ring; and
$R^6$ is chosen from hydrogen, a hydrocarbyl, and a substituted hydrocarbyl.

In certain embodiments, a compound of the invention may be a compound of formula (II) wherein $R^1$ is O. In other embodiments, a compound of the invention may be a compound of formula (II) wherein $R^1$ is N. In still other embodiments, a compound of the invention may be a compound of formula (II) wherein $R^1$ is S.

In particular embodiments, a compound of the invention may be a compound listed in Table 2.

TABLE 2

Selected compounds from Formula (II)

| | R1 | R2 | R4 | R5 | R6 |
|---|---|---|---|---|---|
| II.1 | N | N | $(CH_2)$ | Aromatic ring | Hydrogen |
| II.2 | N | N | $(CH_2)$ | Aromatic ring | Hydrocarbyl |
| II.3 | N | N | $(CH_2)$ | Aromatic ring | Substituted hydrocarbyl |
| II.4 | N | N | $(CH_2)$ | Cylic ring | Hydrogen |
| II.5 | N | N | $(CH_2)$ | Cylic ring | Hydrocarbyl |
| II.6 | N | N | $(CH_2)$ | Cylic ring | Substituted hydrocarbyl |
| II.7 | N | N | $(CH_2)$ | Heterocyclic ring | Hydrogen |
| II.8 | N | N | $(CH_2)$ | Heterocyclic ring | Hydrocarbyl |
| II.9 | N | N | $(CH_2)$ | Heterocyclic ring | Substituted hydrocarbyl |
| II.10 | N | N | $(CH_2)_2$ | Aromatic ring | Hydrogen |
| II.11 | N | N | $(CH_2)_2$ | Aromatic ring | Hydrocarbyl |
| II.12 | N | N | $(CH_2)_2$ | Aromatic ring | Substituted hydrocarbyl |
| II.13 | N | N | $(CH_2)_2$ | Cylic ring | Hydrogen |
| II.14 | N | N | $(CH_2)_2$ | Cylic ring | Hydrocarbyl |
| II.15 | N | N | $(CH_2)_2$ | Cylic ring | Substituted hydrocarbyl |
| II.16 | N | N | $(CH_2)_2$ | Heterocyclic ring | Hydrogen |
| II.17 | N | N | $(CH_2)_2$ | Heterocyclic ring | Hydrocarbyl |
| II.18 | N | N | $(CH_2)_2$ | Heterocyclic ring | Substituted hydrocarbyl |

TABLE 2-continued

Selected compounds from Formula (II)

| | R1 | R2 | R4 | R5 | R6 |
|---|---|---|---|---|---|
| II.19 | N | N | $(CH_2)_3$ | Aromatic ring | Hydrogen |
| II.20 | N | N | $(CH_2)_3$ | Aromatic ring | Hydrocarbyl |
| II.21 | N | N | $(CH_2)_3$ | Aromatic ring | Substituted hydrocarbyl |
| II.22 | N | N | $(CH_2)_3$ | Cylic ring | Hydrogen |
| II.23 | N | N | $(CH_2)_3$ | Cylic ring | Hydrocarbyl |
| II.24 | N | N | $(CH_2)_3$ | Cylic ring | Substituted hydrocarbyl |
| II.25 | N | N | $(CH_2)_3$ | Heterocyclic ring | Hydrogen |
| II.26 | N | N | $(CH_2)_3$ | Heterocyclic ring | Hydrocarbyl |
| II.27 | N | N | $(CH_2)_3$ | Heterocyclic ring | Substituted hydrocarbyl |
| II.28 | N | N | $((CH_2)O)$ | Aromatic ring | Hydrogen |
| II.29 | N | N | $((CH_2)O)$ | Aromatic ring | Hydrocarbyl |
| II.30 | N | N | $((CH_2)O)$ | Aromatic ring | Substituted hydrocarbyl |
| II.31 | N | N | $((CH_2)O)$ | Cylic ring | Hydrogen |
| II.32 | N | N | $((CH_2)O)$ | Cylic ring | Hydrocarbyl |
| II.33 | N | N | $((CH_2)O)$ | Cylic ring | Substituted hydrocarbyl |
| II.34 | N | N | $((CH_2)O)$ | Heterocyclic ring | Hydrogen |
| II.35 | N | N | $((CH_2)O)$ | Heterocyclic ring | Hydrocarbyl |
| II.36 | N | N | $((CH_2)O)$ | Heterocyclic ring | Substituted hydrocarbyl |
| II.37 | N | N | $((CH_2)O)_2$ | Aromatic ring | Hydrogen |
| II.38 | N | N | $((CH_2)O)_2$ | Aromatic ring | Hydrocarbyl |
| II.39 | N | N | $((CH_2)O)_2$ | Aromatic ring | Substituted hydrocarbyl |
| II.40 | N | N | $((CH_2)O)_2$ | Cylic ring | Hydrogen |
| II.41 | N | N | $((CH_2)O)_2$ | Cylic ring | Hydrocarbyl |
| II.42 | N | N | $((CH_2)O)_2$ | Cylic ring | Substituted hydrocarbyl |
| II.43 | N | N | $((CH_2)O)_2$ | Heterocyclic ring | Hydrogen |
| II.44 | N | N | $((CH_2)O)_2$ | Heterocyclic ring | Hydrocarbyl |
| II.45 | N | N | $((CH_2)O)_2$ | Heterocyclic ring | Substituted hydrocarbyl |
| II.46 | N | N | $((CH_2)O)_3$ | Aromatic ring | Hydrogen |
| II.47 | N | N | $((CH_2)O)_3$ | Aromatic ring | Hydrocarbyl |
| II.48 | N | N | $((CH_2)O)_3$ | Aromatic ring | Substituted hydrocarbyl |
| II.49 | N | N | $((CH_2)O)_3$ | Cylic ring | Hydrogen |
| II.50 | N | N | $((CH_2)O)_3$ | Cylic ring | Hydrocarbyl |
| II.51 | N | N | $((CH_2)O)_3$ | Cylic ring | Substituted hydrocarbyl |
| II.52 | N | N | $((CH_2)O)_3$ | Heterocyclic ring | Hydrogen |
| II.53 | N | N | $((CH_2)O)_3$ | Heterocyclic ring | Hydrocarbyl |
| II.54 | N | N | $((CH_2)O)_3$ | Heterocyclic ring | Substituted hydrocarbyl |
| II.55 | N | N | $((CH_2)_2O)$ | Aromatic ring | Hydrogen |
| II.56 | N | N | $((CH_2)_2O)$ | Aromatic ring | Hydrocarbyl |
| II.57 | N | N | $((CH_2)_2O)$ | Aromatic ring | Substituted hydrocarbyl |
| II.58 | N | N | $((CH_2)_2O)$ | Cylic ring | Hydrogen |
| II.59 | N | N | $((CH_2)_2O)$ | Cylic ring | Hydrocarbyl |
| II.60 | N | N | $((CH_2)_2O)$ | Cylic ring | Substituted hydrocarbyl |
| II.61 | N | N | $((CH_2)_2O)$ | Heterocyclic ring | Hydrogen |
| II.62 | N | N | $((CH_2)_2O)$ | Heterocyclic ring | Hydrocarbyl |
| II.63 | N | N | $((CH_2)_2O)$ | Heterocyclic ring | Substituted hydrocarbyl |
| II.64 | N | N | $((CH_2)_2O)_2$ | Aromatic ring | Hydrogen |
| II.65 | N | N | $((CH_2)_2O)_2$ | Aromatic ring | Hydrocarbyl |
| II.66 | N | N | $((CH_2)_2O)_2$ | Aromatic ring | Substituted hydrocarbyl |
| II.67 | N | N | $((CH_2)_2O)_2$ | Cylic ring | Hydrogen |
| II.68 | N | N | $((CH_2)_2O)_2$ | Cylic ring | Hydrocarbyl |
| II.69 | N | N | $((CH_2)_2O)_2$ | Cylic ring | Substituted hydrocarbyl |
| II.70 | N | N | $((CH_2)_2O)_2$ | Heterocyclic ring | Hydrogen |
| II.71 | N | N | $((CH_2)_2O)_2$ | Heterocyclic ring | Hydrocarbyl |
| II.72 | N | N | $((CH_2)_2O)_2$ | Heterocyclic ring | Substituted hydrocarbyl |
| II.73 | N | N | $((CH_2)_2O)_3$ | Aromatic ring | Hydrogen |
| II.74 | N | N | $((CH_2)_2O)_3$ | Aromatic ring | Hydrocarbyl |
| II.75 | N | N | $((CH_2)_2O)_3$ | Aromatic ring | Substituted hydrocarbyl |
| II.76 | N | N | $((CH_2)_2O)_3$ | Cylic ring | Hydrogen |
| II.77 | N | N | $((CH_2)_2O)_3$ | Cylic ring | Hydrocarbyl |
| II.78 | N | N | $((CH_2)_2O)_3$ | Cylic ring | Substituted hydrocarbyl |
| II.79 | N | N | $((CH_2)_2O)_3$ | Heterocyclic ring | Hydrogen |
| II.80 | N | N | $((CH_2)_2O)_3$ | Heterocyclic ring | Hydrocarbyl |
| II.81 | N | N | $((CH_2)_2O)_3$ | Heterocyclic ring | Substituted hydrocarbyl |
| II.82 | N | N | $((CH_2)_3O)$ | Aromatic ring | Hydrogen |
| II.83 | N | N | $((CH_2)_3O)$ | Aromatic ring | Hydrocarbyl |
| II.84 | N | N | $((CH_2)_3O)$ | Aromatic ring | Substituted hydrocarbyl |
| II.85 | N | N | $((CH_2)_3O)$ | Cylic ring | Hydrogen |
| II.86 | N | N | $((CH_2)_3O)$ | Cylic ring | Hydrocarbyl |
| II.87 | N | N | $((CH_2)_3O)$ | Cylic ring | Substituted hydrocarbyl |
| II.88 | N | N | $((CH_2)_3O)$ | Heterocyclic ring | Hydrogen |
| II.89 | N | N | $((CH_2)_3O)$ | Heterocyclic ring | Hydrocarbyl |
| II.90 | N | N | $((CH_2)_3O)$ | Heterocyclic ring | Substituted hydrocarbyl |
| II.91 | N | N | $((CH_2)_3O)_2$ | Aromatic ring | Hydrogen |
| II.92 | N | N | $((CH_2)_3O)_2$ | Aromatic ring | Hydrocarbyl |
| II.93 | N | N | $((CH_2)_3O)_2$ | Aromatic ring | Substituted hydrocarbyl |
| II.94 | N | N | $((CH_2)_3O)_2$ | Cylic ring | Hydrogen |

TABLE 2-continued

Selected compounds from Formula (II)

| | R1 | R2 | R4 | R5 | R6 |
|---|---|---|---|---|---|
| II.95 | N | N | $((CH_2)_3O)_2$ | Cylic ring | Hydrocarbyl |
| II.96 | N | N | $((CH_2)_3O)_2$ | Cylic ring | Substituted hydrocarbyl |
| II.97 | N | N | $((CH_2)_3O)_2$ | Heterocyclic ring | Hydrogen |
| II.98 | N | N | $((CH_2)_3O)_2$ | Heterocyclic ring | Hydrocarbyl |
| II.99 | N | N | $((CH_2)_3O)_2$ | Heterocyclic ring | Substituted hydrocarbyl |
| II.100 | N | N | $((CH_2)_3O)_3$ | Aromatic ring | Hydrogen |
| II.101 | N | N | $((CH_2)_3O)_3$ | Aromatic ring | Hydrocarbyl |
| II.102 | N | N | $((CH_2)_3O)_3$ | Aromatic ring | Substituted hydrocarbyl |
| II.103 | N | N | $((CH_2)_3O)_3$ | Cylic ring | Hydrogen |
| II.104 | N | N | $((CH_2)_3O)_3$ | Cylic ring | Hydrocarbyl |
| II.105 | N | N | $((CH_2)_3O)_3$ | Cylic ring | Substituted hydrocarbyl |
| II.106 | N | N | $((CH_2)_3O)_3$ | Heterocyclic ring | Hydrogen |
| II.107 | N | N | $((CH_2)_3O)_3$ | Heterocyclic ring | Hydrocarbyl |
| II.108 | N | N | $((CH_2)_3O)_3$ | Heterocyclic ring | Substituted hydrocarbyl |
| II.109 | N | N | $((CH_2)O(CH_2))$ | Aromatic ring | Hydrogen |
| II.110 | N | N | $((CH_2)O(CH_2))$ | Aromatic ring | Hydrocarbyl |
| II.111 | N | N | $((CH_2)O(CH_2))$ | Aromatic ring | Substituted hydrocarbyl |
| II.112 | N | N | $((CH_2)O(CH_2))$ | Cylic ring | Hydrogen |
| II.113 | N | N | $((CH_2)O(CH_2))$ | Cylic ring | Hydrocarbyl |
| II.114 | N | N | $((CH_2)O(CH_2))$ | Cylic ring | Substituted hydrocarbyl |
| II.115 | N | N | $((CH_2)O(CH_2))$ | Heterocyclic ring | Hydrogen |
| II.116 | N | N | $((CH_2)O(CH_2))$ | Heterocyclic ring | Hydrocarbyl |
| II.117 | N | N | $((CH_2)O(CH_2))$ | Heterocyclic ring | Substituted hydrocarbyl |
| II.118 | N | N | $((CH_2)O(CH_2))_2$ | Aromatic ring | Hydrogen |
| II.119 | N | N | $((CH_2)O(CH_2))_2$ | Aromatic ring | Hydrocarbyl |
| II.120 | N | N | $((CH_2)O(CH_2))_2$ | Aromatic ring | Substituted hydrocarbyl |
| II.121 | N | N | $((CH_2)O(CH_2))_2$ | Cylic ring | Hydrogen |
| II.122 | N | N | $((CH_2)O(CH_2))_2$ | Cylic ring | Hydrocarbyl |
| II.123 | N | N | $((CH_2)O(CH_2))_2$ | Cylic ring | Substituted hydrocarbyl |
| II.124 | N | N | $((CH_2)O(CH_2))_2$ | Heterocyclic ring | Hydrogen |
| II.125 | N | N | $((CH_2)O(CH_2))_2$ | Heterocyclic ring | Hydrocarbyl |
| II.126 | N | N | $((CH_2)O(CH_2))_2$ | Heterocyclic ring | Substituted hydrocarbyl |
| II.127 | N | N | $((CH_2)O(CH_2))_3$ | Aromatic ring | Hydrogen |
| II.128 | N | N | $((CH_2)O(CH_2))_3$ | Aromatic ring | Hydrocarbyl |
| II.129 | N | N | $((CH_2)O(CH_2))_3$ | Aromatic ring | Substituted hydrocarbyl |
| II.130 | N | N | $((CH_2)O(CH_2))_3$ | Cylic ring | Hydrogen |
| II.131 | N | N | $((CH_2)O(CH_2))_3$ | Cylic ring | Hydrocarbyl |
| II.132 | N | N | $((CH_2)O(CH_2))_3$ | Cylic ring | Substituted hydrocarbyl |
| II.133 | N | N | $((CH_2)O(CH_2))_3$ | Heterocyclic ring | Hydrogen |
| II.134 | N | N | $((CH_2)O(CH_2))_3$ | Heterocyclic ring | Hydrocarbyl |
| II.135 | N | N | $((CH_2)O(CH_2))_3$ | Heterocyclic ring | Substituted hydrocarbyl |
| II.136 | N | N | $((CH_2)O(CH_2)_2)$ | Aromatic ring | Hydrogen |
| II.137 | N | N | $((CH_2)O(CH_2)_2)$ | Aromatic ring | Hydrocarbyl |
| II.138 | N | N | $((CH_2)O(CH_2)_2)$ | Aromatic ring | Substituted hydrocarbyl |
| II.139 | N | N | $((CH_2)O(CH_2)_2)$ | Cylic ring | Hydrogen |
| II.140 | N | N | $((CH_2)O(CH_2)_2)$ | Cylic ring | Hydrocarbyl |
| II.141 | N | N | $((CH_2)O(CH_2)_2)$ | Cylic ring | Substituted hydrocarbyl |
| II.142 | N | N | $((CH_2)O(CH_2)_2)$ | Heterocyclic ring | Hydrogen |
| II.143 | N | N | $((CH_2)O(CH_2)_2)$ | Heterocyclic ring | Hydrocarbyl |
| II.144 | N | N | $((CH_2)O(CH_2)_2)$ | Heterocyclic ring | Substituted hydrocarbyl |
| II.145 | N | N | $((CH_2)O(CH_2)_2)_2$ | Aromatic ring | Hydrogen |
| II.146 | N | N | $((CH_2)O(CH_2)_2)_2$ | Aromatic ring | Hydrocarbyl |
| II.147 | N | N | $((CH_2)O(CH_2)_2)_2$ | Aromatic ring | Substituted hydrocarbyl |
| II.148 | N | N | $((CH_2)O(CH_2)_2)_2$ | Cylic ring | Hydrogen |
| II.149 | N | N | $((CH_2)O(CH_2)_2)_2$ | Cylic ring | Hydrocarbyl |
| II.150 | N | N | $((CH_2)O(CH_2)_2)_2$ | Cylic ring | Substituted hydrocarbyl |
| II.151 | N | N | $((CH_2)O(CH_2)_2)_2$ | Heterocyclic ring | Hydrogen |
| II.152 | N | N | $((CH_2)O(CH_2)_2)_2$ | Heterocyclic ring | Hydrocarbyl |
| II.153 | N | N | $((CH_2)O(CH_2)_2)_2$ | Heterocyclic ring | Substituted hydrocarbyl |
| II.154 | N | N | $((CH_2)O(CH_2)_2)_3$ | Aromatic ring | Hydrogen |
| II.155 | N | N | $((CH_2)O(CH_2)_2)_3$ | Aromatic ring | Hydrocarbyl |
| II.156 | N | N | $((CH_2)O(CH_2)_2)_3$ | Aromatic ring | Substituted hydrocarbyl |
| II.157 | N | N | $((CH_2)O(CH_2)_2)_3$ | Cylic ring | Hydrogen |
| II.158 | N | N | $((CH_2)O(CH_2)_2)_3$ | Cylic ring | Hydrocarbyl |
| II.159 | N | N | $((CH_2)O(CH_2)_2)_3$ | Cylic ring | Substituted hydrocarbyl |
| II.160 | N | N | $((CH_2)O(CH_2)_2)_3$ | Heterocyclic ring | Hydrogen |
| II.161 | N | N | $((CH_2)O(CH_2)_2)_3$ | Heterocyclic ring | Hydrocarbyl |
| II.162 | N | N | $((CH_2)O(CH_2)_2)_3$ | Heterocyclic ring | Substituted hydrocarbyl |
| II.163 | N | N | $((CH_2)O(CH_2)_3)$ | Aromatic ring | Hydrogen |
| II.164 | N | N | $((CH_2)O(CH_2)_3)$ | Aromatic ring | Hydrocarbyl |
| II.165 | N | N | $((CH_2)O(CH_2)_3)$ | Aromatic ring | Substituted hydrocarbyl |
| II.166 | N | N | $((CH_2)O(CH_2)_3)$ | Cylic ring | Hydrogen |
| II.167 | N | N | $((CH_2)O(CH_2)_3)$ | Cylic ring | Hydrocarbyl |
| II.168 | N | N | $((CH_2)O(CH_2)_3)$ | Cylic ring | Substituted hydrocarbyl |
| II.169 | N | N | $((CH_2)O(CH_2)_3)$ | Heterocyclic ring | Hydrogen |
| II.170 | N | N | $((CH_2)O(CH_2)_3)$ | Heterocyclic ring | Hydrocarbyl |

TABLE 2-continued

Selected compounds from Formula (II)

| | R1 | R2 | R4 | R5 | R6 |
|---|---|---|---|---|---|
| II.171 | N | N | ((CH$_2$)O(CH$_2$)$_3$) | Heterocyclic ring | Substituted hydrocarbyl |
| II.172 | N | N | ((CH$_2$)O(CH$_2$)$_3$)$_2$ | Aromatic ring | Hydrogen |
| II.173 | N | N | ((CH$_2$)O(CH$_2$)$_3$)$_2$ | Aromatic ring | Hydrocarbyl |
| II.174 | N | N | ((CH$_2$)O(CH$_2$)$_3$)$_2$ | Aromatic ring | Substituted hydrocarbyl |
| II.175 | N | N | ((CH$_2$)O(CH$_2$)$_3$)$_2$ | Cylic ring | Hydrogen |
| II.176 | N | N | ((CH$_2$)O(CH$_2$)$_3$)$_2$ | Cylic ring | Hydrocarbyl |
| II.177 | N | N | ((CH$_2$)O(CH$_2$)$_3$)$_2$ | Cylic ring | Substituted hydrocarbyl |
| II.178 | N | N | ((CH$_2$)O(CH$_2$)$_3$)$_2$ | Heterocyclic ring | Hydrogen |
| II.179 | N | N | ((CH$_2$)O(CH$_2$)$_3$)$_2$ | Heterocyclic ring | Hydrocarbyl |
| II.180 | N | N | ((CH$_2$)O(CH$_2$)$_3$)$_2$ | Heterocyclic ring | Substituted hydrocarbyl |
| II.181 | N | N | ((CH$_2$)O(CH$_2$)$_3$)$_3$ | Aromatic ring | Hydrogen |
| II.182 | N | N | ((CH$_2$)O(CH$_2$)$_3$)$_3$ | Aromatic ring | Hydrocarbyl |
| II.183 | N | N | ((CH$_2$)O(CH$_2$)$_3$)$_3$ | Aromatic ring | Substituted hydrocarbyl |
| II.184 | N | N | ((CH$_2$)O(CH$_2$)$_3$)$_3$ | Cylic ring | Hydrogen |
| II.185 | N | N | ((CH$_2$)O(CH$_2$)$_3$)$_3$ | Cylic ring | Hydrocarbyl |
| II.186 | N | N | ((CH$_2$)O(CH$_2$)$_3$)$_3$ | Cylic ring | Substituted hydrocarbyl |
| II.187 | N | N | ((CH$_2$)O(CH$_2$)$_3$)$_3$ | Heterocyclic ring | Hydrogen |
| II.188 | N | N | ((CH$_2$)O(CH$_2$)$_3$)$_3$ | Heterocyclic ring | Hydrocarbyl |
| II.189 | N | N | ((CH$_2$)O(CH$_2$)$_3$)$_3$ | Heterocyclic ring | Substituted hydrocarbyl |
| II.190 | N | N | ((CH$_2$)$_2$O(CH$_2$)) | Aromatic ring | Hydrogen |
| II.191 | N | N | ((CH$_2$)$_2$O(CH$_2$)) | Aromatic ring | Hydrocarbyl |
| II.192 | N | N | ((CH$_2$)$_2$O(CH$_2$)) | Aromatic ring | Substituted hydrocarbyl |
| II.193 | N | N | ((CH$_2$)$_2$O(CH$_2$)) | Cylic ring | Hydrogen |
| II.194 | N | N | ((CH$_2$)$_2$O(CH$_2$)) | Cylic ring | Hydrocarbyl |
| II.195 | N | N | ((CH$_2$)$_2$O(CH$_2$)) | Cylic ring | Substituted hydrocarbyl |
| II.196 | N | N | ((CH$_2$)$_2$O(CH$_2$)) | Heterocyclic ring | Hydrogen |
| II.197 | N | N | ((CH$_2$)$_2$O(CH$_2$)) | Heterocyclic ring | Hydrocarbyl |
| II.198 | N | N | ((CH$_2$)$_2$O(CH$_2$)) | Heterocyclic ring | Substituted hydrocarbyl |
| II.199 | N | N | ((CH$_2$)$_2$O(CH$_2$))$_2$ | Aromatic ring | Hydrogen |
| II.200 | N | N | ((CH$_2$)$_2$O(CH$_2$))$_2$ | Aromatic ring | Hydrocarbyl |
| II.201 | N | N | ((CH$_2$)$_2$O(CH$_2$))$_2$ | Aromatic ring | Substituted hydrocarbyl |
| II.202 | N | N | ((CH$_2$)$_2$O(CH$_2$))$_2$ | Cylic ring | Hydrogen |
| II.203 | N | N | ((CH$_2$)$_2$O(CH$_2$))$_2$ | Cylic ring | Hydrocarbyl |
| II.204 | N | N | ((CH$_2$)$_2$O(CH$_2$))$_2$ | Cylic ring | Substituted hydrocarbyl |
| II.205 | N | N | ((CH$_2$)$_2$O(CH$_2$))$_2$ | Heterocyclic ring | Hydrogen |
| II.206 | N | N | ((CH$_2$)$_2$O(CH$_2$))$_2$ | Heterocyclic ring | Hydrocarbyl |
| II.207 | N | N | ((CH$_2$)$_2$O(CH$_2$))$_2$ | Heterocyclic ring | Substituted hydrocarbyl |
| II.208 | N | N | ((CH$_2$)$_2$O(CH$_2$))$_3$ | Aromatic ring | Hydrogen |
| II.209 | N | N | ((CH$_2$)$_2$O(CH$_2$))$_3$ | Aromatic ring | Hydrocarbyl |
| II.210 | N | N | ((CH$_2$)$_2$O(CH$_2$))$_3$ | Aromatic ring | Substituted hydrocarbyl |
| II.211 | N | N | ((CH$_2$)$_2$O(CH$_2$))$_3$ | Cylic ring | Hydrogen |
| II.212 | N | N | ((CH$_2$)$_2$O(CH$_2$))$_3$ | Cylic ring | Hydrocarbyl |
| II.213 | N | N | ((CH$_2$)$_2$O(CH$_2$))$_3$ | Cylic ring | Substituted hydrocarbyl |
| II.214 | N | N | ((CH$_2$)$_2$O(CH$_2$))$_3$ | Heterocyclic ring | Hydrogen |
| II.215 | N | N | ((CH$_2$)$_2$O(CH$_2$))$_3$ | Heterocyclic ring | Hydrocarbyl |
| II.216 | N | N | ((CH$_2$)$_2$O(CH$_2$))$_3$ | Heterocyclic ring | Substituted hydrocarbyl |
| II.217 | N | N | ((CH$_2$)$_2$O(CH$_2$)$_2$) | Aromatic ring | Hydrogen |
| II.218 | N | N | ((CH$_2$)$_2$O(CH$_2$)$_2$) | Aromatic ring | Hydrocarbyl |
| II.219 | N | N | ((CH$_2$)$_2$O(CH$_2$)$_2$) | Aromatic ring | Substituted hydrocarbyl |
| II.220 | N | N | ((CH$_2$)$_2$O(CH$_2$)$_2$) | Cylic ring | Hydrogen |
| II.221 | N | N | ((CH$_2$)$_2$O(CH$_2$)$_2$) | Cylic ring | Hydrocarbyl |
| II.222 | N | N | ((CH$_2$)$_2$O(CH$_2$)$_2$) | Cylic ring | Substituted hydrocarbyl |
| II.223 | N | N | ((CH$_2$)$_2$O(CH$_2$)$_2$) | Heterocyclic ring | Hydrogen |
| II.224 | N | N | ((CH$_2$)$_2$O(CH$_2$)$_2$) | Heterocyclic ring | Hydrocarbyl |
| II.225 | N | N | ((CH$_2$)$_2$O(CH$_2$)$_2$) | Heterocyclic ring | Substituted hydrocarbyl |
| II.226 | N | N | ((CH$_2$)$_2$O(CH$_2$)$_2$)$_2$ | Aromatic ring | Hydrogen |
| II.227 | N | N | ((CH$_2$)$_2$O(CH$_2$)$_2$)$_2$ | Aromatic ring | Hydrocarbyl |
| II.228 | N | N | ((CH$_2$)$_2$O(CH$_2$)$_2$)$_2$ | Aromatic ring | Substituted hydrocarbyl |
| II.229 | N | N | ((CH$_2$)$_2$O(CH$_2$)$_2$)$_2$ | Cylic ring | Hydrogen |
| II.230 | N | N | ((CH$_2$)$_2$O(CH$_2$)$_2$)$_2$ | Cylic ring | Hydrocarbyl |
| II.231 | N | N | ((CH$_2$)$_2$O(CH$_2$)$_2$)$_2$ | Cylic ring | Substituted hydrocarbyl |
| II.232 | N | N | ((CH$_2$)$_2$O(CH$_2$)$_2$)$_2$ | Heterocyclic ring | Hydrogen |
| II.233 | N | N | ((CH$_2$)$_2$O(CH$_2$)$_2$)$_2$ | Heterocyclic ring | Hydrocarbyl |
| II.234 | N | N | ((CH$_2$)$_2$O(CH$_2$)$_2$)$_2$ | Heterocyclic ring | Substituted hydrocarbyl |
| II.235 | N | N | ((CH$_2$)$_2$O(CH$_2$)$_2$)$_3$ | Aromatic ring | Hydrogen |
| II.236 | N | N | ((CH$_2$)$_2$O(CH$_2$)$_2$)$_3$ | Aromatic ring | Hydrocarbyl |
| II.237 | N | N | ((CH$_2$)$_2$O(CH$_2$)$_2$)$_3$ | Aromatic ring | Substituted hydrocarbyl |
| II.238 | N | N | ((CH$_2$)$_2$O(CH$_2$)$_2$)$_3$ | Cylic ring | Hydrogen |
| II.239 | N | N | ((CH$_2$)$_2$O(CH$_2$)$_2$)$_3$ | Cylic ring | Hydrocarbyl |
| II.240 | N | N | ((CH$_2$)$_2$O(CH$_2$)$_2$)$_3$ | Cylic ring | Substituted hydrocarbyl |
| II.241 | N | N | ((CH$_2$)$_2$O(CH$_2$)$_2$)$_3$ | Heterocyclic ring | Hydrogen |
| II.242 | N | N | ((CH$_2$)$_2$O(CH$_2$)$_2$)$_3$ | Heterocyclic ring | Hydrocarbyl |
| II.243 | N | N | ((CH$_2$)$_2$O(CH$_2$)$_2$)$_3$ | Heterocyclic ring | Substituted hydrocarbyl |
| II.244 | N | N | ((CH$_2$)$_2$O(CH$_2$)$_3$) | Aromatic ring | Hydrogen |
| II.245 | N | N | ((CH$_2$)$_2$O(CH$_2$)$_3$) | Aromatic ring | Hydrocarbyl |
| II.246 | N | N | ((CH$_2$)$_2$O(CH$_2$)$_3$) | Aromatic ring | Substituted hydrocarbyl |

TABLE 2-continued

Selected compounds from Formula (II)

| | R1 | R2 | R4 | R5 | R6 |
|---|---|---|---|---|---|
| II.247 | N | N | ((CH$_2$)$_2$O(CH$_2$)$_3$) | Cylic ring | Hydrogen |
| II.248 | N | N | ((CH$_2$)$_2$O(CH$_2$)$_3$) | Cylic ring | Hydrocarbyl |
| II.249 | N | N | ((CH$_2$)$_2$O(CH$_2$)$_3$) | Cylic ring | Substituted hydrocarbyl |
| II.250 | N | N | ((CH$_2$)$_2$O(CH$_2$)$_3$) | Heterocyclic ring | Hydrogen |
| II.251 | N | N | ((CH$_2$)$_2$O(CH$_2$)$_3$) | Heterocyclic ring | Hydrocarbyl |
| II.252 | N | N | ((CH$_2$)$_2$O(CH$_2$)$_3$) | Heterocyclic ring | Substituted hydrocarbyl |
| II.253 | N | N | ((CH$_2$)$_2$O(CH$_2$)$_3$)$_2$ | Aromatic ring | Hydrogen |
| II.254 | N | N | ((CH$_2$)$_2$O(CH$_2$)$_3$)$_2$ | Aromatic ring | Hydrocarbyl |
| II.255 | N | N | ((CH$_2$)$_2$O(CH$_2$)$_3$)$_2$ | Aromatic ring | Substituted hydrocarbyl |
| II.256 | N | N | ((CH$_2$)$_2$O(CH$_2$)$_3$)$_2$ | Cylic ring | Hydrogen |
| II.257 | N | N | ((CH$_2$)$_2$O(CH$_2$)$_3$)$_2$ | Cylic ring | Hydrocarbyl |
| II.258 | N | N | ((CH$_2$)$_2$O(CH$_2$)$_3$)$_2$ | Cylic ring | Substituted hydrocarbyl |
| II.259 | N | N | ((CH$_2$)$_2$O(CH$_2$)$_3$)$_2$ | Heterocyclic ring | Hydrogen |
| II.260 | N | N | ((CH$_2$)$_2$O(CH$_2$)$_3$)$_2$ | Heterocyclic ring | Hydrocarbyl |
| II.261 | N | N | ((CH$_2$)$_2$O(CH$_2$)$_3$)$_2$ | Heterocyclic ring | Substituted hydrocarbyl |
| II.262 | N | N | ((CH$_2$)$_2$O(CH$_2$)$_3$)$_3$ | Aromatic ring | Hydrogen |
| II.263 | N | N | ((CH$_2$)$_2$O(CH$_2$)$_3$)$_3$ | Aromatic ring | Hydrocarbyl |
| II.264 | N | N | ((CH$_2$)$_2$O(CH$_2$)$_3$)$_3$ | Aromatic ring | Substituted hydrocarbyl |
| II.265 | N | N | ((CH$_2$)$_2$O(CH$_2$)$_3$)$_3$ | Cylic ring | Hydrogen |
| II.266 | N | N | ((CH$_2$)$_2$O(CH$_2$)$_3$)$_3$ | Cylic ring | Hydrocarbyl |
| II.267 | N | N | ((CH$_2$)$_2$O(CH$_2$)$_3$)$_3$ | Cylic ring | Substituted hydrocarbyl |
| II.268 | N | N | ((CH$_2$)$_2$O(CH$_2$)$_3$)$_3$ | Heterocyclic ring | Hydrogen |
| II.269 | N | N | ((CH$_2$)$_2$O(CH$_2$)$_3$)$_3$ | Heterocyclic ring | Hydrocarbyl |
| II.270 | N | N | ((CH$_2$)$_2$O(CH$_2$)$_3$)$_3$ | Heterocyclic ring | Substituted hydrocarbyl |
| II.271 | N | N | ((CH$_2$)$_3$O(CH$_2$)) | Aromatic ring | Hydrogen |
| II.272 | N | N | ((CH$_2$)$_3$O(CH$_2$)) | Aromatic ring | Hydrocarbyl |
| II.273 | N | N | ((CH$_2$)$_3$O(CH$_2$)) | Aromatic ring | Substituted hydrocarbyl |
| II.274 | N | N | ((CH$_2$)$_3$O(CH$_2$)) | Cylic ring | Hydrogen |
| II.275 | N | N | ((CH$_2$)$_3$O(CH$_2$)) | Cylic ring | Hydrocarbyl |
| II.276 | N | N | ((CH$_2$)$_3$O(CH$_2$)) | Cylic ring | Substituted hydrocarbyl |
| II.277 | N | N | ((CH$_2$)$_3$O(CH$_2$)) | Heterocyclic ring | Hydrogen |
| II.278 | N | N | ((CH$_2$)$_3$O(CH$_2$)) | Heterocyclic ring | Hydrocarbyl |
| II.279 | N | N | ((CH$_2$)$_3$O(CH$_2$)) | Heterocyclic ring | Substituted hydrocarbyl |
| II.280 | N | N | ((CH$_2$)$_3$O(CH$_2$))$_2$ | Aromatic ring | Hydrogen |
| II.281 | N | N | ((CH$_2$)$_3$O(CH$_2$))$_2$ | Aromatic ring | Hydrocarbyl |
| II.282 | N | N | ((CH$_2$)$_3$O(CH$_2$))$_2$ | Aromatic ring | Substituted hydrocarbyl |
| II.283 | N | N | ((CH$_2$)$_3$O(CH$_2$))$_2$ | Cylic ring | Hydrogen |
| II.284 | N | N | ((CH$_2$)$_3$O(CH$_2$))$_2$ | Cylic ring | Hydrocarbyl |
| II.285 | N | N | ((CH$_2$)$_3$O(CH$_2$))$_2$ | Cylic ring | Substituted hydrocarbyl |
| II.286 | N | N | ((CH$_2$)$_3$O(CH$_2$))$_2$ | Heterocyclic ring | Hydrogen |
| II.287 | N | N | ((CH$_2$)$_3$O(CH$_2$))$_2$ | Heterocyclic ring | Hydrocarbyl |
| II.288 | N | N | ((CH$_2$)$_3$O(CH$_2$))$_2$ | Heterocyclic ring | Substituted hydrocarbyl |
| II.289 | N | N | ((CH$_2$)$_3$O(CH$_2$))$_3$ | Aromatic ring | Hydrogen |
| II.290 | N | N | ((CH$_2$)$_3$O(CH$_2$))$_3$ | Aromatic ring | Hydrocarbyl |
| II.291 | N | N | ((CH$_2$)$_3$O(CH$_2$))$_3$ | Aromatic ring | Substituted hydrocarbyl |
| II.292 | N | N | ((CH$_2$)$_3$O(CH$_2$))$_3$ | Cylic ring | Hydrogen |
| II.293 | N | N | ((CH$_2$)$_3$O(CH$_2$))$_3$ | Cylic ring | Hydrocarbyl |
| II.294 | N | N | ((CH$_2$)$_3$O(CH$_2$))$_3$ | Cylic ring | Substituted hydrocarbyl |
| II.295 | N | N | ((CH$_2$)$_3$O(CH$_2$))$_3$ | Heterocyclic ring | Hydrogen |
| II.296 | N | N | ((CH$_2$)$_3$O(CH$_2$))$_3$ | Heterocyclic ring | Hydrocarbyl |
| II.297 | N | N | ((CH$_2$)$_3$O(CH$_2$))$_3$ | Heterocyclic ring | Substituted hydrocarbyl |
| II.298 | N | N | ((CH$_2$)$_3$O(CH$_2$)$_2$) | Aromatic ring | Hydrogen |
| II.299 | N | N | ((CH$_2$)$_3$O(CH$_2$)$_2$) | Aromatic ring | Hydrocarbyl |
| II.300 | N | N | ((CH$_2$)$_3$O(CH$_2$)$_2$) | Aromatic ring | Substituted hydrocarbyl |
| II.301 | N | N | ((CH$_2$)$_3$O(CH$_2$)$_2$) | Cylic ring | Hydrogen |
| II.302 | N | N | ((CH$_2$)$_3$O(CH$_2$)$_2$) | Cylic ring | Hydrocarbyl |
| II.303 | N | N | ((CH$_2$)$_3$O(CH$_2$)$_2$) | Cylic ring | Substituted hydrocarbyl |
| II.304 | N | N | ((CH$_2$)$_3$O(CH$_2$)$_2$) | Heterocyclic ring | Hydrogen |
| II.305 | N | N | ((CH$_2$)$_3$O(CH$_2$)$_2$) | Heterocyclic ring | Hydrocarbyl |
| II.306 | N | N | ((CH$_2$)$_3$O(CH$_2$)$_2$) | Heterocyclic ring | Substituted hydrocarbyl |
| II.307 | N | N | ((CH$_2$)$_3$O(CH$_2$)$_2$)$_2$ | Aromatic ring | Hydrogen |
| II.308 | N | N | ((CH$_2$)$_3$O(CH$_2$)$_2$)$_2$ | Aromatic ring | Hydrocarbyl |
| II.309 | N | N | ((CH$_2$)$_3$O(CH$_2$)$_2$)$_2$ | Aromatic ring | Substituted hydrocarbyl |
| II.310 | N | N | ((CH$_2$)$_3$O(CH$_2$)$_2$)$_2$ | Cylic ring | Hydrogen |
| II.311 | N | N | ((CH$_2$)$_3$O(CH$_2$)$_2$)$_2$ | Cylic ring | Hydrocarbyl |
| II.312 | N | N | ((CH$_2$)$_3$O(CH$_2$)$_2$)$_2$ | Cylic ring | Substituted hydrocarbyl |
| II.313 | N | N | ((CH$_2$)$_3$O(CH$_2$)$_2$)$_2$ | Heterocyclic ring | Hydrogen |
| II.314 | N | N | ((CH$_2$)$_3$O(CH$_2$)$_2$)$_2$ | Heterocyclic ring | Hydrocarbyl |
| II.315 | N | N | ((CH$_2$)$_3$O(CH$_2$)$_2$)$_2$ | Heterocyclic ring | Substituted hydrocarbyl |
| II.316 | N | N | ((CH$_2$)$_3$O(CH$_2$)$_2$)$_3$ | Aromatic ring | Hydrogen |
| II.317 | N | N | ((CH$_2$)$_3$O(CH$_2$)$_2$)$_3$ | Aromatic ring | Hydrocarbyl |
| II.318 | N | N | ((CH$_2$)$_3$O(CH$_2$)$_2$)$_3$ | Aromatic ring | Substituted hydrocarbyl |
| II.319 | N | N | ((CH$_2$)$_3$O(CH$_2$)$_2$)$_3$ | Cylic ring | Hydrogen |
| II.320 | N | N | ((CH$_2$)$_3$O(CH$_2$)$_2$)$_3$ | Cylic ring | Hydrocarbyl |
| II.321 | N | N | ((CH$_2$)$_3$O(CH$_2$)$_2$)$_3$ | Cylic ring | Substituted hydrocarbyl |
| II.322 | N | N | ((CH$_2$)$_3$O(CH$_2$)$_2$)$_3$ | Heterocyclic ring | Hydrogen |

TABLE 2-continued

Selected compounds from Formula (II)

| | R1 | R2 | R4 | R5 | R6 |
|---|---|---|---|---|---|
| II.323 | N | N | $((CH_2)_3O(CH_2)_2)_3$ | Heterocyclic ring | Hydrocarbyl |
| II.324 | N | N | $((CH_2)_3O(CH_2)_2)_3$ | Heterocyclic ring | Substituted hydrocarbyl |
| II.325 | N | N | $((CH_2)_3O(CH_2)_3)$ | Aromatic ring | Hydrogen |
| II.326 | N | N | $((CH_2)_3O(CH_2)_3)$ | Aromatic ring | Hydrocarbyl |
| II.327 | N | N | $((CH_2)_3O(CH_2)_3)$ | Aromatic ring | Substituted hydrocarbyl |
| II.328 | N | N | $((CH_2)_3O(CH_2)_3)$ | Cylic ring | Hydrogen |
| II.329 | N | N | $((CH_2)_3O(CH_2)_3)$ | Cylic ring | Hydrocarbyl |
| II.330 | N | N | $((CH_2)_3O(CH_2)_3)$ | Cylic ring | Substituted hydrocarbyl |
| II.331 | N | N | $((CH_2)_3O(CH_2)_3)$ | Heterocyclic ring | Hydrogen |
| II.332 | N | N | $((CH_2)_3O(CH_2)_3)$ | Heterocyclic ring | Hydrocarbyl |
| II.333 | N | N | $((CH_2)_3O(CH_2)_3)$ | Heterocyclic ring | Substituted hydrocarbyl |
| II.334 | N | N | $((CH_2)_3O(CH_2)_3)_2$ | Aromatic ring | Hydrogen |
| II.335 | N | N | $((CH_2)_3O(CH_2)_3)_2$ | Aromatic ring | Hydrocarbyl |
| II.336 | N | N | $((CH_2)_3O(CH_2)_3)_2$ | Aromatic ring | Substituted hydrocarbyl |
| II.337 | N | N | $((CH_2)_3O(CH_2)_3)_2$ | Cylic ring | Hydrogen |
| II.338 | N | N | $((CH_2)_3O(CH_2)_3)_2$ | Cylic ring | Hydrocarbyl |
| II.339 | N | N | $((CH_2)_3O(CH_2)_3)_2$ | Cylic ring | Substituted hydrocarbyl |
| II.340 | N | N | $((CH_2)_3O(CH_2)_3)_2$ | Heterocyclic ring | Hydrogen |
| II.341 | N | N | $((CH_2)_3O(CH_2)_3)_2$ | Heterocyclic ring | Hydrocarbyl |
| II.342 | N | N | $((CH_2)_3O(CH_2)_3)_2$ | Heterocyclic ring | Substituted hydrocarbyl |
| II.343 | N | N | $((CH_2)_3O(CH_2)_3)_3$ | Aromatic ring | Hydrogen |
| II.344 | N | N | $((CH_2)_3O(CH_2)_3)_3$ | Aromatic ring | Hydrocarbyl |
| II.345 | N | N | $((CH_2)_3O(CH_2)_3)_3$ | Aromatic ring | Substituted hydrocarbyl |
| II.346 | N | N | $((CH_2)_3O(CH_2)_3)_3$ | Cylic ring | Hydrogen |
| II.347 | N | N | $((CH_2)_3O(CH_2)_3)_3$ | Cylic ring | Hydrocarbyl |
| II.348 | N | N | $((CH_2)_3O(CH_2)_3)_3$ | Cylic ring | Substituted hydrocarbyl |
| II.349 | N | N | $((CH_2)_3O(CH_2)_3)_3$ | Heterocyclic ring | Hydrogen |
| II.350 | N | N | $((CH_2)_3O(CH_2)_3)_3$ | Heterocyclic ring | Hydrocarbyl |
| II.351 | N | N | $((CH_2)_3O(CH_2)_3)_3$ | Heterocyclic ring | Substituted hydrocarbyl |
| II.352 | N | S | $(CH_2)$ | Aromatic ring | Hydrogen |
| II.353 | N | S | $(CH_2)$ | Aromatic ring | Hydrocarbyl |
| II.354 | N | S | $(CH_2)$ | Aromatic ring | Substituted hydrocarbyl |
| II.355 | N | S | $(CH_2)$ | Cylic ring | Hydrogen |
| II.356 | N | S | $(CH_2)$ | Cylic ring | Hydrocarbyl |
| II.357 | N | S | $(CH_2)$ | Cylic ring | Substituted hydrocarbyl |
| II.358 | N | S | $(CH_2)$ | Heterocyclic ring | Hydrogen |
| II.359 | N | S | $(CH_2)$ | Heterocyclic ring | Hydrocarbyl |
| II.360 | N | S | $(CH_2)$ | Heterocyclic ring | Substituted hydrocarbyl |
| II.361 | N | S | $(CH_2)_2$ | Aromatic ring | Hydrogen |
| II.362 | N | S | $(CH_2)_2$ | Aromatic ring | Hydrocarbyl |
| II.363 | N | S | $(CH_2)_2$ | Aromatic ring | Substituted hydrocarbyl |
| II.364 | N | S | $(CH_2)_2$ | Cylic ring | Hydrogen |
| II.365 | N | S | $(CH_2)_2$ | Cylic ring | Hydrocarbyl |
| II.366 | N | S | $(CH_2)_2$ | Cylic ring | Substituted hydrocarbyl |
| II.367 | N | S | $(CH_2)_2$ | Heterocyclic ring | Hydrogen |
| II.368 | N | S | $(CH_2)_2$ | Heterocyclic ring | Hydrocarbyl |
| II.369 | N | S | $(CH_2)_2$ | Heterocyclic ring | Substituted hydrocarbyl |
| II.370 | N | S | $(CH_2)_3$ | Aromatic ring | Hydrogen |
| II.371 | N | S | $(CH_2)_3$ | Aromatic ring | Hydrocarbyl |
| II.372 | N | S | $(CH_2)_3$ | Aromatic ring | Substituted hydrocarbyl |
| II.373 | N | S | $(CH_2)_3$ | Cylic ring | Hydrogen |
| II.374 | N | S | $(CH_2)_3$ | Cylic ring | Hydrocarbyl |
| II.375 | N | S | $(CH_2)_3$ | Cylic ring | Substituted hydrocarbyl |
| II.376 | N | S | $(CH_2)_3$ | Heterocyclic ring | Hydrogen |
| II.377 | N | S | $(CH_2)_3$ | Heterocyclic ring | Hydrocarbyl |
| II.378 | N | S | $(CH_2)_3$ | Heterocyclic ring | Substituted hydrocarbyl |
| II.379 | N | S | $((CH_2)O)$ | Aromatic ring | Hydrogen |
| II.380 | N | S | $((CH_2)O)$ | Aromatic ring | Hydrocarbyl |
| II.381 | N | S | $((CH_2)O)$ | Aromatic ring | Substituted hydrocarbyl |
| II.382 | N | S | $((CH_2)O)$ | Cylic ring | Hydrogen |
| II.383 | N | S | $((CH_2)O)$ | Cylic ring | Hydrocarbyl |
| II.384 | N | S | $((CH_2)O)$ | Cylic ring | Substituted hydrocarbyl |
| II.385 | N | S | $((CH_2)O)$ | Heterocyclic ring | Hydrogen |
| II.386 | N | S | $((CH_2)O)$ | Heterocyclic ring | Hydrocarbyl |
| II.387 | N | S | $((CH_2)O)$ | Heterocyclic ring | Substituted hydrocarbyl |
| II.388 | N | S | $((CH_2)O)_2$ | Aromatic ring | Hydrogen |
| II.389 | N | S | $((CH_2)O)_2$ | Aromatic ring | Hydrocarbyl |
| II.390 | N | S | $((CH_2)O)_2$ | Aromatic ring | Substituted hydrocarbyl |
| II.391 | N | S | $((CH_2)O)_2$ | Cylic ring | Hydrogen |
| II.392 | N | S | $((CH_2)O)_2$ | Cylic ring | Hydrocarbyl |
| II.393 | N | S | $((CH_2)O)_2$ | Cylic ring | Substituted hydrocarbyl |
| II.394 | N | S | $((CH_2)O)_2$ | Heterocyclic ring | Hydrogen |
| II.395 | N | S | $((CH_2)O)_2$ | Heterocyclic ring | Hydrocarbyl |
| II.396 | N | S | $((CH_2)O)_2$ | Heterocyclic ring | Substituted hydrocarbyl |
| II.397 | N | S | $((CH_2)O)_3$ | Aromatic ring | Hydrogen |
| II.398 | N | S | $((CH_2)O)_3$ | Aromatic ring | Hydrocarbyl |

TABLE 2-continued

Selected compounds from Formula (II)

| | R1 | R2 | R4 | R5 | R6 |
|---|---|---|---|---|---|
| II.399 | N | S | $((CH_2)O)_3$ | Aromatic ring | Substituted hydrocarbyl |
| II.400 | N | S | $((CH_2)O)_3$ | Cylic ring | Hydrogen |
| II.401 | N | S | $((CH_2)O)_3$ | Cylic ring | Hydrocarbyl |
| II.402 | N | S | $((CH_2)O)_3$ | Cylic ring | Substituted hydrocarbyl |
| II.403 | N | S | $((CH_2)O)_3$ | Heterocyclic ring | Hydrogen |
| II.404 | N | S | $((CH_2)O)_3$ | Heterocyclic ring | Hydrocarbyl |
| II.405 | N | S | $((CH_2)O)_3$ | Heterocyclic ring | Substituted hydrocarbyl |
| II.406 | N | S | $((CH_2)_2O)$ | Aromatic ring | Hydrogen |
| II.407 | N | S | $((CH_2)_2O)$ | Aromatic ring | Hydrocarbyl |
| II.408 | N | S | $((CH_2)_2O)$ | Aromatic ring | Substituted hydrocarbyl |
| II.409 | N | S | $((CH_2)_2O)$ | Cylic ring | Hydrogen |
| II.410 | N | S | $((CH_2)_2O)$ | Cylic ring | Hydrocarbyl |
| II.411 | N | S | $((CH_2)_2O)$ | Cylic ring | Substituted hydrocarbyl |
| II.412 | N | S | $((CH_2)_2O)$ | Heterocyclic ring | Hydrogen |
| II.413 | N | S | $((CH_2)_2O)$ | Heterocyclic ring | Hydrocarbyl |
| II.414 | N | S | $((CH_2)_2O)$ | Heterocyclic ring | Substituted hydrocarbyl |
| II.415 | N | S | $((CH_2)_2O)_2$ | Aromatic ring | Hydrogen |
| II.416 | N | S | $((CH_2)_2O)_2$ | Aromatic ring | Hydrocarbyl |
| II.417 | N | S | $((CH_2)_2O)_2$ | Aromatic ring | Substituted hydrocarbyl |
| II.418 | N | S | $((CH_2)_2O)_2$ | Cylic ring | Hydrogen |
| II.419 | N | S | $((CH_2)_2O)_2$ | Cylic ring | Hydrocarbyl |
| II.420 | N | S | $((CH_2)_2O)_2$ | Cylic ring | Substituted hydrocarbyl |
| II.421 | N | S | $((CH_2)_2O)_2$ | Heterocyclic ring | Hydrogen |
| II.422 | N | S | $((CH_2)_2O)_2$ | Heterocyclic ring | Hydrocarbyl |
| II.423 | N | S | $((CH_2)_2O)_2$ | Heterocyclic ring | Substituted hydrocarbyl |
| II.424 | N | S | $((CH_2)_2O)_3$ | Aromatic ring | Hydrogen |
| II.425 | N | S | $((CH_2)_2O)_3$ | Aromatic ring | Hydrocarbyl |
| II.426 | N | S | $((CH_2)_2O)_3$ | Aromatic ring | Substituted hydrocarbyl |
| II.427 | N | S | $((CH_2)_2O)_3$ | Cylic ring | Hydrogen |
| II.428 | N | S | $((CH_2)_2O)_3$ | Cylic ring | Hydrocarbyl |
| II.429 | N | S | $((CH_2)_2O)_3$ | Cylic ring | Substituted hydrocarbyl |
| II.430 | N | S | $((CH_2)_2O)_3$ | Heterocyclic ring | Hydrogen |
| II.431 | N | S | $((CH_2)_2O)_3$ | Heterocyclic ring | Hydrocarbyl |
| II.432 | N | S | $((CH_2)_2O)_3$ | Heterocyclic ring | Substituted hydrocarbyl |
| II.433 | N | S | $((CH_2)_3O)$ | Aromatic ring | Hydrogen |
| II.434 | N | S | $((CH_2)_3O)$ | Aromatic ring | Hydrocarbyl |
| II.435 | N | S | $((CH_2)_3O)$ | Aromatic ring | Substituted hydrocarbyl |
| II.436 | N | S | $((CH_2)_3O)$ | Cylic ring | Hydrogen |
| II.437 | N | S | $((CH_2)_3O)$ | Cylic ring | Hydrocarbyl |
| II.438 | N | S | $((CH_2)_3O)$ | Cylic ring | Substituted hydrocarbyl |
| II.439 | N | S | $((CH_2)_3O)$ | Heterocyclic ring | Hydrogen |
| II.440 | N | S | $((CH_2)_3O)$ | Heterocyclic ring | Hydrocarbyl |
| II.441 | N | S | $((CH_2)_3O)$ | Heterocyclic ring | Substituted hydrocarbyl |
| II.442 | N | S | $((CH_2)_3O)_2$ | Aromatic ring | Hydrogen |
| II.443 | N | S | $((CH_2)_3O)_2$ | Aromatic ring | Hydrocarbyl |
| II.444 | N | S | $((CH_2)_3O)_2$ | Aromatic ring | Substituted hydrocarbyl |
| II.445 | N | S | $((CH_2)_3O)_2$ | Cylic ring | Hydrogen |
| II.446 | N | S | $((CH_2)_3O)_2$ | Cylic ring | Hydrocarbyl |
| II.447 | N | S | $((CH_2)_3O)_2$ | Cylic ring | Substituted hydrocarbyl |
| II.448 | N | S | $((CH_2)_3O)_2$ | Heterocyclic ring | Hydrogen |
| II.449 | N | S | $((CH_2)_3O)_2$ | Heterocyclic ring | Hydrocarbyl |
| II.450 | N | S | $((CH_2)_3O)_2$ | Heterocyclic ring | Substituted hydrocarbyl |
| II.451 | N | S | $((CH_2)_3O)_3$ | Aromatic ring | Hydrogen |
| II.452 | N | S | $((CH_2)_3O)_3$ | Aromatic ring | Hydrocarbyl |
| II.453 | N | S | $((CH_2)_3O)_3$ | Aromatic ring | Substituted hydrocarbyl |
| II.454 | N | S | $((CH_2)_3O)_3$ | Cylic ring | Hydrogen |
| II.455 | N | S | $((CH_2)_3O)_3$ | Cylic ring | Hydrocarbyl |
| II.456 | N | S | $((CH_2)_3O)_3$ | Cylic ring | Substituted hydrocarbyl |
| II.457 | N | S | $((CH_2)_3O)_3$ | Heterocyclic ring | Hydrogen |
| II.458 | N | S | $((CH_2)_3O)_3$ | Heterocyclic ring | Hydrocarbyl |
| II.459 | N | S | $((CH_2)_3O)_3$ | Heterocyclic ring | Substituted hydrocarbyl |
| II.460 | N | S | $((CH_2)O(CH_2))$ | Aromatic ring | Hydrogen |
| II.461 | N | S | $((CH_2)O(CH_2))$ | Aromatic ring | Hydrocarbyl |
| II.462 | N | S | $((CH_2)O(CH_2))$ | Aromatic ring | Substituted hydrocarbyl |
| II.463 | N | S | $((CH_2)O(CH_2))$ | Cylic ring | Hydrogen |
| II.464 | N | S | $((CH_2)O(CH_2))$ | Cylic ring | Hydrocarbyl |
| II.465 | N | S | $((CH_2)O(CH_2))$ | Cylic ring | Substituted hydrocarbyl |
| II.466 | N | S | $((CH_2)O(CH_2))$ | Heterocyclic ring | Hydrogen |
| II.467 | N | S | $((CH_2)O(CH_2))$ | Heterocyclic ring | Hydrocarbyl |
| II.468 | N | S | $((CH_2)O(CH_2))$ | Heterocyclic ring | Substituted hydrocarbyl |
| II.469 | N | S | $((CH_2)O(CH_2))_2$ | Aromatic ring | Hydrogen |
| II.470 | N | S | $((CH_2)O(CH_2))_2$ | Aromatic ring | Hydrocarbyl |
| II.471 | N | S | $((CH_2)O(CH_2))_2$ | Aromatic ring | Substituted hydrocarbyl |
| II.472 | N | S | $((CH_2)O(CH_2))_2$ | Cylic ring | Hydrogen |
| II.473 | N | S | $((CH_2)O(CH_2))_2$ | Cylic ring | Hydrocarbyl |
| II.474 | N | S | $((CH_2)O(CH_2))_2$ | Cylic ring | Substituted hydrocarbyl |

TABLE 2-continued

Selected compounds from Formula (II)

|  | R1 | R2 | R4 | R5 | R6 |
|---|---|---|---|---|---|
| II.475 | N | S | ((CH$_2$)O(CH$_2$))$_2$ | Heterocyclic ring | Hydrogen |
| II.476 | N | S | ((CH$_2$)O(CH$_2$))$_2$ | Heterocyclic ring | Hydrocarbyl |
| II.477 | N | S | ((CH$_2$)O(CH$_2$))$_2$ | Heterocyclic ring | Substituted hydrocarbyl |
| II.478 | N | S | ((CH$_2$)O(CH$_2$))$_3$ | Aromatic ring | Hydrogen |
| II.479 | N | S | ((CH$_2$)O(CH$_2$))$_3$ | Aromatic ring | Hydrocarbyl |
| II.480 | N | S | ((CH$_2$)O(CH$_2$))$_3$ | Aromatic ring | Substituted hydrocarbyl |
| II.481 | N | S | ((CH$_2$)O(CH$_2$))$_3$ | Cylic ring | Hydrogen |
| II.482 | N | S | ((CH$_2$)O(CH$_2$))$_3$ | Cylic ring | Hydrocarbyl |
| II.483 | N | S | ((CH$_2$)O(CH$_2$))$_3$ | Cylic ring | Substituted hydrocarbyl |
| II.484 | N | S | ((CH$_2$)O(CH$_2$))$_3$ | Heterocyclic ring | Hydrogen |
| II.485 | N | S | ((CH$_2$)O(CH$_2$))$_3$ | Heterocyclic ring | Hydrocarbyl |
| II.486 | N | S | ((CH$_2$)O(CH$_2$))$_3$ | Heterocyclic ring | Substituted hydrocarbyl |
| II.487 | N | S | ((CH$_2$)O(CH$_2$)$_2$) | Aromatic ring | Hydrogen |
| II.488 | N | S | ((CH$_2$)O(CH$_2$)$_2$) | Aromatic ring | Hydrocarbyl |
| II.489 | N | S | ((CH$_2$)O(CH$_2$)$_2$) | Aromatic ring | Substituted hydrocarbyl |
| II.490 | N | S | ((CH$_2$)O(CH$_2$)$_2$) | Cylic ring | Hydrogen |
| II.491 | N | S | ((CH$_2$)O(CH$_2$)$_2$) | Cylic ring | Hydrocarbyl |
| II.492 | N | S | ((CH$_2$)O(CH$_2$)$_2$) | Cylic ring | Substituted hydrocarbyl |
| II.493 | N | S | ((CH$_2$)O(CH$_2$)$_2$) | Heterocyclic ring | Hydrogen |
| II.494 | N | S | ((CH$_2$)O(CH$_2$)$_2$) | Heterocyclic ring | Hydrocarbyl |
| II.495 | N | S | ((CH$_2$)O(CH$_2$)$_2$) | Heterocyclic ring | Substituted hydrocarbyl |
| II.496 | N | S | ((CH$_2$)O(CH$_2$)$_2$)$_2$ | Aromatic ring | Hydrogen |
| II.497 | N | S | ((CH$_2$)O(CH$_2$)$_2$)$_2$ | Aromatic ring | Hydrocarbyl |
| II.498 | N | S | ((CH$_2$)O(CH$_2$)$_2$)$_2$ | Aromatic ring | Substituted hydrocarbyl |
| II.499 | N | S | ((CH$_2$)O(CH$_2$)$_2$)$_2$ | Cylic ring | Hydrogen |
| II.500 | N | S | ((CH$_2$)O(CH$_2$)$_2$)$_2$ | Cylic ring | Hydrocarbyl |
| II.501 | N | S | ((CH$_2$)O(CH$_2$)$_2$)$_2$ | Cylic ring | Substituted hydrocarbyl |
| II.502 | N | S | ((CH$_2$)O(CH$_2$)$_2$)$_2$ | Heterocyclic ring | Hydrogen |
| II.503 | N | S | ((CH$_2$)O(CH$_2$)$_2$)$_2$ | Heterocyclic ring | Hydrocarbyl |
| II.504 | N | S | ((CH$_2$)O(CH$_2$)$_2$)$_2$ | Heterocyclic ring | Substituted hydrocarbyl |
| II.505 | N | S | ((CH$_2$)O(CH$_2$)$_2$)$_3$ | Aromatic ring | Hydrogen |
| II.506 | N | S | ((CH$_2$)O(CH$_2$)$_2$)$_3$ | Aromatic ring | Hydrocarbyl |
| II.507 | N | S | ((CH$_2$)O(CH$_2$)$_2$)$_3$ | Aromatic ring | Substituted hydrocarbyl |
| II.508 | N | S | ((CH$_2$)O(CH$_2$)$_2$)$_3$ | Cylic ring | Hydrogen |
| II.509 | N | S | ((CH$_2$)O(CH$_2$)$_2$)$_3$ | Cylic ring | Hydrocarbyl |
| II.510 | N | S | ((CH$_2$)O(CH$_2$)$_2$)$_3$ | Cylic ring | Substituted hydrocarbyl |
| II.511 | N | S | ((CH$_2$)O(CH$_2$)$_2$)$_3$ | Heterocyclic ring | Hydrogen |
| II.512 | N | S | ((CH$_2$)O(CH$_2$)$_2$)$_3$ | Heterocyclic ring | Hydrocarbyl |
| II.513 | N | S | ((CH$_2$)O(CH$_2$)$_2$)$_3$ | Heterocyclic ring | Substituted hydrocarbyl |
| II.514 | N | S | ((CH$_2$)O(CH$_2$)$_3$) | Aromatic ring | Hydrogen |
| II.515 | N | S | ((CH$_2$)O(CH$_2$)$_3$) | Aromatic ring | Hydrocarbyl |
| II.516 | N | S | ((CH$_2$)O(CH$_2$)$_3$) | Aromatic ring | Substituted hydrocarbyl |
| II.517 | N | S | ((CH$_2$)O(CH$_2$)$_3$) | Cylic ring | Hydrogen |
| II.518 | N | S | ((CH$_2$)O(CH$_2$)$_3$) | Cylic ring | Hydrocarbyl |
| II.519 | N | S | ((CH$_2$)O(CH$_2$)$_3$) | Cylic ring | Substituted hydrocarbyl |
| II.520 | N | S | ((CH$_2$)O(CH$_2$)$_3$) | Heterocyclic ring | Hydrogen |
| II.521 | N | S | ((CH$_2$)O(CH$_2$)$_3$) | Heterocyclic ring | Hydrocarbyl |
| II.522 | N | S | ((CH$_2$)O(CH$_2$)$_3$) | Heterocyclic ring | Substituted hydrocarbyl |
| II.523 | N | S | ((CH$_2$)O(CH$_2$)$_3$)$_2$ | Aromatic ring | Hydrogen |
| II.524 | N | S | ((CH$_2$)O(CH$_2$)$_3$)$_2$ | Aromatic ring | Hydrocarbyl |
| II.525 | N | S | ((CH$_2$)O(CH$_2$)$_3$)$_2$ | Aromatic ring | Substituted hydrocarbyl |
| II.526 | N | S | ((CH$_2$)O(CH$_2$)$_3$)$_2$ | Cylic ring | Hydrogen |
| II.527 | N | S | ((CH$_2$)O(CH$_2$)$_3$)$_2$ | Cylic ring | Hydrocarbyl |
| II.528 | N | S | ((CH$_2$)O(CH$_2$)$_3$)$_2$ | Cylic ring | Substituted hydrocarbyl |
| II.529 | N | S | ((CH$_2$)O(CH$_2$)$_3$)$_2$ | Heterocyclic ring | Hydrogen |
| II.530 | N | S | ((CH$_2$)O(CH$_2$)$_3$)$_2$ | Heterocyclic ring | Hydrocarbyl |
| II.531 | N | S | ((CH$_2$)O(CH$_2$)$_3$)$_2$ | Heterocyclic ring | Substituted hydrocarbyl |
| II.532 | N | S | ((CH$_2$)O(CH$_2$)$_3$)$_3$ | Aromatic ring | Hydrogen |
| II.533 | N | S | ((CH$_2$)O(CH$_2$)$_3$)$_3$ | Aromatic ring | Hydrocarbyl |
| II.534 | N | S | ((CH$_2$)O(CH$_2$)$_3$)$_3$ | Aromatic ring | Substituted hydrocarbyl |
| II.535 | N | S | ((CH$_2$)O(CH$_2$)$_3$)$_3$ | Cylic ring | Hydrogen |
| II.536 | N | S | ((CH$_2$)O(CH$_2$)$_3$)$_3$ | Cylic ring | Hydrocarbyl |
| II.537 | N | S | ((CH$_2$)O(CH$_2$)$_3$)$_3$ | Cylic ring | Substituted hydrocarbyl |
| II.538 | N | S | ((CH$_2$)O(CH$_2$)$_3$)$_3$ | Heterocyclic ring | Hydrogen |
| II.539 | N | S | ((CH$_2$)O(CH$_2$)$_3$)$_3$ | Heterocyclic ring | Hydrocarbyl |
| II.540 | N | S | ((CH$_2$)O(CH$_2$)$_3$)$_3$ | Heterocyclic ring | Substituted hydrocarbyl |
| II.541 | N | S | ((CH$_2$)$_2$O(CH$_2$)) | Aromatic ring | Hydrogen |
| II.542 | N | S | ((CH$_2$)$_2$O(CH$_2$)) | Aromatic ring | Hydrocarbyl |
| II.543 | N | S | ((CH$_2$)$_2$O(CH$_2$)) | Aromatic ring | Substituted hydrocarbyl |
| II.544 | N | S | ((CH$_2$)$_2$O(CH$_2$)) | Cylic ring | Hydrogen |
| II.545 | N | S | ((CH$_2$)$_2$O(CH$_2$)) | Cylic ring | Hydrocarbyl |
| II.546 | N | S | ((CH$_2$)$_2$O(CH$_2$)) | Cylic ring | Substituted hydrocarbyl |
| II.547 | N | S | ((CH$_2$)$_2$O(CH$_2$)) | Heterocyclic ring | Hydrogen |
| II.548 | N | S | ((CH$_2$)$_2$O(CH$_2$)) | Heterocyclic ring | Hydrocarbyl |
| II.549 | N | S | ((CH$_2$)$_2$O(CH$_2$)) | Heterocyclic ring | Substituted hydrocarbyl |
| II.550 | N | S | ((CH$_2$)$_2$O(CH$_2$))$_2$ | Aromatic ring | Hydrogen |

TABLE 2-continued

Selected compounds from Formula (II)

| | R1 | R2 | R4 | R5 | R6 |
|---|---|---|---|---|---|
| II.551 | N | S | $((CH_2)_2O(CH_2))_2$ | Aromatic ring | Hydrocarbyl |
| II.552 | N | S | $((CH_2)_2O(CH_2))_2$ | Aromatic ring | Substituted hydrocarbyl |
| II.553 | N | S | $((CH_2)_2O(CH_2))_2$ | Cylic ring | Hydrogen |
| II.554 | N | S | $((CH_2)_2O(CH_2))_2$ | Cylic ring | Hydrocarbyl |
| II.555 | N | S | $((CH_2)_2O(CH_2))_2$ | Cylic ring | Substituted hydrocarbyl |
| II.556 | N | S | $((CH_2)_2O(CH_2))_2$ | Heterocyclic ring | Hydrogen |
| II.557 | N | S | $((CH_2)_2O(CH_2))_2$ | Heterocyclic ring | Hydrocarbyl |
| II.558 | N | S | $((CH_2)_2O(CH_2))_2$ | Heterocyclic ring | Substituted hydrocarbyl |
| II.559 | N | S | $((CH_2)_2O(CH_2))_3$ | Aromatic ring | Hydrogen |
| II.560 | N | S | $((CH_2)_2O(CH_2))_3$ | Aromatic ring | Hydrocarbyl |
| II.561 | N | S | $((CH_2)_2O(CH_2))_3$ | Aromatic ring | Substituted hydrocarbyl |
| II.562 | N | S | $((CH_2)_2O(CH_2))_3$ | Cylic ring | Hydrogen |
| II.563 | N | S | $((CH_2)_2O(CH_2))_3$ | Cylic ring | Hydrocarbyl |
| II.564 | N | S | $((CH_2)_2O(CH_2))_3$ | Cylic ring | Substituted hydrocarbyl |
| II.565 | N | S | $((CH_2)_2O(CH_2))_3$ | Heterocyclic ring | Hydrogen |
| II.566 | N | S | $((CH_2)_2O(CH_2))_3$ | Heterocyclic ring | Hydrocarbyl |
| II.567 | N | S | $((CH_2)_2O(CH_2))_3$ | Heterocyclic ring | Substituted hydrocarbyl |
| II.568 | N | S | $((CH_2)_2O(CH_2)_2)$ | Aromatic ring | Hydrogen |
| II.569 | N | S | $((CH_2)_2O(CH_2)_2)$ | Aromatic ring | Hydrocarbyl |
| II.570 | N | S | $((CH_2)_2O(CH_2)_2)$ | Aromatic ring | Substituted hydrocarbyl |
| II.571 | N | S | $((CH_2)_2O(CH_2)_2)$ | Cylic ring | Hydrogen |
| II.572 | N | S | $((CH_2)_2O(CH_2)_2)$ | Cylic ring | Hydrocarbyl |
| II.573 | N | S | $((CH_2)_2O(CH_2)_2)$ | Cylic ring | Substituted hydrocarbyl |
| II.574 | N | S | $((CH_2)_2O(CH_2)_2)$ | Heterocyclic ring | Hydrogen |
| II.575 | N | S | $((CH_2)_2O(CH_2)_2)$ | Heterocyclic ring | Hydrocarbyl |
| II.576 | N | S | $((CH_2)_2O(CH_2)_2)$ | Heterocyclic ring | Substituted hydrocarbyl |
| II.577 | N | S | $((CH_2)_2O(CH_2)_2)_2$ | Aromatic ring | Hydrogen |
| II.578 | N | S | $((CH_2)_2O(CH_2)_2)_2$ | Aromatic ring | Hydrocarbyl |
| II.579 | N | S | $((CH_2)_2O(CH_2)_2)_2$ | Aromatic ring | Substituted hydrocarbyl |
| II.580 | N | S | $((CH_2)_2O(CH_2)_2)_2$ | Cylic ring | Hydrogen |
| II.581 | N | S | $((CH_2)_2O(CH_2)_2)_2$ | Cylic ring | Hydrocarbyl |
| II.582 | N | S | $((CH_2)_2O(CH_2)_2)_2$ | Cylic ring | Substituted hydrocarbyl |
| II.583 | N | S | $((CH_2)_2O(CH_2)_2)_2$ | Heterocyclic ring | Hydrogen |
| II.584 | N | S | $((CH_2)_2O(CH_2)_2)_2$ | Heterocyclic ring | Hydrocarbyl |
| II.585 | N | S | $((CH_2)_2O(CH_2)_2)_2$ | Heterocyclic ring | Substituted hydrocarbyl |
| II.586 | N | S | $((CH_2)_2O(CH_2)_2)_3$ | Aromatic ring | Hydrogen |
| II.587 | N | S | $((CH_2)_2O(CH_2)_2)_3$ | Aromatic ring | Hydrocarbyl |
| II.588 | N | S | $((CH_2)_2O(CH_2)_2)_3$ | Aromatic ring | Substituted hydrocarbyl |
| II.589 | N | S | $((CH_2)_2O(CH_2)_2)_3$ | Cylic ring | Hydrogen |
| II.590 | N | S | $((CH_2)_2O(CH_2)_2)_3$ | Cylic ring | Hydrocarbyl |
| II.591 | N | S | $((CH_2)_2O(CH_2)_2)_3$ | Cylic ring | Substituted hydrocarbyl |
| II.592 | N | S | $((CH_2)_2O(CH_2)_2)_3$ | Heterocyclic ring | Hydrogen |
| II.593 | N | S | $((CH_2)_2O(CH_2)_2)_3$ | Heterocyclic ring | Hydrocarbyl |
| II.594 | N | S | $((CH_2)_2O(CH_2)_2)_3$ | Heterocyclic ring | Substituted hydrocarbyl |
| II.595 | N | S | $((CH_2)_2O(CH_2)_3)$ | Aromatic ring | Hydrogen |
| II.596 | N | S | $((CH_2)_2O(CH_2)_3)$ | Aromatic ring | Hydrocarbyl |
| II.597 | N | S | $((CH_2)_2O(CH_2)_3)$ | Aromatic ring | Substituted hydrocarbyl |
| II.598 | N | S | $((CH_2)_2O(CH_2)_3)$ | Cylic ring | Hydrogen |
| II.599 | N | S | $((CH_2)_2O(CH_2)_3)$ | Cylic ring | Hydrocarbyl |
| II.600 | N | S | $((CH_2)_2O(CH_2)_3)$ | Cylic ring | Substituted hydrocarbyl |
| II.601 | N | S | $((CH_2)_2O(CH_2)_3)$ | Heterocyclic ring | Hydrogen |
| II.602 | N | S | $((CH_2)_2O(CH_2)_3)$ | Heterocyclic ring | Hydrocarbyl |
| II.603 | N | S | $((CH_2)_2O(CH_2)_3)$ | Heterocyclic ring | Substituted hydrocarbyl |
| II.604 | N | S | $((CH_2)_2O(CH_2)_3)_2$ | Aromatic ring | Hydrogen |
| II.605 | N | S | $((CH_2)_2O(CH_2)_3)_2$ | Aromatic ring | Hydrocarbyl |
| II.606 | N | S | $((CH_2)_2O(CH_2)_3)_2$ | Aromatic ring | Substituted hydrocarbyl |
| II.607 | N | S | $((CH_2)_2O(CH_2)_3)_2$ | Cylic ring | Hydrogen |
| II.608 | N | S | $((CH_2)_2O(CH_2)_3)_2$ | Cylic ring | Hydrocarbyl |
| II.609 | N | S | $((CH_2)_2O(CH_2)_3)_2$ | Cylic ring | Substituted hydrocarbyl |
| II.610 | N | S | $((CH_2)_2O(CH_2)_3)_2$ | Heterocyclic ring | Hydrogen |
| II.611 | N | S | $((CH_2)_2O(CH_2)_3)_2$ | Heterocyclic ring | Hydrocarbyl |
| II.612 | N | S | $((CH_2)_2O(CH_2)_3)_2$ | Heterocyclic ring | Substituted hydrocarbyl |
| II.613 | N | S | $((CH_2)_2O(CH_2)_3)_3$ | Aromatic ring | Hydrogen |
| II.614 | N | S | $((CH_2)_2O(CH_2)_3)_3$ | Aromatic ring | Hydrocarbyl |
| II.615 | N | S | $((CH_2)_2O(CH_2)_3)_3$ | Aromatic ring | Substituted hydrocarbyl |
| II.616 | N | S | $((CH_2)_2O(CH_2)_3)_3$ | Cylic ring | Hydrogen |
| II.617 | N | S | $((CH_2)_2O(CH_2)_3)_3$ | Cylic ring | Hydrocarbyl |
| II.618 | N | S | $((CH_2)_2O(CH_2)_3)_3$ | Cylic ring | Substituted hydrocarbyl |
| II.619 | N | S | $((CH_2)_2O(CH_2)_3)_3$ | Heterocyclic ring | Hydrogen |
| II.620 | N | S | $((CH_2)_2O(CH_2)_3)_3$ | Heterocyclic ring | Hydrocarbyl |
| II.621 | N | S | $((CH_2)_2O(CH_2)_3)_3$ | Heterocyclic ring | Substituted hydrocarbyl |
| II.622 | N | S | $((CH_2)_3O(CH_2))$ | Aromatic ring | Hydrogen |
| II.623 | N | S | $((CH_2)_3O(CH_2))$ | Aromatic ring | Hydrocarbyl |
| II.624 | N | S | $((CH_2)_3O(CH_2))$ | Aromatic ring | Substituted hydrocarbyl |
| II.625 | N | S | $((CH_2)_3O(CH_2))$ | Cylic ring | Hydrogen |
| II.626 | N | S | $((CH_2)_3O(CH_2))$ | Cylic ring | Hydrocarbyl |

TABLE 2-continued

Selected compounds from Formula (II)

| | R1 | R2 | R4 | R5 | R6 |
|---|---|---|---|---|---|
| II.627 | N | S | $((CH_2)_3O(CH_2))$ | Cylic ring | Substituted hydrocarbyl |
| II.628 | N | S | $((CH_2)_3O(CH_2))$ | Heterocyclic ring | Hydrogen |
| II.629 | N | S | $((CH_2)_3O(CH_2))$ | Heterocyclic ring | Hydrocarbyl |
| II.630 | N | S | $((CH_2)_3O(CH_2))$ | Heterocyclic ring | Substituted hydrocarbyl |
| II.631 | N | S | $((CH_2)_3O(CH_2))_2$ | Aromatic ring | Hydrogen |
| II.632 | N | S | $((CH_2)_3O(CH_2))_2$ | Aromatic ring | Hydrocarbyl |
| II.633 | N | S | $((CH_2)_3O(CH_2))_2$ | Aromatic ring | Substituted hydrocarbyl |
| II.634 | N | S | $((CH_2)_3O(CH_2))_2$ | Cylic ring | Hydrogen |
| II.635 | N | S | $((CH_2)_3O(CH_2))_2$ | Cylic ring | Hydrocarbyl |
| II.636 | N | S | $((CH_2)_3O(CH_2))_2$ | Cylic ring | Substituted hydrocarbyl |
| II.637 | N | S | $((CH_2)_3O(CH_2))_2$ | Heterocyclic ring | Hydrogen |
| II.638 | N | S | $((CH_2)_3O(CH_2))_2$ | Heterocyclic ring | Hydrocarbyl |
| II.639 | N | S | $((CH_2)_3O(CH_2))_2$ | Heterocyclic ring | Substituted hydrocarbyl |
| II.640 | N | S | $((CH_2)_3O(CH_2))_3$ | Aromatic ring | Hydrogen |
| II.641 | N | S | $((CH_2)_3O(CH_2))_3$ | Aromatic ring | Hydrocarbyl |
| II.642 | N | S | $((CH_2)_3O(CH_2))_3$ | Aromatic ring | Substituted hydrocarbyl |
| II.643 | N | S | $((CH_2)_3O(CH_2))_3$ | Cylic ring | Hydrogen |
| II.644 | N | S | $((CH_2)_3O(CH_2))_3$ | Cylic ring | Hydrocarbyl |
| II.645 | N | S | $((CH_2)_3O(CH_2))_3$ | Cylic ring | Substituted hydrocarbyl |
| II.646 | N | S | $((CH_2)_3O(CH_2))_3$ | Heterocyclic ring | Hydrogen |
| II.647 | N | S | $((CH_2)_3O(CH_2))_3$ | Heterocyclic ring | Hydrocarbyl |
| II.648 | N | S | $((CH_2)_3O(CH_2))_3$ | Heterocyclic ring | Substituted hydrocarbyl |
| II.649 | N | S | $((CH_2)_3O(CH_2)_2)$ | Aromatic ring | Hydrogen |
| II.650 | N | S | $((CH_2)_3O(CH_2)_2)$ | Aromatic ring | Hydrocarbyl |
| II.651 | N | S | $((CH_2)_3O(CH_2)_2)$ | Aromatic ring | Substituted hydrocarbyl |
| II.652 | N | S | $((CH_2)_3O(CH_2)_2)$ | Cylic ring | Hydrogen |
| II.653 | N | S | $((CH_2)_3O(CH_2)_2)$ | Cylic ring | Hydrocarbyl |
| II.654 | N | S | $((CH_2)_3O(CH_2)_2)$ | Cylic ring | Substituted hydrocarbyl |
| II.655 | N | S | $((CH_2)_3O(CH_2)_2)$ | Heterocyclic ring | Hydrogen |
| II.656 | N | S | $((CH_2)_3O(CH_2)_2)$ | Heterocyclic ring | Hydrocarbyl |
| II.657 | N | S | $((CH_2)_3O(CH_2)_2)$ | Heterocyclic ring | Substituted hydrocarbyl |
| II.658 | N | S | $((CH_2)_3O(CH_2)_2)_2$ | Aromatic ring | Hydrogen |
| II.659 | N | S | $((CH_2)_3O(CH_2)_2)_2$ | Aromatic ring | Hydrocarbyl |
| II.660 | N | S | $((CH_2)_3O(CH_2)_2)_2$ | Aromatic ring | Substituted hydrocarbyl |
| II.661 | N | S | $((CH_2)_3O(CH_2)_2)_2$ | Cylic ring | Hydrogen |
| II.662 | N | S | $((CH_2)_3O(CH_2)_2)_2$ | Cylic ring | Hydrocarbyl |
| II.663 | N | S | $((CH_2)_3O(CH_2)_2)_2$ | Cylic ring | Substituted hydrocarbyl |
| II.664 | N | S | $((CH_2)_3O(CH_2)_2)_2$ | Heterocyclic ring | Hydrogen |
| II.665 | N | S | $((CH_2)_3O(CH_2)_2)_2$ | Heterocyclic ring | Hydrocarbyl |
| II.666 | N | S | $((CH_2)_3O(CH_2)_2)_2$ | Heterocyclic ring | Substituted hydrocarbyl |
| II.667 | N | S | $((CH_2)_3O(CH_2)_2)_3$ | Aromatic ring | Hydrogen |
| II.668 | N | S | $((CH_2)_3O(CH_2)_2)_3$ | Aromatic ring | Hydrocarbyl |
| II.669 | N | S | $((CH_2)_3O(CH_2)_2)_3$ | Aromatic ring | Substituted hydrocarbyl |
| II.670 | N | S | $((CH_2)_3O(CH_2)_2)_3$ | Cylic ring | Hydrogen |
| II.671 | N | S | $((CH_2)_3O(CH_2)_2)_3$ | Cylic ring | Hydrocarbyl |
| II.672 | N | S | $((CH_2)_3O(CH_2)_2)_3$ | Cylic ring | Substituted hydrocarbyl |
| II.673 | N | S | $((CH_2)_3O(CH_2)_2)_3$ | Heterocyclic ring | Hydrogen |
| II.674 | N | S | $((CH_2)_3O(CH_2)_2)_3$ | Heterocyclic ring | Hydrocarbyl |
| II.675 | N | S | $((CH_2)_3O(CH_2)_2)_3$ | Heterocyclic ring | Substituted hydrocarbyl |
| II.676 | N | S | $((CH_2)_3O(CH_2)_3)$ | Aromatic ring | Hydrogen |
| II.677 | N | S | $((CH_2)_3O(CH_2)_3)$ | Aromatic ring | Hydrocarbyl |
| II.678 | N | S | $((CH_2)_3O(CH_2)_3)$ | Aromatic ring | Substituted hydrocarbyl |
| II.679 | N | S | $((CH_2)_3O(CH_2)_3)$ | Cylic ring | Hydrogen |
| II.680 | N | S | $((CH_2)_3O(CH_2)_3)$ | Cylic ring | Hydrocarbyl |
| II.681 | N | S | $((CH_2)_3O(CH_2)_3)$ | Cylic ring | Substituted hydrocarbyl |
| II.682 | N | S | $((CH_2)_3O(CH_2)_3)$ | Heterocyclic ring | Hydrogen |
| II.683 | N | S | $((CH_2)_3O(CH_2)_3)$ | Heterocyclic ring | Hydrocarbyl |
| II.684 | N | S | $((CH_2)_3O(CH_2)_3)$ | Heterocyclic ring | Substituted hydrocarbyl |
| II.685 | N | S | $((CH_2)_3O(CH_2)_3)_2$ | Aromatic ring | Hydrogen |
| II.686 | N | S | $((CH_2)_3O(CH_2)_3)_2$ | Aromatic ring | Hydrocarbyl |
| II.687 | N | S | $((CH_2)_3O(CH_2)_3)_2$ | Aromatic ring | Substituted hydrocarbyl |
| II.688 | N | S | $((CH_2)_3O(CH_2)_3)_2$ | Cylic ring | Hydrogen |
| II.689 | N | S | $((CH_2)_3O(CH_2)_3)_2$ | Cylic ring | Hydrocarbyl |
| II.690 | N | S | $((CH_2)_3O(CH_2)_3)_2$ | Cylic ring | Substituted hydrocarbyl |
| II.691 | N | S | $((CH_2)_3O(CH_2)_3)_2$ | Heterocyclic ring | Hydrogen |
| II.692 | N | S | $((CH_2)_3O(CH_2)_3)_2$ | Heterocyclic ring | Hydrocarbyl |
| II.693 | N | S | $((CH_2)_3O(CH_2)_3)_2$ | Heterocyclic ring | Substituted hydrocarbyl |
| II.694 | N | S | $((CH_2)_3O(CH_2)_3)_3$ | Aromatic ring | Hydrogen |
| II.695 | N | S | $((CH_2)_3O(CH_2)_3)_3$ | Aromatic ring | Hydrocarbyl |
| II.696 | N | S | $((CH_2)_3O(CH_2)_3)_3$ | Aromatic ring | Substituted hydrocarbyl |
| II.697 | N | S | $((CH_2)_3O(CH_2)_3)_3$ | Cylic ring | Hydrogen |
| II.698 | N | S | $((CH_2)_3O(CH_2)_3)_3$ | Cylic ring | Hydrocarbyl |
| II.699 | N | S | $((CH_2)_3O(CH_2)_3)_3$ | Cylic ring | Substituted hydrocarbyl |
| II.700 | N | S | $((CH_2)_3O(CH_2)_3)_3$ | Heterocyclic ring | Hydrogen |
| II.701 | N | S | $((CH_2)_3O(CH_2)_3)_3$ | Heterocyclic ring | Hydrocarbyl |
| II.702 | N | S | $((CH_2)_3O(CH_2)_3)_3$ | Heterocyclic ring | Substituted hydrocarbyl |

TABLE 2-continued

Selected compounds from Formula (II)

|        | R1 | R2 | R4          | R5               | R6                     |
|--------|----|----|-------------|------------------|------------------------|
| II.703 | N  | O  | (CH$_2$)    | Aromatic ring    | Hydrogen               |
| II.704 | N  | O  | (CH$_2$)    | Aromatic ring    | Hydrocarbyl            |
| II.705 | N  | O  | (CH$_2$)    | Aromatic ring    | Substituted hydrocarbyl |
| II.706 | N  | O  | (CH$_2$)    | Cylic ring       | Hydrogen               |
| II.707 | N  | O  | (CH$_2$)    | Cylic ring       | Hydrocarbyl            |
| II.708 | N  | O  | (CH$_2$)    | Cylic ring       | Substituted hydrocarbyl |
| II.709 | N  | O  | (CH$_2$)    | Heterocyclic ring | Hydrogen              |
| II.710 | N  | O  | (CH$_2$)    | Heterocyclic ring | Hydrocarbyl           |
| II.711 | N  | O  | (CH$_2$)    | Heterocyclic ring | Substituted hydrocarbyl |
| II.712 | N  | O  | (CH$_2$)$_2$ | Aromatic ring    | Hydrogen               |
| II.713 | N  | O  | (CH$_2$)$_2$ | Aromatic ring    | Hydrocarbyl            |
| II.714 | N  | O  | (CH$_2$)$_2$ | Aromatic ring    | Substituted hydrocarbyl |
| II.715 | N  | O  | (CH$_2$)$_2$ | Cylic ring       | Hydrogen               |
| II.716 | N  | O  | (CH$_2$)$_2$ | Cylic ring       | Hydrocarbyl            |
| II.717 | N  | O  | (CH$_2$)$_2$ | Cylic ring       | Substituted hydrocarbyl |
| II.718 | N  | O  | (CH$_2$)$_2$ | Heterocyclic ring | Hydrogen              |
| II.719 | N  | O  | (CH$_2$)$_2$ | Heterocyclic ring | Hydrocarbyl           |
| II.720 | N  | O  | (CH$_2$)$_2$ | Heterocyclic ring | Substituted hydrocarbyl |
| II.721 | N  | O  | (CH$_2$)$_3$ | Aromatic ring    | Hydrogen               |
| II.722 | N  | O  | (CH$_2$)$_3$ | Aromatic ring    | Hydrocarbyl            |
| II.723 | N  | O  | (CH$_2$)$_3$ | Aromatic ring    | Substituted hydrocarbyl |
| II.724 | N  | O  | (CH$_2$)$_3$ | Cylic ring       | Hydrogen               |
| II.725 | N  | O  | (CH$_2$)$_3$ | Cylic ring       | Hydrocarbyl            |
| II.726 | N  | O  | (CH$_2$)$_3$ | Cylic ring       | Substituted hydrocarbyl |
| II.727 | N  | O  | (CH$_2$)$_3$ | Heterocyclic ring | Hydrogen              |
| II.728 | N  | O  | (CH$_2$)$_3$ | Heterocyclic ring | Hydrocarbyl           |
| II.729 | N  | O  | (CH$_2$)$_3$ | Heterocyclic ring | Substituted hydrocarbyl |
| II.730 | N  | O  | ((CH$_2$)O) | Aromatic ring    | Hydrogen               |
| II.731 | N  | O  | ((CH$_2$)O) | Aromatic ring    | Hydrocarbyl            |
| II.732 | N  | O  | ((CH$_2$)O) | Aromatic ring    | Substituted hydrocarbyl |
| II.733 | N  | O  | ((CH$_2$)O) | Cylic ring       | Hydrogen               |
| II.734 | N  | O  | ((CH$_2$)O) | Cylic ring       | Hydrocarbyl            |
| II.735 | N  | O  | ((CH$_2$)O) | Cylic ring       | Substituted hydrocarbyl |
| II.736 | N  | O  | ((CH$_2$)O) | Heterocyclic ring | Hydrogen              |
| II.737 | N  | O  | ((CH$_2$)O) | Heterocyclic ring | Hydrocarbyl           |
| II.738 | N  | O  | ((CH$_2$)O) | Heterocyclic ring | Substituted hydrocarbyl |
| II.739 | N  | O  | ((CH$_2$)O)$_2$ | Aromatic ring | Hydrogen               |
| II.740 | N  | O  | ((CH$_2$)O)$_2$ | Aromatic ring | Hydrocarbyl            |
| II.741 | N  | O  | ((CH$_2$)O)$_2$ | Aromatic ring | Substituted hydrocarbyl |
| II.742 | N  | O  | ((CH$_2$)O)$_2$ | Cylic ring    | Hydrogen               |
| II.743 | N  | O  | ((CH$_2$)O)$_2$ | Cylic ring    | Hydrocarbyl            |
| II.744 | N  | O  | ((CH$_2$)O)$_2$ | Cylic ring    | Substituted hydrocarbyl |
| II.745 | N  | O  | ((CH$_2$)O)$_2$ | Heterocyclic ring | Hydrogen          |
| II.746 | N  | O  | ((CH$_2$)O)$_2$ | Heterocyclic ring | Hydrocarbyl       |
| II.747 | N  | O  | ((CH$_2$)O)$_2$ | Heterocyclic ring | Substituted hydrocarbyl |
| II.748 | N  | O  | ((CH$_2$)O)$_3$ | Aromatic ring | Hydrogen               |
| II.749 | N  | O  | ((CH$_2$)O)$_3$ | Aromatic ring | Hydrocarbyl            |
| II.750 | N  | O  | ((CH$_2$)O)$_3$ | Aromatic ring | Substituted hydrocarbyl |
| II.751 | N  | O  | ((CH$_2$)O)$_3$ | Cylic ring    | Hydrogen               |
| II.752 | N  | O  | ((CH$_2$)O)$_3$ | Cylic ring    | Hydrocarbyl            |
| II.753 | N  | O  | ((CH$_2$)O)$_3$ | Cylic ring    | Substituted hydrocarbyl |
| II.754 | N  | O  | ((CH$_2$)O)$_3$ | Heterocyclic ring | Hydrogen          |
| II.755 | N  | O  | ((CH$_2$)O)$_3$ | Heterocyclic ring | Hydrocarbyl       |
| II.756 | N  | O  | ((CH$_2$)O)$_3$ | Heterocyclic ring | Substituted hydrocarbyl |
| II.757 | N  | O  | ((CH$_2$)$_2$O) | Aromatic ring | Hydrogen              |
| II.758 | N  | O  | ((CH$_2$)$_2$O) | Aromatic ring | Hydrocarbyl           |
| II.759 | N  | O  | ((CH$_2$)$_2$O) | Aromatic ring | Substituted hydrocarbyl |
| II.760 | N  | O  | ((CH$_2$)$_2$O) | Cylic ring    | Hydrogen              |
| II.761 | N  | O  | ((CH$_2$)$_2$O) | Cylic ring    | Hydrocarbyl           |
| II.762 | N  | O  | ((CH$_2$)$_2$O) | Cylic ring    | Substituted hydrocarbyl |
| II.763 | N  | O  | ((CH$_2$)$_2$O) | Heterocyclic ring | Hydrogen         |
| II.764 | N  | O  | ((CH$_2$)$_2$O) | Heterocyclic ring | Hydrocarbyl      |
| II.765 | N  | O  | ((CH$_2$)$_2$O) | Heterocyclic ring | Substituted hydrocarbyl |
| II.766 | N  | O  | ((CH$_2$)$_2$O)$_2$ | Aromatic ring | Hydrogen          |
| II.767 | N  | O  | ((CH$_2$)$_2$O)$_2$ | Aromatic ring | Hydrocarbyl       |
| II.768 | N  | O  | ((CH$_2$)$_2$O)$_2$ | Aromatic ring | Substituted hydrocarbyl |
| II.769 | N  | O  | ((CH$_2$)$_2$O)$_2$ | Cylic ring    | Hydrogen          |
| II.770 | N  | O  | ((CH$_2$)$_2$O)$_2$ | Cylic ring    | Hydrocarbyl       |
| II.771 | N  | O  | ((CH$_2$)$_2$O)$_2$ | Cylic ring    | Substituted hydrocarbyl |
| II.772 | N  | O  | ((CH$_2$)$_2$O)$_2$ | Heterocyclic ring | Hydrogen     |
| II.773 | N  | O  | ((CH$_2$)$_2$O)$_2$ | Heterocyclic ring | Hydrocarbyl  |
| II.774 | N  | O  | ((CH$_2$)$_2$O)$_2$ | Heterocyclic ring | Substituted hydrocarbyl |
| II.775 | N  | O  | ((CH$_2$)$_2$O)$_3$ | Aromatic ring | Hydrogen          |
| II.776 | N  | O  | ((CH$_2$)$_2$O)$_3$ | Aromatic ring | Hydrocarbyl       |
| II.777 | N  | O  | ((CH$_2$)$_2$O)$_3$ | Aromatic ring | Substituted hydrocarbyl |
| II.778 | N  | O  | ((CH$_2$)$_2$O)$_3$ | Cylic ring    | Hydrogen          |

TABLE 2-continued

Selected compounds from Formula (II)

| | R1 | R2 | R4 | R5 | R6 |
|---|---|---|---|---|---|
| II.779 | N | O | $((CH_2)_2O)_3$ | Cylic ring | Hydrocarbyl |
| II.780 | N | O | $((CH_2)_2O)_3$ | Cylic ring | Substituted hydrocarbyl |
| II.781 | N | O | $((CH_2)_2O)_3$ | Heterocyclic ring | Hydrogen |
| II.782 | N | O | $((CH_2)_2O)_3$ | Heterocyclic ring | Hydrocarbyl |
| II.783 | N | O | $((CH_2)_2O)_3$ | Heterocyclic ring | Substituted hydrocarbyl |
| II.784 | N | O | $((CH_2)_3O)$ | Aromatic ring | Hydrogen |
| II.785 | N | O | $((CH_2)_3O)$ | Aromatic ring | Hydrocarbyl |
| II.786 | N | O | $((CH_2)_3O)$ | Aromatic ring | Substituted hydrocarbyl |
| II.787 | N | O | $((CH_2)_3O)$ | Cylic ring | Hydrogen |
| II.788 | N | O | $((CH_2)_3O)$ | Cylic ring | Hydrocarbyl |
| II.789 | N | O | $((CH_2)_3O)$ | Cylic ring | Substituted hydrocarbyl |
| II.790 | N | O | $((CH_2)_3O)$ | Heterocyclic ring | Hydrogen |
| II.791 | N | O | $((CH_2)_3O)$ | Heterocyclic ring | Hydrocarbyl |
| II.792 | N | O | $((CH_2)_3O)$ | Heterocyclic ring | Substituted hydrocarbyl |
| II.793 | N | O | $((CH_2)_3O)_2$ | Aromatic ring | Hydrogen |
| II.794 | N | O | $((CH_2)_3O)_2$ | Aromatic ring | Hydrocarbyl |
| II.795 | N | O | $((CH_2)_3O)_2$ | Aromatic ring | Substituted hydrocarbyl |
| II.796 | N | O | $((CH_2)_3O)_2$ | Cylic ring | Hydrogen |
| II.797 | N | O | $((CH_2)_3O)_2$ | Cylic ring | Hydrocarbyl |
| II.798 | N | O | $((CH_2)_3O)_2$ | Cylic ring | Substituted hydrocarbyl |
| II.799 | N | O | $((CH_2)_3O)_2$ | Heterocyclic ring | Hydrogen |
| II.800 | N | O | $((CH_2)_3O)_2$ | Heterocyclic ring | Hydrocarbyl |
| II.801 | N | O | $((CH_2)_3O)_2$ | Heterocyclic ring | Substituted hydrocarbyl |
| II.802 | N | O | $((CH_2)_3O)_3$ | Aromatic ring | Hydrogen |
| II.803 | N | O | $((CH_2)_3O)_3$ | Aromatic ring | Hydrocarbyl |
| II.804 | N | O | $((CH_2)_3O)_3$ | Aromatic ring | Substituted hydrocarbyl |
| II.805 | N | O | $((CH_2)_3O)_3$ | Cylic ring | Hydrogen |
| II.806 | N | O | $((CH_2)_3O)_3$ | Cylic ring | Hydrocarbyl |
| II.807 | N | O | $((CH_2)_3O)_3$ | Cylic ring | Substituted hydrocarbyl |
| II.808 | N | O | $((CH_2)_3O)_3$ | Heterocyclic ring | Hydrogen |
| II.809 | N | O | $((CH_2)_3O)_3$ | Heterocyclic ring | Hydrocarbyl |
| II.810 | N | O | $((CH_2)_3O)_3$ | Heterocyclic ring | Substituted hydrocarbyl |
| II.811 | N | O | $((CH_2)O(CH_2))$ | Aromatic ring | Hydrogen |
| II.812 | N | O | $((CH_2)O(CH_2))$ | Aromatic ring | Hydrocarbyl |
| II.813 | N | O | $((CH_2)O(CH_2))$ | Aromatic ring | Substituted hydrocarbyl |
| II.814 | N | O | $((CH_2)O(CH_2))$ | Cylic ring | Hydrogen |
| II.815 | N | O | $((CH_2)O(CH_2))$ | Cylic ring | Hydrocarbyl |
| II.816 | N | O | $((CH_2)O(CH_2))$ | Cylic ring | Substituted hydrocarbyl |
| II.817 | N | O | $((CH_2)O(CH_2))$ | Heterocyclic ring | Hydrogen |
| II.818 | N | O | $((CH_2)O(CH_2))$ | Heterocyclic ring | Hydrocarbyl |
| II.819 | N | O | $((CH_2)O(CH_2))$ | Heterocyclic ring | Substituted hydrocarbyl |
| II.820 | N | O | $((CH_2)O(CH_2))_2$ | Aromatic ring | Hydrogen |
| II.821 | N | O | $((CH_2)O(CH_2))_2$ | Aromatic ring | Hydrocarbyl |
| II.822 | N | O | $((CH_2)O(CH_2))_2$ | Aromatic ring | Substituted hydrocarbyl |
| II.823 | N | O | $((CH_2)O(CH_2))_2$ | Cylic ring | Hydrogen |
| II.824 | N | O | $((CH_2)O(CH_2))_2$ | Cylic ring | Hydrocarbyl |
| II.825 | N | O | $((CH_2)O(CH_2))_2$ | Cylic ring | Substituted hydrocarbyl |
| II.826 | N | O | $((CH_2)O(CH_2))_2$ | Heterocyclic ring | Hydrogen |
| II.827 | N | O | $((CH_2)O(CH_2))_2$ | Heterocyclic ring | Hydrocarbyl |
| II.828 | N | O | $((CH_2)O(CH_2))_2$ | Heterocyclic ring | Substituted hydrocarbyl |
| II.829 | N | O | $((CH_2)O(CH_2))_3$ | Aromatic ring | Hydrogen |
| II.830 | N | O | $((CH_2)O(CH_2))_3$ | Aromatic ring | Hydrocarbyl |
| II.831 | N | O | $((CH_2)O(CH_2))_3$ | Aromatic ring | Substituted hydrocarbyl |
| II.832 | N | O | $((CH_2)O(CH_2))_3$ | Cylic ring | Hydrogen |
| II.833 | N | O | $((CH_2)O(CH_2))_3$ | Cylic ring | Hydrocarbyl |
| II.834 | N | O | $((CH_2)O(CH_2))_3$ | Cylic ring | Substituted hydrocarbyl |
| II.835 | N | O | $((CH_2)O(CH_2))_3$ | Heterocyclic ring | Hydrogen |
| II.836 | N | O | $((CH_2)O(CH_2))_3$ | Heterocyclic ring | Hydrocarbyl |
| II.837 | N | O | $((CH_2)O(CH_2))_3$ | Heterocyclic ring | Substituted hydrocarbyl |
| II.838 | N | O | $((CH_2)O(CH_2)_2)$ | Aromatic ring | Hydrogen |
| II.839 | N | O | $((CH_2)O(CH_2)_2)$ | Aromatic ring | Hydrocarbyl |
| II.840 | N | O | $((CH_2)O(CH_2)_2)$ | Aromatic ring | Substituted hydrocarbyl |
| II.841 | N | O | $((CH_2)O(CH_2)_2)$ | Cylic ring | Hydrogen |
| II.842 | N | O | $((CH_2)O(CH_2)_2)$ | Cylic ring | Hydrocarbyl |
| II.843 | N | O | $((CH_2)O(CH_2)_2)$ | Cylic ring | Substituted hydrocarbyl |
| II.844 | N | O | $((CH_2)O(CH_2)_2)$ | Heterocyclic ring | Hydrogen |
| II.845 | N | O | $((CH_2)O(CH_2)_2)$ | Heterocyclic ring | Hydrocarbyl |
| II.846 | N | O | $((CH_2)O(CH_2)_2)$ | Heterocyclic ring | Substituted hydrocarbyl |
| II.847 | N | O | $((CH_2)O(CH_2)_2)_2$ | Aromatic ring | Hydrogen |
| II.848 | N | O | $((CH_2)O(CH_2)_2)_2$ | Aromatic ring | Hydrocarbyl |
| II.849 | N | O | $((CH_2)O(CH_2)_2)_2$ | Aromatic ring | Substituted hydrocarbyl |
| II.850 | N | O | $((CH_2)O(CH_2)_2)_2$ | Cylic ring | Hydrogen |
| II.851 | N | O | $((CH_2)O(CH_2)_2)_2$ | Cylic ring | Hydrocarbyl |
| II.852 | N | O | $((CH_2)O(CH_2)_2)_2$ | Cylic ring | Substituted hydrocarbyl |
| II.853 | N | O | $((CH_2)O(CH_2)_2)_2$ | Heterocyclic ring | Hydrogen |
| II.854 | N | O | $((CH_2)O(CH_2)_2)_2$ | Heterocyclic ring | Hydrocarbyl |

TABLE 2-continued

Selected compounds from Formula (II)

| | R1 | R2 | R4 | R5 | R6 |
|---|---|---|---|---|---|
| II.855 | N | O | $((CH_2)O(CH_2)_2)_2$ | Heterocyclic ring | Substituted hydrocarbyl |
| II.856 | N | O | $((CH_2)O(CH_2)_2)_3$ | Aromatic ring | Hydrogen |
| II.857 | N | O | $((CH_2)O(CH_2)_2)_3$ | Aromatic ring | Hydrocarbyl |
| II.858 | N | O | $((CH_2)O(CH_2)_2)_3$ | Aromatic ring | Substituted hydrocarbyl |
| II.859 | N | O | $((CH_2)O(CH_2)_2)_3$ | Cylic ring | Hydrogen |
| II.860 | N | O | $((CH_2)O(CH_2)_2)_3$ | Cylic ring | Hydrocarbyl |
| II.861 | N | O | $((CH_2)O(CH_2)_2)_3$ | Cylic ring | Substituted hydrocarbyl |
| II.862 | N | O | $((CH_2)O(CH_2)_2)_3$ | Heterocyclic ring | Hydrogen |
| II.863 | N | O | $((CH_2)O(CH_2)_2)_3$ | Heterocyclic ring | Hydrocarbyl |
| II.864 | N | O | $((CH_2)O(CH_2)_2)_3$ | Heterocyclic ring | Substituted hydrocarbyl |
| II.865 | N | O | $((CH_2)O(CH_2)_3)$ | Aromatic ring | Hydrogen |
| II.866 | N | O | $((CH_2)O(CH_2)_3)$ | Aromatic ring | Hydrocarbyl |
| II.867 | N | O | $((CH_2)O(CH_2)_3)$ | Aromatic ring | Substituted hydrocarbyl |
| II.868 | N | O | $((CH_2)O(CH_2)_3)$ | Cylic ring | Hydrogen |
| II.869 | N | O | $((CH_2)O(CH_2)_3)$ | Cylic ring | Hydrocarbyl |
| II.870 | N | O | $((CH_2)O(CH_2)_3)$ | Cylic ring | Substituted hydrocarbyl |
| II.871 | N | O | $((CH_2)O(CH_2)_3)$ | Heterocyclic ring | Hydrogen |
| II.872 | N | O | $((CH_2)O(CH_2)_3)$ | Heterocyclic ring | Hydrocarbyl |
| II.873 | N | O | $((CH_2)O(CH_2)_3)$ | Heterocyclic ring | Substituted hydrocarbyl |
| II.874 | N | O | $((CH_2)O(CH_2)_3)_2$ | Aromatic ring | Hydrogen |
| II.875 | N | O | $((CH_2)O(CH_2)_3)_2$ | Aromatic ring | Hydrocarbyl |
| II.876 | N | O | $((CH_2)O(CH_2)_3)_2$ | Aromatic ring | Substituted hydrocarbyl |
| II.877 | N | O | $((CH_2)O(CH_2)_3)_2$ | Cylic ring | Hydrogen |
| II.878 | N | O | $((CH_2)O(CH_2)_3)_2$ | Cylic ring | Hydrocarbyl |
| II.879 | N | O | $((CH_2)O(CH_2)_3)_2$ | Cylic ring | Substituted hydrocarbyl |
| II.880 | N | O | $((CH_2)O(CH_2)_3)_2$ | Heterocyclic ring | Hydrogen |
| II.881 | N | O | $((CH_2)O(CH_2)_3)_2$ | Heterocyclic ring | Hydrocarbyl |
| II.882 | N | O | $((CH_2)O(CH_2)_3)_2$ | Heterocyclic ring | Substituted hydrocarbyl |
| II.883 | N | O | $((CH_2)O(CH_2)_3)_3$ | Aromatic ring | Hydrogen |
| II.884 | N | O | $((CH_2)O(CH_2)_3)_3$ | Aromatic ring | Hydrocarbyl |
| II.885 | N | O | $((CH_2)O(CH_2)_3)_3$ | Aromatic ring | Substituted hydrocarbyl |
| II.886 | N | O | $((CH_2)O(CH_2)_3)_3$ | Cylic ring | Hydrogen |
| II.887 | N | O | $((CH_2)O(CH_2)_3)_3$ | Cylic ring | Hydrocarbyl |
| II.888 | N | O | $((CH_2)O(CH_2)_3)_3$ | Cylic ring | Substituted hydrocarbyl |
| II.889 | N | O | $((CH_2)O(CH_2)_3)_3$ | Heterocyclic ring | Hydrogen |
| II.890 | N | O | $((CH_2)O(CH_2)_3)_3$ | Heterocyclic ring | Hydrocarbyl |
| II.891 | N | O | $((CH_2)O(CH_2)_3)_3$ | Heterocyclic ring | Substituted hydrocarbyl |
| II.892 | N | O | $((CH_2)_2O(CH_2))$ | Aromatic ring | Hydrogen |
| II.893 | N | O | $((CH_2)_2O(CH_2))$ | Aromatic ring | Hydrocarbyl |
| II.894 | N | O | $((CH_2)_2O(CH_2))$ | Aromatic ring | Substituted hydrocarbyl |
| II.895 | N | O | $((CH_2)_2O(CH_2))$ | Cylic ring | Hydrogen |
| II.896 | N | O | $((CH_2)_2O(CH_2))$ | Cylic ring | Hydrocarbyl |
| II.897 | N | O | $((CH_2)_2O(CH_2))$ | Cylic ring | Substituted hydrocarbyl |
| II.898 | N | O | $((CH_2)_2O(CH_2))$ | Heterocyclic ring | Hydrogen |
| II.899 | N | O | $((CH_2)_2O(CH_2))$ | Heterocyclic ring | Hydrocarbyl |
| II.900 | N | O | $((CH_2)_2O(CH_2))$ | Heterocyclic ring | Substituted hydrocarbyl |
| II.901 | N | O | $((CH_2)_2O(CH_2))_2$ | Aromatic ring | Hydrogen |
| II.902 | N | O | $((CH_2)_2O(CH_2))_2$ | Aromatic ring | Hydrocarbyl |
| II.903 | N | O | $((CH_2)_2O(CH_2))_2$ | Aromatic ring | Substituted hydrocarbyl |
| II.904 | N | O | $((CH_2)_2O(CH_2))_2$ | Cylic ring | Hydrogen |
| II.905 | N | O | $((CH_2)_2O(CH_2))_2$ | Cylic ring | Hydrocarbyl |
| II.906 | N | O | $((CH_2)_2O(CH_2))_2$ | Cylic ring | Substituted hydrocarbyl |
| II.907 | N | O | $((CH_2)_2O(CH_2))_2$ | Heterocyclic ring | Hydrogen |
| II.908 | N | O | $((CH_2)_2O(CH_2))_2$ | Heterocyclic ring | Hydrocarbyl |
| II.909 | N | O | $((CH_2)_2O(CH_2))_2$ | Heterocyclic ring | Substituted hydrocarbyl |
| II.910 | N | O | $((CH_2)_2O(CH_2))_3$ | Aromatic ring | Hydrogen |
| II.911 | N | O | $((CH_2)_2O(CH_2))_3$ | Aromatic ring | Hydrocarbyl |
| II.912 | N | O | $((CH_2)_2O(CH_2))_3$ | Aromatic ring | Substituted hydrocarbyl |
| II.913 | N | O | $((CH_2)_2O(CH_2))_3$ | Cylic ring | Hydrogen |
| II.914 | N | O | $((CH_2)_2O(CH_2))_3$ | Cylic ring | Hydrocarbyl |
| II.915 | N | O | $((CH_2)_2O(CH_2))_3$ | Cylic ring | Substituted hydrocarbyl |
| II.916 | N | O | $((CH_2)_2O(CH_2))_3$ | Heterocyclic ring | Hydrogen |
| II.917 | N | O | $((CH_2)_2O(CH_2))_3$ | Heterocyclic ring | Hydrocarbyl |
| II.918 | N | O | $((CH_2)_2O(CH_2))_3$ | Heterocyclic ring | Substituted hydrocarbyl |
| II.919 | N | O | $((CH_2)_2O(CH_2)_2)$ | Aromatic ring | Hydrogen |
| II.920 | N | O | $((CH_2)_2O(CH_2)_2)$ | Aromatic ring | Hydrocarbyl |
| II.921 | N | O | $((CH_2)_2O(CH_2)_2)$ | Aromatic ring | Substituted hydrocarbyl |
| II.922 | N | O | $((CH_2)_2O(CH_2)_2)$ | Cylic ring | Hydrogen |
| II.923 | N | O | $((CH_2)_2O(CH_2)_2)$ | Cylic ring | Hydrocarbyl |
| II.924 | N | O | $((CH_2)_2O(CH_2)_2)$ | Cylic ring | Substituted hydrocarbyl |
| II.925 | N | O | $((CH_2)_2O(CH_2)_2)$ | Heterocyclic ring | Hydrogen |
| II.926 | N | O | $((CH_2)_2O(CH_2)_2)$ | Heterocyclic ring | Hydrocarbyl |
| II.927 | N | O | $((CH_2)_2O(CH_2)_2)$ | Heterocyclic ring | Substituted hydrocarbyl |
| II.928 | N | O | $((CH_2)_2O(CH_2)_2)_2$ | Aromatic ring | Hydrogen |
| II.929 | N | O | $((CH_2)_2O(CH_2)_2)_2$ | Aromatic ring | Hydrocarbyl |
| II.930 | N | O | $((CH_2)_2O(CH_2)_2)_2$ | Aromatic ring | Substituted hydrocarbyl |

TABLE 2-continued

Selected compounds from Formula (II)

|  | R1 | R2 | R4 | R5 | R6 |
|---|---|---|---|---|---|
| II.931 | N | O | $((CH_2)_2O(CH_2)_2)_2$ | Cylic ring | Hydrogen |
| II.932 | N | O | $((CH_2)_2O(CH_2)_2)_2$ | Cylic ring | Hydrocarbyl |
| II.933 | N | O | $((CH_2)_2O(CH_2)_2)_2$ | Cylic ring | Substituted hydrocarbyl |
| II.934 | N | O | $((CH_2)_2O(CH_2)_2)_2$ | Heterocyclic ring | Hydrogen |
| II.935 | N | O | $((CH_2)_2O(CH_2)_2)_2$ | Heterocyclic ring | Hydrocarbyl |
| II.936 | N | O | $((CH_2)_2O(CH_2)_2)_2$ | Heterocyclic ring | Substituted hydrocarbyl |
| II.937 | N | O | $((CH_2)_2O(CH_2)_2)_3$ | Aromatic ring | Hydrogen |
| II.938 | N | O | $((CH_2)_2O(CH_2)_2)_3$ | Aromatic ring | Hydrocarbyl |
| II.939 | N | O | $((CH_2)_2O(CH_2)_2)_3$ | Aromatic ring | Substituted hydrocarbyl |
| II.940 | N | O | $((CH_2)_2O(CH_2)_2)_3$ | Cylic ring | Hydrogen |
| II.941 | N | O | $((CH_2)_2O(CH_2)_2)_3$ | Cylic ring | Hydrocarbyl |
| II.942 | N | O | $((CH_2)_2O(CH_2)_2)_3$ | Cylic ring | Substituted hydrocarbyl |
| II.943 | N | O | $((CH_2)_2O(CH_2)_2)_3$ | Heterocyclic ring | Hydrogen |
| II.944 | N | O | $((CH_2)_2O(CH_2)_2)_3$ | Heterocyclic ring | Hydrocarbyl |
| II.945 | N | O | $((CH_2)_2O(CH_2)_2)_3$ | Heterocyclic ring | Substituted hydrocarbyl |
| II.946 | N | O | $((CH_2)_2O(CH_2)_3)$ | Aromatic ring | Hydrogen |
| II.947 | N | O | $((CH_2)_2O(CH_2)_3)$ | Aromatic ring | Hydrocarbyl |
| II.948 | N | O | $((CH_2)_2O(CH_2)_3)$ | Aromatic ring | Substituted hydrocarbyl |
| II.949 | N | O | $((CH_2)_2O(CH_2)_3)$ | Cylic ring | Hydrogen |
| II.950 | N | O | $((CH_2)_2O(CH_2)_3)$ | Cylic ring | Hydrocarbyl |
| II.951 | N | O | $((CH_2)_2O(CH_2)_3)$ | Cylic ring | Substituted hydrocarbyl |
| II.952 | N | O | $((CH_2)_2O(CH_2)_3)$ | Heterocyclic ring | Hydrogen |
| II.953 | N | O | $((CH_2)_2O(CH_2)_3)$ | Heterocyclic ring | Hydrocarbyl |
| II.954 | N | O | $((CH_2)_2O(CH_2)_3)$ | Heterocyclic ring | Substituted hydrocarbyl |
| II.955 | N | O | $((CH_2)_2O(CH_2)_3)_2$ | Aromatic ring | Hydrogen |
| II.956 | N | O | $((CH_2)_2O(CH_2)_3)_2$ | Aromatic ring | Hydrocarbyl |
| II.957 | N | O | $((CH_2)_2O(CH_2)_3)_2$ | Aromatic ring | Substituted hydrocarbyl |
| II.958 | N | O | $((CH_2)_2O(CH_2)_3)_2$ | Cylic ring | Hydrogen |
| II.959 | N | O | $((CH_2)_2O(CH_2)_3)_2$ | Cylic ring | Hydrocarbyl |
| II.960 | N | O | $((CH_2)_2O(CH_2)_3)_2$ | Cylic ring | Substituted hydrocarbyl |
| II.961 | N | O | $((CH_2)_2O(CH_2)_3)_2$ | Heterocyclic ring | Hydrogen |
| II.962 | N | O | $((CH_2)_2O(CH_2)_3)_2$ | Heterocyclic ring | Hydrocarbyl |
| II.963 | N | O | $((CH_2)_2O(CH_2)_3)_2$ | Heterocyclic ring | Substituted hydrocarbyl |
| II.964 | N | O | $((CH_2)_2O(CH_2)_3)_3$ | Aromatic ring | Hydrogen |
| II.965 | N | O | $((CH_2)_2O(CH_2)_3)_3$ | Aromatic ring | Hydrocarbyl |
| II.966 | N | O | $((CH_2)_2O(CH_2)_3)_3$ | Aromatic ring | Substituted hydrocarbyl |
| II.967 | N | O | $((CH_2)_2O(CH_2)_3)_3$ | Cylic ring | Hydrogen |
| II.968 | N | O | $((CH_2)_2O(CH_2)_3)_3$ | Cylic ring | Hydrocarbyl |
| II.969 | N | O | $((CH_2)_2O(CH_2)_3)_3$ | Cylic ring | Substituted hydrocarbyl |
| II.970 | N | O | $((CH_2)_2O(CH_2)_3)_3$ | Heterocyclic ring | Hydrogen |
| II.971 | N | O | $((CH_2)_2O(CH_2)_3)_3$ | Heterocyclic ring | Hydrocarbyl |
| II.972 | N | O | $((CH_2)_2O(CH_2)_3)_3$ | Heterocyclic ring | Substituted hydrocarbyl |
| II.973 | N | O | $((CH_2)_3O(CH_2))$ | Aromatic ring | Hydrogen |
| II.974 | N | O | $((CH_2)_3O(CH_2))$ | Aromatic ring | Hydrocarbyl |
| II.975 | N | O | $((CH_2)_3O(CH_2))$ | Aromatic ring | Substituted hydrocarbyl |
| II.976 | N | O | $((CH_2)_3O(CH_2))$ | Cylic ring | Hydrogen |
| II.977 | N | O | $((CH_2)_3O(CH_2))$ | Cylic ring | Hydrocarbyl |
| II.978 | N | O | $((CH_2)_3O(CH_2))$ | Cylic ring | Substituted hydrocarbyl |
| II.979 | N | O | $((CH_2)_3O(CH_2))$ | Heterocyclic ring | Hydrogen |
| II.980 | N | O | $((CH_2)_3O(CH_2))$ | Heterocyclic ring | Hydrocarbyl |
| II.981 | N | O | $((CH_2)_3O(CH_2))$ | Heterocyclic ring | Substituted hydrocarbyl |
| II.982 | N | O | $((CH_2)_3O(CH_2))_2$ | Aromatic ring | Hydrogen |
| II.983 | N | O | $((CH_2)_3O(CH_2))_2$ | Aromatic ring | Hydrocarbyl |
| II.984 | N | O | $((CH_2)_3O(CH_2))_2$ | Aromatic ring | Substituted hydrocarbyl |
| II.985 | N | O | $((CH_2)_3O(CH_2))_2$ | Cylic ring | Hydrogen |
| II.986 | N | O | $((CH_2)_3O(CH_2))_2$ | Cylic ring | Hydrocarbyl |
| II.987 | N | O | $((CH_2)_3O(CH_2))_2$ | Cylic ring | Substituted hydrocarbyl |
| II.988 | N | O | $((CH_2)_3O(CH_2))_2$ | Heterocyclic ring | Hydrogen |
| II.989 | N | O | $((CH_2)_3O(CH_2))_2$ | Heterocyclic ring | Hydrocarbyl |
| II.990 | N | O | $((CH_2)_3O(CH_2))_2$ | Heterocyclic ring | Substituted hydrocarbyl |
| II.991 | N | O | $((CH_2)_3O(CH_2))_3$ | Aromatic ring | Hydrogen |
| II.992 | N | O | $((CH_2)_3O(CH_2))_3$ | Aromatic ring | Hydrocarbyl |
| II.993 | N | O | $((CH_2)_3O(CH_2))_3$ | Aromatic ring | Substituted hydrocarbyl |
| II.994 | N | O | $((CH_2)_3O(CH_2))_3$ | Cylic ring | Hydrogen |
| II.995 | N | O | $((CH_2)_3O(CH_2))_3$ | Cylic ring | Hydrocarbyl |
| II.996 | N | O | $((CH_2)_3O(CH_2))_3$ | Cylic ring | Substituted hydrocarbyl |
| II.997 | N | O | $((CH_2)_3O(CH_2))_3$ | Heterocyclic ring | Hydrogen |
| II.998 | N | O | $((CH_2)_3O(CH_2))_3$ | Heterocyclic ring | Hydrocarbyl |
| II.999 | N | O | $((CH_2)_3O(CH_2))_3$ | Heterocyclic ring | Substituted hydrocarbyl |
| II.1000 | N | O | $((CH_2)_3O(CH_2)_2)$ | Aromatic ring | Hydrogen |
| II.1001 | N | O | $((CH_2)_3O(CH_2)_2)$ | Aromatic ring | Hydrocarbyl |
| II.1002 | N | O | $((CH_2)_3O(CH_2)_2)$ | Aromatic ring | Substituted hydrocarbyl |
| II.1003 | N | O | $((CH_2)_3O(CH_2)_2)$ | Cylic ring | Hydrogen |
| II.1004 | N | O | $((CH_2)_3O(CH_2)_2)$ | Cylic ring | Hydrocarbyl |
| II.1005 | N | O | $((CH_2)_3O(CH_2)_2)$ | Cylic ring | Substituted hydrocarbyl |
| II.1006 | N | O | $((CH_2)_3O(CH_2)_2)$ | Heterocyclic ring | Hydrogen |

TABLE 2-continued

Selected compounds from Formula (II)

| | R1 | R2 | R4 | R5 | R6 |
|---|---|---|---|---|---|
| II.1007 | N | O | $((CH_2)_3O(CH_2)_2)$ | Heterocyclic ring | Hydrocarbyl |
| II.1008 | N | O | $((CH_2)_3O(CH_2)_2)$ | Heterocyclic ring | Substituted hydrocarbyl |
| II.1009 | N | O | $((CH_2)_3O(CH_2)_2)_2$ | Aromatic ring | Hydrogen |
| II.1010 | N | O | $((CH_2)_3O(CH_2)_2)_2$ | Aromatic ring | Hydrocarbyl |
| II.1011 | N | O | $((CH_2)_3O(CH_2)_2)_2$ | Aromatic ring | Substituted hydrocarbyl |
| II.1012 | N | O | $((CH_2)_3O(CH_2)_2)_2$ | Cylic ring | Hydrogen |
| II.1013 | N | O | $((CH_2)_3O(CH_2)_2)_2$ | Cylic ring | Hydrocarbyl |
| II.1014 | N | O | $((CH_2)_3O(CH_2)_2)_2$ | Cylic ring | Substituted hydrocarbyl |
| II.1015 | N | O | $((CH_2)_3O(CH_2)_2)_2$ | Heterocyclic ring | Hydrogen |
| II.1016 | N | O | $((CH_2)_3O(CH_2)_2)_2$ | Heterocyclic ring | Hydrocarbyl |
| II.1017 | N | O | $((CH_2)_3O(CH_2)_2)_2$ | Heterocyclic ring | Substituted hydrocarbyl |
| II.1018 | N | O | $((CH_2)_3O(CH_2)_2)_3$ | Aromatic ring | Hydrogen |
| II.1019 | N | O | $((CH_2)_3O(CH_2)_2)_3$ | Aromatic ring | Hydrocarbyl |
| II.1020 | N | O | $((CH_2)_3O(CH_2)_2)_3$ | Aromatic ring | Substituted hydrocarbyl |
| II.1021 | N | O | $((CH_2)_3O(CH_2)_2)_3$ | Cylic ring | Hydrogen |
| II.1022 | N | O | $((CH_2)_3O(CH_2)_2)_3$ | Cylic ring | Hydrocarbyl |
| II.1023 | N | O | $((CH_2)_3O(CH_2)_2)_3$ | Cylic ring | Substituted hydrocarbyl |
| II.1024 | N | O | $((CH_2)_3O(CH_2)_2)_3$ | Heterocyclic ring | Hydrogen |
| II.1025 | N | O | $((CH_2)_3O(CH_2)_2)_3$ | Heterocyclic ring | Hydrocarbyl |
| II.1026 | N | O | $((CH_2)_3O(CH_2)_2)_3$ | Heterocyclic ring | Substituted hydrocarbyl |
| II.1027 | N | O | $((CH_2)_3O(CH_2)_3)$ | Aromatic ring | Hydrogen |
| II.1028 | N | O | $((CH_2)_3O(CH_2)_3)$ | Aromatic ring | Hydrocarbyl |
| II.1029 | N | O | $((CH_2)_3O(CH_2)_3)$ | Aromatic ring | Substituted hydrocarbyl |
| II.1030 | N | O | $((CH_2)_3O(CH_2)_3)$ | Cylic ring | Hydrogen |
| II.1031 | N | O | $((CH_2)_3O(CH_2)_3)$ | Cylic ring | Hydrocarbyl |
| II.1032 | N | O | $((CH_2)_3O(CH_2)_3)$ | Cylic ring | Substituted hydrocarbyl |
| II.1033 | N | O | $((CH_2)_3O(CH_2)_3)$ | Heterocyclic ring | Hydrogen |
| II.1034 | N | O | $((CH_2)_3O(CH_2)_3)$ | Heterocyclic ring | Hydrocarbyl |
| II.1035 | N | O | $((CH_2)_3O(CH_2)_3)$ | Heterocyclic ring | Substituted hydrocarbyl |
| II.1036 | N | O | $((CH_2)_3O(CH_2)_3)_2$ | Aromatic ring | Hydrogen |
| II.1037 | N | O | $((CH_2)_3O(CH_2)_3)_2$ | Aromatic ring | Hydrocarbyl |
| II.1038 | N | O | $((CH_2)_3O(CH_2)_3)_2$ | Aromatic ring | Substituted hydrocarbyl |
| II.1039 | N | O | $((CH_2)_3O(CH_2)_3)_2$ | Cylic ring | Hydrogen |
| II.1040 | N | O | $((CH_2)_3O(CH_2)_3)_2$ | Cylic ring | Hydrocarbyl |
| II.1041 | N | O | $((CH_2)_3O(CH_2)_3)_2$ | Cylic ring | Substituted hydrocarbyl |
| II.1042 | N | O | $((CH_2)_3O(CH_2)_3)_2$ | Heterocyclic ring | Hydrogen |
| II.1043 | N | O | $((CH_2)_3O(CH_2)_3)_2$ | Heterocyclic ring | Hydrocarbyl |
| II.1044 | N | O | $((CH_2)_3O(CH_2)_3)_2$ | Heterocyclic ring | Substituted hydrocarbyl |
| II.1045 | N | O | $((CH_2)_3O(CH_2)_3)_3$ | Aromatic ring | Hydrogen |
| II.1046 | N | O | $((CH_2)_3O(CH_2)_3)_3$ | Aromatic ring | Hydrocarbyl |
| II.1047 | N | O | $((CH_2)_3O(CH_2)_3)_3$ | Aromatic ring | Substituted hydrocarbyl |
| II.1048 | N | O | $((CH_2)_3O(CH_2)_3)_3$ | Cylic ring | Hydrogen |
| II.1049 | N | O | $((CH_2)_3O(CH_2)_3)_3$ | Cylic ring | Hydrocarbyl |
| II.1050 | N | O | $((CH_2)_3O(CH_2)_3)_3$ | Cylic ring | Substituted hydrocarbyl |
| II.1051 | N | O | $((CH_2)_3O(CH_2)_3)_3$ | Heterocyclic ring | Hydrogen |
| II.1052 | N | O | $((CH_2)_3O(CH_2)_3)_3$ | Heterocyclic ring | Hydrocarbyl |
| II.1053 | N | O | $((CH_2)_3O(CH_2)_3)_3$ | Heterocyclic ring | Substituted hydrocarbyl |
| II.1054 | S | N | $(CH_2)$ | Aromatic ring | Hydrogen |
| II.1055 | S | N | $(CH_2)$ | Aromatic ring | Hydrocarbyl |
| II.1056 | S | N | $(CH_2)$ | Aromatic ring | Substituted hydrocarbyl |
| II.1057 | S | N | $(CH_2)$ | Cylic ring | Hydrogen |
| II.1058 | S | N | $(CH_2)$ | Cylic ring | Hydrocarbyl |
| II.1059 | S | N | $(CH_2)$ | Cylic ring | Substituted hydrocarbyl |
| II.1060 | S | N | $(CH_2)$ | Heterocyclic ring | Hydrogen |
| II.1061 | S | N | $(CH_2)$ | Heterocyclic ring | Hydrocarbyl |
| II.1062 | S | N | $(CH_2)$ | Heterocyclic ring | Substituted hydrocarbyl |
| II.1063 | S | N | $(CH_2)_2$ | Aromatic ring | Hydrogen |
| II.1064 | S | N | $(CH_2)_2$ | Aromatic ring | Hydrocarbyl |
| II.1065 | S | N | $(CH_2)_2$ | Aromatic ring | Substituted hydrocarbyl |
| II.1066 | S | N | $(CH_2)_2$ | Cylic ring | Hydrogen |
| II.1067 | S | N | $(CH_2)_2$ | Cylic ring | Hydrocarbyl |
| II.1068 | S | N | $(CH_2)_2$ | Cylic ring | Substituted hydrocarbyl |
| II.1069 | S | N | $(CH_2)_2$ | Heterocyclic ring | Hydrogen |
| II.1070 | S | N | $(CH_2)_2$ | Heterocyclic ring | Hydrocarbyl |
| II.1071 | S | N | $(CH_2)_2$ | Heterocyclic ring | Substituted hydrocarbyl |
| II.1072 | S | N | $(CH_2)_3$ | Aromatic ring | Hydrogen |
| II.1073 | S | N | $(CH_2)_3$ | Aromatic ring | Hydrocarbyl |
| II.1074 | S | N | $(CH_2)_3$ | Aromatic ring | Substituted hydrocarbyl |
| II.1075 | S | N | $(CH_2)_3$ | Cylic ring | Hydrogen |
| II.1076 | S | N | $(CH_2)_3$ | Cylic ring | Hydrocarbyl |
| II.1077 | S | N | $(CH_2)_3$ | Cylic ring | Substituted hydrocarbyl |
| II.1078 | S | N | $(CH_2)_3$ | Heterocyclic ring | Hydrogen |
| II.1079 | S | N | $(CH_2)_3$ | Heterocyclic ring | Hydrocarbyl |
| II.1080 | S | N | $(CH_2)_3$ | Heterocyclic ring | Substituted hydrocarbyl |
| II.1081 | S | N | $((CH_2)O)$ | Aromatic ring | Hydrogen |
| II.1082 | S | N | $((CH_2)O)$ | Aromatic ring | Hydrocarbyl |

TABLE 2-continued

Selected compounds from Formula (II)

| | R1 | R2 | R4 | R5 | R6 |
|---|---|---|---|---|---|
| II.1083 | S | N | $((CH_2)O)$ | Aromatic ring | Substituted hydrocarbyl |
| II.1084 | S | N | $((CH_2)O)$ | Cylic ring | Hydrogen |
| II.1085 | S | N | $((CH_2)O)$ | Cylic ring | Hydrocarbyl |
| II.1086 | S | N | $((CH_2)O)$ | Cylic ring | Substituted hydrocarbyl |
| II.1087 | S | N | $((CH_2)O)$ | Heterocyclic ring | Hydrogen |
| II.1088 | S | N | $((CH_2)O)$ | Heterocyclic ring | Hydrocarbyl |
| II.1089 | S | N | $((CH_2)O)$ | Heterocyclic ring | Substituted hydrocarbyl |
| II.1090 | S | N | $((CH_2)O)_2$ | Aromatic ring | Hydrogen |
| II.1091 | S | N | $((CH_2)O)_2$ | Aromatic ring | Hydrocarbyl |
| II.1092 | S | N | $((CH_2)O)_2$ | Aromatic ring | Substituted hydrocarbyl |
| II.1093 | S | N | $((CH_2)O)_2$ | Cylic ring | Hydrogen |
| II.1094 | S | N | $((CH_2)O)_2$ | Cylic ring | Hydrocarbyl |
| II.1095 | S | N | $((CH_2)O)_2$ | Cylic ring | Substituted hydrocarbyl |
| II.1096 | S | N | $((CH_2)O)_2$ | Heterocyclic ring | Hydrogen |
| II.1097 | S | N | $((CH_2)O)_2$ | Heterocyclic ring | Hydrocarbyl |
| II.1098 | S | N | $((CH_2)O)_2$ | Heterocyclic ring | Substituted hydrocarbyl |
| II.1099 | S | N | $((CH_2)O)_3$ | Aromatic ring | Hydrogen |
| II.1100 | S | N | $((CH_2)O)_3$ | Aromatic ring | Hydrocarbyl |
| II.1101 | S | N | $((CH_2)O)_3$ | Aromatic ring | Substituted hydrocarbyl |
| II.1102 | S | N | $((CH_2)O)_3$ | Cylic ring | Hydrogen |
| II.1103 | S | N | $((CH_2)O)_3$ | Cylic ring | Hydrocarbyl |
| II.1104 | S | N | $((CH_2)O)_3$ | Cylic ring | Substituted hydrocarbyl |
| II.1105 | S | N | $((CH_2)O)_3$ | Heterocyclic ring | Hydrogen |
| II.1106 | S | N | $((CH_2)O)_3$ | Heterocyclic ring | Hydrocarbyl |
| II.1107 | S | N | $((CH_2)O)_3$ | Heterocyclic ring | Substituted hydrocarbyl |
| II.1108 | S | N | $((CH_2)_2O)$ | Aromatic ring | Hydrogen |
| II.1109 | S | N | $((CH_2)_2O)$ | Aromatic ring | Hydrocarbyl |
| II.1110 | S | N | $((CH_2)_2O)$ | Aromatic ring | Substituted hydrocarbyl |
| II.1111 | S | N | $((CH_2)_2O)$ | Cylic ring | Hydrogen |
| II.1112 | S | N | $((CH_2)_2O)$ | Cylic ring | Hydrocarbyl |
| II.1113 | S | N | $((CH_2)_2O)$ | Cylic ring | Substituted hydrocarbyl |
| II.1114 | S | N | $((CH_2)_2O)$ | Heterocyclic ring | Hydrogen |
| II.1115 | S | N | $((CH_2)_2O)$ | Heterocyclic ring | Hydrocarbyl |
| II.1116 | S | N | $((CH_2)_2O)$ | Heterocyclic ring | Substituted hydrocarbyl |
| II.1117 | S | N | $((CH_2)_2O)_2$ | Aromatic ring | Hydrogen |
| II.1118 | S | N | $((CH_2)_2O)_2$ | Aromatic ring | Hydrocarbyl |
| II.1119 | S | N | $((CH_2)_2O)_2$ | Aromatic ring | Substituted hydrocarbyl |
| II.1120 | S | N | $((CH_2)_2O)_2$ | Cylic ring | Hydrogen |
| II.1121 | S | N | $((CH_2)_2O)_2$ | Cylic ring | Hydrocarbyl |
| II.1122 | S | N | $((CH_2)_2O)_2$ | Cylic ring | Substituted hydrocarbyl |
| II.1123 | S | N | $((CH_2)_2O)_2$ | Heterocyclic ring | Hydrogen |
| II.1124 | S | N | $((CH_2)_2O)_2$ | Heterocyclic ring | Hydrocarbyl |
| II.1125 | S | N | $((CH_2)_2O)_2$ | Heterocyclic ring | Substituted hydrocarbyl |
| II.1126 | S | N | $((CH_2)_2O)_3$ | Aromatic ring | Hydrogen |
| II.1127 | S | N | $((CH_2)_2O)_3$ | Aromatic ring | Hydrocarbyl |
| II.1128 | S | N | $((CH_2)_2O)_3$ | Aromatic ring | Substituted hydrocarbyl |
| II.1129 | S | N | $((CH_2)_2O)_3$ | Cylic ring | Hydrogen |
| II.1130 | S | N | $((CH_2)_2O)_3$ | Cylic ring | Hydrocarbyl |
| II.1131 | S | N | $((CH_2)_2O)_3$ | Cylic ring | Substituted hydrocarbyl |
| II.1132 | S | N | $((CH_2)_2O)_3$ | Heterocyclic ring | Hydrogen |
| II.1133 | S | N | $((CH_2)_2O)_3$ | Heterocyclic ring | Hydrocarbyl |
| II.1134 | S | N | $((CH_2)_2O)_3$ | Heterocyclic ring | Substituted hydrocarbyl |
| II.1135 | S | N | $((CH_2)_3O)$ | Aromatic ring | Hydrogen |
| II.1136 | S | N | $((CH_2)_3O)$ | Aromatic ring | Hydrocarbyl |
| II.1137 | S | N | $((CH_2)_3O)$ | Aromatic ring | Substituted hydrocarbyl |
| II.1138 | S | N | $((CH_2)_3O)$ | Cylic ring | Hydrogen |
| II.1139 | S | N | $((CH_2)_3O)$ | Cylic ring | Hydrocarbyl |
| II.1140 | S | N | $((CH_2)_3O)$ | Cylic ring | Substituted hydrocarbyl |
| II.1141 | S | N | $((CH_2)_3O)$ | Heterocyclic ring | Hydrogen |
| II.1142 | S | N | $((CH_2)_3O)$ | Heterocyclic ring | Hydrocarbyl |
| II.1143 | S | N | $((CH_2)_3O)$ | Heterocyclic ring | Substituted hydrocarbyl |
| II.1144 | S | N | $((CH_2)_3O)_2$ | Aromatic ring | Hydrogen |
| II.1145 | S | N | $((CH_2)_3O)_2$ | Aromatic ring | Hydrocarbyl |
| II.1146 | S | N | $((CH_2)_3O)_2$ | Aromatic ring | Substituted hydrocarbyl |
| II.1147 | S | N | $((CH_2)_3O)_2$ | Cylic ring | Hydrogen |
| II.1148 | S | N | $((CH_2)_3O)_2$ | Cylic ring | Hydrocarbyl |
| II.1149 | S | N | $((CH_2)_3O)_2$ | Cylic ring | Substituted hydrocarbyl |
| II.1150 | S | N | $((CH_2)_3O)_2$ | Heterocyclic ring | Hydrogen |
| II.1151 | S | N | $((CH_2)_3O)_2$ | Heterocyclic ring | Hydrocarbyl |
| II.1152 | S | N | $((CH_2)_3O)_2$ | Heterocyclic ring | Substituted hydrocarbyl |
| II.1153 | S | N | $((CH_2)_3O)_3$ | Aromatic ring | Hydrogen |
| II.1154 | S | N | $((CH_2)_3O)_3$ | Aromatic ring | Hydrocarbyl |
| II.1155 | S | N | $((CH_2)_3O)_3$ | Aromatic ring | Substituted hydrocarbyl |
| II.1156 | S | N | $((CH_2)_3O)_3$ | Cylic ring | Hydrogen |
| II.1157 | S | N | $((CH_2)_3O)_3$ | Cylic ring | Hydrocarbyl |
| II.1158 | S | N | $((CH_2)_3O)_3$ | Cylic ring | Substituted hydrocarbyl |

TABLE 2-continued

Selected compounds from Formula (II)

| | R1 | R2 | R4 | R5 | R6 |
|---|---|---|---|---|---|
| II.1159 | S | N | $((CH_2)_3O)_3$ | Heterocyclic ring | Hydrogen |
| II.1160 | S | N | $((CH_2)_3O)_3$ | Heterocyclic ring | Hydrocarbyl |
| II.1161 | S | N | $((CH_2)_3O)_3$ | Heterocyclic ring | Substituted hydrocarbyl |
| II.1162 | S | N | $((CH_2)O(CH_2))$ | Aromatic ring | Hydrogen |
| II.1163 | S | N | $((CH_2)O(CH_2))$ | Aromatic ring | Hydrocarbyl |
| II.1164 | S | N | $((CH_2)O(CH_2))$ | Aromatic ring | Substituted hydrocarbyl |
| II.1165 | S | N | $((CH_2)O(CH_2))$ | Cylic ring | Hydrogen |
| II.1166 | S | N | $((CH_2)O(CH_2))$ | Cylic ring | Hydrocarbyl |
| II.1167 | S | N | $((CH_2)O(CH_2))$ | Cylic ring | Substituted hydrocarbyl |
| II.1168 | S | N | $((CH_2)O(CH_2))$ | Heterocyclic ring | Hydrogen |
| II.1169 | S | N | $((CH_2)O(CH_2))$ | Heterocyclic ring | Hydrocarbyl |
| II.1170 | S | N | $((CH_2)O(CH_2))$ | Heterocyclic ring | Substituted hydrocarbyl |
| II.1171 | S | N | $((CH_2)O(CH_2))_2$ | Aromatic ring | Hydrogen |
| II.1172 | S | N | $((CH_2)O(CH_2))_2$ | Aromatic ring | Hydrocarbyl |
| II.1173 | S | N | $((CH_2)O(CH_2))_2$ | Aromatic ring | Substituted hydrocarbyl |
| II.1174 | S | N | $((CH_2)O(CH_2))_2$ | Cylic ring | Hydrogen |
| II.1175 | S | N | $((CH_2)O(CH_2))_2$ | Cylic ring | Hydrocarbyl |
| II.1176 | S | N | $((CH_2)O(CH_2))_2$ | Cylic ring | Substituted hydrocarbyl |
| II.1177 | S | N | $((CH_2)O(CH_2))_2$ | Heterocyclic ring | Hydrogen |
| II.1178 | S | N | $((CH_2)O(CH_2))_2$ | Heterocyclic ring | Hydrocarbyl |
| II.1179 | S | N | $((CH_2)O(CH_2))_2$ | Heterocyclic ring | Substituted hydrocarbyl |
| II.1180 | S | N | $((CH_2)O(CH_2))_3$ | Aromatic ring | Hydrogen |
| II.1181 | S | N | $((CH_2)O(CH_2))_3$ | Aromatic ring | Hydrocarbyl |
| II.1182 | S | N | $((CH_2)O(CH_2))_3$ | Aromatic ring | Substituted hydrocarbyl |
| II.1183 | S | N | $((CH_2)O(CH_2))_3$ | Cylic ring | Hydrogen |
| II.1184 | S | N | $((CH_2)O(CH_2))_3$ | Cylic ring | Hydrocarbyl |
| II.1185 | S | N | $((CH_2)O(CH_2))_3$ | Cylic ring | Substituted hydrocarbyl |
| II.1186 | S | N | $((CH_2)O(CH_2))_3$ | Heterocyclic ring | Hydrogen |
| II.1187 | S | N | $((CH_2)O(CH_2))_3$ | Heterocyclic ring | Hydrocarbyl |
| II.1188 | S | N | $((CH_2)O(CH_2))_3$ | Heterocyclic ring | Substituted hydrocarbyl |
| II.1189 | S | N | $((CH_2)O(CH_2)_2)$ | Aromatic ring | Hydrogen |
| II.1190 | S | N | $((CH_2)O(CH_2)_2)$ | Aromatic ring | Hydrocarbyl |
| II.1191 | S | N | $((CH_2)O(CH_2)_2)$ | Aromatic ring | Substituted hydrocarbyl |
| II.1192 | S | N | $((CH_2)O(CH_2)_2)$ | Cylic ring | Hydrogen |
| II.1193 | S | N | $((CH_2)O(CH_2)_2)$ | Cylic ring | Hydrocarbyl |
| II.1194 | S | N | $((CH_2)O(CH_2)_2)$ | Cylic ring | Substituted hydrocarbyl |
| II.1195 | S | N | $((CH_2)O(CH_2)_2)$ | Heterocyclic ring | Hydrogen |
| II.1196 | S | N | $((CH_2)O(CH_2)_2)$ | Heterocyclic ring | Hydrocarbyl |
| II.1197 | S | N | $((CH_2)O(CH_2)_2)$ | Heterocyclic ring | Substituted hydrocarbyl |
| II.1198 | S | N | $((CH_2)O(CH_2)_2)_2$ | Aromatic ring | Hydrogen |
| II.1199 | S | N | $((CH_2)O(CH_2)_2)_2$ | Aromatic ring | Hydrocarbyl |
| II.1200 | S | N | $((CH_2)O(CH_2)_2)_2$ | Aromatic ring | Substituted hydrocarbyl |
| II.1201 | S | N | $((CH_2)O(CH_2)_2)_2$ | Cylic ring | Hydrogen |
| II.1202 | S | N | $((CH_2)O(CH_2)_2)_2$ | Cylic ring | Hydrocarbyl |
| II.1203 | S | N | $((CH_2)O(CH_2)_2)_2$ | Cylic ring | Substituted hydrocarbyl |
| II.1204 | S | N | $((CH_2)O(CH_2)_2)_2$ | Heterocyclic ring | Hydrogen |
| II.1205 | S | N | $((CH_2)O(CH_2)_2)_2$ | Heterocyclic ring | Hydrocarbyl |
| II.1206 | S | N | $((CH_2)O(CH_2)_2)_2$ | Heterocyclic ring | Substituted hydrocarbyl |
| II.1207 | S | N | $((CH_2)O(CH_2)_2)_3$ | Aromatic ring | Hydrogen |
| II.1208 | S | N | $((CH_2)O(CH_2)_2)_3$ | Aromatic ring | Hydrocarbyl |
| II.1209 | S | N | $((CH_2)O(CH_2)_2)_3$ | Aromatic ring | Substituted hydrocarbyl |
| II.1210 | S | N | $((CH_2)O(CH_2)_2)_3$ | Cylic ring | Hydrogen |
| II.1211 | S | N | $((CH_2)O(CH_2)_2)_3$ | Cylic ring | Hydrocarbyl |
| II.1212 | S | N | $((CH_2)O(CH_2)_2)_3$ | Cylic ring | Substituted hydrocarbyl |
| II.1213 | S | N | $((CH_2)O(CH_2)_2)_3$ | Heterocyclic ring | Hydrogen |
| II.1214 | S | N | $((CH_2)O(CH_2)_2)_3$ | Heterocyclic ring | Hydrocarbyl |
| II.1215 | S | N | $((CH_2)O(CH_2)_2)_3$ | Heterocyclic ring | Substituted hydrocarbyl |
| II.1216 | S | N | $((CH_2)O(CH_2)_3)$ | Aromatic ring | Hydrogen |
| II.1217 | S | N | $((CH_2)O(CH_2)_3)$ | Aromatic ring | Hydrocarbyl |
| II.1218 | S | N | $((CH_2)O(CH_2)_3)$ | Aromatic ring | Substituted hydrocarbyl |
| II.1219 | S | N | $((CH_2)O(CH_2)_3)$ | Cylic ring | Hydrogen |
| II.1220 | S | N | $((CH_2)O(CH_2)_3)$ | Cylic ring | Hydrocarbyl |
| II.1221 | S | N | $((CH_2)O(CH_2)_3)$ | Cylic ring | Substituted hydrocarbyl |
| II.1222 | S | N | $((CH_2)O(CH_2)_3)$ | Heterocyclic ring | Hydrogen |
| II.1223 | S | N | $((CH_2)O(CH_2)_3)$ | Heterocyclic ring | Hydrocarbyl |
| II.1224 | S | N | $((CH_2)O(CH_2)_3)$ | Heterocyclic ring | Substituted hydrocarbyl |
| II.1225 | S | N | $((CH_2)O(CH_2)_3)_2$ | Aromatic ring | Hydrogen |
| II.1226 | S | N | $((CH_2)O(CH_2)_3)_2$ | Aromatic ring | Hydrocarbyl |
| II.1227 | S | N | $((CH_2)O(CH_2)_3)_2$ | Aromatic ring | Substituted hydrocarbyl |
| II.1228 | S | N | $((CH_2)O(CH_2)_3)_2$ | Cylic ring | Hydrogen |
| II.1229 | S | N | $((CH_2)O(CH_2)_3)_2$ | Cylic ring | Hydrocarbyl |
| II.1230 | S | N | $((CH_2)O(CH_2)_3)_2$ | Cylic ring | Substituted hydrocarbyl |
| II.1231 | S | N | $((CH_2)O(CH_2)_3)_2$ | Heterocyclic ring | Hydrogen |
| II.1232 | S | N | $((CH_2)O(CH_2)_3)_2$ | Heterocyclic ring | Hydrocarbyl |
| II.1233 | S | N | $((CH_2)O(CH_2)_3)_2$ | Heterocyclic ring | Substituted hydrocarbyl |
| II.1234 | S | N | $((CH_2)O(CH_2)_3)_3$ | Aromatic ring | Hydrogen |

TABLE 2-continued

Selected compounds from Formula (II)

| | R1 | R2 | R4 | R5 | R6 |
|---|---|---|---|---|---|
| II.1235 | S | N | $((CH_2)O(CH_2)_3)_3$ | Aromatic ring | Hydrogen |
| II.1236 | S | N | $((CH_2)O(CH_2)_3)_3$ | Aromatic ring | Hydrocarbyl |
| II.1237 | S | N | $((CH_2)O(CH_2)_3)_3$ | Cylic ring | Hydrogen |
| II.1238 | S | N | $((CH_2)O(CH_2)_3)_3$ | Cylic ring | Hydrocarbyl |
| II.1239 | S | N | $((CH_2)O(CH_2)_3)_3$ | Cylic ring | Substituted hydrocarbyl |
| II.1240 | S | N | $((CH_2)O(CH_2)_3)_3$ | Heterocyclic ring | Hydrogen |
| II.1241 | S | N | $((CH_2)O(CH_2)_3)_3$ | Heterocyclic ring | Hydrocarbyl |
| II.1242 | S | N | $((CH_2)O(CH_2)_3)_3$ | Heterocyclic ring | Substituted hydrocarbyl |
| II.1243 | S | N | $((CH_2)_2O(CH_2))$ | Aromatic ring | Hydrogen |
| II.1244 | S | N | $((CH_2)_2O(CH_2))$ | Aromatic ring | Hydrocarbyl |
| II.1245 | S | N | $((CH_2)_2O(CH_2))$ | Aromatic ring | Substituted hydrocarbyl |
| II.1246 | S | N | $((CH_2)_2O(CH_2))$ | Cylic ring | Hydrogen |
| II.1247 | S | N | $((CH_2)_2O(CH_2))$ | Cylic ring | Hydrocarbyl |
| II.1248 | S | N | $((CH_2)_2O(CH_2))$ | Cylic ring | Substituted hydrocarbyl |
| II.1249 | S | N | $((CH_2)_2O(CH_2))$ | Heterocyclic ring | Hydrogen |
| II.1250 | S | N | $((CH_2)_2O(CH_2))$ | Heterocyclic ring | Hydrocarbyl |
| II.1251 | S | N | $((CH_2)_2O(CH_2))$ | Heterocyclic ring | Substituted hydrocarbyl |
| II.1252 | S | N | $((CH_2)_2O(CH_2))_2$ | Aromatic ring | Hydrogen |
| II.1253 | S | N | $((CH_2)_2O(CH_2))_2$ | Aromatic ring | Hydrocarbyl |
| II.1254 | S | N | $((CH_2)_2O(CH_2))_2$ | Aromatic ring | Substituted hydrocarbyl |
| II.1255 | S | N | $((CH_2)_2O(CH_2))_2$ | Cylic ring | Hydrogen |
| II.1256 | S | N | $((CH_2)_2O(CH_2))_2$ | Cylic ring | Hydrocarbyl |
| II.1257 | S | N | $((CH_2)_2O(CH_2))_2$ | Cylic ring | Substituted hydrocarbyl |
| II.1258 | S | N | $((CH_2)_2O(CH_2))_2$ | Heterocyclic ring | Hydrogen |
| II.1259 | S | N | $((CH_2)_2O(CH_2))_2$ | Heterocyclic ring | Hydrocarbyl |
| II.1260 | S | N | $((CH_2)_2O(CH_2))_2$ | Heterocyclic ring | Substituted hydrocarbyl |
| II.1261 | S | N | $((CH_2)_2O(CH_2))_3$ | Aromatic ring | Hydrogen |
| II.1262 | S | N | $((CH_2)_2O(CH_2))_3$ | Aromatic ring | Hydrocarbyl |
| II.1263 | S | N | $((CH_2)_2O(CH_2))_3$ | Aromatic ring | Substituted hydrocarbyl |
| II.1264 | S | N | $((CH_2)_2O(CH_2))_3$ | Cylic ring | Hydrogen |
| II.1265 | S | N | $((CH_2)_2O(CH_2))_3$ | Cylic ring | Hydrocarbyl |
| II.1266 | S | N | $((CH_2)_2O(CH_2))_3$ | Cylic ring | Substituted hydrocarbyl |
| II.1267 | S | N | $((CH_2)_2O(CH_2))_3$ | Heterocyclic ring | Hydrogen |
| II.1268 | S | N | $((CH_2)_2O(CH_2))_3$ | Heterocyclic ring | Hydrocarbyl |
| II.1269 | S | N | $((CH_2)_2O(CH_2))_3$ | Heterocyclic ring | Substituted hydrocarbyl |
| II.1270 | S | N | $((CH_2)_2O(CH_2)_2)$ | Aromatic ring | Hydrogen |
| II.1271 | S | N | $((CH_2)_2O(CH_2)_2)$ | Aromatic ring | Hydrocarbyl |
| II.1272 | S | N | $((CH_2)_2O(CH_2)_2)$ | Aromatic ring | Substituted hydrocarbyl |
| II.1273 | S | N | $((CH_2)_2O(CH_2)_2)$ | Cylic ring | Hydrogen |
| II.1274 | S | N | $((CH_2)_2O(CH_2)_2)$ | Cylic ring | Hydrocarbyl |
| II.1275 | S | N | $((CH_2)_2O(CH_2)_2)$ | Cylic ring | Substituted hydrocarbyl |
| II.1276 | S | N | $((CH_2)_2O(CH_2)_2)$ | Heterocyclic ring | Hydrogen |
| II.1277 | S | N | $((CH_2)_2O(CH_2)_2)$ | Heterocyclic ring | Hydrocarbyl |
| II.1278 | S | N | $((CH_2)_2O(CH_2)_2)$ | Heterocyclic ring | Substituted hydrocarbyl |
| II.1279 | S | N | $((CH_2)_2O(CH_2)_2)_2$ | Aromatic ring | Hydrogen |
| II.1280 | S | N | $((CH_2)_2O(CH_2)_2)_2$ | Aromatic ring | Hydrocarbyl |
| II.1281 | S | N | $((CH_2)_2O(CH_2)_2)_2$ | Aromatic ring | Substituted hydrocarbyl |
| II.1282 | S | N | $((CH_2)_2O(CH_2)_2)_2$ | Cylic ring | Hydrogen |
| II.1283 | S | N | $((CH_2)_2O(CH_2)_2)_2$ | Cylic ring | Hydrocarbyl |
| II.1284 | S | N | $((CH_2)_2O(CH_2)_2)_2$ | Cylic ring | Substituted hydrocarbyl |
| II.1285 | S | N | $((CH_2)_2O(CH_2)_2)_2$ | Heterocyclic ring | Hydrogen |
| II.1286 | S | N | $((CH_2)_2O(CH_2)_2)_2$ | Heterocyclic ring | Hydrocarbyl |
| II.1287 | S | N | $((CH_2)_2O(CH_2)_2)_2$ | Heterocyclic ring | Substituted hydrocarbyl |
| II.1288 | S | N | $((CH_2)_2O(CH_2)_2)_3$ | Aromatic ring | Hydrogen |
| II.1289 | S | N | $((CH_2)_2O(CH_2)_2)_3$ | Aromatic ring | Hydrocarbyl |
| II.1290 | S | N | $((CH_2)_2O(CH_2)_2)_3$ | Aromatic ring | Substituted hydrocarbyl |
| II.1291 | S | N | $((CH_2)_2O(CH_2)_2)_3$ | Cylic ring | Hydrogen |
| II.1292 | S | N | $((CH_2)_2O(CH_2)_2)_3$ | Cylic ring | Hydrocarbyl |
| II.1293 | S | N | $((CH_2)_2O(CH_2)_2)_3$ | Cylic ring | Substituted hydrocarbyl |
| II.1294 | S | N | $((CH_2)_2O(CH_2)_2)_3$ | Heterocyclic ring | Hydrogen |
| II.1295 | S | N | $((CH_2)_2O(CH_2)_2)_3$ | Heterocyclic ring | Hydrocarbyl |
| II.1296 | S | N | $((CH_2)_2O(CH_2)_2)_3$ | Heterocyclic ring | Substituted hydrocarbyl |
| II.1297 | S | N | $((CH_2)_2O(CH_2)_3)$ | Aromatic ring | Hydrogen |
| II.1298 | S | N | $((CH_2)_2O(CH_2)_3)$ | Aromatic ring | Hydrocarbyl |
| II.1299 | S | N | $((CH_2)_2O(CH_2)_3)$ | Aromatic ring | Substituted hydrocarbyl |
| II.1300 | S | N | $((CH_2)_2O(CH_2)_3)$ | Cylic ring | Hydrogen |
| II.1301 | S | N | $((CH_2)_2O(CH_2)_3)$ | Cylic ring | Hydrocarbyl |
| II.1302 | S | N | $((CH_2)_2O(CH_2)_3)$ | Cylic ring | Substituted hydrocarbyl |
| II.1303 | S | N | $((CH_2)_2O(CH_2)_3)$ | Heterocyclic ring | Hydrogen |
| II.1304 | S | N | $((CH_2)_2O(CH_2)_3)$ | Heterocyclic ring | Hydrocarbyl |
| II.1305 | S | N | $((CH_2)_2O(CH_2)_3)$ | Heterocyclic ring | Substituted hydrocarbyl |
| II.1306 | S | N | $((CH_2)_2O(CH_2)_3)_2$ | Aromatic ring | Hydrogen |
| II.1307 | S | N | $((CH_2)_2O(CH_2)_3)_2$ | Aromatic ring | Hydrocarbyl |
| II.1308 | S | N | $((CH_2)_2O(CH_2)_3)_2$ | Aromatic ring | Substituted hydrocarbyl |
| II.1309 | S | N | $((CH_2)_2O(CH_2)_3)_2$ | Cylic ring | Hydrogen |
| II.1310 | S | N | $((CH_2)_2O(CH_2)_3)_2$ | Cylic ring | Hydrocarbyl |

TABLE 2-continued

Selected compounds from Formula (II)

| | R1 | R2 | R4 | R5 | R6 |
|---|---|---|---|---|---|
| II.1311 | S | N | ((CH$_2$)$_2$O(CH$_2$)$_3$)$_2$ | Cylic ring | Substituted hydrocarbyl |
| II.1312 | S | N | ((CH$_2$)$_2$O(CH$_2$)$_3$)$_2$ | Heterocyclic ring | Hydrogen |
| II.1313 | S | N | ((CH$_2$)$_2$O(CH$_2$)$_3$)$_2$ | Heterocyclic ring | Hydrocarbyl |
| II.1314 | S | N | ((CH$_2$)$_2$O(CH$_2$)$_3$)$_2$ | Heterocyclic ring | Substituted hydrocarbyl |
| II.1315 | S | N | ((CH$_2$)$_2$O(CH$_2$)$_3$)$_3$ | Aromatic ring | Hydrogen |
| II.1316 | S | N | ((CH$_2$)$_2$O(CH$_2$)$_3$)$_3$ | Aromatic ring | Hydrocarbyl |
| II.1317 | S | N | ((CH$_2$)$_2$O(CH$_2$)$_3$)$_3$ | Aromatic ring | Substituted hydrocarbyl |
| II.1318 | S | N | ((CH$_2$)$_2$O(CH$_2$)$_3$)$_3$ | Cylic ring | Hydrogen |
| II.1319 | S | N | ((CH$_2$)$_2$O(CH$_2$)$_3$)$_3$ | Cylic ring | Hydrocarbyl |
| II.1320 | S | N | ((CH$_2$)$_2$O(CH$_2$)$_3$)$_3$ | Cylic ring | Substituted hydrocarbyl |
| II.1321 | S | N | ((CH$_2$)$_2$O(CH$_2$)$_3$)$_3$ | Heterocyclic ring | Hydrogen |
| II.1322 | S | N | ((CH$_2$)$_2$O(CH$_2$)$_3$)$_3$ | Heterocyclic ring | Hydrocarbyl |
| II.1323 | S | N | ((CH$_2$)$_2$O(CH$_2$)$_3$)$_3$ | Heterocyclic ring | Substituted hydrocarbyl |
| II.1324 | S | N | ((CH$_2$)$_3$O(CH$_2$)) | Aromatic ring | Hydrogen |
| II.1325 | S | N | ((CH$_2$)$_3$O(CH$_2$)) | Aromatic ring | Hydrocarbyl |
| II.1326 | S | N | ((CH$_2$)$_3$O(CH$_2$)) | Aromatic ring | Substituted hydrocarbyl |
| II.1327 | S | N | ((CH$_2$)$_3$O(CH$_2$)) | Cylic ring | Hydrogen |
| II.1328 | S | N | ((CH$_2$)$_3$O(CH$_2$)) | Cylic ring | Hydrocarbyl |
| II.1329 | S | N | ((CH$_2$)$_3$O(CH$_2$)) | Cylic ring | Substituted hydrocarbyl |
| II.1330 | S | N | ((CH$_2$)$_3$O(CH$_2$)) | Heterocyclic ring | Hydrogen |
| II.1331 | S | N | ((CH$_2$)$_3$O(CH$_2$)) | Heterocyclic ring | Hydrocarbyl |
| II.1332 | S | N | ((CH$_2$)$_3$O(CH$_2$)) | Heterocyclic ring | Substituted hydrocarbyl |
| II.1333 | S | N | ((CH$_2$)$_3$O(CH$_2$))$_2$ | Aromatic ring | Hydrogen |
| II.1334 | S | N | ((CH$_2$)$_3$O(CH$_2$))$_2$ | Aromatic ring | Hydrocarbyl |
| II.1335 | S | N | ((CH$_2$)$_3$O(CH$_2$))$_2$ | Aromatic ring | Substituted hydrocarbyl |
| II.1336 | S | N | ((CH$_2$)$_3$O(CH$_2$))$_2$ | Cylic ring | Hydrogen |
| II.1337 | S | N | ((CH$_2$)$_3$O(CH$_2$))$_2$ | Cylic ring | Hydrocarbyl |
| II.1338 | S | N | ((CH$_2$)$_3$O(CH$_2$))$_2$ | Cylic ring | Substituted hydrocarbyl |
| II.1339 | S | N | ((CH$_2$)$_3$O(CH$_2$))$_2$ | Heterocyclic ring | Hydrogen |
| II.1340 | S | N | ((CH$_2$)$_3$O(CH$_2$))$_2$ | Heterocyclic ring | Hydrocarbyl |
| II.1341 | S | N | ((CH$_2$)$_3$O(CH$_2$))$_2$ | Heterocyclic ring | Substituted hydrocarbyl |
| II.1342 | S | N | ((CH$_2$)$_3$O(CH$_2$))$_3$ | Aromatic ring | Hydrogen |
| II.1343 | S | N | ((CH$_2$)$_3$O(CH$_2$))$_3$ | Aromatic ring | Hydrocarbyl |
| II.1344 | S | N | ((CH$_2$)$_3$O(CH$_2$))$_3$ | Aromatic ring | Substituted hydrocarbyl |
| II.1345 | S | N | ((CH$_2$)$_3$O(CH$_2$))$_3$ | Cylic ring | Hydrogen |
| II.1346 | S | N | ((CH$_2$)$_3$O(CH$_2$))$_3$ | Cylic ring | Hydrocarbyl |
| II.1347 | S | N | ((CH$_2$)$_3$O(CH$_2$))$_3$ | Cylic ring | Substituted hydrocarbyl |
| II.1348 | S | N | ((CH$_2$)$_3$O(CH$_2$))$_3$ | Heterocyclic ring | Hydrogen |
| II.1349 | S | N | ((CH$_2$)$_3$O(CH$_2$))$_3$ | Heterocyclic ring | Hydrocarbyl |
| II.1350 | S | N | ((CH$_2$)$_3$O(CH$_2$))$_3$ | Heterocyclic ring | Substituted hydrocarbyl |
| II.1351 | S | N | ((CH$_2$)$_3$O(CH$_2$)$_2$) | Aromatic ring | Hydrogen |
| II.1352 | S | N | ((CH$_2$)$_3$O(CH$_2$)$_2$) | Aromatic ring | Hydrocarbyl |
| II.1353 | S | N | ((CH$_2$)$_3$O(CH$_2$)$_2$) | Aromatic ring | Substituted hydrocarbyl |
| II.1354 | S | N | ((CH$_2$)$_3$O(CH$_2$)$_2$) | Cylic ring | Hydrogen |
| II.1355 | S | N | ((CH$_2$)$_3$O(CH$_2$)$_2$) | Cylic ring | Hydrocarbyl |
| II.1356 | S | N | ((CH$_2$)$_3$O(CH$_2$)$_2$) | Cylic ring | Substituted hydrocarbyl |
| II.1357 | S | N | ((CH$_2$)$_3$O(CH$_2$)$_2$) | Heterocyclic ring | Hydrogen |
| II.1358 | S | N | ((CH$_2$)$_3$O(CH$_2$)$_2$) | Heterocyclic ring | Hydrocarbyl |
| II.1359 | S | N | ((CH$_2$)$_3$O(CH$_2$)$_2$) | Heterocyclic ring | Substituted hydrocarbyl |
| II.1360 | S | N | ((CH$_2$)$_3$O(CH$_2$)$_2$)$_2$ | Aromatic ring | Hydrogen |
| II.1361 | S | N | ((CH$_2$)$_3$O(CH$_2$)$_2$)$_2$ | Aromatic ring | Hydrocarbyl |
| II.1362 | S | N | ((CH$_2$)$_3$O(CH$_2$)$_2$)$_2$ | Aromatic ring | Substituted hydrocarbyl |
| II.1363 | S | N | ((CH$_2$)$_3$O(CH$_2$)$_2$)$_2$ | Cylic ring | Hydrogen |
| II.1364 | S | N | ((CH$_2$)$_3$O(CH$_2$)$_2$)$_2$ | Cylic ring | Hydrocarbyl |
| II.1365 | S | N | ((CH$_2$)$_3$O(CH$_2$)$_2$)$_2$ | Cylic ring | Substituted hydrocarbyl |
| II.1366 | S | N | ((CH$_2$)$_3$O(CH$_2$)$_2$)$_2$ | Heterocyclic ring | Hydrogen |
| II.1367 | S | N | ((CH$_2$)$_3$O(CH$_2$)$_2$)$_2$ | Heterocyclic ring | Hydrocarbyl |
| II.1368 | S | N | ((CH$_2$)$_3$O(CH$_2$)$_2$)$_2$ | Heterocyclic ring | Substituted hydrocarbyl |
| II.1369 | S | N | ((CH$_2$)$_3$O(CH$_2$)$_2$)$_3$ | Aromatic ring | Hydrogen |
| II.1370 | S | N | ((CH$_2$)$_3$O(CH$_2$)$_2$)$_3$ | Aromatic ring | Hydrocarbyl |
| II.1371 | S | N | ((CH$_2$)$_3$O(CH$_2$)$_2$)$_3$ | Aromatic ring | Substituted hydrocarbyl |
| II.1372 | S | N | ((CH$_2$)$_3$O(CH$_2$)$_2$)$_3$ | Cylic ring | Hydrogen |
| II.1373 | S | N | ((CH$_2$)$_3$O(CH$_2$)$_2$)$_3$ | Cylic ring | Hydrocarbyl |
| II.1374 | S | N | ((CH$_2$)$_3$O(CH$_2$)$_2$)$_3$ | Cylic ring | Substituted hydrocarbyl |
| II.1375 | S | N | ((CH$_2$)$_3$O(CH$_2$)$_2$)$_3$ | Heterocyclic ring | Hydrogen |
| II.1376 | S | N | ((CH$_2$)$_3$O(CH$_2$)$_2$)$_3$ | Heterocyclic ring | Hydrocarbyl |
| II.1377 | S | N | ((CH$_2$)$_3$O(CH$_2$)$_2$)$_3$ | Heterocyclic ring | Substituted hydrocarbyl |
| II.1378 | S | N | ((CH$_2$)$_3$O(CH$_2$)$_3$) | Aromatic ring | Hydrogen |
| II.1379 | S | N | ((CH$_2$)$_3$O(CH$_2$)$_3$) | Aromatic ring | Hydrocarbyl |
| II.1380 | S | N | ((CH$_2$)$_3$O(CH$_2$)$_3$) | Aromatic ring | Substituted hydrocarbyl |
| II.1381 | S | N | ((CH$_2$)$_3$O(CH$_2$)$_3$) | Cylic ring | Hydrogen |
| II.1382 | S | N | ((CH$_2$)$_3$O(CH$_2$)$_3$) | Cylic ring | Hydrocarbyl |
| II.1383 | S | N | ((CH$_2$)$_3$O(CH$_2$)$_3$) | Cylic ring | Substituted hydrocarbyl |
| II.1384 | S | N | ((CH$_2$)$_3$O(CH$_2$)$_3$) | Heterocyclic ring | Hydrogen |
| II.1385 | S | N | ((CH$_2$)$_3$O(CH$_2$)$_3$) | Heterocyclic ring | Hydrocarbyl |
| II.1386 | S | N | ((CH$_2$)$_3$O(CH$_2$)$_3$) | Heterocyclic ring | Substituted hydrocarbyl |

TABLE 2-continued

Selected compounds from Formula (II)

| | R1 | R2 | R4 | R5 | R6 |
|---|---|---|---|---|---|
| II.1387 | S | N | $((CH_2)_3O(CH_2)_3)_2$ | Aromatic ring | Hydrogen |
| II.1388 | S | N | $((CH_2)_3O(CH_2)_3)_2$ | Aromatic ring | Hydrocarbyl |
| II.1389 | S | N | $((CH_2)_3O(CH_2)_3)_2$ | Aromatic ring | Substituted hydrocarbyl |
| II.1390 | S | N | $((CH_2)_3O(CH_2)_3)_2$ | Cylic ring | Hydrogen |
| II.1391 | S | N | $((CH_2)_3O(CH_2)_3)_2$ | Cylic ring | Hydrocarbyl |
| II.1392 | S | N | $((CH_2)_3O(CH_2)_3)_2$ | Cylic ring | Substituted hydrocarbyl |
| II.1393 | S | N | $((CH_2)_3O(CH_2)_3)_2$ | Heterocyclic ring | Hydrogen |
| II.1394 | S | N | $((CH_2)_3O(CH_2)_3)_2$ | Heterocyclic ring | Hydrocarbyl |
| II.1395 | S | N | $((CH_2)_3O(CH_2)_3)_2$ | Heterocyclic ring | Substituted hydrocarbyl |
| II.1396 | S | N | $((CH_2)_3O(CH_2)_3)_3$ | Aromatic ring | Hydrogen |
| II.1397 | S | N | $((CH_2)_3O(CH_2)_3)_3$ | Aromatic ring | Hydrocarbyl |
| II.1398 | S | N | $((CH_2)_3O(CH_2)_3)_3$ | Aromatic ring | Substituted hydrocarbyl |
| II.1399 | S | N | $((CH_2)_3O(CH_2)_3)_3$ | Cylic ring | Hydrogen |
| II.1400 | S | N | $((CH_2)_3O(CH_2)_3)_3$ | Cylic ring | Hydrocarbyl |
| II.1401 | S | N | $((CH_2)_3O(CH_2)_3)_3$ | Cylic ring | Substituted hydrocarbyl |
| II.1402 | S | N | $((CH_2)_3O(CH_2)_3)_3$ | Heterocyclic ring | Hydrogen |
| II.1403 | S | N | $((CH_2)_3O(CH_2)_3)_3$ | Heterocyclic ring | Hydrocarbyl |
| II.1404 | S | N | $((CH_2)_3O(CH_2)_3)_3$ | Heterocyclic ring | Substituted hydrocarbyl |
| II.1405 | S | S | $(CH_2)$ | Aromatic ring | Hydrogen |
| II.1406 | S | S | $(CH_2)$ | Aromatic ring | Hydrocarbyl |
| II.1407 | S | S | $(CH_2)$ | Aromatic ring | Substituted hydrocarbyl |
| II.1408 | S | S | $(CH_2)$ | Cylic ring | Hydrogen |
| II.1409 | S | S | $(CH_2)$ | Cylic ring | Hydrocarbyl |
| II.1410 | S | S | $(CH_2)$ | Cylic ring | Substituted hydrocarbyl |
| II.1411 | S | S | $(CH_2)$ | Heterocyclic ring | Hydrogen |
| II.1412 | S | S | $(CH_2)$ | Heterocyclic ring | Hydrocarbyl |
| II.1413 | S | S | $(CH_2)$ | Heterocyclic ring | Substituted hydrocarbyl |
| II.1414 | S | S | $(CH_2)_2$ | Aromatic ring | Hydrogen |
| II.1415 | S | S | $(CH_2)_2$ | Aromatic ring | Hydrocarbyl |
| II.1416 | S | S | $(CH_2)_2$ | Aromatic ring | Substituted hydrocarbyl |
| II.1417 | S | S | $(CH_2)_2$ | Cylic ring | Hydrogen |
| II.1418 | S | S | $(CH_2)_2$ | Cylic ring | Hydrocarbyl |
| II.1419 | S | S | $(CH_2)_2$ | Cylic ring | Substituted hydrocarbyl |
| II.1420 | S | S | $(CH_2)_2$ | Heterocyclic ring | Hydrogen |
| II.1421 | S | S | $(CH_2)_2$ | Heterocyclic ring | Hydrocarbyl |
| II.1422 | S | S | $(CH_2)_2$ | Heterocyclic ring | Substituted hydrocarbyl |
| II.1423 | S | S | $(CH_2)_3$ | Aromatic ring | Hydrogen |
| II.1424 | S | S | $(CH_2)_3$ | Aromatic ring | Hydrocarbyl |
| II.1425 | S | S | $(CH_2)_3$ | Aromatic ring | Substituted hydrocarbyl |
| II.1426 | S | S | $(CH_2)_3$ | Cylic ring | Hydrogen |
| II.1427 | S | S | $(CH_2)_3$ | Cylic ring | Hydrocarbyl |
| II.1428 | S | S | $(CH_2)_3$ | Cylic ring | Substituted hydrocarbyl |
| II.1429 | S | S | $(CH_2)_3$ | Heterocyclic ring | Hydrogen |
| II.1430 | S | S | $(CH_2)_3$ | Heterocyclic ring | Hydrocarbyl |
| II.1431 | S | S | $(CH_2)_3$ | Heterocyclic ring | Substituted hydrocarbyl |
| II.1432 | S | S | $((CH_2)O)$ | Aromatic ring | Hydrogen |
| II.1433 | S | S | $((CH_2)O)$ | Aromatic ring | Hydrocarbyl |
| II.1434 | S | S | $((CH_2)O)$ | Aromatic ring | Substituted hydrocarbyl |
| II.1435 | S | S | $((CH_2)O)$ | Cylic ring | Hydrogen |
| II.1436 | S | S | $((CH_2)O)$ | Cylic ring | Hydrocarbyl |
| II.1437 | S | S | $((CH_2)O)$ | Cylic ring | Substituted hydrocarbyl |
| II.1438 | S | S | $((CH_2)O)$ | Heterocyclic ring | Hydrogen |
| II.1439 | S | S | $((CH_2)O)$ | Heterocyclic ring | Hydrocarbyl |
| II.1440 | S | S | $((CH_2)O)$ | Heterocyclic ring | Substituted hydrocarbyl |
| II.1441 | S | S | $((CH_2)O)_2$ | Aromatic ring | Hydrogen |
| II.1442 | S | S | $((CH_2)O)_2$ | Aromatic ring | Hydrocarbyl |
| II.1443 | S | S | $((CH_2)O)_2$ | Aromatic ring | Substituted hydrocarbyl |
| II.1444 | S | S | $((CH_2)O)_2$ | Cylic ring | Hydrogen |
| II.1445 | S | S | $((CH_2)O)_2$ | Cylic ring | Hydrocarbyl |
| II.1446 | S | S | $((CH_2)O)_2$ | Cylic ring | Substituted hydrocarbyl |
| II.1447 | S | S | $((CH_2)O)_2$ | Heterocyclic ring | Hydrogen |
| II.1448 | S | S | $((CH_2)O)_2$ | Heterocyclic ring | Hydrocarbyl |
| II.1449 | S | S | $((CH_2)O)_2$ | Heterocyclic ring | Substituted hydrocarbyl |
| II.1450 | S | S | $((CH_2)O)_3$ | Aromatic ring | Hydrogen |
| II.1451 | S | S | $((CH_2)O)_3$ | Aromatic ring | Hydrocarbyl |
| II.1452 | S | S | $((CH_2)O)_3$ | Aromatic ring | Substituted hydrocarbyl |
| II.1453 | S | S | $((CH_2)O)_3$ | Cylic ring | Hydrogen |
| II.1454 | S | S | $((CH_2)O)_3$ | Cylic ring | Hydrocarbyl |
| II.1455 | S | S | $((CH_2)O)_3$ | Cylic ring | Substituted hydrocarbyl |
| II.1456 | S | S | $((CH_2)O)_3$ | Heterocyclic ring | Hydrogen |
| II.1457 | S | S | $((CH_2)O)_3$ | Heterocyclic ring | Hydrocarbyl |
| II.1458 | S | S | $((CH_2)O)_3$ | Heterocyclic ring | Substituted hydrocarbyl |
| II.1459 | S | S | $((CH_2)_2O)$ | Aromatic ring | Hydrogen |
| II.1460 | S | S | $((CH_2)_2O)$ | Aromatic ring | Hydrocarbyl |
| II.1461 | S | S | $((CH_2)_2O)$ | Aromatic ring | Substituted hydrocarbyl |
| II.1462 | S | S | $((CH_2)_2O)$ | Cylic ring | Hydrogen |

TABLE 2-continued

Selected compounds from Formula (II)

| | R1 | R2 | R4 | R5 | R6 |
|---|---|---|---|---|---|
| II.1463 | S | S | ((CH$_2$)$_2$O) | Cylic ring | Hydrocarbyl |
| II.1464 | S | S | ((CH$_2$)$_2$O) | Cylic ring | Substituted hydrocarbyl |
| II.1465 | S | S | ((CH$_2$)$_2$O) | Heterocyclic ring | Hydrogen |
| II.1466 | S | S | ((CH$_2$)$_2$O) | Heterocyclic ring | Hydrocarbyl |
| II.1467 | S | S | ((CH$_2$)$_2$O) | Heterocyclic ring | Substituted hydrocarbyl |
| II.1468 | S | S | ((CH$_2$)$_2$O)$_2$ | Aromatic ring | Hydrogen |
| II.1469 | S | S | ((CH$_2$)$_2$O)$_2$ | Aromatic ring | Hydrocarbyl |
| II.1470 | S | S | ((CH$_2$)$_2$O)$_2$ | Aromatic ring | Substituted hydrocarbyl |
| II.1471 | S | S | ((CH$_2$)$_2$O)$_2$ | Cylic ring | Hydrogen |
| II.1472 | S | S | ((CH$_2$)$_2$O)$_2$ | Cylic ring | Hydrocarbyl |
| II.1473 | S | S | ((CH$_2$)$_2$O)$_2$ | Cylic ring | Substituted hydrocarbyl |
| II.1474 | S | S | ((CH$_2$)$_2$O)$_2$ | Heterocyclic ring | Hydrogen |
| II.1475 | S | S | ((CH$_2$)$_2$O)$_2$ | Heterocyclic ring | Hydrocarbyl |
| II.1476 | S | S | ((CH$_2$)$_2$O)$_2$ | Heterocyclic ring | Substituted hydrocarbyl |
| II.1477 | S | S | ((CH$_2$)$_2$O)$_3$ | Aromatic ring | Hydrogen |
| II.1478 | S | S | ((CH$_2$)$_2$O)$_3$ | Aromatic ring | Hydrocarbyl |
| II.1479 | S | S | ((CH$_2$)$_2$O)$_3$ | Aromatic ring | Substituted hydrocarbyl |
| II.1480 | S | S | ((CH$_2$)$_2$O)$_3$ | Cylic ring | Hydrogen |
| II.1481 | S | S | ((CH$_2$)$_2$O)$_3$ | Cylic ring | Hydrocarbyl |
| II.1482 | S | S | ((CH$_2$)$_2$O)$_3$ | Cylic ring | Substituted hydrocarbyl |
| II.1483 | S | S | ((CH$_2$)$_2$O)$_3$ | Heterocyclic ring | Hydrogen |
| II.1484 | S | S | ((CH$_2$)$_2$O)$_3$ | Heterocyclic ring | Hydrocarbyl |
| II.1485 | S | S | ((CH$_2$)$_2$O)$_3$ | Heterocyclic ring | Substituted hydrocarbyl |
| II.1486 | S | S | ((CH$_2$)$_3$O) | Aromatic ring | Hydrogen |
| II.1487 | S | S | ((CH$_2$)$_3$O) | Aromatic ring | Hydrocarbyl |
| II.1488 | S | S | ((CH$_2$)$_3$O) | Aromatic ring | Substituted hydrocarbyl |
| II.1489 | S | S | ((CH$_2$)$_3$O) | Cylic ring | Hydrogen |
| II.1490 | S | S | ((CH$_2$)$_3$O) | Cylic ring | Hydrocarbyl |
| II.1491 | S | S | ((CH$_2$)$_3$O) | Cylic ring | Substituted hydrocarbyl |
| II.1492 | S | S | ((CH$_2$)$_3$O) | Heterocyclic ring | Hydrogen |
| II.1493 | S | S | ((CH$_2$)$_3$O) | Heterocyclic ring | Hydrocarbyl |
| II.1494 | S | S | ((CH$_2$)$_3$O) | Heterocyclic ring | Substituted hydrocarbyl |
| II.1495 | S | S | ((CH$_2$)$_3$O)$_2$ | Aromatic ring | Hydrogen |
| II.1496 | S | S | ((CH$_2$)$_3$O)$_2$ | Aromatic ring | Hydrocarbyl |
| II.1497 | S | S | ((CH$_2$)$_3$O)$_2$ | Aromatic ring | Substituted hydrocarbyl |
| II.1498 | S | S | ((CH$_2$)$_3$O)$_2$ | Cylic ring | Hydrogen |
| II.1499 | S | S | ((CH$_2$)$_3$O)$_2$ | Cylic ring | Hydrocarbyl |
| II.1500 | S | S | ((CH$_2$)$_3$O)$_2$ | Cylic ring | Substituted hydrocarbyl |
| II.1501 | S | S | ((CH$_2$)$_3$O)$_2$ | Heterocyclic ring | Hydrogen |
| II.1502 | S | S | ((CH$_2$)$_3$O)$_2$ | Heterocyclic ring | Hydrocarbyl |
| II.1503 | S | S | ((CH$_2$)$_3$O)$_2$ | Heterocyclic ring | Substituted hydrocarbyl |
| II.1504 | S | S | ((CH$_2$)$_3$O)$_3$ | Aromatic ring | Hydrogen |
| II.1505 | S | S | ((CH$_2$)$_3$O)$_3$ | Aromatic ring | Hydrocarbyl |
| II.1506 | S | S | ((CH$_2$)$_3$O)$_3$ | Aromatic ring | Substituted hydrocarbyl |
| II.1507 | S | S | ((CH$_2$)$_3$O)$_3$ | Cylic ring | Hydrogen |
| II.1508 | S | S | ((CH$_2$)$_3$O)$_3$ | Cylic ring | Hydrocarbyl |
| II.1509 | S | S | ((CH$_2$)$_3$O)$_3$ | Cylic ring | Substituted hydrocarbyl |
| II.1510 | S | S | ((CH$_2$)$_3$O)$_3$ | Heterocyclic ring | Hydrogen |
| II.1511 | S | S | ((CH$_2$)$_3$O)$_3$ | Heterocyclic ring | Hydrocarbyl |
| II.1512 | S | S | ((CH$_2$)$_3$O)$_3$ | Heterocyclic ring | Substituted hydrocarbyl |
| II.1513 | S | S | ((CH$_2$)O(CH$_2$)) | Aromatic ring | Hydrogen |
| II.1514 | S | S | ((CH$_2$)O(CH$_2$)) | Aromatic ring | Hydrocarbyl |
| II.1515 | S | S | ((CH$_2$)O(CH$_2$)) | Aromatic ring | Substituted hydrocarbyl |
| II.1516 | S | S | ((CH$_2$)O(CH$_2$)) | Cylic ring | Hydrogen |
| II.1517 | S | S | ((CH$_2$)O(CH$_2$)) | Cylic ring | Hydrocarbyl |
| II.1518 | S | S | ((CH$_2$)O(CH$_2$)) | Cylic ring | Substituted hydrocarbyl |
| II.1519 | S | S | ((CH$_2$)O(CH$_2$)) | Heterocyclic ring | Hydrogen |
| II.1520 | S | S | ((CH$_2$)O(CH$_2$)) | Heterocyclic ring | Hydrocarbyl |
| II.1521 | S | S | ((CH$_2$)O(CH$_2$)) | Heterocyclic ring | Substituted hydrocarbyl |
| II.1522 | S | S | ((CH$_2$)O(CH$_2$))$_2$ | Aromatic ring | Hydrogen |
| II.1523 | S | S | ((CH$_2$)O(CH$_2$))$_2$ | Aromatic ring | Hydrocarbyl |
| II.1524 | S | S | ((CH$_2$)O(CH$_2$))$_2$ | Aromatic ring | Substituted hydrocarbyl |
| II.1525 | S | S | ((CH$_2$)O(CH$_2$))$_2$ | Cylic ring | Hydrogen |
| II.1526 | S | S | ((CH$_2$)O(CH$_2$))$_2$ | Cylic ring | Hydrocarbyl |
| II.1527 | S | S | ((CH$_2$)O(CH$_2$))$_2$ | Cylic ring | Substituted hydrocarbyl |
| II.1528 | S | S | ((CH$_2$)O(CH$_2$))$_2$ | Heterocyclic ring | Hydrogen |
| II.1529 | S | S | ((CH$_2$)O(CH$_2$))$_2$ | Heterocyclic ring | Hydrocarbyl |
| II.1530 | S | S | ((CH$_2$)O(CH$_2$))$_2$ | Heterocyclic ring | Substituted hydrocarbyl |
| II.1531 | S | S | ((CH$_2$)O(CH$_2$))$_3$ | Aromatic ring | Hydrogen |
| II.1532 | S | S | ((CH$_2$)O(CH$_2$))$_3$ | Aromatic ring | Hydrocarbyl |
| II.1533 | S | S | ((CH$_2$)O(CH$_2$))$_3$ | Aromatic ring | Substituted hydrocarbyl |
| II.1534 | S | S | ((CH$_2$)O(CH$_2$))$_3$ | Cylic ring | Hydrogen |
| II.1535 | S | S | ((CH$_2$)O(CH$_2$))$_3$ | Cylic ring | Hydrocarbyl |
| II.1536 | S | S | ((CH$_2$)O(CH$_2$))$_3$ | Cylic ring | Substituted hydrocarbyl |
| II.1537 | S | S | ((CH$_2$)O(CH$_2$))$_3$ | Heterocyclic ring | Hydrogen |
| II.1538 | S | S | ((CH$_2$)O(CH$_2$))$_3$ | Heterocyclic ring | Hydrocarbyl |

TABLE 2-continued

Selected compounds from Formula (II)

| | R1 | R2 | R4 | R5 | R6 |
|---|---|---|---|---|---|
| II.1539 | S | S | $((CH_2)O(CH_2))_3$ | Heterocyclic ring | Substituted hydrocarbyl |
| II.1540 | S | S | $((CH_2)O(CH_2)_2)$ | Aromatic ring | Hydrogen |
| II.1541 | S | S | $((CH_2)O(CH_2)_2)$ | Aromatic ring | Hydrocarbyl |
| II.1542 | S | S | $((CH_2)O(CH_2)_2)$ | Aromatic ring | Substituted hydrocarbyl |
| II.1543 | S | S | $((CH_2)O(CH_2)_2)$ | Cylic ring | Hydrogen |
| II.1544 | S | S | $((CH_2)O(CH_2)_2)$ | Cylic ring | Hydrocarbyl |
| II.1545 | S | S | $((CH_2)O(CH_2)_2)$ | Cylic ring | Substituted hydrocarbyl |
| II.1546 | S | S | $((CH_2)O(CH_2)_2)$ | Heterocyclic ring | Hydrogen |
| II.1547 | S | S | $((CH_2)O(CH_2)_2)$ | Heterocyclic ring | Hydrocarbyl |
| II.1548 | S | S | $((CH_2)O(CH_2)_2)$ | Heterocyclic ring | Substituted hydrocarbyl |
| II.1549 | S | S | $((CH_2)O(CH_2)_2)_2$ | Aromatic ring | Hydrogen |
| II.1550 | S | S | $((CH_2)O(CH_2)_2)_2$ | Aromatic ring | Hydrocarbyl |
| II.1551 | S | S | $((CH_2)O(CH_2)_2)_2$ | Aromatic ring | Substituted hydrocarbyl |
| II.1552 | S | S | $((CH_2)O(CH_2)_2)_2$ | Cylic ring | Hydrogen |
| II.1553 | S | S | $((CH_2)O(CH_2)_2)_2$ | Cylic ring | Hydrocarbyl |
| II.1554 | S | S | $((CH_2)O(CH_2)_2)_2$ | Cylic ring | Substituted hydrocarbyl |
| II.1555 | S | S | $((CH_2)O(CH_2)_2)_2$ | Heterocyclic ring | Hydrogen |
| II.1556 | S | S | $((CH_2)O(CH_2)_2)_2$ | Heterocyclic ring | Hydrocarbyl |
| II.1557 | S | S | $((CH_2)O(CH_2)_2)_2$ | Heterocyclic ring | Substituted hydrocarbyl |
| II.1558 | S | S | $((CH_2)O(CH_2)_2)_3$ | Aromatic ring | Hydrogen |
| II.1559 | S | S | $((CH_2)O(CH_2)_2)_3$ | Aromatic ring | Hydrocarbyl |
| II.1560 | S | S | $((CH_2)O(CH_2)_2)_3$ | Aromatic ring | Substituted hydrocarbyl |
| II.1561 | S | S | $((CH_2)O(CH_2)_2)_3$ | Cylic ring | Hydrogen |
| II.1562 | S | S | $((CH_2)O(CH_2)_2)_3$ | Cylic ring | Hydrocarbyl |
| II.1563 | S | S | $((CH_2)O(CH_2)_2)_3$ | Cylic ring | Substituted hydrocarbyl |
| II.1564 | S | S | $((CH_2)O(CH_2)_2)_3$ | Heterocyclic ring | Hydrogen |
| II.1565 | S | S | $((CH_2)O(CH_2)_2)_3$ | Heterocyclic ring | Hydrocarbyl |
| II.1566 | S | S | $((CH_2)O(CH_2)_2)_3$ | Heterocyclic ring | Substituted hydrocarbyl |
| II.1567 | S | S | $((CH_2)O(CH_2)_3)$ | Aromatic ring | Hydrogen |
| II.1568 | S | S | $((CH_2)O(CH_2)_3)$ | Aromatic ring | Hydrocarbyl |
| II.1569 | S | S | $((CH_2)O(CH_2)_3)$ | Aromatic ring | Substituted hydrocarbyl |
| II.1570 | S | S | $((CH_2)O(CH_2)_3)$ | Cylic ring | Hydrogen |
| II.1571 | S | S | $((CH_2)O(CH_2)_3)$ | Cylic ring | Hydrocarbyl |
| II.1572 | S | S | $((CH_2)O(CH_2)_3)$ | Cylic ring | Substituted hydrocarbyl |
| II.1573 | S | S | $((CH_2)O(CH_2)_3)$ | Heterocyclic ring | Hydrogen |
| II.1574 | S | S | $((CH_2)O(CH_2)_3)$ | Heterocyclic ring | Hydrocarbyl |
| II.1575 | S | S | $((CH_2)O(CH_2)_3)$ | Heterocyclic ring | Substituted hydrocarbyl |
| II.1576 | S | S | $((CH_2)O(CH_2)_3)_2$ | Aromatic ring | Hydrogen |
| II.1577 | S | S | $((CH_2)O(CH_2)_3)_2$ | Aromatic ring | Hydrocarbyl |
| II.1578 | S | S | $((CH_2)O(CH_2)_3)_2$ | Aromatic ring | Substituted hydrocarbyl |
| II.1579 | S | S | $((CH_2)O(CH_2)_3)_2$ | Cylic ring | Hydrogen |
| II.1580 | S | S | $((CH_2)O(CH_2)_3)_2$ | Cylic ring | Hydrocarbyl |
| II.1581 | S | S | $((CH_2)O(CH_2)_3)_2$ | Cylic ring | Substituted hydrocarbyl |
| II.1582 | S | S | $((CH_2)O(CH_2)_3)_2$ | Heterocyclic ring | Hydrogen |
| II.1583 | S | S | $((CH_2)O(CH_2)_3)_2$ | Heterocyclic ring | Hydrocarbyl |
| II.1584 | S | S | $((CH_2)O(CH_2)_3)_2$ | Heterocyclic ring | Substituted hydrocarbyl |
| II.1585 | S | S | $((CH_2)O(CH_2)_3)_3$ | Aromatic ring | Hydrogen |
| II.1586 | S | S | $((CH_2)O(CH_2)_3)_3$ | Aromatic ring | Hydrocarbyl |
| II.1587 | S | S | $((CH_2)O(CH_2)_3)_3$ | Aromatic ring | Substituted hydrocarbyl |
| II.1588 | S | S | $((CH_2)O(CH_2)_3)_3$ | Cylic ring | Hydrogen |
| II.1589 | S | S | $((CH_2)O(CH_2)_3)_3$ | Cylic ring | Hydrocarbyl |
| II.1590 | S | S | $((CH_2)O(CH_2)_3)_3$ | Cylic ring | Substituted hydrocarbyl |
| II.1591 | S | S | $((CH_2)O(CH_2)_3)_3$ | Heterocyclic ring | Hydrogen |
| II.1592 | S | S | $((CH_2)O(CH_2)_3)_3$ | Heterocyclic ring | Hydrocarbyl |
| II.1593 | S | S | $((CH_2)O(CH_2)_3)_3$ | Heterocyclic ring | Substituted hydrocarbyl |
| II.1594 | S | S | $((CH_2)_2O(CH_2))$ | Aromatic ring | Hydrogen |
| II.1595 | S | S | $((CH_2)_2O(CH_2))$ | Aromatic ring | Hydrocarbyl |
| II.1596 | S | S | $((CH_2)_2O(CH_2))$ | Aromatic ring | Substituted hydrocarbyl |
| II.1597 | S | S | $((CH_2)_2O(CH_2))$ | Cylic ring | Hydrogen |
| II.1598 | S | S | $((CH_2)_2O(CH_2))$ | Cylic ring | Hydrocarbyl |
| II.1599 | S | S | $((CH_2)_2O(CH_2))$ | Cylic ring | Substituted hydrocarbyl |
| II.1600 | S | S | $((CH_2)_2O(CH_2))$ | Heterocyclic ring | Hydrogen |
| II.1601 | S | S | $((CH_2)_2O(CH_2))$ | Heterocyclic ring | Hydrocarbyl |
| II.1602 | S | S | $((CH_2)_2O(CH_2))$ | Heterocyclic ring | Substituted hydrocarbyl |
| II.1603 | S | S | $((CH_2)_2O(CH_2))_2$ | Aromatic ring | Hydrogen |
| II.1604 | S | S | $((CH_2)_2O(CH_2))_2$ | Aromatic ring | Hydrocarbyl |
| II.1605 | S | S | $((CH_2)_2O(CH_2))_2$ | Aromatic ring | Substituted hydrocarbyl |
| II.1606 | S | S | $((CH_2)_2O(CH_2))_2$ | Cylic ring | Hydrogen |
| II.1607 | S | S | $((CH_2)_2O(CH_2))_2$ | Cylic ring | Hydrocarbyl |
| II.1608 | S | S | $((CH_2)_2O(CH_2))_2$ | Cylic ring | Substituted hydrocarbyl |
| II.1609 | S | S | $((CH_2)_2O(CH_2))_2$ | Heterocyclic ring | Hydrogen |
| II.1610 | S | S | $((CH_2)_2O(CH_2))_2$ | Heterocyclic ring | Hydrocarbyl |
| II.1611 | S | S | $((CH_2)_2O(CH_2))_2$ | Heterocyclic ring | Substituted hydrocarbyl |
| II.1612 | S | S | $((CH_2)_2O(CH_2))_3$ | Aromatic ring | Hydrogen |
| II.1613 | S | S | $((CH_2)_2O(CH_2))_3$ | Aromatic ring | Hydrocarbyl |
| II.1614 | S | S | $((CH_2)_2O(CH_2))_3$ | Aromatic ring | Substituted hydrocarbyl |

TABLE 2-continued

Selected compounds from Formula (II)

| | R1 | R2 | R4 | R5 | R6 |
|---|---|---|---|---|---|
| II.1615 | S | S | $((CH_2)_2O(CH_2))_3$ | Cylic ring | Hydrogen |
| II.1616 | S | S | $((CH_2)_2O(CH_2))_3$ | Cylic ring | Hydrocarbyl |
| II.1617 | S | S | $((CH_2)_2O(CH_2))_3$ | Cylic ring | Substituted hydrocarbyl |
| II.1618 | S | S | $((CH_2)_2O(CH_2))_3$ | Heterocyclic ring | Hydrogen |
| II.1619 | S | S | $((CH_2)_2O(CH_2))_3$ | Heterocyclic ring | Hydrocarbyl |
| II.1620 | S | S | $((CH_2)_2O(CH_2))_3$ | Heterocyclic ring | Substituted hydrocarbyl |
| II.1621 | S | S | $((CH_2)_2O(CH_2)_2)$ | Aromatic ring | Hydrogen |
| II.1622 | S | S | $((CH_2)_2O(CH_2)_2)$ | Aromatic ring | Hydrocarbyl |
| II.1623 | S | S | $((CH_2)_2O(CH_2)_2)$ | Aromatic ring | Substituted hydrocarbyl |
| II.1624 | S | S | $((CH_2)_2O(CH_2)_2)$ | Cylic ring | Hydrogen |
| II.1625 | S | S | $((CH_2)_2O(CH_2)_2)$ | Cylic ring | Hydrocarbyl |
| II.1626 | S | S | $((CH_2)_2O(CH_2)_2)$ | Cylic ring | Substituted hydrocarbyl |
| II.1627 | S | S | $((CH_2)_2O(CH_2)_2)$ | Heterocyclic ring | Hydrogen |
| II.1628 | S | S | $((CH_2)_2O(CH_2)_2)$ | Heterocyclic ring | Hydrocarbyl |
| II.1629 | S | S | $((CH_2)_2O(CH_2)_2)$ | Heterocyclic ring | Substituted hydrocarbyl |
| II.1630 | S | S | $((CH_2)_2O(CH_2)_2)_2$ | Aromatic ring | Hydrogen |
| II.1631 | S | S | $((CH_2)_2O(CH_2)_2)_2$ | Aromatic ring | Hydrocarbyl |
| II.1632 | S | S | $((CH_2)_2O(CH_2)_2)_2$ | Aromatic ring | Substituted hydrocarbyl |
| II.1633 | S | S | $((CH_2)_2O(CH_2)_2)_2$ | Cylic ring | Hydrogen |
| II.1634 | S | S | $((CH_2)_2O(CH_2)_2)_2$ | Cylic ring | Hydrocarbyl |
| II.1635 | S | S | $((CH_2)_2O(CH_2)_2)_2$ | Cylic ring | Substituted hydrocarbyl |
| II.1636 | S | S | $((CH_2)_2O(CH_2)_2)_2$ | Heterocyclic ring | Hydrogen |
| II.1637 | S | S | $((CH_2)_2O(CH_2)_2)_2$ | Heterocyclic ring | Hydrocarbyl |
| II.1638 | S | S | $((CH_2)_2O(CH_2)_2)_2$ | Heterocyclic ring | Substituted hydrocarbyl |
| II.1639 | S | S | $((CH_2)_2O(CH_2)_2)_3$ | Aromatic ring | Hydrogen |
| II.1640 | S | S | $((CH_2)_2O(CH_2)_2)_3$ | Aromatic ring | Hydrocarbyl |
| II.1641 | S | S | $((CH_2)_2O(CH_2)_2)_3$ | Aromatic ring | Substituted hydrocarbyl |
| II.1642 | S | S | $((CH_2)_2O(CH_2)_2)_3$ | Cylic ring | Hydrogen |
| II.1643 | S | S | $((CH_2)_2O(CH_2)_2)_3$ | Cylic ring | Hydrocarbyl |
| II.1644 | S | S | $((CH_2)_2O(CH_2)_2)_3$ | Cylic ring | Substituted hydrocarbyl |
| II.1645 | S | S | $((CH_2)_2O(CH_2)_2)_3$ | Heterocyclic ring | Hydrogen |
| II.1646 | S | S | $((CH_2)_2O(CH_2)_2)_3$ | Heterocyclic ring | Hydrocarbyl |
| II.1647 | S | S | $((CH_2)_2O(CH_2)_2)_3$ | Heterocyclic ring | Substituted hydrocarbyl |
| II.1648 | S | S | $((CH_2)_2O(CH_2)_3)$ | Aromatic ring | Hydrogen |
| II.1649 | S | S | $((CH_2)_2O(CH_2)_3)$ | Aromatic ring | Hydrocarbyl |
| II.1650 | S | S | $((CH_2)_2O(CH_2)_3)$ | Aromatic ring | Substituted hydrocarbyl |
| II.1651 | S | S | $((CH_2)_2O(CH_2)_3)$ | Cylic ring | Hydrogen |
| II.1652 | S | S | $((CH_2)_2O(CH_2)_3)$ | Cylic ring | Hydrocarbyl |
| II.1653 | S | S | $((CH_2)_2O(CH_2)_3)$ | Cylic ring | Substituted hydrocarbyl |
| II.1654 | S | S | $((CH_2)_2O(CH_2)_3)$ | Heterocyclic ring | Hydrogen |
| II.1655 | S | S | $((CH_2)_2O(CH_2)_3)$ | Heterocyclic ring | Hydrocarbyl |
| II.1656 | S | S | $((CH_2)_2O(CH_2)_3)$ | Heterocyclic ring | Substituted hydrocarbyl |
| II.1657 | S | S | $((CH_2)_2O(CH_2)_3)_2$ | Aromatic ring | Hydrogen |
| II.1658 | S | S | $((CH_2)_2O(CH_2)_3)_2$ | Aromatic ring | Hydrocarbyl |
| II.1659 | S | S | $((CH_2)_2O(CH_2)_3)_2$ | Aromatic ring | Substituted hydrocarbyl |
| II.1660 | S | S | $((CH_2)_2O(CH_2)_3)_2$ | Cylic ring | Hydrogen |
| II.1661 | S | S | $((CH_2)_2O(CH_2)_3)_2$ | Cylic ring | Hydrocarbyl |
| II.1662 | S | S | $((CH_2)_2O(CH_2)_3)_2$ | Cylic ring | Substituted hydrocarbyl |
| II.1663 | S | S | $((CH_2)_2O(CH_2)_3)_2$ | Heterocyclic ring | Hydrogen |
| II.1664 | S | S | $((CH_2)_2O(CH_2)_3)_2$ | Heterocyclic ring | Hydrocarbyl |
| II.1665 | S | S | $((CH_2)_2O(CH_2)_3)_2$ | Heterocyclic ring | Substituted hydrocarbyl |
| II.1666 | S | S | $((CH_2)_2O(CH_2)_3)_3$ | Aromatic ring | Hydrogen |
| II.1667 | S | S | $((CH_2)_2O(CH_2)_3)_3$ | Aromatic ring | Hydrocarbyl |
| II.1668 | S | S | $((CH_2)_2O(CH_2)_3)_3$ | Aromatic ring | Substituted hydrocarbyl |
| II.1669 | S | S | $((CH_2)_2O(CH_2)_3)_3$ | Cylic ring | Hydrogen |
| II.1670 | S | S | $((CH_2)_2O(CH_2)_3)_3$ | Cylic ring | Hydrocarbyl |
| II.1671 | S | S | $((CH_2)_2O(CH_2)_3)_3$ | Cylic ring | Substituted hydrocarbyl |
| II.1672 | S | S | $((CH_2)_2O(CH_2)_3)_3$ | Heterocyclic ring | Hydrogen |
| II.1673 | S | S | $((CH_2)_2O(CH_2)_3)_3$ | Heterocyclic ring | Hydrocarbyl |
| II.1674 | S | S | $((CH_2)_2O(CH_2)_3)_3$ | Heterocyclic ring | Substituted hydrocarbyl |
| II.1675 | S | S | $((CH_2)_3O(CH_2))$ | Aromatic ring | Hydrogen |
| II.1676 | S | S | $((CH_2)_3O(CH_2))$ | Aromatic ring | Hydrocarbyl |
| II.1677 | S | S | $((CH_2)_3O(CH_2))$ | Aromatic ring | Substituted hydrocarbyl |
| II.1678 | S | S | $((CH_2)_3O(CH_2))$ | Cylic ring | Hydrogen |
| II.1679 | S | S | $((CH_2)_3O(CH_2))$ | Cylic ring | Hydrocarbyl |
| II.1680 | S | S | $((CH_2)_3O(CH_2))$ | Cylic ring | Substituted hydrocarbyl |
| II.1681 | S | S | $((CH_2)_3O(CH_2))$ | Heterocyclic ring | Hydrogen |
| II.1682 | S | S | $((CH_2)_3O(CH_2))$ | Heterocyclic ring | Hydrocarbyl |
| II.1683 | S | S | $((CH_2)_3O(CH_2))$ | Heterocyclic ring | Substituted hydrocarbyl |
| II.1684 | S | S | $((CH_2)_3O(CH_2))_2$ | Aromatic ring | Hydrogen |
| II.1685 | S | S | $((CH_2)_3O(CH_2))_2$ | Aromatic ring | Hydrocarbyl |
| II.1686 | S | S | $((CH_2)_3O(CH_2))_2$ | Aromatic ring | Substituted hydrocarbyl |
| II.1687 | S | S | $((CH_2)_3O(CH_2))_2$ | Cylic ring | Hydrogen |
| II.1688 | S | S | $((CH_2)_3O(CH_2))_2$ | Cylic ring | Hydrocarbyl |
| II.1689 | S | S | $((CH_2)_3O(CH_2))_2$ | Cylic ring | Substituted hydrocarbyl |
| II.1690 | S | S | $((CH_2)_3O(CH_2))_2$ | Heterocyclic ring | Hydrogen |

TABLE 2-continued

Selected compounds from Formula (II)

| | R1 | R2 | R4 | R5 | R6 |
|---|---|---|---|---|---|
| II.1691 | S | S | ((CH$_2$)$_3$O(CH$_2$))$_2$ | Heterocyclic ring | Hydrocarbyl |
| II.1692 | S | S | ((CH$_2$)$_3$O(CH$_2$))$_2$ | Heterocyclic ring | Substituted hydrocarbyl |
| II.1693 | S | S | ((CH$_2$)$_3$O(CH$_2$))$_3$ | Aromatic ring | Hydrogen |
| II.1694 | S | S | ((CH$_2$)$_3$O(CH$_2$))$_3$ | Aromatic ring | Hydrocarbyl |
| II.1695 | S | S | ((CH$_2$)$_3$O(CH$_2$))$_3$ | Aromatic ring | Substituted hydrocarbyl |
| II.1696 | S | S | ((CH$_2$)$_3$O(CH$_2$))$_3$ | Cylic ring | Hydrogen |
| II.1697 | S | S | ((CH$_2$)$_3$O(CH$_2$))$_3$ | Cylic ring | Hydrocarbyl |
| II.1698 | S | S | ((CH$_2$)$_3$O(CH$_2$))$_3$ | Cylic ring | Substituted hydrocarbyl |
| II.1699 | S | S | ((CH$_2$)$_3$O(CH$_2$))$_3$ | Heterocyclic ring | Hydrogen |
| II.1700 | S | S | ((CH$_2$)$_3$O(CH$_2$))$_3$ | Heterocyclic ring | Hydrocarbyl |
| II.1701 | S | S | ((CH$_2$)$_3$O(CH$_2$))$_3$ | Heterocyclic ring | Substituted hydrocarbyl |
| II.1702 | S | S | ((CH$_2$)$_3$O(CH$_2$)$_2$) | Aromatic ring | Hydrogen |
| II.1703 | S | S | ((CH$_2$)$_3$O(CH$_2$)$_2$) | Aromatic ring | Hydrocarbyl |
| II.1704 | S | S | ((CH$_2$)$_3$O(CH$_2$)$_2$) | Aromatic ring | Substituted hydrocarbyl |
| II.1705 | S | S | ((CH$_2$)$_3$O(CH$_2$)$_2$) | Cylic ring | Hydrogen |
| II.1706 | S | S | ((CH$_2$)$_3$O(CH$_2$)$_2$) | Cylic ring | Hydrocarbyl |
| II.1707 | S | S | ((CH$_2$)$_3$O(CH$_2$)$_2$) | Cylic ring | Substituted hydrocarbyl |
| II.1708 | S | S | ((CH$_2$)$_3$O(CH$_2$)$_2$) | Heterocyclic ring | Hydrogen |
| II.1709 | S | S | ((CH$_2$)$_3$O(CH$_2$)$_2$) | Heterocyclic ring | Hydrocarbyl |
| II.1710 | S | S | ((CH$_2$)$_3$O(CH$_2$)$_2$) | Heterocyclic ring | Substituted hydrocarbyl |
| II.1711 | S | S | ((CH$_2$)$_3$O(CH$_2$)$_2$)$_2$ | Aromatic ring | Hydrogen |
| II.1712 | S | S | ((CH$_2$)$_3$O(CH$_2$)$_2$)$_2$ | Aromatic ring | Hydrocarbyl |
| II.1713 | S | S | ((CH$_2$)$_3$O(CH$_2$)$_2$)$_2$ | Aromatic ring | Substituted hydrocarbyl |
| II.1714 | S | S | ((CH$_2$)$_3$O(CH$_2$)$_2$)$_2$ | Cylic ring | Hydrogen |
| II.1715 | S | S | ((CH$_2$)$_3$O(CH$_2$)$_2$)$_2$ | Cylic ring | Hydrocarbyl |
| II.1716 | S | S | ((CH$_2$)$_3$O(CH$_2$)$_2$)$_2$ | Cylic ring | Substituted hydrocarbyl |
| II.1717 | S | S | ((CH$_2$)$_3$O(CH$_2$)$_2$)$_2$ | Heterocyclic ring | Hydrogen |
| II.1718 | S | S | ((CH$_2$)$_3$O(CH$_2$)$_2$)$_2$ | Heterocyclic ring | Hydrocarbyl |
| II.1719 | S | S | ((CH$_2$)$_3$O(CH$_2$)$_2$)$_2$ | Heterocyclic ring | Substituted hydrocarbyl |
| II.1720 | S | S | ((CH$_2$)$_3$O(CH$_2$)$_2$)$_3$ | Aromatic ring | Hydrogen |
| II.1721 | S | S | ((CH$_2$)$_3$O(CH$_2$)$_2$)$_3$ | Aromatic ring | Hydrocarbyl |
| II.1722 | S | S | ((CH$_2$)$_3$O(CH$_2$)$_2$)$_3$ | Aromatic ring | Substituted hydrocarbyl |
| II.1723 | S | S | ((CH$_2$)$_3$O(CH$_2$)$_2$)$_3$ | Cylic ring | Hydrogen |
| II.1724 | S | S | ((CH$_2$)$_3$O(CH$_2$)$_2$)$_3$ | Cylic ring | Hydrocarbyl |
| II.1725 | S | S | ((CH$_2$)$_3$O(CH$_2$)$_2$)$_3$ | Cylic ring | Substituted hydrocarbyl |
| II.1726 | S | S | ((CH$_2$)$_3$O(CH$_2$)$_2$)$_3$ | Heterocyclic ring | Hydrogen |
| II.1727 | S | S | ((CH$_2$)$_3$O(CH$_2$)$_2$)$_3$ | Heterocyclic ring | Hydrocarbyl |
| II.1728 | S | S | ((CH$_2$)$_3$O(CH$_2$)$_2$)$_3$ | Heterocyclic ring | Substituted hydrocarbyl |
| II.1729 | S | S | ((CH$_2$)$_3$O(CH$_2$)$_3$) | Aromatic ring | Hydrogen |
| II.1730 | S | S | ((CH$_2$)$_3$O(CH$_2$)$_3$) | Aromatic ring | Hydrocarbyl |
| II.1731 | S | S | ((CH$_2$)$_3$O(CH$_2$)$_3$) | Aromatic ring | Substituted hydrocarbyl |
| II.1732 | S | S | ((CH$_2$)$_3$O(CH$_2$)$_3$) | Cylic ring | Hydrogen |
| II.1733 | S | S | ((CH$_2$)$_3$O(CH$_2$)$_3$) | Cylic ring | Hydrocarbyl |
| II.1734 | S | S | ((CH$_2$)$_3$O(CH$_2$)$_3$) | Cylic ring | Substituted hydrocarbyl |
| II.1735 | S | S | ((CH$_2$)$_3$O(CH$_2$)$_3$) | Heterocyclic ring | Hydrogen |
| II.1736 | S | S | ((CH$_2$)$_3$O(CH$_2$)$_3$) | Heterocyclic ring | Hydrocarbyl |
| II.1737 | S | S | ((CH$_2$)$_3$O(CH$_2$)$_3$) | Heterocyclic ring | Substituted hydrocarbyl |
| II.1738 | S | S | ((CH$_2$)$_3$O(CH$_2$)$_3$)$_2$ | Aromatic ring | Hydrogen |
| II.1739 | S | S | ((CH$_2$)$_3$O(CH$_2$)$_3$)$_2$ | Aromatic ring | Hydrocarbyl |
| II.1740 | S | S | ((CH$_2$)$_3$O(CH$_2$)$_3$)$_2$ | Aromatic ring | Substituted hydrocarbyl |
| II.1741 | S | S | ((CH$_2$)$_3$O(CH$_2$)$_3$)$_2$ | Cylic ring | Hydrogen |
| II.1742 | S | S | ((CH$_2$)$_3$O(CH$_2$)$_3$)$_2$ | Cylic ring | Hydrocarbyl |
| II.1743 | S | S | ((CH$_2$)$_3$O(CH$_2$)$_3$)$_2$ | Cylic ring | Substituted hydrocarbyl |
| II.1744 | S | S | ((CH$_2$)$_3$O(CH$_2$)$_3$)$_2$ | Heterocyclic ring | Hydrogen |
| II.1745 | S | S | ((CH$_2$)$_3$O(CH$_2$)$_3$)$_2$ | Heterocyclic ring | Hydrocarbyl |
| II.1746 | S | S | ((CH$_2$)$_3$O(CH$_2$)$_3$)$_2$ | Heterocyclic ring | Substituted hydrocarbyl |
| II.1747 | S | S | ((CH$_2$)$_3$O(CH$_2$)$_3$)$_3$ | Aromatic ring | Hydrogen |
| II.1748 | S | S | ((CH$_2$)$_3$O(CH$_2$)$_3$)$_3$ | Aromatic ring | Hydrocarbyl |
| II.1749 | S | S | ((CH$_2$)$_3$O(CH$_2$)$_3$)$_3$ | Aromatic ring | Substituted hydrocarbyl |
| II.1750 | S | S | ((CH$_2$)$_3$O(CH$_2$)$_3$)$_3$ | Cylic ring | Hydrogen |
| II.1751 | S | S | ((CH$_2$)$_3$O(CH$_2$)$_3$)$_3$ | Cylic ring | Hydrocarbyl |
| II.1752 | S | S | ((CH$_2$)$_3$O(CH$_2$)$_3$)$_3$ | Cylic ring | Substituted hydrocarbyl |
| II.1753 | S | S | ((CH$_2$)$_3$O(CH$_2$)$_3$)$_3$ | Heterocyclic ring | Hydrogen |
| II.1754 | S | S | ((CH$_2$)$_3$O(CH$_2$)$_3$)$_3$ | Heterocyclic ring | Hydrocarbyl |
| II.1755 | S | S | ((CH$_2$)$_3$O(CH$_2$)$_3$)$_3$ | Heterocyclic ring | Substituted hydrocarbyl |
| II.1756 | S | O | (CH$_2$) | Aromatic ring | Hydrogen |
| II.1757 | S | O | (CH$_2$) | Aromatic ring | Hydrocarbyl |
| II.1758 | S | O | (CH$_2$) | Aromatic ring | Substituted hydrocarbyl |
| II.1759 | S | O | (CH$_2$) | Cylic ring | Hydrogen |
| II.1760 | S | O | (CH$_2$) | Cylic ring | Hydrocarbyl |
| II.1761 | S | O | (CH$_2$) | Cylic ring | Substituted hydrocarbyl |
| II.1762 | S | O | (CH$_2$) | Heterocyclic ring | Hydrogen |
| II.1763 | S | O | (CH$_2$) | Heterocyclic ring | Hydrocarbyl |
| II.1764 | S | O | (CH$_2$) | Heterocyclic ring | Substituted hydrocarbyl |
| II.1765 | S | O | (CH$_2$)$_2$ | Aromatic ring | Hydrogen |
| II.1766 | S | O | (CH$_2$)$_2$ | Aromatic ring | Hydrocarbyl |

TABLE 2-continued

Selected compounds from Formula (II)

| | R1 | R2 | R4 | R5 | R6 |
|---|---|---|---|---|---|
| II.1767 | S | O | $(CH_2)_2$ | Aromatic ring | Substituted hydrocarbyl |
| II.1768 | S | O | $(CH_2)_2$ | Cylic ring | Hydrogen |
| II.1769 | S | O | $(CH_2)_2$ | Cylic ring | Hydrocarbyl |
| II.1770 | S | O | $(CH_2)_2$ | Cylic ring | Substituted hydrocarbyl |
| II.1771 | S | O | $(CH_2)_2$ | Heterocyclic ring | Hydrogen |
| II.1772 | S | O | $(CH_2)_2$ | Heterocyclic ring | Hydrocarbyl |
| II.1773 | S | O | $(CH_2)_2$ | Heterocyclic ring | Substituted hydrocarbyl |
| II.1774 | S | O | $(CH_2)_3$ | Aromatic ring | Hydrogen |
| II.1775 | S | O | $(CH_2)_3$ | Aromatic ring | Hydrocarbyl |
| II.1776 | S | O | $(CH_2)_3$ | Aromatic ring | Substituted hydrocarbyl |
| II.1777 | S | O | $(CH_2)_3$ | Cylic ring | Hydrogen |
| II.1778 | S | O | $(CH_2)_3$ | Cylic ring | Hydrocarbyl |
| II.1779 | S | O | $(CH_2)_3$ | Cylic ring | Substituted hydrocarbyl |
| II.1780 | S | O | $(CH_2)_3$ | Heterocyclic ring | Hydrogen |
| II.1781 | S | O | $(CH_2)_3$ | Heterocyclic ring | Hydrocarbyl |
| II.1782 | S | O | $(CH_2)_3$ | Heterocyclic ring | Substituted hydrocarbyl |
| II.1783 | S | O | $((CH_2)O)$ | Aromatic ring | Hydrogen |
| II.1784 | S | O | $((CH_2)O)$ | Aromatic ring | Hydrocarbyl |
| II.1785 | S | O | $((CH_2)O)$ | Aromatic ring | Substituted hydrocarbyl |
| II.1786 | S | O | $((CH_2)O)$ | Cylic ring | Hydrogen |
| II.1787 | S | O | $((CH_2)O)$ | Cylic ring | Hydrocarbyl |
| II.1788 | S | O | $((CH_2)O)$ | Cylic ring | Substituted hydrocarbyl |
| II.1789 | S | O | $((CH_2)O)$ | Heterocyclic ring | Hydrogen |
| II.1790 | S | O | $((CH_2)O)$ | Heterocyclic ring | Hydrocarbyl |
| II.1791 | S | O | $((CH_2)O)$ | Heterocyclic ring | Substituted hydrocarbyl |
| II.1792 | S | O | $((CH_2)O)_2$ | Aromatic ring | Hydrogen |
| II.1793 | S | O | $((CH_2)O)_2$ | Aromatic ring | Hydrocarbyl |
| II.1794 | S | O | $((CH_2)O)_2$ | Aromatic ring | Substituted hydrocarbyl |
| II.1795 | S | O | $((CH_2)O)_2$ | Cylic ring | Hydrogen |
| II.1796 | S | O | $((CH_2)O)_2$ | Cylic ring | Hydrocarbyl |
| II.1797 | S | O | $((CH_2)O)_2$ | Cylic ring | Substituted hydrocarbyl |
| II.1798 | S | O | $((CH_2)O)_2$ | Heterocyclic ring | Hydrogen |
| II.1799 | S | O | $((CH_2)O)_2$ | Heterocyclic ring | Hydrocarbyl |
| II.1800 | S | O | $((CH_2)O)_2$ | Heterocyclic ring | Substituted hydrocarbyl |
| II.1801 | S | O | $((CH_2)O)_3$ | Aromatic ring | Hydrogen |
| II.1802 | S | O | $((CH_2)O)_3$ | Aromatic ring | Hydrocarbyl |
| II.1803 | S | O | $((CH_2)O)_3$ | Aromatic ring | Substituted hydrocarbyl |
| II.1804 | S | O | $((CH_2)O)_3$ | Cylic ring | Hydrogen |
| II.1805 | S | O | $((CH_2)O)_3$ | Cylic ring | Hydrocarbyl |
| II.1806 | S | O | $((CH_2)O)_3$ | Cylic ring | Substituted hydrocarbyl |
| II.1807 | S | O | $((CH_2)O)_3$ | Heterocyclic ring | Hydrogen |
| II.1808 | S | O | $((CH_2)O)_3$ | Heterocyclic ring | Hydrocarbyl |
| II.1809 | S | O | $((CH_2)O)_3$ | Heterocyclic ring | Substituted hydrocarbyl |
| II.1810 | S | O | $((CH_2)_2O)$ | Aromatic ring | Hydrogen |
| II.1811 | S | O | $((CH_2)_2O)$ | Aromatic ring | Hydrocarbyl |
| II.1812 | S | O | $((CH_2)_2O)$ | Aromatic ring | Substituted hydrocarbyl |
| II.1813 | S | O | $((CH_2)_2O)$ | Cylic ring | Hydrogen |
| II.1814 | S | O | $((CH_2)_2O)$ | Cylic ring | Hydrocarbyl |
| II.1815 | S | O | $((CH_2)_2O)$ | Cylic ring | Substituted hydrocarbyl |
| II.1816 | S | O | $((CH_2)_2O)$ | Heterocyclic ring | Hydrogen |
| II.1817 | S | O | $((CH_2)_2O)$ | Heterocyclic ring | Hydrocarbyl |
| II.1818 | S | O | $((CH_2)_2O)$ | Heterocyclic ring | Substituted hydrocarbyl |
| II.1819 | S | O | $((CH_2)_2O)_2$ | Aromatic ring | Hydrogen |
| II.1820 | S | O | $((CH_2)_2O)_2$ | Aromatic ring | Hydrocarbyl |
| II.1821 | S | O | $((CH_2)_2O)_2$ | Aromatic ring | Substituted hydrocarbyl |
| II.1822 | S | O | $((CH_2)_2O)_2$ | Cylic ring | Hydrogen |
| II.1823 | S | O | $((CH_2)_2O)_2$ | Cylic ring | Hydrocarbyl |
| II.1824 | S | O | $((CH_2)_2O)_2$ | Cylic ring | Substituted hydrocarbyl |
| II.1825 | S | O | $((CH_2)_2O)_2$ | Heterocyclic ring | Hydrogen |
| II.1826 | S | O | $((CH_2)_2O)_2$ | Heterocyclic ring | Hydrocarbyl |
| II.1827 | S | O | $((CH_2)_2O)_2$ | Heterocyclic ring | Substituted hydrocarbyl |
| II.1828 | S | O | $((CH_2)_2O)_3$ | Aromatic ring | Hydrogen |
| II.1829 | S | O | $((CH_2)_2O)_3$ | Aromatic ring | Hydrocarbyl |
| II.1830 | S | O | $((CH_2)_2O)_3$ | Aromatic ring | Substituted hydrocarbyl |
| II.1831 | S | O | $((CH_2)_2O)_3$ | Cylic ring | Hydrogen |
| II.1832 | S | O | $((CH_2)_2O)_3$ | Cylic ring | Hydrocarbyl |
| II.1833 | S | O | $((CH_2)_2O)_3$ | Cylic ring | Substituted hydrocarbyl |
| II.1834 | S | O | $((CH_2)_2O)_3$ | Heterocyclic ring | Hydrogen |
| II.1835 | S | O | $((CH_2)_2O)_3$ | Heterocyclic ring | Hydrocarbyl |
| II.1836 | S | O | $((CH_2)_2O)_3$ | Heterocyclic ring | Substituted hydrocarbyl |
| II.1837 | S | O | $((CH_2)_3O)$ | Aromatic ring | Hydrogen |
| II.1838 | S | O | $((CH_2)_3O)$ | Aromatic ring | Hydrocarbyl |
| II.1839 | S | O | $((CH_2)_3O)$ | Aromatic ring | Substituted hydrocarbyl |
| II.1840 | S | O | $((CH_2)_3O)$ | Cylic ring | Hydrogen |
| II.1841 | S | O | $((CH_2)_3O)$ | Cylic ring | Hydrocarbyl |
| II.1842 | S | O | $((CH_2)_3O)$ | Cylic ring | Substituted hydrocarbyl |

TABLE 2-continued

Selected compounds from Formula (II)

| | R1 | R2 | R4 | R5 | R6 |
|---|---|---|---|---|---|
| II.1843 | S | O | $((CH_2)_3O)$ | Heterocyclic ring | Hydrogen |
| II.1844 | S | O | $((CH_2)_3O)$ | Heterocyclic ring | Hydrocarbyl |
| II.1845 | S | O | $((CH_2)_3O)$ | Heterocyclic ring | Substituted hydrocarbyl |
| II.1846 | S | O | $((CH_2)_3O)_2$ | Aromatic ring | Hydrogen |
| II.1847 | S | O | $((CH_2)_3O)_2$ | Aromatic ring | Hydrocarbyl |
| II.1848 | S | O | $((CH_2)_3O)_2$ | Aromatic ring | Substituted hydrocarbyl |
| II.1849 | S | O | $((CH_2)_3O)_2$ | Cylic ring | Hydrogen |
| II.1850 | S | O | $((CH_2)_3O)_2$ | Cylic ring | Hydrocarbyl |
| II.1851 | S | O | $((CH_2)_3O)_2$ | Cylic ring | Substituted hydrocarbyl |
| II.1852 | S | O | $((CH_2)_3O)_2$ | Heterocyclic ring | Hydrogen |
| II.1853 | S | O | $((CH_2)_3O)_2$ | Heterocyclic ring | Hydrocarbyl |
| II.1854 | S | O | $((CH_2)_3O)_2$ | Heterocyclic ring | Substituted hydrocarbyl |
| II.1855 | S | O | $((CH_2)_3O)_3$ | Aromatic ring | Hydrogen |
| II.1856 | S | O | $((CH_2)_3O)_3$ | Aromatic ring | Hydrocarbyl |
| II.1857 | S | O | $((CH_2)_3O)_3$ | Aromatic ring | Substituted hydrocarbyl |
| II.1858 | S | O | $((CH_2)_3O)_3$ | Cylic ring | Hydrogen |
| II.1859 | S | O | $((CH_2)_3O)_3$ | Cylic ring | Hydrocarbyl |
| II.1860 | S | O | $((CH_2)_3O)_3$ | Cylic ring | Substituted hydrocarbyl |
| II.1861 | S | O | $((CH_2)_3O)_3$ | Heterocyclic ring | Hydrogen |
| II.1862 | S | O | $((CH_2)_3O)_3$ | Heterocyclic ring | Hydrocarbyl |
| II.1863 | S | O | $((CH_2)_3O)_3$ | Heterocyclic ring | Substituted hydrocarbyl |
| II.1864 | S | O | $((CH_2)O(CH_2))$ | Aromatic ring | Hydrogen |
| II.1865 | S | O | $((CH_2)O(CH_2))$ | Aromatic ring | Hydrocarbyl |
| II.1866 | S | O | $((CH_2)O(CH_2))$ | Aromatic ring | Substituted hydrocarbyl |
| II.1867 | S | O | $((CH_2)O(CH_2))$ | Cylic ring | Hydrogen |
| II.1868 | S | O | $((CH_2)O(CH_2))$ | Cylic ring | Hydrocarbyl |
| II.1869 | S | O | $((CH_2)O(CH_2))$ | Cylic ring | Substituted hydrocarbyl |
| II.1870 | S | O | $((CH_2)O(CH_2))$ | Heterocyclic ring | Hydrogen |
| II.1871 | S | O | $((CH_2)O(CH_2))$ | Heterocyclic ring | Hydrocarbyl |
| II.1872 | S | O | $((CH_2)O(CH_2))$ | Heterocyclic ring | Substituted hydrocarbyl |
| II.1873 | S | O | $((CH_2)O(CH_2))_2$ | Aromatic ring | Hydrogen |
| II.1874 | S | O | $((CH_2)O(CH_2))_2$ | Aromatic ring | Hydrocarbyl |
| II.1875 | S | O | $((CH_2)O(CH_2))_2$ | Aromatic ring | Substituted hydrocarbyl |
| II.1876 | S | O | $((CH_2)O(CH_2))_2$ | Cylic ring | Hydrogen |
| II.1877 | S | O | $((CH_2)O(CH_2))_2$ | Cylic ring | Hydrocarbyl |
| II.1878 | S | O | $((CH_2)O(CH_2))_2$ | Cylic ring | Substituted hydrocarbyl |
| II.1879 | S | O | $((CH_2)O(CH_2))_2$ | Heterocyclic ring | Hydrogen |
| II.1880 | S | O | $((CH_2)O(CH_2))_2$ | Heterocyclic ring | Hydrocarbyl |
| II.1881 | S | O | $((CH_2)O(CH_2))_2$ | Heterocyclic ring | Substituted hydrocarbyl |
| II.1882 | S | O | $((CH_2)O(CH_2))_3$ | Aromatic ring | Hydrogen |
| II.1883 | S | O | $((CH_2)O(CH_2))_3$ | Aromatic ring | Hydrocarbyl |
| II.1884 | S | O | $((CH_2)O(CH_2))_3$ | Aromatic ring | Substituted hydrocarbyl |
| II.1885 | S | O | $((CH_2)O(CH_2))_3$ | Cylic ring | Hydrogen |
| II.1886 | S | O | $((CH_2)O(CH_2))_3$ | Cylic ring | Hydrocarbyl |
| II.1887 | S | O | $((CH_2)O(CH_2))_3$ | Cylic ring | Substituted hydrocarbyl |
| II.1888 | S | O | $((CH_2)O(CH_2))_3$ | Heterocyclic ring | Hydrogen |
| II.1889 | S | O | $((CH_2)O(CH_2))_3$ | Heterocyclic ring | Hydrocarbyl |
| II.1890 | S | O | $((CH_2)O(CH_2))_3$ | Heterocyclic ring | Substituted hydrocarbyl |
| II.1891 | S | O | $((CH_2)O(CH_2)_2)$ | Aromatic ring | Hydrogen |
| II.1892 | S | O | $((CH_2)O(CH_2)_2)$ | Aromatic ring | Hydrocarbyl |
| II.1893 | S | O | $((CH_2)O(CH_2)_2)$ | Aromatic ring | Substituted hydrocarbyl |
| II.1894 | S | O | $((CH_2)O(CH_2)_2)$ | Cylic ring | Hydrogen |
| II.1895 | S | O | $((CH_2)O(CH_2)_2)$ | Cylic ring | Hydrocarbyl |
| II.1896 | S | O | $((CH_2)O(CH_2)_2)$ | Cylic ring | Substituted hydrocarbyl |
| II.1897 | S | O | $((CH_2)O(CH_2)_2)$ | Heterocyclic ring | Hydrogen |
| II.1898 | S | O | $((CH_2)O(CH_2)_2)$ | Heterocyclic ring | Hydrocarbyl |
| II.1899 | S | O | $((CH_2)O(CH_2)_2)$ | Heterocyclic ring | Substituted hydrocarbyl |
| II.1900 | S | O | $((CH_2)O(CH_2)_2)_2$ | Aromatic ring | Hydrogen |
| II.1901 | S | O | $((CH_2)O(CH_2)_2)_2$ | Aromatic ring | Hydrocarbyl |
| II.1902 | S | O | $((CH_2)O(CH_2)_2)_2$ | Aromatic ring | Substituted hydrocarbyl |
| II.1903 | S | O | $((CH_2)O(CH_2)_2)_2$ | Cylic ring | Hydrogen |
| II.1904 | S | O | $((CH_2)O(CH_2)_2)_2$ | Cylic ring | Hydrocarbyl |
| II.1905 | S | O | $((CH_2)O(CH_2)_2)_2$ | Cylic ring | Substituted hydrocarbyl |
| II.1906 | S | O | $((CH_2)O(CH_2)_2)_2$ | Heterocyclic ring | Hydrogen |
| II.1907 | S | O | $((CH_2)O(CH_2)_2)_2$ | Heterocyclic ring | Hydrocarbyl |
| II.1908 | S | O | $((CH_2)O(CH_2)_2)_2$ | Heterocyclic ring | Substituted hydrocarbyl |
| II.1909 | S | O | $((CH_2)O(CH_2)_2)_3$ | Aromatic ring | Hydrogen |
| II.1910 | S | O | $((CH_2)O(CH_2)_2)_3$ | Aromatic ring | Hydrocarbyl |
| II.1911 | S | O | $((CH_2)O(CH_2)_2)_3$ | Aromatic ring | Substituted hydrocarbyl |
| II.1912 | S | O | $((CH_2)O(CH_2)_2)_3$ | Cylic ring | Hydrogen |
| II.1913 | S | O | $((CH_2)O(CH_2)_2)_3$ | Cylic ring | Hydrocarbyl |
| II.1914 | S | O | $((CH_2)O(CH_2)_2)_3$ | Cylic ring | Substituted hydrocarbyl |
| II.1915 | S | O | $((CH_2)O(CH_2)_2)_3$ | Heterocyclic ring | Hydrogen |
| II.1916 | S | O | $((CH_2)O(CH_2)_2)_3$ | Heterocyclic ring | Hydrocarbyl |
| II.1917 | S | O | $((CH_2)O(CH_2)_2)_3$ | Heterocyclic ring | Substituted hydrocarbyl |
| II.1918 | S | O | $((CH_2)O(CH_2)_3)$ | Aromatic ring | Hydrogen |

TABLE 2-continued

Selected compounds from Formula (II)

| | R1 | R2 | R4 | R5 | R6 |
|---|---|---|---|---|---|
| II. 1919 | S | O | ((CH$_2$)O(CH$_2$)$_3$) | Aromatic ring | Hydrogen |
| II. 1920 | S | O | ((CH$_2$)O(CH$_2$)$_3$) | Aromatic ring | Substituted hydrocarbyl |
| II. 1921 | S | O | ((CH$_2$)O(CH$_2$)$_3$) | Cylic ring | Hydrogen |
| II. 1922 | S | O | ((CH$_2$)O(CH$_2$)$_3$) | Cylic ring | Hydrocarbyl |
| II. 1923 | S | O | ((CH$_2$)O(CH$_2$)$_3$) | Cylic ring | Substituted hydrocarbyl |
| II. 1924 | S | O | ((CH$_2$)O(CH$_2$)$_3$) | Heterocyclic ring | Hydrogen |
| II. 1925 | S | O | ((CH$_2$)O(CH$_2$)$_3$) | Heterocyclic ring | Hydrocarbyl |
| II. 1926 | S | O | ((CH$_2$)O(CH$_2$)$_3$) | Heterocyclic ring | Substituted hydrocarbyl |
| II. 1927 | S | O | ((CH$_2$)O(CH$_2$)$_3$)$_2$ | Aromatic ring | Hydrogen |
| II. 1928 | S | O | ((CH$_2$)O(CH$_2$)$_3$)$_2$ | Aromatic ring | Hydrocarbyl |
| II. 1929 | S | O | ((CH$_2$)O(CH$_2$)$_3$)$_2$ | Aromatic ring | Substituted hydrocarbyl |
| II. 1930 | S | O | ((CH$_2$)O(CH$_2$)$_3$)$_2$ | Cylic ring | Hydrogen |
| II. 1931 | S | O | ((CH$_2$)O(CH$_2$)$_3$)$_2$ | Cylic ring | Hydrocarbyl |
| II. 1932 | S | O | ((CH$_2$)O(CH$_2$)$_3$)$_2$ | Cylic ring | Substituted hydrocarbyl |
| II. 1933 | S | O | ((CH$_2$)O(CH$_2$)$_3$)$_2$ | Heterocyclic ring | Hydrogen |
| II. 1934 | S | O | ((CH$_2$)O(CH$_2$)$_3$)$_2$ | Heterocyclic ring | Hydrocarbyl |
| II. 1935 | S | O | ((CH$_2$)O(CH$_2$)$_3$)$_2$ | Heterocyclic ring | Substituted hydrocarbyl |
| II. 1936 | S | O | ((CH$_2$)O(CH$_2$)$_3$)$_3$ | Aromatic ring | Hydrogen |
| II. 1937 | S | O | ((CH$_2$)O(CH$_2$)$_3$)$_3$ | Aromatic ring | Hydrocarbyl |
| II. 1938 | S | O | ((CH$_2$)O(CH$_2$)$_3$)$_3$ | Aromatic ring | Substituted hydrocarbyl |
| II. 1939 | S | O | ((CH$_2$)O(CH$_2$)$_3$)$_3$ | Cylic ring | Hydrogen |
| II. 1940 | S | O | ((CH$_2$)O(CH$_2$)$_3$)$_3$ | Cylic ring | Hydrocarbyl |
| II. 1941 | S | O | ((CH$_2$)O(CH$_2$)$_3$)$_3$ | Cylic ring | Substituted hydrocarbyl |
| II. 1942 | S | O | ((CH$_2$)O(CH$_2$)$_3$)$_3$ | Heterocyclic ring | Hydrogen |
| II. 1943 | S | O | ((CH$_2$)O(CH$_2$)$_3$)$_3$ | Heterocyclic ring | Hydrocarbyl |
| II. 1944 | S | O | ((CH$_2$)O(CH$_2$)$_3$)$_3$ | Heterocyclic ring | Substituted hydrocarbyl |
| II. 1945 | S | O | ((CH$_2$)$_2$O(CH$_2$)) | Aromatic ring | Hydrogen |
| II. 1946 | S | O | ((CH$_2$)$_2$O(CH$_2$)) | Aromatic ring | Hydrocarbyl |
| II. 1947 | S | O | ((CH$_2$)$_2$O(CH$_2$)) | Aromatic ring | Substituted hydrocarbyl |
| II. 1948 | S | O | ((CH$_2$)$_2$O(CH$_2$)) | Cylic ring | Hydrogen |
| II. 1949 | S | O | ((CH$_2$)$_2$O(CH$_2$)) | Cylic ring | Hydrocarbyl |
| II. 1950 | S | O | ((CH$_2$)$_2$O(CH$_2$)) | Cylic ring | Substituted hydrocarbyl |
| II. 1951 | S | O | ((CH$_2$)$_2$O(CH$_2$)) | Heterocyclic ring | Hydrogen |
| II. 1952 | S | O | ((CH$_2$)$_2$O(CH$_2$)) | Heterocyclic ring | Hydrocarbyl |
| II. 1953 | S | O | ((CH$_2$)$_2$O(CH$_2$)) | Heterocyclic ring | Substituted hydrocarbyl |
| II. 1954 | S | O | ((CH$_2$)$_2$O(CH$_2$))$_2$ | Aromatic ring | Hydrogen |
| II. 1955 | S | O | ((CH$_2$)$_2$O(CH$_2$))$_2$ | Aromatic ring | Hydrocarbyl |
| II. 1956 | S | O | ((CH$_2$)$_2$O(CH$_2$))$_2$ | Aromatic ring | Substituted hydrocarbyl |
| II. 1957 | S | O | ((CH$_2$)$_2$O(CH$_2$))$_2$ | Cylic ring | Hydrogen |
| II. 1958 | S | O | ((CH$_2$)$_2$O(CH$_2$))$_2$ | Cylic ring | Hydrocarbyl |
| II. 1959 | S | O | ((CH$_2$)$_2$O(CH$_2$))$_2$ | Cylic ring | Substituted hydrocarbyl |
| II. 1960 | S | O | ((CH$_2$)$_2$O(CH$_2$))$_2$ | Heterocyclic ring | Hydrogen |
| II. 1961 | S | O | ((CH$_2$)$_2$O(CH$_2$))$_2$ | Heterocyclic ring | Hydrocarbyl |
| II. 1962 | S | O | ((CH$_2$)$_2$O(CH$_2$))$_2$ | Heterocyclic ring | Substituted hydrocarbyl |
| II. 1963 | S | O | ((CH$_2$)$_2$O(CH$_2$))$_3$ | Aromatic ring | Hydrogen |
| II. 1964 | S | O | ((CH$_2$)$_2$O(CH$_2$))$_3$ | Aromatic ring | Hydrocarbyl |
| II. 1965 | S | O | ((CH$_2$)$_2$O(CH$_2$))$_3$ | Aromatic ring | Substituted hydrocarbyl |
| II. 1966 | S | O | ((CH$_2$)$_2$O(CH$_2$))$_3$ | Cylic ring | Hydrogen |
| II. 1967 | S | O | ((CH$_2$)$_2$O(CH$_2$))$_3$ | Cylic ring | Hydrocarbyl |
| II. 1968 | S | O | ((CH$_2$)$_2$O(CH$_2$))$_3$ | Cylic ring | Substituted hydrocarbyl |
| II. 1969 | S | O | ((CH$_2$)$_2$O(CH$_2$))$_3$ | Heterocyclic ring | Hydrogen |
| II. 1970 | S | O | ((CH$_2$)$_2$O(CH$_2$))$_3$ | Heterocyclic ring | Hydrocarbyl |
| II. 1971 | S | O | ((CH$_2$)$_2$O(CH$_2$))$_3$ | Heterocyclic ring | Substituted hydrocarbyl |
| II. 1972 | S | O | ((CH$_2$)$_2$O(CH$_2$)$_2$) | Aromatic ring | Hydrogen |
| II. 1973 | S | O | ((CH$_2$)$_2$O(CH$_2$)$_2$) | Aromatic ring | Hydrocarbyl |
| II. 1974 | S | O | ((CH$_2$)$_2$O(CH$_2$)$_2$) | Aromatic ring | Substituted hydrocarbyl |
| II. 1975 | S | O | ((CH$_2$)$_2$O(CH$_2$)$_2$) | Cylic ring | Hydrogen |
| II. 1976 | S | O | ((CH$_2$)$_2$O(CH$_2$)$_2$) | Cylic ring | Hydrocarbyl |
| II. 1977 | S | O | ((CH$_2$)$_2$O(CH$_2$)$_2$) | Cylic ring | Substituted hydrocarbyl |
| II. 1978 | S | O | ((CH$_2$)$_2$O(CH$_2$)$_2$) | Heterocyclic ring | Hydrogen |
| II. 1979 | S | O | ((CH$_2$)$_2$O(CH$_2$)$_2$) | Heterocyclic ring | Hydrocarbyl |
| II. 1980 | S | O | ((CH$_2$)$_2$O(CH$_2$)$_2$) | Heterocyclic ring | Substituted hydrocarbyl |
| II. 1981 | S | O | ((CH$_2$)$_2$O(CH$_2$)$_2$)$_2$ | Aromatic ring | Hydrogen |
| II. 1982 | S | O | ((CH$_2$)$_2$O(CH$_2$)$_2$)$_2$ | Aromatic ring | Hydrocarbyl |
| II. 1983 | S | O | ((CH$_2$)$_2$O(CH$_2$)$_2$)$_2$ | Aromatic ring | Substituted hydrocarbyl |
| II. 1984 | S | O | ((CH$_2$)$_2$O(CH$_2$)$_2$)$_2$ | Cylic ring | Hydrogen |
| II. 1985 | S | O | ((CH$_2$)$_2$O(CH$_2$)$_2$)$_2$ | Cylic ring | Hydrocarbyl |
| II. 1986 | S | O | ((CH$_2$)$_2$O(CH$_2$)$_2$)$_2$ | Cylic ring | Substituted hydrocarbyl |
| II. 1987 | S | O | ((CH$_2$)$_2$O(CH$_2$)$_2$)$_2$ | Heterocyclic ring | Hydrogen |
| II. 1988 | S | O | ((CH$_2$)$_2$O(CH$_2$)$_2$)$_2$ | Heterocyclic ring | Hydrocarbyl |
| II. 1989 | S | O | ((CH$_2$)$_2$O(CH$_2$)$_2$)$_2$ | Heterocyclic ring | Substituted hydrocarbyl |
| II. 1990 | S | O | ((CH$_2$)$_2$O(CH$_2$)$_2$)$_3$ | Aromatic ring | Hydrogen |
| II. 1991 | S | O | ((CH$_2$)$_2$O(CH$_2$)$_2$)$_3$ | Aromatic ring | Hydrocarbyl |
| II. 1992 | S | O | ((CH$_2$)$_2$O(CH$_2$)$_2$)$_3$ | Aromatic ring | Substituted hydrocarbyl |
| II. 1993 | S | O | ((CH$_2$)$_2$O(CH$_2$)$_2$)$_3$ | Cylic ring | Hydrogen |
| II. 1994 | S | O | ((CH$_2$)$_2$O(CH$_2$)$_2$)$_3$ | Cylic ring | Hydrocarbyl |

TABLE 2-continued

Selected compounds from Formula (II)

| | R1 | R2 | R4 | R5 | R6 |
|---|---|---|---|---|---|
| II. 1995 | S | O | $((CH_2)_2O(CH_2)_2)_3$ | Cylic ring | Substituted hydrocarbyl |
| II. 1996 | S | O | $((CH_2)_2O(CH_2)_2)_3$ | Heterocyclic ring | Hydrogen |
| II. 1997 | S | O | $((CH_2)_2O(CH_2)_2)_3$ | Heterocyclic ring | Hydrocarbyl |
| II. 1998 | S | O | $((CH_2)_2O(CH_2)_2)_3$ | Heterocyclic ring | Substituted hydrocarbyl |
| II. 1999 | S | O | $((CH_2)_2O(CH_2)_3)$ | Aromatic ring | Hydrogen |
| II. 2000 | S | O | $((CH_2)_2O(CH_2)_3)$ | Aromatic ring | Hydrocarbyl |
| II. 2001 | S | O | $((CH_2)_2O(CH_2)_3)$ | Aromatic ring | Substituted hydrocarbyl |
| II. 2002 | S | O | $((CH_2)_2O(CH_2)_3)$ | Cylic ring | Hydrogen |
| II. 2003 | S | O | $((CH_2)_2O(CH_2)_3)$ | Cylic ring | Hydrocarbyl |
| II. 2004 | S | O | $((CH_2)_2O(CH_2)_3)$ | Cylic ring | Substituted hydrocarbyl |
| II. 2005 | S | O | $((CH_2)_2O(CH_2)_3)$ | Heterocyclic ring | Hydrogen |
| II. 2006 | S | O | $((CH_2)_2O(CH_2)_3)$ | Heterocyclic ring | Hydrocarbyl |
| II. 2007 | S | O | $((CH_2)_2O(CH_2)_3)$ | Heterocyclic ring | Substituted hydrocarbyl |
| II. 2008 | S | O | $((CH_2)_2O(CH_2)_3)_2$ | Aromatic ring | Hydrogen |
| II. 2009 | S | O | $((CH_2)_2O(CH_2)_3)_2$ | Aromatic ring | Hydrocarbyl |
| II. 2010 | S | O | $((CH_2)_2O(CH_2)_3)_2$ | Aromatic ring | Substituted hydrocarbyl |
| II. 2011 | S | O | $((CH_2)_2O(CH_2)_3)_2$ | Cylic ring | Hydrogen |
| II. 2012 | S | O | $((CH_2)_2O(CH_2)_3)_2$ | Cylic ring | Hydrocarbyl |
| II. 2013 | S | O | $((CH_2)_2O(CH_2)_3)_2$ | Cylic ring | Substituted hydrocarbyl |
| II. 2014 | S | O | $((CH_2)_2O(CH_2)_3)_2$ | Heterocyclic ring | Hydrogen |
| II. 2015 | S | O | $((CH_2)_2O(CH_2)_3)_2$ | Heterocyclic ring | Hydrocarbyl |
| II. 2016 | S | O | $((CH_2)_2O(CH_2)_3)_2$ | Heterocyclic ring | Substituted hydrocarbyl |
| II. 2017 | S | O | $((CH_2)_2O(CH_2)_3)_3$ | Aromatic ring | Hydrogen |
| II. 2018 | S | O | $((CH_2)_2O(CH_2)_3)_3$ | Aromatic ring | Hydrocarbyl |
| II. 2019 | S | O | $((CH_2)_2O(CH_2)_3)_3$ | Aromatic ring | Substituted hydrocarbyl |
| II. 2020 | S | O | $((CH_2)_2O(CH_2)_3)_3$ | Cylic ring | Hydrogen |
| II. 2021 | S | O | $((CH_2)_2O(CH_2)_3)_3$ | Cylic ring | Hydrocarbyl |
| II. 2022 | S | O | $((CH_2)_2O(CH_2)_3)_3$ | Cylic ring | Substituted hydrocarbyl |
| II. 2023 | S | O | $((CH_2)_2O(CH_2)_3)_3$ | Heterocyclic ring | Hydrogen |
| II. 2024 | S | O | $((CH_2)_2O(CH_2)_3)_3$ | Heterocyclic ring | Hydrocarbyl |
| II. 2025 | S | O | $((CH_2)_2O(CH_2)_3)_3$ | Heterocyclic ring | Substituted hydrocarbyl |
| II. 2026 | S | O | $((CH_2)_3O(CH_2))$ | Aromatic ring | Hydrogen |
| II. 2027 | S | O | $((CH_2)_3O(CH_2))$ | Aromatic ring | Hydrocarbyl |
| II. 2028 | S | O | $((CH_2)_3O(CH_2))$ | Aromatic ring | Substituted hydrocarbyl |
| II. 2029 | S | O | $((CH_2)_3O(CH_2))$ | Cylic ring | Hydrogen |
| II. 2030 | S | O | $((CH_2)_3O(CH_2))$ | Cylic ring | Hydrocarbyl |
| II. 2031 | S | O | $((CH_2)_3O(CH_2))$ | Cylic ring | Substituted hydrocarbyl |
| II. 2032 | S | O | $((CH_2)_3O(CH_2))$ | Heterocyclic ring | Hydrogen |
| II. 2033 | S | O | $((CH_2)_3O(CH_2))$ | Heterocyclic ring | Hydrocarbyl |
| II. 2034 | S | O | $((CH_2)_3O(CH_2))$ | Heterocyclic ring | Substituted hydrocarbyl |
| II. 2035 | S | O | $((CH_2)_3O(CH_2))_2$ | Aromatic ring | Hydrogen |
| II. 2036 | S | O | $((CH_2)_3O(CH_2))_2$ | Aromatic ring | Hydrocarbyl |
| II. 2037 | S | O | $((CH_2)_3O(CH_2))_2$ | Aromatic ring | Substituted hydrocarbyl |
| II. 2038 | S | O | $((CH_2)_3O(CH_2))_2$ | Cylic ring | Hydrogen |
| II. 2039 | S | O | $((CH_2)_3O(CH_2))_2$ | Cylic ring | Hydrocarbyl |
| II. 2040 | S | O | $((CH_2)_3O(CH_2))_2$ | Cylic ring | Substituted hydrocarbyl |
| II. 2041 | S | O | $((CH_2)_3O(CH_2))_2$ | Heterocyclic ring | Hydrogen |
| II. 2042 | S | O | $((CH_2)_3O(CH_2))_2$ | Heterocyclic ring | Hydrocarbyl |
| II. 2043 | S | O | $((CH_2)_3O(CH_2))_2$ | Heterocyclic ring | Substituted hydrocarbyl |
| II. 2044 | S | O | $((CH_2)_3O(CH_2))_3$ | Aromatic ring | Hydrogen |
| II. 2045 | S | O | $((CH_2)_3O(CH_2))_3$ | Aromatic ring | Hydrocarbyl |
| II. 2046 | S | O | $((CH_2)_3O(CH_2))_3$ | Aromatic ring | Substituted hydrocarbyl |
| II. 2047 | S | O | $((CH_2)_3O(CH_2))_3$ | Cylic ring | Hydrogen |
| II. 2048 | S | O | $((CH_2)_3O(CH_2))_3$ | Cylic ring | Hydrocarbyl |
| II. 2049 | S | O | $((CH_2)_3O(CH_2))_3$ | Cylic ring | Substituted hydrocarbyl |
| II. 2050 | S | O | $((CH_2)_3O(CH_2))_3$ | Heterocyclic ring | Hydrogen |
| II. 2051 | S | O | $((CH_2)_3O(CH_2))_3$ | Heterocyclic ring | Hydrocarbyl |
| II. 2052 | S | O | $((CH_2)_3O(CH_2))_3$ | Heterocyclic ring | Substituted hydrocarbyl |
| II. 2053 | S | O | $((CH_2)_3O(CH_2)_2)$ | Aromatic ring | Hydrogen |
| II. 2054 | S | O | $((CH_2)_3O(CH_2)_2)$ | Aromatic ring | Hydrocarbyl |
| II. 2055 | S | O | $((CH_2)_3O(CH_2)_2)$ | Aromatic ring | Substituted hydrocarbyl |
| II. 2056 | S | O | $((CH_2)_3O(CH_2)_2)$ | Cylic ring | Hydrogen |
| II. 2057 | S | O | $((CH_2)_3O(CH_2)_2)$ | Cylic ring | Hydrocarbyl |
| II. 2058 | S | O | $((CH_2)_3O(CH_2)_2)$ | Cylic ring | Substituted hydrocarbyl |
| II. 2059 | S | O | $((CH_2)_3O(CH_2)_2)$ | Heterocyclic ring | Hydrogen |
| II. 2060 | S | O | $((CH_2)_3O(CH_2)_2)$ | Heterocyclic ring | Hydrocarbyl |
| II. 2061 | S | O | $((CH_2)_3O(CH_2)_2)$ | Heterocyclic ring | Substituted hydrocarbyl |
| II. 2062 | S | O | $((CH_2)_3O(CH_2)_2)_2$ | Aromatic ring | Hydrogen |
| II. 2063 | S | O | $((CH_2)_3O(CH_2)_2)_2$ | Aromatic ring | Hydrocarbyl |
| II. 2064 | S | O | $((CH_2)_3O(CH_2)_2)_2$ | Aromatic ring | Substituted hydrocarbyl |
| II. 2065 | S | O | $((CH_2)_3O(CH_2)_2)_2$ | Cylic ring | Hydrogen |
| II. 2066 | S | O | $((CH_2)_3O(CH_2)_2)_2$ | Cylic ring | Hydrocarbyl |
| II. 2067 | S | O | $((CH_2)_3O(CH_2)_2)_2$ | Cylic ring | Substituted hydrocarbyl |
| II. 2068 | S | O | $((CH_2)_3O(CH_2)_2)_2$ | Heterocyclic ring | Hydrogen |
| II. 2069 | S | O | $((CH_2)_3O(CH_2)_2)_2$ | Heterocyclic ring | Hydrocarbyl |
| II. 2070 | S | O | $((CH_2)_3O(CH_2)_2)_2$ | Heterocyclic ring | Substituted hydrocarbyl |

TABLE 2-continued

Selected compounds from Formula (II)

| | R1 | R2 | R4 | R5 | R6 |
|---|---|---|---|---|---|
| II. 2071 | S | O | $((CH_2)_3O(CH_2)_2)_3$ | Aromatic ring | Hydrogen |
| II. 2072 | S | O | $((CH_2)_3O(CH_2)_2)_3$ | Aromatic ring | Hydrocarbyl |
| II. 2073 | S | O | $((CH_2)_3O(CH_2)_2)_3$ | Aromatic ring | Substituted hydrocarbyl |
| II. 2074 | S | O | $((CH_2)_3O(CH_2)_2)_3$ | Cylic ring | Hydrogen |
| II. 2075 | S | O | $((CH_2)_3O(CH_2)_2)_3$ | Cylic ring | Hydrocarbyl |
| II. 2076 | S | O | $((CH_2)_3O(CH_2)_2)_3$ | Cylic ring | Substituted hydrocarbyl |
| II. 2077 | S | O | $((CH_2)_3O(CH_2)_2)_3$ | Heterocyclic ring | Hydrogen |
| II. 2078 | S | O | $((CH_2)_3O(CH_2)_2)_3$ | Heterocyclic ring | Hydrocarbyl |
| II. 2079 | S | O | $((CH_2)_3O(CH_2)_2)_3$ | Heterocyclic ring | Substituted hydrocarbyl |
| II. 2080 | S | O | $((CH_2)_3O(CH_2)_3)$ | Aromatic ring | Hydrogen |
| II. 2081 | S | O | $((CH_2)_3O(CH_2)_3)$ | Aromatic ring | Hydrocarbyl |
| II. 2082 | S | O | $((CH_2)_3O(CH_2)_3)$ | Aromatic ring | Substituted hydrocarbyl |
| II. 2083 | S | O | $((CH_2)_3O(CH_2)_3)$ | Cylic ring | Hydrogen |
| II. 2084 | S | O | $((CH_2)_3O(CH_2)_3)$ | Cylic ring | Hydrocarbyl |
| II. 2085 | S | O | $((CH_2)_3O(CH_2)_3)$ | Cylic ring | Substituted hydrocarbyl |
| II. 2086 | S | O | $((CH_2)_3O(CH_2)_3)$ | Heterocyclic ring | Hydrogen |
| II. 2087 | S | O | $((CH_2)_3O(CH_2)_3)$ | Heterocyclic ring | Hydrocarbyl |
| II. 2088 | S | O | $((CH_2)_3O(CH_2)_3)$ | Heterocyclic ring | Substituted hydrocarbyl |
| II. 2089 | S | O | $((CH_2)_3O(CH_2)_3)_2$ | Aromatic ring | Hydrogen |
| II. 2090 | S | O | $((CH_2)_3O(CH_2)_3)_2$ | Aromatic ring | Hydrocarbyl |
| II. 2091 | S | O | $((CH_2)_3O(CH_2)_3)_2$ | Aromatic ring | Substituted hydrocarbyl |
| II. 2092 | S | O | $((CH_2)_3O(CH_2)_3)_2$ | Cylic ring | Hydrogen |
| II. 2093 | S | O | $((CH_2)_3O(CH_2)_3)_2$ | Cylic ring | Hydrocarbyl |
| II. 2094 | S | O | $((CH_2)_3O(CH_2)_3)_2$ | Cylic ring | Substituted hydrocarbyl |
| II. 2095 | S | O | $((CH_2)_3O(CH_2)_3)_2$ | Heterocyclic ring | Hydrogen |
| II. 2096 | S | O | $((CH_2)_3O(CH_2)_3)_2$ | Heterocyclic ring | Hydrocarbyl |
| II. 2097 | S | O | $((CH_2)_3O(CH_2)_3)_2$ | Heterocyclic ring | Substituted hydrocarbyl |
| II. 2098 | S | O | $((CH_2)_3O(CH_2)_3)_3$ | Aromatic ring | Hydrogen |
| II. 2099 | S | O | $((CH_2)_3O(CH_2)_3)_3$ | Aromatic ring | Hydrocarbyl |
| II. 2100 | S | O | $((CH_2)_3O(CH_2)_3)_3$ | Aromatic ring | Substituted hydrocarbyl |
| II. 2101 | S | O | $((CH_2)_3O(CH_2)_3)_3$ | Cylic ring | Hydrogen |
| II. 2102 | S | O | $((CH_2)_3O(CH_2)_3)_3$ | Cylic ring | Hydrocarbyl |
| II. 2103 | S | O | $((CH_2)_3O(CH_2)_3)_3$ | Cylic ring | Substituted hydrocarbyl |
| II. 2104 | S | O | $((CH_2)_3O(CH_2)_3)_3$ | Heterocyclic ring | Hydrogen |
| II. 2105 | S | O | $((CH_2)_3O(CH_2)_3)_3$ | Heterocyclic ring | Hydrocarbyl |
| II. 2106 | S | O | $((CH_2)_3O(CH_2)_3)_3$ | Heterocyclic ring | Substituted hydrocarbyl |
| II. 2107 | O | N | $(CH_2)$ | Aromatic ring | Hydrogen |
| II. 2108 | O | N | $(CH_2)$ | Aromatic ring | Hydrocarbyl |
| II. 2109 | O | N | $(CH_2)$ | Aromatic ring | Substituted hydrocarbyl |
| II. 2110 | O | N | $(CH_2)$ | Cylic ring | Hydrogen |
| II. 2111 | O | N | $(CH_2)$ | Cylic ring | Hydrocarbyl |
| II. 2112 | O | N | $(CH_2)$ | Cylic ring | Substituted hydrocarbyl |
| II. 2113 | O | N | $(CH_2)$ | Heterocyclic ring | Hydrogen |
| II. 2114 | O | N | $(CH_2)$ | Heterocyclic ring | Hydrocarbyl |
| II. 2115 | O | N | $(CH_2)$ | Heterocyclic ring | Substituted hydrocarbyl |
| II. 2116 | O | N | $(CH_2)_2$ | Aromatic ring | Hydrogen |
| II. 2117 | O | N | $(CH_2)_2$ | Aromatic ring | Hydrocarbyl |
| II. 2118 | O | N | $(CH_2)_2$ | Aromatic ring | Substituted hydrocarbyl |
| II. 2119 | O | N | $(CH_2)_2$ | Cylic ring | Hydrogen |
| II. 2120 | O | N | $(CH_2)_2$ | Cylic ring | Hydrocarbyl |
| II. 2121 | O | N | $(CH_2)_2$ | Cylic ring | Substituted hydrocarbyl |
| II. 2122 | O | N | $(CH_2)_2$ | Heterocyclic ring | Hydrogen |
| II. 2123 | O | N | $(CH_2)_2$ | Heterocyclic ring | Hydrocarbyl |
| II. 2124 | O | N | $(CH_2)_2$ | Heterocyclic ring | Substituted hydrocarbyl |
| II. 2125 | O | N | $(CH_2)_3$ | Aromatic ring | Hydrogen |
| II. 2126 | O | N | $(CH_2)_3$ | Aromatic ring | Hydrocarbyl |
| II. 2127 | O | N | $(CH_2)_3$ | Aromatic ring | Substituted hydrocarbyl |
| II. 2128 | O | N | $(CH_2)_3$ | Cylic ring | Hydrogen |
| II. 2129 | O | N | $(CH_2)_3$ | Cylic ring | Hydrocarbyl |
| II. 2130 | O | N | $(CH_2)_3$ | Cylic ring | Substituted hydrocarbyl |
| II. 2131 | O | N | $(CH_2)_3$ | Heterocyclic ring | Hydrogen |
| II. 2132 | O | N | $(CH_2)_3$ | Heterocyclic ring | Hydrocarbyl |
| II. 2133 | O | N | $(CH_2)_3$ | Heterocyclic ring | Substituted hydrocarbyl |
| II. 2134 | O | N | $((CH_2)O)$ | Aromatic ring | Hydrogen |
| II. 2135 | O | N | $((CH_2)O)$ | Aromatic ring | Hydrocarbyl |
| II. 2136 | O | N | $((CH_2)O)$ | Aromatic ring | Substituted hydrocarbyl |
| II. 2137 | O | N | $((CH_2)O)$ | Cylic ring | Hydrogen |
| II. 2138 | O | N | $((CH_2)O)$ | Cylic ring | Hydrocarbyl |
| II. 2139 | O | N | $((CH_2)O)$ | Cylic ring | Substituted hydrocarbyl |
| II. 2140 | O | N | $((CH_2)O)$ | Heterocyclic ring | Hydrogen |
| II. 2141 | O | N | $((CH_2)O)$ | Heterocyclic ring | Hydrocarbyl |
| II. 2142 | O | N | $((CH_2)O)$ | Heterocyclic ring | Substituted hydrocarbyl |
| II. 2143 | O | N | $((CH_2)O)_2$ | Aromatic ring | Hydrogen |
| II. 2144 | O | N | $((CH_2)O)_2$ | Aromatic ring | Hydrocarbyl |
| II. 2145 | O | N | $((CH_2)O)_2$ | Aromatic ring | Substituted hydrocarbyl |
| II. 2146 | O | N | $((CH_2)O)_2$ | Cylic ring | Hydrogen |

TABLE 2-continued

Selected compounds from Formula (II)

| | R1 | R2 | R4 | R5 | R6 |
|---|---|---|---|---|---|
| II. 2147 | O | N | $((CH_2)O)_2$ | Cylic ring | Hydrocarbyl |
| II. 2148 | O | N | $((CH_2)O)_2$ | Cylic ring | Substituted hydrocarbyl |
| II. 2149 | O | N | $((CH_2)O)_2$ | Heterocyclic ring | Hydrogen |
| II. 2150 | O | N | $((CH_2)O)_2$ | Heterocyclic ring | Hydrocarbyl |
| II. 2151 | O | N | $((CH_2)O)_2$ | Heterocyclic ring | Substituted hydrocarbyl |
| II. 2152 | O | N | $((CH_2)O)_3$ | Aromatic ring | Hydrogen |
| II. 2153 | O | N | $((CH_2)O)_3$ | Aromatic ring | Hydrocarbyl |
| II. 2154 | O | N | $((CH_2)O)_3$ | Aromatic ring | Substituted hydrocarbyl |
| II. 2155 | O | N | $((CH_2)O)_3$ | Cylic ring | Hydrogen |
| II. 2156 | O | N | $((CH_2)O)_3$ | Cylic ring | Hydrocarbyl |
| II. 2157 | O | N | $((CH_2)O)_3$ | Cylic ring | Substituted hydrocarbyl |
| II. 2158 | O | N | $((CH_2)O)_3$ | Heterocyclic ring | Hydrogen |
| II. 2159 | O | N | $((CH_2)O)_3$ | Heterocyclic ring | Hydrocarbyl |
| II. 2160 | O | N | $((CH_2)O)_3$ | Heterocyclic ring | Substituted hydrocarbyl |
| II. 2161 | O | N | $((CH_2)_2O)$ | Aromatic ring | Hydrogen |
| II. 2162 | O | N | $((CH_2)_2O)$ | Aromatic ring | Hydrocarbyl |
| II. 2163 | O | N | $((CH_2)_2O)$ | Aromatic ring | Substituted hydrocarbyl |
| II. 2164 | O | N | $((CH_2)_2O)$ | Cylic ring | Hydrogen |
| II. 2165 | O | N | $((CH_2)_2O)$ | Cylic ring | Hydrocarbyl |
| II. 2166 | O | N | $((CH_2)_2O)$ | Cylic ring | Substituted hydrocarbyl |
| II. 2167 | O | N | $((CH_2)_2O)$ | Heterocyclic ring | Hydrogen |
| II. 2168 | O | N | $((CH_2)_2O)$ | Heterocyclic ring | Hydrocarbyl |
| II. 2169 | O | N | $((CH_2)_2O)$ | Heterocyclic ring | Substituted hydrocarbyl |
| II. 2170 | O | N | $((CH_2)_2O)_2$ | Aromatic ring | Hydrogen |
| II. 2171 | O | N | $((CH_2)_2O)_2$ | Aromatic ring | Hydrocarbyl |
| II. 2172 | O | N | $((CH_2)_2O)_2$ | Aromatic ring | Substituted hydrocarbyl |
| II. 2173 | O | N | $((CH_2)_2O)_2$ | Cylic ring | Hydrogen |
| II. 2174 | O | N | $((CH_2)_2O)_2$ | Cylic ring | Hydrocarbyl |
| II. 2175 | O | N | $((CH_2)_2O)_2$ | Cylic ring | Substituted hydrocarbyl |
| II. 2176 | O | N | $((CH_2)_2O)_2$ | Heterocyclic ring | Hydrogen |
| II. 2177 | O | N | $((CH_2)_2O)_2$ | Heterocyclic ring | Hydrocarbyl |
| II. 2178 | O | N | $((CH_2)_2O)_2$ | Heterocyclic ring | Substituted hydrocarbyl |
| II. 2179 | O | N | $((CH_2)_2O)_3$ | Aromatic ring | Hydrogen |
| II. 2180 | O | N | $((CH_2)_2O)_3$ | Aromatic ring | Hydrocarbyl |
| II. 2181 | O | N | $((CH_2)_2O)_3$ | Aromatic ring | Substituted hydrocarbyl |
| II. 2182 | O | N | $((CH_2)_2O)_3$ | Cylic ring | Hydrogen |
| II. 2183 | O | N | $((CH_2)_2O)_3$ | Cylic ring | Hydrocarbyl |
| II. 2184 | O | N | $((CH_2)_2O)_3$ | Cylic ring | Substituted hydrocarbyl |
| II. 2185 | O | N | $((CH_2)_2O)_3$ | Heterocyclic ring | Hydrogen |
| II. 2186 | O | N | $((CH_2)_2O)_3$ | Heterocyclic ring | Hydrocarbyl |
| II. 2187 | O | N | $((CH_2)_2O)_3$ | Heterocyclic ring | Substituted hydrocarbyl |
| II. 2188 | O | N | $((CH_2)_3O)$ | Aromatic ring | Hydrogen |
| II. 2189 | O | N | $((CH_2)_3O)$ | Aromatic ring | Hydrocarbyl |
| II. 2190 | O | N | $((CH_2)_3O)$ | Aromatic ring | Substituted hydrocarbyl |
| II. 2191 | O | N | $((CH_2)_3O)$ | Cylic ring | Hydrogen |
| II. 2192 | O | N | $((CH_2)_3O)$ | Cylic ring | Hydrocarbyl |
| II. 2193 | O | N | $((CH_2)_3O)$ | Cylic ring | Substituted hydrocarbyl |
| II. 2194 | O | N | $((CH_2)_3O)$ | Heterocyclic ring | Hydrogen |
| II. 2195 | O | N | $((CH_2)_3O)$ | Heterocyclic ring | Hydrocarbyl |
| II. 2196 | O | N | $((CH_2)_3O)$ | Heterocyclic ring | Substituted hydrocarbyl |
| II. 2197 | O | N | $((CH_2)_3O)_2$ | Aromatic ring | Hydrogen |
| II. 2198 | O | N | $((CH_2)_3O)_2$ | Aromatic ring | Hydrocarbyl |
| II. 2199 | O | N | $((CH_2)_3O)_2$ | Aromatic ring | Substituted hydrocarbyl |
| II. 2200 | O | N | $((CH_2)_3O)_2$ | Cylic ring | Hydrogen |
| II. 2201 | O | N | $((CH_2)_3O)_2$ | Cylic ring | Hydrocarbyl |
| II. 2202 | O | N | $((CH_2)_3O)_2$ | Cylic ring | Substituted hydrocarbyl |
| II. 2203 | O | N | $((CH_2)_3O)_2$ | Heterocyclic ring | Hydrogen |
| II. 2204 | O | N | $((CH_2)_3O)_2$ | Heterocyclic ring | Hydrocarbyl |
| II. 2205 | O | N | $((CH_2)_3O)_2$ | Heterocyclic ring | Substituted hydrocarbyl |
| II. 2206 | O | N | $((CH_2)_3O)_3$ | Aromatic ring | Hydrogen |
| II. 2207 | O | N | $((CH_2)_3O)_3$ | Aromatic ring | Hydrocarbyl |
| II. 2208 | O | N | $((CH_2)_3O)_3$ | Aromatic ring | Substituted hydrocarbyl |
| II. 2209 | O | N | $((CH_2)_3O)_3$ | Cylic ring | Hydrogen |
| II. 2210 | O | N | $((CH_2)_3O)_3$ | Cylic ring | Hydrocarbyl |
| II. 2211 | O | N | $((CH_2)_3O)_3$ | Cylic ring | Substituted hydrocarbyl |
| II. 2212 | O | N | $((CH_2)_3O)_3$ | Heterocyclic ring | Hydrogen |
| II. 2213 | O | N | $((CH_2)_3O)_3$ | Heterocyclic ring | Hydrocarbyl |
| II. 2214 | O | N | $((CH_2)_3O)_3$ | Heterocyclic ring | Substituted hydrocarbyl |
| II. 2215 | O | N | $((CH_2)O(CH_2))$ | Aromatic ring | Hydrogen |
| II. 2216 | O | N | $((CH_2)O(CH_2))$ | Aromatic ring | Hydrocarbyl |
| II. 2217 | O | N | $((CH_2)O(CH_2))$ | Aromatic ring | Substituted hydrocarbyl |
| II. 2218 | O | N | $((CH_2)O(CH_2))$ | Cylic ring | Hydrogen |
| II. 2219 | O | N | $((CH_2)O(CH_2))$ | Cylic ring | Hydrocarbyl |
| II. 2220 | O | N | $((CH_2)O(CH_2))$ | Cylic ring | Substituted hydrocarbyl |
| II. 2221 | O | N | $((CH_2)O(CH_2))$ | Heterocyclic ring | Hydrogen |
| II. 2222 | O | N | $((CH_2)O(CH_2))$ | Heterocyclic ring | Hydrocarbyl |

TABLE 2-continued

Selected compounds from Formula (II)

| | R1 | R2 | R4 | R5 | R6 |
|---|---|---|---|---|---|
| II. 2223 | O | N | $((CH_2)O(CH_2))$ | Heterocyclic ring | Substituted hydrocarbyl |
| II. 2224 | O | N | $((CH_2)O(CH_2))_2$ | Aromatic ring | Hydrogen |
| II. 2225 | O | N | $((CH_2)O(CH_2))_2$ | Aromatic ring | Hydrocarbyl |
| II. 2226 | O | N | $((CH_2)O(CH_2))_2$ | Aromatic ring | Substituted hydrocarbyl |
| II. 2227 | O | N | $((CH_2)O(CH_2))_2$ | Cylic ring | Hydrogen |
| II. 2228 | O | N | $((CH_2)O(CH_2))_2$ | Cylic ring | Hydrocarbyl |
| II. 2229 | O | N | $((CH_2)O(CH_2))_2$ | Cylic ring | Substituted hydrocarbyl |
| II. 2230 | O | N | $((CH_2)O(CH_2))_2$ | Heterocyclic ring | Hydrogen |
| II. 2231 | O | N | $((CH_2)O(CH_2))_2$ | Heterocyclic ring | Hydrocarbyl |
| II. 2232 | O | N | $((CH_2)O(CH_2))_2$ | Heterocyclic ring | Substituted hydrocarbyl |
| II. 2233 | O | N | $((CH_2)O(CH_2))_3$ | Aromatic ring | Hydrogen |
| II. 2234 | O | N | $((CH_2)O(CH_2))_3$ | Aromatic ring | Hydrocarbyl |
| II. 2235 | O | N | $((CH_2)O(CH_2))_3$ | Aromatic ring | Substituted hydrocarbyl |
| II. 2236 | O | N | $((CH_2)O(CH_2))_3$ | Cylic ring | Hydrogen |
| II. 2237 | O | N | $((CH_2)O(CH_2))_3$ | Cylic ring | Hydrocarbyl |
| II. 2238 | O | N | $((CH_2)O(CH_2))_3$ | Cylic ring | Substituted hydrocarbyl |
| II. 2239 | O | N | $((CH_2)O(CH_2))_3$ | Heterocyclic ring | Hydrogen |
| II. 2240 | O | N | $((CH_2)O(CH_2))_3$ | Heterocyclic ring | Hydrocarbyl |
| II. 2241 | O | N | $((CH_2)O(CH_2))_3$ | Heterocyclic ring | Substituted hydrocarbyl |
| II. 2242 | O | N | $((CH_2)O(CH_2)_2)$ | Aromatic ring | Hydrogen |
| II. 2243 | O | N | $((CH_2)O(CH_2)_2)$ | Aromatic ring | Hydrocarbyl |
| II. 2244 | O | N | $((CH_2)O(CH_2)_2)$ | Aromatic ring | Substituted hydrocarbyl |
| II. 2245 | O | N | $((CH_2)O(CH_2)_2)$ | Cylic ring | Hydrogen |
| II. 2246 | O | N | $((CH_2)O(CH_2)_2)$ | Cylic ring | Hydrocarbyl |
| II. 2247 | O | N | $((CH_2)O(CH_2)_2)$ | Cylic ring | Substituted hydrocarbyl |
| II. 2248 | O | N | $((CH_2)O(CH_2)_2)$ | Heterocyclic ring | Hydrogen |
| II. 2249 | O | N | $((CH_2)O(CH_2)_2)$ | Heterocyclic ring | Hydrocarbyl |
| II. 2250 | O | N | $((CH_2)O(CH_2)_2)$ | Heterocyclic ring | Substituted hydrocarbyl |
| II. 2251 | O | N | $((CH_2)O(CH_2)_2)_2$ | Aromatic ring | Hydrogen |
| II. 2252 | O | N | $((CH_2)O(CH_2)_2)_2$ | Aromatic ring | Hydrocarbyl |
| II. 2253 | O | N | $((CH_2)O(CH_2)_2)_2$ | Aromatic ring | Substituted hydrocarbyl |
| II. 2254 | O | N | $((CH_2)O(CH_2)_2)_2$ | Cylic ring | Hydrogen |
| II. 2255 | O | N | $((CH_2)O(CH_2)_2)_2$ | Cylic ring | Hydrocarbyl |
| II. 2256 | O | N | $((CH_2)O(CH_2)_2)_2$ | Cylic ring | Substituted hydrocarbyl |
| II. 2257 | O | N | $((CH_2)O(CH_2)_2)_2$ | Heterocyclic ring | Hydrogen |
| II. 2258 | O | N | $((CH_2)O(CH_2)_2)_2$ | Heterocyclic ring | Hydrocarbyl |
| II. 2259 | O | N | $((CH_2)O(CH_2)_2)_2$ | Heterocyclic ring | Substituted hydrocarbyl |
| II. 2260 | O | N | $((CH_2)O(CH_2)_2)_3$ | Aromatic ring | Hydrogen |
| II. 2261 | O | N | $((CH_2)O(CH_2)_2)_3$ | Aromatic ring | Hydrocarbyl |
| II. 2262 | O | N | $((CH_2)O(CH_2)_2)_3$ | Aromatic ring | Substituted hydrocarbyl |
| II. 2263 | O | N | $((CH_2)O(CH_2)_2)_3$ | Cylic ring | Hydrogen |
| II. 2264 | O | N | $((CH_2)O(CH_2)_2)_3$ | Cylic ring | Hydrocarbyl |
| II. 2265 | O | N | $((CH_2)O(CH_2)_2)_3$ | Cylic ring | Substituted hydrocarbyl |
| II. 2266 | O | N | $((CH_2)O(CH_2)_2)_3$ | Heterocyclic ring | Hydrogen |
| II. 2267 | O | N | $((CH_2)O(CH_2)_2)_3$ | Heterocyclic ring | Hydrocarbyl |
| II. 2268 | O | N | $((CH_2)O(CH_2)_2)_3$ | Heterocyclic ring | Substituted hydrocarbyl |
| II. 2269 | O | N | $((CH_2)O(CH_2)_3)$ | Aromatic ring | Hydrogen |
| II. 2270 | O | N | $((CH_2)O(CH_2)_3)$ | Aromatic ring | Hydrocarbyl |
| II. 2271 | O | N | $((CH_2)O(CH_2)_3)$ | Aromatic ring | Substituted hydrocarbyl |
| II. 2272 | O | N | $((CH_2)O(CH_2)_3)$ | Cylic ring | Hydrogen |
| II. 2273 | O | N | $((CH_2)O(CH_2)_3)$ | Cylic ring | Hydrocarbyl |
| II. 2274 | O | N | $((CH_2)O(CH_2)_3)$ | Cylic ring | Substituted hydrocarbyl |
| II. 2275 | O | N | $((CH_2)O(CH_2)_3)$ | Heterocyclic ring | Hydrogen |
| II. 2276 | O | N | $((CH_2)O(CH_2)_3)$ | Heterocyclic ring | Hydrocarbyl |
| II. 2277 | O | N | $((CH_2)O(CH_2)_3)$ | Heterocyclic ring | Substituted hydrocarbyl |
| II. 2278 | O | N | $((CH_2)O(CH_2)_3)_2$ | Aromatic ring | Hydrogen |
| II. 2279 | O | N | $((CH_2)O(CH_2)_3)_2$ | Aromatic ring | Hydrocarbyl |
| II. 2280 | O | N | $((CH_2)O(CH_2)_3)_2$ | Aromatic ring | Substituted hydrocarbyl |
| II. 2281 | O | N | $((CH_2)O(CH_2)_3)_2$ | Cylic ring | Hydrogen |
| II. 2282 | O | N | $((CH_2)O(CH_2)_3)_2$ | Cylic ring | Hydrocarbyl |
| II. 2283 | O | N | $((CH_2)O(CH_2)_3)_2$ | Cylic ring | Substituted hydrocarbyl |
| II. 2284 | O | N | $((CH_2)O(CH_2)_3)_2$ | Heterocyclic ring | Hydrogen |
| II. 2285 | O | N | $((CH_2)O(CH_2)_3)_2$ | Heterocyclic ring | Hydrocarbyl |
| II. 2286 | O | N | $((CH_2)O(CH_2)_3)_2$ | Heterocyclic ring | Substituted hydrocarbyl |
| II. 2287 | O | N | $((CH_2)O(CH_2)_3)_3$ | Aromatic ring | Hydrogen |
| II. 2288 | O | N | $((CH_2)O(CH_2)_3)_3$ | Aromatic ring | Hydrocarbyl |
| II. 2289 | O | N | $((CH_2)O(CH_2)_3)_3$ | Aromatic ring | Substituted hydrocarbyl |
| II. 2290 | O | N | $((CH_2)O(CH_2)_3)_3$ | Cylic ring | Hydrogen |
| II. 2291 | O | N | $((CH_2)O(CH_2)_3)_3$ | Cylic ring | Hydrocarbyl |
| II. 2292 | O | N | $((CH_2)O(CH_2)_3)_3$ | Cylic ring | Substituted hydrocarbyl |
| II. 2293 | O | N | $((CH_2)O(CH_2)_3)_3$ | Heterocyclic ring | Hydrogen |
| II. 2294 | O | N | $((CH_2)O(CH_2)_3)_3$ | Heterocyclic ring | Hydrocarbyl |
| II. 2295 | O | N | $((CH_2)O(CH_2)_3)_3$ | Heterocyclic ring | Substituted hydrocarbyl |
| II. 2296 | O | N | $((CH_2)_2O(CH_2))$ | Aromatic ring | Hydrogen |
| II. 2297 | O | N | $((CH_2)_2O(CH_2))$ | Aromatic ring | Hydrocarbyl |
| II. 2298 | O | N | $((CH_2)_2O(CH_2))$ | Aromatic ring | Substituted hydrocarbyl |

TABLE 2-continued

Selected compounds from Formula (II)

| | R1 | R2 | R4 | R5 | R6 |
|---|---|---|---|---|---|
| II. 2299 | O | N | $((CH_2)_2O(CH_2))$ | Cylic ring | Hydrogen |
| II. 2300 | O | N | $((CH_2)_2O(CH_2))$ | Cylic ring | Hydrocarbyl |
| II. 2301 | O | N | $((CH_2)_2O(CH_2))$ | Cylic ring | Substituted hydrocarbyl |
| II. 2302 | O | N | $((CH_2)_2O(CH_2))$ | Heterocyclic ring | Hydrogen |
| II. 2303 | O | N | $((CH_2)_2O(CH_2))$ | Heterocyclic ring | Hydrocarbyl |
| II. 2304 | O | N | $((CH_2)_2O(CH_2))$ | Heterocyclic ring | Substituted hydrocarbyl |
| II. 2305 | O | N | $((CH_2)_2O(CH_2))_2$ | Aromatic ring | Hydrogen |
| II. 2306 | O | N | $((CH_2)_2O(CH_2))_2$ | Aromatic ring | Hydrocarbyl |
| II. 2307 | O | N | $((CH_2)_2O(CH_2))_2$ | Aromatic ring | Substituted hydrocarbyl |
| II. 2308 | O | N | $((CH_2)_2O(CH_2))_2$ | Cylic ring | Hydrogen |
| II. 2309 | O | N | $((CH_2)_2O(CH_2))_2$ | Cylic ring | Hydrocarbyl |
| II. 2310 | O | N | $((CH_2)_2O(CH_2))_2$ | Cylic ring | Substituted hydrocarbyl |
| II. 2311 | O | N | $((CH_2)_2O(CH_2))_2$ | Heterocyclic ring | Hydrogen |
| II. 2312 | O | N | $((CH_2)_2O(CH_2))_2$ | Heterocyclic ring | Hydrocarbyl |
| II. 2313 | O | N | $((CH_2)_2O(CH_2))_2$ | Heterocyclic ring | Substituted hydrocarbyl |
| II. 2314 | O | N | $((CH_2)_2O(CH_2))_3$ | Aromatic ring | Hydrogen |
| II. 2315 | O | N | $((CH_2)_2O(CH_2))_3$ | Aromatic ring | Hydrocarbyl |
| II. 2316 | O | N | $((CH_2)_2O(CH_2))_3$ | Aromatic ring | Substituted hydrocarbyl |
| II. 2317 | O | N | $((CH_2)_2O(CH_2))_3$ | Cylic ring | Hydrogen |
| II. 2318 | O | N | $((CH_2)_2O(CH_2))_3$ | Cylic ring | Hydrocarbyl |
| II. 2319 | O | N | $((CH_2)_2O(CH_2))_3$ | Cylic ring | Substituted hydrocarbyl |
| II. 2320 | O | N | $((CH_2)_2O(CH_2))_3$ | Heterocyclic ring | Hydrogen |
| II. 2321 | O | N | $((CH_2)_2O(CH_2))_3$ | Heterocyclic ring | Hydrocarbyl |
| II. 2322 | O | N | $((CH_2)_2O(CH_2))_3$ | Heterocyclic ring | Substituted hydrocarbyl |
| II. 2323 | O | N | $((CH_2)_2O(CH_2)_2)$ | Aromatic ring | Hydrogen |
| II. 2324 | O | N | $((CH_2)_2O(CH_2)_2)$ | Aromatic ring | Hydrocarbyl |
| II. 2325 | O | N | $((CH_2)_2O(CH_2)_2)$ | Aromatic ring | Substituted hydrocarbyl |
| II. 2326 | O | N | $((CH_2)_2O(CH_2)_2)$ | Cylic ring | Hydrogen. |
| II. 2327 | O | N | $((CH_2)_2O(CH_2)_2)$ | Cylic ring | Hydrocarbyl |
| II. 2328 | O | N | $((CH_2)_2O(CH_2)_2)$ | Cylic ring | Substituted hydrocarbyl |
| II. 2329 | O | N | $((CH_2)_2O(CH_2)_2)$ | Heterocyclic ring | Hydrogen |
| II. 2330 | O | N | $((CH_2)_2O(CH_2)_2)$ | Heterocyclic ring | Hydrocarbyl |
| II. 2331 | O | N | $((CH_2)_2O(CH_2)_2)$ | Heterocyclic ring | Substituted hydrocarbyl |
| II. 2332 | O | N | $((CH_2)_2O(CH_2)_2)_2$ | Aromatic ring | Hydrogen |
| II. 2333 | O | N | $((CH_2)_2O(CH_2)_2)_2$ | Aromatic ring | Hydrocarbyl |
| II. 2334 | O | N | $((CH_2)_2O(CH_2)_2)_2$ | Aromatic ring | Substituted hydrocarbyl |
| II. 2335 | O | N | $((CH_2)_2O(CH_2)_2)_2$ | Cylic ring | Hydrogen |
| II. 2336 | O | N | $((CH_2)_2O(CH_2)_2)_2$ | Cylic ring | Hydrocarbyl |
| II. 2337 | O | N | $((CH_2)_2O(CH_2)_2)_2$ | Cylic ring | Substituted hydrocarbyl |
| II. 2338 | O | N | $((CH_2)_2O(CH_2)_2)_2$ | Heterocyclic ring | Hydrogen |
| II. 2339 | O | N | $((CH_2)_2O(CH_2)_2)_2$ | Heterocyclic ring | Hydrocarbyl |
| II. 2340 | O | N | $((CH_2)_2O(CH_2)_2)_2$ | Heterocyclic ring | Substituted hydrocarbyl |
| II. 2341 | O | N | $((CH_2)_2O(CH_2)_2)_3$ | Aromatic ring | Hydrogen |
| II. 2342 | O | N | $((CH_2)_2O(CH_2)_2)_3$ | Aromatic ring | Hydrocarbyl |
| II. 2343 | O | N | $((CH_2)_2O(CH_2)_2)_3$ | Aromatic ring | Substituted hydrocarbyl |
| II. 2344 | O | N | $((CH_2)_2O(CH_2)_2)_3$ | Cylic ring | Hydrogen |
| II. 2345 | O | N | $((CH_2)_2O(CH_2)_2)_3$ | Cylic ring | Hydrocarbyl |
| II. 2346 | O | N | $((CH_2)_2O(CH_2)_2)_3$ | Cylic ring | Substituted hydrocarbyl |
| II. 2347 | O | N | $((CH_2)_2O(CH_2)_2)_3$ | Heterocyclic ring | Hydrogen |
| II. 2348 | O | N | $((CH_2)_2O(CH_2)_2)_3$ | Heterocyclic ring | Hydrocarbyl |
| II. 2349 | O | N | $((CH_2)_2O(CH_2)_2)_3$ | Heterocyclic ring | Substituted hydrocarbyl |
| II. 2350 | O | N | $((CH_2)_2O(CH_2)_3)$ | Aromatic ring | Hydrogen |
| II. 2351 | O | N | $((CH_2)_2O(CH_2)_3)$ | Aromatic ring | Hydrocarbyl |
| II. 2352 | O | N | $((CH_2)_2O(CH_2)_3)$ | Aromatic ring | Substituted hydrocarbyl |
| II. 2353 | O | N | $((CH_2)_2O(CH_2)_3)$ | Cylic ring | Hydrogen |
| II. 2354 | O | N | $((CH_2)_2O(CH_2)_3)$ | Cylic ring | Hydrocarbyl |
| II. 2355 | O | N | $((CH_2)_2O(CH_2)_3)$ | Cylic ring | Substituted hydrocarbyl |
| II. 2356 | O | N | $((CH_2)_2O(CH_2)_3)$ | Heterocyclic ring | Hydrogen |
| II. 2357 | O | N | $((CH_2)_2O(CH_2)_3)$ | Heterocyclic ring | Hydrocarbyl |
| II. 2358 | O | N | $((CH_2)_2O(CH_2)_3)$ | Heterocyclic ring | Substituted hydrocarbyl |
| II. 2359 | O | N | $((CH_2)_2O(CH_2)_3)_2$ | Aromatic ring | Hydrogen |
| II. 2360 | O | N | $((CH_2)_2O(CH_2)_3)_2$ | Aromatic ring | Hydrocarbyl |
| II. 2361 | O | N | $((CH_2)_2O(CH_2)_3)_2$ | Aromatic ring | Substituted hydrocarbyl |
| II. 2362 | O | N | $((CH_2)_2O(CH_2)_3)_2$ | Cylic ring | Hydrogen |
| II. 2363 | O | N | $((CH_2)_2O(CH_2)_3)_2$ | Cylic ring | Hydrocarbyl |
| II. 2364 | O | N | $((CH_2)_2O(CH_2)_3)_2$ | Cylic ring | Substituted hydrocarbyl |
| II. 2365 | O | N | $((CH_2)_2O(CH_2)_3)_2$ | Heterocyclic ring | Hydrogen |
| II. 2366 | O | N | $((CH_2)_2O(CH_2)_3)_2$ | Heterocyclic ring | Hydrocarbyl |
| II. 2367 | O | N | $((CH_2)_2O(CH_2)_3)_2$ | Heterocyclic ring | Substituted hydrocarbyl |
| II. 2368 | O | N | $((CH_2)_2O(CH_2)_3)_3$ | Aromatic ring | Hydrogen |
| II. 2369 | O | N | $((CH_2)_2O(CH_2)_3)_3$ | Aromatic ring | Hydrocarbyl |
| II. 2370 | O | N | $((CH_2)_2O(CH_2)_3)_3$ | Aromatic ring | Substituted hydrocarbyl |
| II. 2371 | O | N | $((CH_2)_2O(CH_2)_3)_3$ | Cylic ring | Hydrogen |
| II. 2372 | O | N | $((CH_2)_2O(CH_2)_3)_3$ | Cylic ring | Hydrocarbyl |
| II. 2373 | O | N | $((CH_2)_2O(CH_2)_3)_3$ | Cylic ring | Substituted hydrocarbyl |
| II. 2374 | O | N | $((CH_2)_2O(CH_2)_3)_3$ | Heterocyclic ring | Hydrogen |

TABLE 2-continued

Selected compounds from Formula (II)

| | R1 | R2 | R4 | R5 | R6 |
|---|---|---|---|---|---|
| II. 2375 | O | N | ((CH$_2$)$_2$O(CH$_2$)$_3$)$_3$ | Heterocyclic ring | Hydrogen |
| II. 2376 | O | N | ((CH$_2$)$_2$O(CH$_2$)$_3$)$_3$ | Heterocyclic ring | Substituted hydrocarbyl |
| II. 2377 | O | N | ((CH$_2$)$_3$O(CH$_2$)) | Aromatic ring | Hydrogen |
| II. 2378 | O | N | ((CH$_2$)$_3$O(CH$_2$)) | Aromatic ring | Hydrocarbyl |
| II. 2379 | O | N | ((CH$_2$)$_3$O(CH$_2$)) | Aromatic ring | Substituted hydrocarbyl |
| II. 2380 | O | N | ((CH$_2$)$_3$O(CH$_2$)) | Cylic ring | Hydrogen |
| II. 2381 | O | N | ((CH$_2$)$_3$O(CH$_2$)) | Cylic ring | Hydrocarbyl |
| II. 2382 | O | N | ((CH$_2$)$_3$O(CH$_2$)) | Cylic ring | Substituted hydrocarbyl |
| II. 2383 | O | N | ((CH$_2$)$_3$O(CH$_2$)) | Heterocyclic ring | Hydrogen |
| II. 2384 | O | N | ((CH$_2$)$_3$O(CH$_2$)) | Heterocyclic ring | Hydrocarbyl |
| II. 2385 | O | N | ((CH$_2$)$_3$O(CH$_2$)) | Heterocyclic ring | Substituted hydrocarbyl |
| II. 2386 | O | N | ((CH$_2$)$_3$O(CH$_2$))$_2$ | Aromatic ring | Hydrogen |
| II. 2387 | O | N | ((CH$_2$)$_3$O(CH$_2$))$_2$ | Aromatic ring | Hydrocarbyl |
| II. 2388 | O | N | ((CH$_2$)$_3$O(CH$_2$))$_2$ | Aromatic ring | Substituted hydrocarbyl |
| II. 2389 | O | N | ((CH$_2$)$_3$O(CH$_2$))$_2$ | Cylic ring | Hydrogen |
| II. 2390 | O | N | ((CH$_2$)$_3$O(CH$_2$))$_2$ | Cylic ring | Hydrocarbyl |
| II. 2391 | O | N | ((CH$_2$)$_3$O(CH$_2$))$_2$ | Cylic ring | Substituted hydrocarbyl |
| II. 2392 | O | N | ((CH$_2$)$_3$O(CH$_2$))$_2$ | Heterocyclic ring | Hydrogen |
| II. 2393 | O | N | ((CH$_2$)$_3$O(CH$_2$))$_2$ | Heterocyclic ring | Hydrocarbyl |
| II. 2394 | O | N | ((CH$_2$)$_3$O(CH$_2$))$_2$ | Heterocyclic ring | Substituted hydrocarbyl |
| II. 2395 | O | N | ((CH$_2$)$_3$O(CH$_2$))$_3$ | Aromatic ring | Hydrogen |
| II. 2396 | O | N | ((CH$_2$)$_3$O(CH$_2$))$_3$ | Aromatic ring | Hydrocarbyl |
| II. 2397 | O | N | ((CH$_2$)$_3$O(CH$_2$))$_3$ | Aromatic ring | Substituted hydrocarbyl |
| II. 2398 | O | N | ((CH$_2$)$_3$O(CH$_2$))$_3$ | Cylic ring | Hydrogen |
| II. 2399 | O | N | ((CH$_2$)$_3$O(CH$_2$))$_3$ | Cylic ring | Hydrocarbyl |
| II. 2400 | O | N | ((CH$_2$)$_3$O(CH$_2$))$_3$ | Cylic ring | Substituted hydrocarbyl |
| II. 2401 | O | N | ((CH$_2$)$_3$O(CH$_2$))$_3$ | Heterocyclic ring | Hydrogen |
| II. 2402 | O | N | ((CH$_2$)$_3$O(CH$_2$))$_3$ | Heterocyclic ring | Hydrocarbyl |
| II. 2403 | O | N | ((CH$_2$)$_3$O(CH$_2$))$_3$ | Heterocyclic ring | Substituted hydrocarbyl |
| II. 2404 | O | N | ((CH$_2$)$_3$O(CH$_2$)$_2$) | Aromatic ring | Hydrogen |
| II. 2405 | O | N | ((CH$_2$)$_3$O(CH$_2$)$_2$) | Aromatic ring | Hydrocarbyl |
| II. 2406 | O | N | ((CH$_2$)$_3$O(CH$_2$)$_2$) | Aromatic ring | Substituted hydrocarbyl |
| II. 2407 | O | N | ((CH$_2$)$_3$O(CH$_2$)$_2$) | Cylic ring | Hydrogen |
| II. 2408 | O | N | ((CH$_2$)$_3$O(CH$_2$)$_2$) | Cylic ring | Hydrocarbyl |
| II. 2409 | O | N | ((CH$_2$)$_3$O(CH$_2$)$_2$) | Cylic ring | Substituted hydrocarbyl |
| II. 2410 | O | N | ((CH$_2$)$_3$O(CH$_2$)$_2$) | Heterocyclic ring | Hydrogen |
| II. 2411 | O | N | ((CH$_2$)$_3$O(CH$_2$)$_2$) | Heterocyclic ring | Hydrocarbyl |
| II. 2412 | O | N | ((CH$_2$)$_3$O(CH$_2$)$_2$) | Heterocyclic ring | Substituted hydrocarbyl |
| II. 2413 | O | N | ((CH$_2$)$_3$O(CH$_2$)$_2$)$_2$ | Aromatic ring | Hydrogen |
| II. 2414 | O | N | ((CH$_2$)$_3$O(CH$_2$)$_2$)$_2$ | Aromatic ring | Hydrocarbyl |
| II. 2415 | O | N | ((CH$_2$)$_3$O(CH$_2$)$_2$)$_2$ | Aromatic ring | Substituted hydrocarbyl |
| II. 2416 | O | N | ((CH$_2$)$_3$O(CH$_2$)$_2$)$_2$ | Cylic ring | Hydrogen |
| II. 2417 | O | N | ((CH$_2$)$_3$O(CH$_2$)$_2$)$_2$ | Cylic ring | Hydrocarbyl |
| II. 2418 | O | N | ((CH$_2$)$_3$O(CH$_2$)$_2$)$_2$ | Cylic ring | Substituted hydrocarbyl |
| II. 2419 | O | N | ((CH$_2$)$_3$O(CH$_2$)$_2$)$_2$ | Heterocyclic ring | Hydrogen |
| II. 2420 | O | N | ((CH$_2$)$_3$O(CH$_2$)$_2$)$_2$ | Heterocyclic ring | Hydrocarbyl |
| II. 2421 | O | N | ((CH$_2$)$_3$O(CH$_2$)$_2$)$_2$ | Heterocyclic ring | Substituted hydrocarbyl |
| II. 2422 | O | N | ((CH$_2$)$_3$O(CH$_2$)$_2$)$_3$ | Aromatic ring | Hydrogen |
| II. 2423 | O | N | ((CH$_2$)$_3$O(CH$_2$)$_2$)$_3$ | Aromatic ring | Hydrocarbyl |
| II. 2424 | O | N | ((CH$_2$)$_3$O(CH$_2$)$_2$)$_3$ | Aromatic ring | Substituted hydrocarbyl |
| II. 2425 | O | N | ((CH$_2$)$_3$O(CH$_2$)$_2$)$_3$ | Cylic ring | Hydrogen |
| II. 2426 | O | N | ((CH$_2$)$_3$O(CH$_2$)$_2$)$_3$ | Cylic ring | Hydrocarbyl |
| II. 2427 | O | N | ((CH$_2$)$_3$O(CH$_2$)$_2$)$_3$ | Cylic ring | Substituted hydrocarbyl |
| II. 2428 | O | N | ((CH$_2$)$_3$O(CH$_2$)$_2$)$_3$ | Heterocyclic ring | Hydrogen |
| II. 2429 | O | N | ((CH$_2$)$_3$O(CH$_2$)$_2$)$_3$ | Heterocyclic ring | Hydrocarbyl |
| II. 2430 | O | N | ((CH$_2$)$_3$O(CH$_2$)$_2$)$_3$ | Heterocyclic ring | Substituted hydrocarbyl |
| II. 2431 | O | N | ((CH$_2$)$_3$O(CH$_2$)$_3$) | Aromatic ring | Hydrogen |
| II. 2432 | O | N | ((CH$_2$)$_3$O(CH$_2$)$_3$) | Aromatic ring | Hydrocarbyl |
| II. 2433 | O | N | ((CH$_2$)$_3$O(CH$_2$)$_3$) | Aromatic ring | Substituted hydrocarbyl |
| II. 2434 | O | N | ((CH$_2$)$_3$O(CH$_2$)$_3$) | Cylic ring | Hydrogen |
| II. 2435 | O | N | ((CH$_2$)$_3$O(CH$_2$)$_3$) | Cylic ring | Hydrocarbyl |
| II. 2436 | O | N | ((CH$_2$)$_3$O(CH$_2$)$_3$) | Cylic ring | Substituted hydrocarbyl |
| II. 2437 | O | N | ((CH$_2$)$_3$O(CH$_2$)$_3$) | Heterocyclic ring | Hydrogen |
| II. 2438 | O | N | ((CH$_2$)$_3$O(CH$_2$)$_3$) | Heterocyclic ring | Hydrocarbyl |
| II. 2439 | O | N | ((CH$_2$)$_3$O(CH$_2$)$_3$) | Heterocyclic ring | Substituted hydrocarbyl |
| II. 2440 | O | N | ((CH$_2$)$_3$O(CH$_2$)$_3$)$_2$ | Aromatic ring | Hydrogen |
| II. 2441 | O | N | ((CH$_2$)$_3$O(CH$_2$)$_3$)$_2$ | Aromatic ring | Hydrocarbyl |
| II. 2442 | O | N | ((CH$_2$)$_3$O(CH$_2$)$_3$)$_2$ | Aromatic ring | Substituted hydrocarbyl |
| II. 2443 | O | N | ((CH$_2$)$_3$O(CH$_2$)$_3$)$_2$ | Cylic ring | Hydrogen |
| II. 2444 | O | N | ((CH$_2$)$_3$O(CH$_2$)$_3$)$_2$ | Cylic ring | Hydrocarbyl |
| II. 2445 | O | N | ((CH$_2$)$_3$O(CH$_2$)$_3$)$_2$ | Cylic ring | Substituted hydrocarbyl |
| II. 2446 | O | N | ((CH$_2$)$_3$O(CH$_2$)$_3$)$_2$ | Heterocyclic ring | Hydrogen |
| II. 2447 | O | N | ((CH$_2$)$_3$O(CH$_2$)$_3$)$_2$ | Heterocyclic ring | Hydrocarbyl |
| II. 2448 | O | N | ((CH$_2$)$_3$O(CH$_2$)$_3$)$_2$ | Heterocyclic ring | Substituted hydrocarbyl |
| II. 2449 | O | N | ((CH$_2$)$_3$O(CH$_2$)$_3$)$_3$ | Aromatic ring | Hydrogen |
| II. 2450 | O | N | ((CH$_2$)$_3$O(CH$_2$)$_3$)$_3$ | Aromatic ring | Hydrocarbyl |

TABLE 2-continued

Selected compounds from Formula (II)

| | R1 | R2 | R4 | R5 | R6 |
|---|---|---|---|---|---|
| II. 2451 | O | N | $((CH_2)_3O(CH_2)_3)_3$ | Aromatic ring | Substituted hydrocarbyl |
| II. 2452 | O | N | $((CH_2)_3O(CH_2)_3)_3$ | Cylic ring | Hydrogen |
| II. 2453 | O | N | $((CH_2)_3O(CH_2)_3)_3$ | Cylic ring | Hydrocarbyl |
| II. 2454 | O | N | $((CH_2)_3O(CH_2)_3)_3$ | Cylic ring | Substituted hydrocarbyl |
| II. 2455 | O | N | $((CH_2)_3O(CH_2)_3)_3$ | Heterocyclic ring | Hydrogen |
| II. 2456 | O | N | $((CH_2)_3O(CH_2)_3)_3$ | Heterocyclic ring | Hydrocarbyl |
| II. 2457 | O | N | $((CH_2)_3O(CH_2)_3)_3$ | Heterocyclic ring | Substituted hydrocarbyl |
| II. 2458 | O | S | $(CH_2)$ | Aromatic ring | Hydrogen |
| II. 2459 | O | S | $(CH_2)$ | Aromatic ring | Hydrocarbyl |
| II. 2460 | O | S | $(CH_2)$ | Aromatic ring | Substituted hydrocarbyl |
| II. 2461 | O | S | $(CH_2)$ | Cylic ring | Hydrogen |
| II. 2462 | O | S | $(CH_2)$ | Cylic ring | Hydrocarbyl |
| II. 2463 | O | S | $(CH_2)$ | Cylic ring | Substituted hydrocarbyl |
| II. 2464 | O | S | $(CH_2)$ | Heterocyclic ring | Hydrogen |
| II. 2465 | O | S | $(CH_2)$ | Heterocyclic ring | Hydrocarbyl |
| II. 2466 | O | S | $(CH_2)$ | Heterocyclic ring | Substituted hydrocarbyl |
| II. 2467 | O | S | $(CH_2)_2$ | Aromatic ring | Hydrogen |
| II. 2468 | O | S | $(CH_2)_2$ | Aromatic ring | Hydrocarbyl |
| II. 2469 | O | S | $(CH_2)_2$ | Aromatic ring | Substituted hydrocarbyl |
| II. 2470 | O | S | $(CH_2)_2$ | Cylic ring | Hydrogen |
| II. 2471 | O | S | $(CH_2)_2$ | Cylic ring | Hydrocarbyl |
| II. 2472 | O | S | $(CH_2)_2$ | Cylic ring | Substituted hydrocarbyl |
| II. 2473 | O | S | $(CH_2)_2$ | Heterocyclic ring | Hydrogen |
| II. 2474 | O | S | $(CH_2)_2$ | Heterocyclic ring | Hydrocarbyl |
| II. 2475 | O | S | $(CH_2)_2$ | Heterocyclic ring | Substituted hydrocarbyl |
| II. 2476 | O | S | $(CH_2)_3$ | Aromatic ring | Hydrogen |
| II. 2477 | O | S | $(CH_2)_3$ | Aromatic ring | Hydrocarbyl |
| II. 2478 | O | S | $(CH_2)_3$ | Aromatic ring | Substituted hydrocarbyl |
| II. 2479 | O | S | $(CH_2)_3$ | Cylic ring | Hydrogen |
| II. 2480 | O | S | $(CH_2)_3$ | Cylic ring | Hydrocarbyl |
| II. 2481 | O | S | $(CH_2)_3$ | Cylic ring | Substituted hydrocarbyl |
| II. 2482 | O | S | $(CH_2)_3$ | Heterocyclic ring | Hydrogen |
| II. 2483 | O | S | $(CH_2)_3$ | Heterocyclic ring | Hydrocarbyl |
| II. 2484 | O | S | $(CH_2)_3$ | Heterocyclic ring | Substituted hydrocarbyl |
| II. 2485 | O | S | $((CH_2)O)$ | Aromatic ring | Hydrogen |
| II. 2486 | O | S | $((CH_2)O)$ | Aromatic ring | Hydrocarbyl |
| II. 2487 | O | S | $((CH_2)O)$ | Aromatic ring | Substituted hydrocarbyl |
| II. 2488 | O | S | $((CH_2)O)$ | Cylic ring | Hydrogen |
| II. 2489 | O | S | $((CH_2)O)$ | Cylic ring | Hydrocarbyl |
| II. 2490 | O | S | $((CH_2)O)$ | Cylic ring | Substituted hydrocarbyl |
| II. 2491 | O | S | $((CH_2)O)$ | Heterocyclic ring | Hydrogen |
| II. 2492 | O | S | $((CH_2)O)$ | Heterocyclic ring | Hydrocarbyl |
| II. 2493 | O | S | $((CH_2)O)$ | Heterocyclic ring | Substituted hydrocarbyl |
| II. 2494 | O | S | $((CH_2)O)_2$ | Aromatic ring | Hydrogen |
| II. 2495 | O | S | $((CH_2)O)_2$ | Aromatic ring | Hydrocarbyl |
| II. 2496 | O | S | $((CH_2)O)_2$ | Aromatic ring | Substituted hydrocarbyl |
| II. 2497 | O | S | $((CH_2)O)_2$ | Cylic ring | Hydrogen |
| II. 2498 | O | S | $((CH_2)O)_2$ | Cylic ring | Hydrocarbyl |
| II. 2499 | O | S | $((CH_2)O)_2$ | Cylic ring | Substituted hydrocarbyl |
| II. 2500 | O | S | $((CH_2)O)_2$ | Heterocyclic ring | Hydrogen |
| II. 2501 | O | S | $((CH_2)O)_2$ | Heterocyclic ring | Hydrocarbyl |
| II. 2502 | O | S | $((CH_2)O)_2$ | Heterocyclic ring | Substituted hydrocarbyl |
| II. 2503 | O | S | $((CH_2)O)_3$ | Aromatic ring | Hydrogen |
| II. 2504 | O | S | $((CH_2)O)_3$ | Aromatic ring | Hydrocarbyl |
| II. 2505 | O | S | $((CH_2)O)_3$ | Aromatic ring | Substituted hydrocarbyl |
| II. 2506 | O | S | $((CH_2)O)_3$ | Cylic ring | Hydrogen |
| II. 2507 | O | S | $((CH_2)O)_3$ | Cylic ring | Hydrocarbyl |
| II. 2508 | O | S | $((CH_2)O)_3$ | Cylic ring | Substituted hydrocarbyl |
| II. 2509 | O | S | $((CH_2)O)_3$ | Heterocyclic ring | Hydrogen |
| II. 2510 | O | S | $((CH_2)O)_3$ | Heterocyclic ring | Hydrocarbyl |
| II. 2511 | O | S | $((CH_2)O)_3$ | Heterocyclic ring | Substituted hydrocarbyl |
| II. 2512 | O | S | $((CH_2)_2O)$ | Aromatic ring | Hydrogen |
| II. 2513 | O | S | $((CH_2)_2O)$ | Aromatic ring | Hydrocarbyl |
| II. 2514 | O | S | $((CH_2)_2O)$ | Aromatic ring | Substituted hydrocarbyl |
| II. 2515 | O | S | $((CH_2)_2O)$ | Cylic ring | Hydrogen |
| II. 2516 | O | S | $((CH_2)_2O)$ | Cylic ring | Hydrocarbyl |
| II. 2517 | O | S | $((CH_2)_2O)$ | Cylic ring | Substituted hydrocarbyl |
| II. 2518 | O | S | $((CH_2)_2O)$ | Heterocyclic ring | Hydrogen |
| II. 2519 | O | S | $((CH_2)_2O)$ | Heterocyclic ring | Hydrocarbyl |
| II. 2520 | O | S | $((CH_2)_2O)$ | Heterocyclic ring | Substituted hydrocarbyl |
| II. 2521 | O | S | $((CH_2)_2O)_2$ | Aromatic ring | Hydrogen |
| II. 2522 | O | S | $((CH_2)_2O)_2$ | Aromatic ring | Hydrocarbyl |
| II. 2523 | O | S | $((CH_2)_2O)_2$ | Aromatic ring | Substituted hydrocarbyl |
| II. 2524 | O | S | $((CH_2)_2O)_2$ | Cylic ring | Hydrogen |
| II. 2525 | O | S | $((CH_2)_2O)_2$ | Cylic ring | Hydrocarbyl |
| II. 2526 | O | S | $((CH_2)_2O)_2$ | Cylic ring | Substituted hydrocarbyl |

TABLE 2-continued

Selected compounds from Formula (II)

| | R1 | R2 | R4 | R5 | R6 |
|---|---|---|---|---|---|
| II. 2527 | O | S | $((CH_2)_2O)_2$ | Heterocyclic ring | Hydrogen |
| II. 2528 | O | S | $((CH_2)_2O)_2$ | Heterocyclic ring | Hydrocarbyl |
| II. 2529 | O | S | $((CH_2)_2O)_2$ | Heterocyclic ring | Substituted hydrocarbyl |
| II. 2530 | O | S | $((CH_2)_2O)_3$ | Aromatic ring | Hydrogen |
| II. 2531 | O | S | $((CH_2)_2O)_3$ | Aromatic ring | Hydrocarbyl |
| II. 2532 | O | S | $((CH_2)_2O)_3$ | Aromatic ring | Substituted hydrocarbyl |
| II. 2533 | O | S | $((CH_2)_2O)_3$ | Cylic ring | Hydrogen |
| II. 2534 | O | S | $((CH_2)_2O)_3$ | Cylic ring | Hydrocarbyl |
| II. 2535 | O | S | $((CH_2)_2O)_3$ | Cylic ring | Substituted hydrocarbyl |
| II. 2536 | O | S | $((CH_2)_2O)_3$ | Heterocyclic ring | Hydrogen |
| II. 2537 | O | S | $((CH_2)_2O)_3$ | Heterocyclic ring | Hydrocarbyl |
| II. 2538 | O | S | $((CH_2)_2O)_3$ | Heterocyclic ring | Substituted hydrocarbyl |
| II. 2539 | O | S | $((CH_2)_3O)$ | Aromatic ring | Hydrogen |
| II. 2540 | O | S | $((CH_2)_3O)$ | Aromatic ring | Hydrocarbyl |
| II. 2541 | O | S | $((CH_2)_3O)$ | Aromatic ring | Substituted hydrocarbyl |
| II. 2542 | O | S | $((CH_2)_3O)$ | Cylic ring | Hydrogen |
| II. 2543 | O | S | $((CH_2)_3O)$ | Cylic ring | Hydrocarbyl |
| II. 2544 | O | S | $((CH_2)_3O)$ | Cylic ring | Substituted hydrocarbyl |
| II. 2545 | O | S | $((CH_2)_3O)$ | Heterocyclic ring | Hydrogen |
| II. 2546 | O | S | $((CH_2)_3O)$ | Heterocyclic ring | Hydrocarbyl |
| II. 2547 | O | S | $((CH_2)_3O)$ | Heterocyclic ring | Substituted hydrocarbyl |
| II. 2548 | O | S | $((CH_2)_3O)_2$ | Aromatic ring | Hydrogen |
| II. 2549 | O | S | $((CH_2)_3O)_2$ | Aromatic ring | Hydrocarbyl |
| II. 2550 | O | S | $((CH_2)_3O)_2$ | Aromatic ring | Substituted hydrocarbyl |
| II. 2551 | O | S | $((CH_2)_3O)_2$ | Cylic ring | Hydrogen |
| II. 2552 | O | S | $((CH_2)_3O)_2$ | Cylic ring | Hydrocarbyl |
| II. 2553 | O | S | $((CH_2)_3O)_2$ | Cylic ring | Substituted hydrocarbyl |
| II. 2554 | O | S | $((CH_2)_3O)_2$ | Heterocyclic ring | Hydrogen |
| II. 2555 | O | S | $((CH_2)_3O)_2$ | Heterocyclic ring | Hydrocarbyl |
| II. 2556 | O | S | $((CH_2)_3O)_2$ | Heterocyclic ring | Substituted hydrocarbyl |
| II. 2557 | O | S | $((CH_2)_3O)_3$ | Aromatic ring | Hydrogen |
| II. 2558 | O | S | $((CH_2)_3O)_3$ | Aromatic ring | Hydrocarbyl |
| II. 2559 | O | S | $((CH_2)_3O)_3$ | Aromatic ring | Substituted hydrocarbyl |
| II. 2560 | O | S | $((CH_2)_3O)_3$ | Cylic ring | Hydrogen |
| II. 2561 | O | S | $((CH_2)_3O)_3$ | Cylic ring | Hydrocarbyl |
| II. 2562 | O | S | $((CH_2)_3O)_3$ | Cylic ring | Substituted hydrocarbyl |
| II. 2563 | O | S | $((CH_2)_3O)_3$ | Heterocyclic ring | Hydrogen |
| II. 2564 | O | S | $((CH_2)_3O)_3$ | Heterocyclic ring | Hydrocarbyl |
| II. 2565 | O | S | $((CH_2)_3O)_3$ | Heterocyclic ring | Substituted hydrocarbyl |
| II. 2566 | O | S | $((CH_2)O(CH_2))$ | Aromatic ring | Hydrogen |
| II. 2567 | O | S | $((CH_2)O(CH_2))$ | Aromatic ring | Hydrocarbyl |
| II. 2568 | O | S | $((CH_2)O(CH_2))$ | Aromatic ring | Substituted hydrocarbyl |
| II. 2569 | O | S | $((CH_2)O(CH_2))$ | Cylic ring | Hydrogen |
| II. 2570 | O | S | $((CH_2)O(CH_2))$ | Cylic ring | Hydrocarbyl |
| II. 2571 | O | S | $((CH_2)O(CH_2))$ | Cylic ring | Substituted hydrocarbyl |
| II. 2572 | O | S | $((CH_2)O(CH_2))$ | Heterocyclic ring | Hydrogen |
| II. 2573 | O | S | $((CH_2)O(CH_2))$ | Heterocyclic ring | Hydrocarbyl |
| II. 2574 | O | S | $((CH_2)O(CH_2))$ | Heterocyclic ring | Substituted hydrocarbyl |
| II. 2575 | O | S | $((CH_2)O(CH_2))_2$ | Aromatic ring | Hydrogen |
| II. 2576 | O | S | $((CH_2)O(CH_2))_2$ | Aromatic ring | Hydrocarbyl |
| II. 2577 | O | S | $((CH_2)O(CH_2))_2$ | Aromatic ring | Substituted hydrocarbyl |
| II. 2578 | O | S | $((CH_2)O(CH_2))_2$ | Cylic ring | Hydrogen |
| II. 2579 | O | S | $((CH_2)O(CH_2))_2$ | Cylic ring | Hydrocarbyl |
| II. 2580 | O | S | $((CH_2)O(CH_2))_2$ | Cylic ring | Substituted hydrocarbyl |
| II. 2581 | O | S | $((CH_2)O(CH_2))_2$ | Heterocyclic ring | Hydrogen |
| II. 2582 | O | S | $((CH_2)O(CH_2))_2$ | Heterocyclic ring | Hydrocarbyl |
| II. 2583 | O | S | $((CH_2)O(CH_2))_2$ | Heterocyclic ring | Substituted hydrocarbyl |
| II. 2584 | O | S | $((CH_2)O(CH_2))_3$ | Aromatic ring | Hydrogen |
| II. 2585 | O | S | $((CH_2)O(CH_2))_3$ | Aromatic ring | Hydrocarbyl |
| II. 2586 | O | S | $((CH_2)O(CH_2))_3$ | Aromatic ring | Substituted hydrocarbyl |
| II. 2587 | O | S | $((CH_2)O(CH_2))_3$ | Cylic ring | Hydrogen |
| II. 2588 | O | S | $((CH_2)O(CH_2))_3$ | Cylic ring | Hydrocarbyl |
| II. 2589 | O | S | $((CH_2)O(CH_2))_3$ | Cylic ring | Substituted hydrocarbyl |
| II. 2590 | O | S | $((CH_2)O(CH_2))_3$ | Heterocyclic ring | Hydrogen |
| II. 2591 | O | S | $((CH_2)O(CH_2))_3$ | Heterocyclic ring | Hydrocarbyl |
| II. 2592 | O | S | $((CH_2)O(CH_2))_3$ | Heterocyclic ring | Substituted hydrocarbyl |
| II. 2593 | O | S | $((CH_2)O(CH_2)_2)$ | Aromatic ring | Hydrogen |
| II. 2594 | O | S | $((CH_2)O(CH_2)_2)$ | Aromatic ring | Hydrocarbyl |
| II. 2595 | O | S | $((CH_2)O(CH_2)_2)$ | Aromatic ring | Substituted hydrocarbyl |
| II. 2596 | O | S | $((CH_2)O(CH_2)_2)$ | Cylic ring | Hydrogen |
| II. 2597 | O | S | $((CH_2)O(CH_2)_2)$ | Cylic ring | Hydrocarbyl |
| II. 2598 | O | S | $((CH_2)O(CH_2)_2)$ | Cylic ring | Substituted hydrocarbyl |
| II. 2599 | O | S | $((CH_2)O(CH_2)_2)$ | Heterocyclic ring | Hydrogen |
| II. 2600 | O | S | $((CH_2)O(CH_2)_2)$ | Heterocyclic ring | Hydrocarbyl |
| II. 2601 | O | S | $((CH_2)O(CH_2)_2)$ | Heterocyclic ring | Substituted hydrocarbyl |
| II. 2602 | O | S | $((CH_2)O(CH_2)_2)_2$ | Aromatic ring | Hydrogen |

TABLE 2-continued

Selected compounds from Formula (II)

| | R1 | R2 | R4 | R5 | R6 |
|---|---|---|---|---|---|
| II. 2603 | O | S | $((CH_2)O(CH_2)_2)_2$ | Aromatic ring | Hydrocarbyl |
| II. 2604 | O | S | $((CH_2)O(CH_2)_2)_2$ | Aromatic ring | Substituted hydrocarbyl |
| II. 2605 | O | S | $((CH_2)O(CH_2)_2)_2$ | Cylic ring | Hydrogen |
| II. 2606 | O | S | $((CH_2)O(CH_2)_2)_2$ | Cylic ring | Hydrocarbyl |
| II. 2607 | O | S | $((CH_2)O(CH_2)_2)_2$ | Cylic ring | Substituted hydrocarbyl |
| II. 2608 | O | S | $((CH_2)O(CH_2)_2)_2$ | Heterocyclic ring | Hydrogen |
| II. 2609 | O | S | $((CH_2)O(CH_2)_2)_2$ | Heterocyclic ring | Hydrocarbyl |
| II. 2610 | O | S | $((CH_2)O(CH_2)_2)_2$ | Heterocyclic ring | Substituted hydrocarbyl |
| II. 2611 | O | S | $((CH_2)O(CH_2)_2)_3$ | Aromatic ring | Hydrogen |
| II. 2612 | O | S | $((CH_2)O(CH_2)_2)_3$ | Aromatic ring | Hydrocarbyl |
| II. 2613 | O | S | $((CH_2)O(CH_2)_2)_3$ | Aromatic ring | Substituted hydrocarbyl |
| II. 2614 | O | S | $((CH_2)O(CH_2)_2)_3$ | Cylic ring | Hydrogen |
| II. 2615 | O | S | $((CH_2)O(CH_2)_2)_3$ | Cylic ring | Hydrocarbyl |
| II. 2616 | O | S | $((CH_2)O(CH_2)_2)_3$ | Cylic ring | Substituted hydrocarbyl |
| II. 2617 | O | S | $((CH_2)O(CH_2)_2)_3$ | Heterocyclic ring | Hydrogen |
| II. 2618 | O | S | $((CH_2)O(CH_2)_2)_3$ | Heterocyclic ring | Hydrocarbyl |
| II. 2619 | O | S | $((CH_2)O(CH_2)_2)_3$ | Heterocyclic ring | Substituted hydrocarbyl |
| II. 2620 | O | S | $((CH_2)O(CH_2)_3)$ | Aromatic ring | Hydrogen |
| II. 2621 | O | S | $((CH_2)O(CH_2)_3)$ | Aromatic ring | Hydrocarbyl |
| II. 2622 | O | S | $((CH_2)O(CH_2)_3)$ | Aromatic ring | Substituted hydrocarbyl |
| II. 2623 | O | S | $((CH_2)O(CH_2)_3)$ | Cylic ring | Hydrogen |
| II. 2624 | O | S | $((CH_2)O(CH_2)_3)$ | Cylic ring | Hydrocarbyl |
| II. 2625 | O | S | $((CH_2)O(CH_2)_3)$ | Cylic ring | Substituted hydrocarbyl |
| II. 2626 | O | S | $((CH_2)O(CH_2)_3)$ | Heterocyclic ring | Hydrogen |
| II. 2627 | O | S | $((CH_2)O(CH_2)_3)$ | Heterocyclic ring | Hydrocarbyl |
| II. 2628 | O | S | $((CH_2)O(CH_2)_3)$ | Heterocyclic ring | Substituted hydrocarbyl |
| II. 2629 | O | S | $((CH_2)O(CH_2)_3)_2$ | Aromatic ring | Hydrogen |
| II. 2630 | O | S | $((CH_2)O(CH_2)_3)_2$ | Aromatic ring | Hydrocarbyl |
| II. 2631 | O | S | $((CH_2)O(CH_2)_3)_2$ | Aromatic ring | Substituted hydrocarbyl |
| II. 2632 | O | S | $((CH_2)O(CH_2)_3)_2$ | Cylic ring | Hydrogen |
| II. 2633 | O | S | $((CH_2)O(CH_2)_3)_2$ | Cylic ring | Hydrocarbyl |
| II. 2634 | O | S | $((CH_2)O(CH_2)_3)_2$ | Cylic ring | Substituted hydrocarbyl |
| II. 2635 | O | S | $((CH_2)O(CH_2)_3)_2$ | Heterocyclic ring | Hydrogen |
| II. 2636 | O | S | $((CH_2)O(CH_2)_3)_2$ | Heterocyclic ring | Hydrocarbyl |
| II. 2637 | O | S | $((CH_2)O(CH_2)_3)_2$ | Heterocyclic ring | Substituted hydrocarbyl |
| II. 2638 | O | S | $((CH_2)O(CH_2)_3)_3$ | Aromatic ring | Hydrogen |
| II. 2639 | O | S | $((CH_2)O(CH_2)_3)_3$ | Aromatic ring | Hydrocarbyl |
| II. 2640 | O | S | $((CH_2)O(CH_2)_3)_3$ | Aromatic ring | Substituted hydrocarbyl |
| II. 2641 | O | S | $((CH_2)O(CH_2)_3)_3$ | Cylic ring | Hydrogen |
| II. 2642 | O | S | $((CH_2)O(CH_2)_3)_3$ | Cylic ring | Hydrocarbyl |
| II. 2643 | O | S | $((CH_2)O(CH_2)_3)_3$ | Cylic ring | Substituted hydrocarbyl |
| II. 2644 | O | S | $((CH_2)O(CH_2)_3)_3$ | Heterocyclic ring | Hydrogen |
| II. 2645 | O | S | $((CH_2)O(CH_2)_3)_3$ | Heterocyclic ring | Hydrocarbyl |
| II. 2646 | O | S | $((CH_2)O(CH_2)_3)_3$ | Heterocyclic ring | Substituted hydrocarbyl |
| II. 2647 | O | S | $((CH_2)_2O(CH_2))$ | Aromatic ring | Hydrogen |
| II. 2648 | O | S | $((CH_2)_2O(CH_2))$ | Aromatic ring | Hydrocarbyl |
| II. 2649 | O | S | $((CH_2)_2O(CH_2))$ | Aromatic ring | Substituted hydrocarbyl |
| II. 2650 | O | S | $((CH_2)_2O(CH_2))$ | Cylic ring | Hydrogen |
| II. 2651 | O | S | $((CH_2)_2O(CH_2))$ | Cylic ring | Hydrocarbyl |
| II. 2652 | O | S | $((CH_2)_2O(CH_2))$ | Cylic ring | Substituted hydrocarbyl |
| II. 2653 | O | S | $((CH_2)_2O(CH_2))$ | Heterocyclic ring | Hydrogen |
| II. 2654 | O | S | $((CH_2)_2O(CH_2))$ | Heterocyclic ring | Hydrocarbyl |
| II. 2655 | O | S | $((CH_2)_2O(CH_2))$ | Heterocyclic ring | Substituted hydrocarbyl |
| II. 2656 | O | S | $((CH_2)_2O(CH_2))_2$ | Aromatic ring | Hydrogen |
| II. 2657 | O | S | $((CH_2)_2O(CH_2))_2$ | Aromatic ring | Hydrocarbyl |
| II. 2658 | O | S | $((CH_2)_2O(CH_2))_2$ | Aromatic ring | Substituted hydrocarbyl |
| II. 2659 | O | S | $((CH_2)_2O(CH_2))_2$ | Cylic ring | Hydrogen |
| II. 2660 | O | S | $((CH_2)_2O(CH_2))_2$ | Cylic ring | Hydrocarbyl |
| II. 2661 | O | S | $((CH_2)_2O(CH_2))_2$ | Cylic ring | Substituted hydrocarbyl |
| II. 2662 | O | S | $((CH_2)_2O(CH_2))_2$ | Heterocyclic ring | Hydrogen |
| II. 2663 | O | S | $((CH_2)_2O(CH_2))_2$ | Heterocyclic ring | Hydrocarbyl |
| II. 2664 | O | S | $((CH_2)_2O(CH_2))_2$ | Heterocyclic ring | Substituted hydrocarbyl |
| II. 2665 | O | S | $((CH_2)_2O(CH_2))_3$ | Aromatic ring | Hydrogen |
| II. 2666 | O | S | $((CH_2)_2O(CH_2))_3$ | Aromatic ring | Hydrocarbyl |
| II. 2667 | O | S | $((CH_2)_2O(CH_2))_3$ | Aromatic ring | Substituted hydrocarbyl |
| II. 2668 | O | S | $((CH_2)_2O(CH_2))_3$ | Cylic ring | Hydrogen |
| II. 2669 | O | S | $((CH_2)_2O(CH_2))_3$ | Cylic ring | Hydrocarbyl |
| II. 2670 | O | S | $((CH_2)_2O(CH_2))_3$ | Cylic ring | Substituted hydrocarbyl |
| II. 2671 | O | S | $((CH_2)_2O(CH_2))_3$ | Heterocyclic ring | Hydrogen |
| II. 2672 | O | S | $((CH_2)_2O(CH_2))_3$ | Heterocyclic ring | Hydrocarbyl |
| II. 2673 | O | S | $((CH_2)_2O(CH_2))_3$ | Heterocyclic ring | Substituted hydrocarbyl |
| II. 2674 | O | S | $((CH_2)_2O(CH_2)_2)$ | Aromatic ring | Hydrogen |
| II. 2675 | O | S | $((CH_2)_2O(CH_2)_2)$ | Aromatic ring | Hydrocarbyl |
| II. 2676 | O | S | $((CH_2)_2O(CH_2)_2)$ | Aromatic ring | Substituted hydrocarbyl |
| II. 2677 | O | S | $((CH_2)_2O(CH_2)_2)$ | Cylic ring | Hydrogen |
| II. 2678 | O | S | $((CH_2)_2O(CH_2)_2)$ | Cylic ring | Hydrocarbyl |

TABLE 2-continued

Selected compounds from Formula (II)

| | R1 | R2 | R4 | R5 | R6 |
|---|---|---|---|---|---|
| II. 2679 | O | S | $((CH_2)_2O(CH_2)_2)$ | Cylic ring | Substituted hydrocarbyl |
| II. 2680 | O | S | $((CH_2)_2O(CH_2)_2)$ | Heterocyclic ring | Hydrogen |
| II. 2681 | O | S | $((CH_2)_2O(CH_2)_2)$ | Heterocyclic ring | Hydrocarbyl |
| II. 2682 | O | S | $((CH_2)_2O(CH_2)_2)$ | Heterocyclic ring | Substituted hydrocarbyl |
| II. 2683 | O | S | $((CH_2)_2O(CH_2)_2)_2$ | Aromatic ring | Hydrogen |
| II. 2684 | O | S | $((CH_2)_2O(CH_2)_2)_2$ | Aromatic ring | Hydrocarbyl |
| II. 2685 | O | S | $((CH_2)_2O(CH_2)_2)_2$ | Aromatic ring | Substituted hydrocarbyl |
| II. 2686 | O | S | $((CH_2)_2O(CH_2)_2)_2$ | Cylic ring | Hydrogen |
| II. 2687 | O | S | $((CH_2)_2O(CH_2)_2)_2$ | Cylic ring | Hydrocarbyl |
| II. 2688 | O | S | $((CH_2)_2O(CH_2)_2)_2$ | Cylic ring | Substituted hydrocarbyl |
| II. 2689 | O | S | $((CH_2)_2O(CH_2)_2)_2$ | Heterocyclic ring | Hydrogen |
| II. 2690 | O | S | $((CH_2)_2O(CH_2)_2)_2$ | Heterocyclic ring | Hydrocarbyl |
| II. 2691 | O | S | $((CH_2)_2O(CH_2)_2)_2$ | Heterocyclic ring | Substituted hydrocarbyl |
| II. 2692 | O | S | $((CH_2)_2O(CH_2)_2)_3$ | Aromatic ring | Hydrogen |
| II. 2693 | O | S | $((CH_2)_2O(CH_2)_2)_3$ | Aromatic ring | Hydrocarbyl |
| II. 2694 | O | S | $((CH_2)_2O(CH_2)_2)_3$ | Aromatic ring | Substituted hydrocarbyl |
| II. 2695 | O | S | $((CH_2)_2O(CH_2)_2)_3$ | Cylic ring | Hydrogen |
| II. 2696 | O | S | $((CH_2)_2O(CH_2)_2)_3$ | Cylic ring | Hydrocarbyl |
| II. 2697 | O | S | $((CH_2)_2O(CH_2)_2)_3$ | Cylic ring | Substituted hydrocarbyl |
| II. 2698 | O | S | $((CH_2)_2O(CH_2)_2)_3$ | Heterocyclic ring | Hydrogen |
| II. 2699 | O | S | $((CH_2)_2O(CH_2)_2)_3$ | Heterocyclic ring | Hydrocarbyl |
| II. 2700 | O | S | $((CH_2)_2O(CH_2)_2)_3$ | Heterocyclic ring | Substituted hydrocarbyl |
| II. 2701 | O | S | $((CH_2)_2O(CH_2)_3)$ | Aromatic ring | Hydrogen |
| II. 2702 | O | S | $((CH_2)_2O(CH_2)_3)$ | Aromatic ring | Hydrocarbyl |
| II. 2703 | O | S | $((CH_2)_2O(CH_2)_3)$ | Aromatic ring | Substituted hydrocarbyl |
| II. 2704 | O | S | $((CH_2)_2O(CH_2)_3)$ | Cylic ring | Hydrogen |
| II. 2705 | O | S | $((CH_2)_2O(CH_2)_3)$ | Cylic ring | Hydrocarbyl |
| II. 2706 | O | S | $((CH_2)_2O(CH_2)_3)$ | Cylic ring | Substituted hydrocarbyl |
| II. 2707 | O | S | $((CH_2)_2O(CH_2)_3)$ | Heterocyclic ring | Hydrogen |
| II. 2708 | O | S | $((CH_2)_2O(CH_2)_3)$ | Heterocyclic ring | Hydrocarbyl |
| II. 2709 | O | S | $((CH_2)_2O(CH_2)_3)$ | Heterocyclic ring | Substituted hydrocarbyl |
| II. 2710 | O | S | $((CH_2)_2O(CH_2)_3)_2$ | Aromatic ring | Hydrogen |
| II. 2711 | O | S | $((CH_2)_2O(CH_2)_3)_2$ | Aromatic ring | Hydrocarbyl |
| II. 2712 | O | S | $((CH_2)_2O(CH_2)_3)_2$ | Aromatic ring | Substituted hydrocarbyl |
| II. 2713 | O | S | $((CH_2)_2O(CH_2)_3)_2$ | Cylic ring | Hydrogen |
| II. 2714 | O | S | $((CH_2)_2O(CH_2)_3)_2$ | Cylic ring | Hydrocarbyl |
| II. 2715 | O | S | $((CH_2)_2O(CH_2)_3)_2$ | Cylic ring | Substituted hydrocarbyl |
| II. 2716 | O | S | $((CH_2)_2O(CH_2)_3)_2$ | Heterocyclic ring | Hydrogen |
| II. 2717 | O | S | $((CH_2)_2O(CH_2)_3)_2$ | Heterocyclic ring | Hydrocarbyl |
| II. 2718 | O | S | $((CH_2)_2O(CH_2)_3)_2$ | Heterocyclic ring | Substituted hydrocarbyl |
| II. 2719 | O | S | $((CH_2)_2O(CH_2)_3)_3$ | Aromatic ring | Hydrogen |
| II. 2720 | O | S | $((CH_2)_2O(CH_2)_3)_3$ | Aromatic ring | Hydrocarbyl |
| II. 2721 | O | S | $((CH_2)_2O(CH_2)_3)_3$ | Aromatic ring | Substituted hydrocarbyl |
| II. 2722 | O | S | $((CH_2)_2O(CH_2)_3)_3$ | Cylic ring | Hydrogen |
| II. 2723 | O | S | $((CH_2)_2O(CH_2)_3)_3$ | Cylic ring | Hydrocarbyl |
| II. 2724 | O | S | $((CH_2)_2O(CH_2)_3)_3$ | Cylic ring | Substituted hydrocarbyl |
| II. 2725 | O | S | $((CH_2)_2O(CH_2)_3)_3$ | Heterocyclic ring | Hydrogen |
| II. 2726 | O | S | $((CH_2)_2O(CH_2)_3)_3$ | Heterocyclic ring | Hydrocarbyl |
| II. 2727 | O | S | $((CH_2)_2O(CH_2)_3)_3$ | Heterocyclic ring | Substituted hydrocarbyl |
| II. 2728 | O | S | $((CH_2)_3O(CH_2))$ | Aromatic ring | Hydrogen |
| II. 2729 | O | S | $((CH_2)_3O(CH_2))$ | Aromatic ring | Hydrocarbyl |
| II. 2730 | O | S | $((CH_2)_3O(CH_2))$ | Aromatic ring | Substituted hydrocarbyl |
| II. 2731 | O | S | $((CH_2)_3O(CH_2))$ | Cylic ring | Hydrogen |
| II. 2732 | O | S | $((CH_2)_3O(CH_2))$ | Cylic ring | Hydrocarbyl |
| II. 2733 | O | S | $((CH_2)_3O(CH_2))$ | Cylic ring | Substituted hydrocarbyl |
| II. 2734 | O | S | $((CH_2)_3O(CH_2))$ | Heterocyclic ring | Hydrogen |
| II. 2735 | O | S | $((CH_2)_3O(CH_2))$ | Heterocyclic ring | Hydrocarbyl |
| II. 2736 | O | S | $((CH_2)_3O(CH_2))$ | Heterocyclic ring | Substituted hydrocarbyl |
| II. 2737 | O | S | $((CH_2)_3O(CH_2))_2$ | Aromatic ring | Hydrogen |
| II. 2738 | O | S | $((CH_2)_3O(CH_2))_2$ | Aromatic ring | Hydrocarbyl |
| II. 2739 | O | S | $((CH_2)_3O(CH_2))_2$ | Aromatic ring | Substituted hydrocarbyl |
| II. 2740 | O | S | $((CH_2)_3O(CH_2))_2$ | Cylic ring | Hydrogen |
| II. 2741 | O | S | $((CH_2)_3O(CH_2))_2$ | Cylic ring | Hydrocarbyl |
| II. 2742 | O | S | $((CH_2)_3O(CH_2))_2$ | Cylic ring | Substituted hydrocarbyl |
| II. 2743 | O | S | $((CH_2)_3O(CH_2))_2$ | Heterocyclic ring | Hydrogen |
| II. 2744 | O | S | $((CH_2)_3O(CH_2))_2$ | Heterocyclic ring | Hydrocarbyl |
| II. 2745 | O | S | $((CH_2)_3O(CH_2))_2$ | Heterocyclic ring | Substituted hydrocarbyl |
| II. 2746 | O | S | $((CH_2)_3O(CH_2))_3$ | Aromatic ring | Hydrogen |
| II. 2747 | O | S | $((CH_2)_3O(CH_2))_3$ | Aromatic ring | Hydrocarbyl |
| II. 2748 | O | S | $((CH_2)_3O(CH_2))_3$ | Aromatic ring | Substituted hydrocarbyl |
| II. 2749 | O | S | $((CH_2)_3O(CH_2))_3$ | Cylic ring | Hydrogen |
| II. 2750 | O | S | $((CH_2)_3O(CH_2))_3$ | Cylic ring | Hydrocarbyl |
| II. 2751 | O | S | $((CH_2)_3O(CH_2))_3$ | Cylic ring | Substituted hydrocarbyl |
| II. 2752 | O | S | $((CH_2)_3O(CH_2))_3$ | Heterocyclic ring | Hydrogen |
| II. 2753 | O | S | $((CH_2)_3O(CH_2))_3$ | Heterocyclic ring | Hydrocarbyl |
| II. 2754 | O | S | $((CH_2)_3O(CH_2))_3$ | Heterocyclic ring | Substituted hydrocarbyl |

TABLE 2-continued

Selected compounds from Formula (II)

| | R1 | R2 | R4 | R5 | R6 |
|---|---|---|---|---|---|
| II. 2755 | O | S | $((CH_2)_3O(CH_2)_2)$ | Aromatic ring | Hydrogen |
| II. 2756 | O | S | $((CH_2)_3O(CH_2)_2)$ | Aromatic ring | Hydrocarbyl |
| II. 2757 | O | S | $((CH_2)_3O(CH_2)_2)$ | Aromatic ring | Substituted hydrocarbyl |
| II. 2758 | O | S | $((CH_2)_3O(CH_2)_2)$ | Cylic ring | Hydrogen |
| II. 2759 | O | S | $((CH_2)_3O(CH_2)_2)$ | Cylic ring | Hydrocarbyl |
| II. 2760 | O | S | $((CH_2)_3O(CH_2)_2)$ | Cylic ring | Substituted hydrocarbyl |
| II. 2761 | O | S | $((CH_2)_3O(CH_2)_2)$ | Heterocyclic ring | Hydrogen |
| II. 2762 | O | S | $((CH_2)_3O(CH_2)_2)$ | Heterocyclic ring | Hydrocarbyl |
| II. 2763 | O | S | $((CH_2)_3O(CH_2)_2)$ | Heterocyclic ring | Substituted hydrocarbyl |
| II. 2764 | O | S | $((CH_2)_3O(CH_2)_2)_2$ | Aromatic ring | Hydrogen |
| II. 2765 | O | S | $((CH_2)_3O(CH_2)_2)_2$ | Aromatic ring | Hydrocarbyl |
| II. 2766 | O | S | $((CH_2)_3O(CH_2)_2)_2$ | Aromatic ring | Substituted hydrocarbyl |
| II. 2767 | O | S | $((CH_2)_3O(CH_2)_2)_2$ | Cylic ring | Hydrogen |
| II. 2768 | O | S | $((CH_2)_3O(CH_2)_2)_2$ | Cylic ring | Hydrocarbyl |
| II. 2769 | O | S | $((CH_2)_3O(CH_2)_2)_2$ | Cylic ring | Substituted hydrocarbyl |
| II. 2770 | O | S | $((CH_2)_3O(CH_2)_2)_2$ | Heterocyclic ring | Hydrogen |
| II. 2771 | O | S | $((CH_2)_3O(CH_2)_2)_2$ | Heterocyclic ring | Hydrocarbyl |
| II. 2772 | O | S | $((CH_2)_3O(CH_2)_2)_2$ | Heterocyclic ring | Substituted hydrocarbyl |
| II. 2773 | O | S | $((CH_2)_3O(CH_2)_2)_3$ | Aromatic ring | Hydrogen |
| II. 2774 | O | S | $((CH_2)_3O(CH_2)_2)_3$ | Aromatic ring | Hydrocarbyl |
| II. 2775 | O | S | $((CH_2)_3O(CH_2)_2)_3$ | Aromatic ring | Substituted hydrocarbyl |
| II. 2776 | O | S | $((CH_2)_3O(CH_2)_2)_3$ | Cylic ring | Hydrogen |
| II. 2777 | O | S | $((CH_2)_3O(CH_2)_2)_3$ | Cylic ring | Hydrocarbyl |
| II. 2778 | O | S | $((CH_2)_3O(CH_2)_2)_3$ | Cylic ring | Substituted hydrocarbyl |
| II. 2779 | O | S | $((CH_2)_3O(CH_2)_2)_3$ | Heterocyclic ring | Hydrogen |
| II. 2780 | O | S | $((CH_2)_3O(CH_2)_2)_3$ | Heterocyclic ring | Hydrocarbyl |
| II. 2781 | O | S | $((CH_2)_3O(CH_2)_2)_3$ | Heterocyclic ring | Substituted hydrocarbyl |
| II. 2782 | O | S | $((CH_2)_3O(CH_2)_3)$ | Aromatic ring | Hydrogen |
| II. 2783 | O | S | $((CH_2)_3O(CH_2)_3)$ | Aromatic ring | Hydrocarbyl |
| II. 2784 | O | S | $((CH_2)_3O(CH_2)_3)$ | Aromatic ring | Substituted hydrocarbyl |
| II. 2785 | O | S | $((CH_2)_3O(CH_2)_3)$ | Cylic ring | Hydrogen |
| II. 2786 | O | S | $((CH_2)_3O(CH_2)_3)$ | Cylic ring | Hydrocarbyl |
| II. 2787 | O | S | $((CH_2)_3O(CH_2)_3)$ | Cylic ring | Substituted hydrocarbyl |
| II. 2788 | O | S | $((CH_2)_3O(CH_2)_3)$ | Heterocyclic ring | Hydrogen |
| II. 2789 | O | S | $((CH_2)_3O(CH_2)_3)$ | Heterocyclic ring | Hydrocarbyl |
| II. 2790 | O | S | $((CH_2)_3O(CH_2)_3)$ | Heterocyclic ring | Substituted hydrocarbyl |
| II. 2791 | O | S | $((CH_2)_3O(CH_2)_3)_2$ | Aromatic ring | Hydrogen |
| II. 2792 | O | S | $((CH_2)_3O(CH_2)_3)_2$ | Aromatic ring | Hydrocarbyl |
| II. 2793 | O | S | $((CH_2)_3O(CH_2)_3)_2$ | Aromatic ring | Substituted hydrocarbyl |
| II. 2794 | O | S | $((CH_2)_3O(CH_2)_3)_2$ | Cylic ring | Hydrogen |
| II. 2795 | O | S | $((CH_2)_3O(CH_2)_3)_2$ | Cylic ring | Hydrocarbyl |
| II. 2796 | O | S | $((CH_2)_3O(CH_2)_3)_2$ | Cylic ring | Substituted hydrocarbyl |
| II. 2797 | O | S | $((CH_2)_3O(CH_2)_3)_2$ | Heterocyclic ring | Hydrogen |
| II. 2798 | O | S | $((CH_2)_3O(CH_2)_3)_2$ | Heterocyclic ring | Hydrocarbyl |
| II. 2799 | O | S | $((CH_2)_3O(CH_2)_3)_2$ | Heterocyclic ring | Substituted hydrocarbyl |
| II. 2800 | O | S | $((CH_2)_3O(CH_2)_3)_3$ | Aromatic ring | Hydrogen |
| II. 2801 | O | S | $((CH_2)_3O(CH_2)_3)_3$ | Aromatic ring | Hydrocarbyl |
| II. 2802 | O | S | $((CH_2)_3O(CH_2)_3)_3$ | Aromatic ring | Substituted hydrocarbyl |
| II. 2803 | O | S | $((CH_2)_3O(CH_2)_3)_3$ | Cylic ring | Hydrogen |
| II. 2804 | O | S | $((CH_2)_3O(CH_2)_3)_3$ | Cylic ring | Hydrocarbyl |
| II. 2805 | O | S | $((CH_2)_3O(CH_2)_3)_3$ | Cylic ring | Substituted hydrocarbyl |
| II. 2806 | O | S | $((CH_2)_3O(CH_2)_3)_3$ | Heterocyclic ring | Hydrogen |
| II. 2807 | O | S | $((CH_2)_3O(CH_2)_3)_3$ | Heterocyclic ring | Hydrocarbyl |
| II. 2808 | O | S | $((CH_2)_3O(CH_2)_3)_3$ | Heterocyclic ring | Substituted hydrocarbyl |
| II. 2809 | O | O | $(CH_2)$ | Aromatic ring | Hydrogen |
| II. 2810 | O | O | $(CH_2)$ | Aromatic ring | Hydrocarbyl |
| II. 2811 | O | O | $(CH_2)$ | Aromatic ring | Substituted hydrocarbyl |
| II. 2812 | O | O | $(CH_2)$ | Cylic ring | Hydrogen |
| II. 2813 | O | O | $(CH_2)$ | Cylic ring | Hydrocarbyl |
| II. 2814 | O | O | $(CH_2)$ | Cylic ring | Substituted hydrocarbyl |
| II. 2815 | O | O | $(CH_2)$ | Heterocyclic ring | Hydrogen |
| II. 2816 | O | O | $(CH_2)$ | Heterocyclic ring | Hydrocarbyl |
| II. 2817 | O | O | $(CH_2)$ | Heterocyclic ring | Substituted hydrocarbyl |
| II. 2818 | O | O | $(CH_2)_2$ | Aromatic ring | Hydrogen |
| II. 2819 | O | O | $(CH_2)_2$ | Aromatic ring | Hydrocarbyl |
| II. 2820 | O | O | $(CH_2)_2$ | Aromatic ring | Substituted hydrocarbyl |
| II. 2821 | O | O | $(CH_2)_2$ | Cylic ring | Hydrogen |
| II. 2822 | O | O | $(CH_2)_2$ | Cylic ring | Hydrocarbyl |
| II. 2823 | O | O | $(CH_2)_2$ | Cylic ring | Substituted hydrocarbyl |
| II. 2824 | O | O | $(CH_2)_2$ | Heterocyclic ring | Hydrogen |
| II. 2825 | O | O | $(CH_2)_2$ | Heterocyclic ring | Hydrocarbyl |
| II. 2826 | O | O | $(CH_2)_2$ | Heterocyclic ring | Substituted hydrocarbyl |
| II. 2827 | O | O | $(CH_2)_3$ | Aromatic ring | Hydrogen |
| II. 2828 | O | O | $(CH_2)_3$ | Aromatic ring | Hydrocarbyl |
| II. 2829 | O | O | $(CH_2)_3$ | Aromatic ring | Substituted hydrocarbyl |
| II. 2830 | O | O | $(CH_2)_3$ | Cylic ring | Hydrogen |

TABLE 2-continued

Selected compounds from Formula (II)

| | R1 | R2 | R4 | R5 | R6 |
|---|---|---|---|---|---|
| II. 2831 | O | O | (CH$_2$)$_3$ | Cylic ring | Hydrocarbyl |
| II. 2832 | O | O | (CH$_2$)$_3$ | Cylic ring | Substituted hydrocarbyl |
| II. 2833 | O | O | (CH$_2$)$_3$ | Heterocyclic ring | Hydrogen |
| II. 2834 | O | O | (CH$_2$)$_3$ | Heterocyclic ring | Hydrocarbyl |
| II. 2835 | O | O | (CH$_2$)$_3$ | Heterocyclic ring | Substituted hydrocarbyl |
| II. 2836 | O | O | ((CH$_2$)O) | Aromatic ring | Hydrogen |
| II. 2837 | O | O | ((CH$_2$)O) | Aromatic ring | Hydrocarbyl |
| II. 2838 | O | O | ((CH$_2$)O) | Aromatic ring | Substituted hydrocarbyl |
| II. 2839 | O | O | ((CH$_2$)O) | Cylic ring | Hydrogen |
| II. 2840 | O | O | ((CH$_2$)O) | Cylic ring | Hydrocarbyl |
| II. 2841 | O | O | ((CH$_2$)O) | Cylic ring | Substituted hydrocarbyl |
| II. 2842 | O | O | ((CH$_2$)O) | Heterocyclic ring | Hydrogen |
| II. 2843 | O | O | ((CH$_2$)O) | Heterocyclic ring | Hydrocarbyl |
| II. 2844 | O | O | ((CH$_2$)O) | Heterocyclic ring | Substituted hydrocarbyl |
| II. 2845 | O | O | ((CH$_2$)O)$_2$ | Aromatic ring | Hydrogen |
| II. 2846 | O | O | ((CH$_2$)O)$_2$ | Aromatic ring | Hydrocarbyl |
| II. 2847 | O | O | ((CH$_2$)O)$_2$ | Aromatic ring | Substituted hydrocarbyl |
| II. 2848 | O | O | ((CH$_2$)O)$_2$ | Cylic ring | Hydrogen |
| II. 2849 | O | O | ((CH$_2$)O)$_2$ | Cylic ring | Hydrocarbyl |
| II. 2850 | O | O | ((CH$_2$)O)$_2$ | Cylic ring | Substituted hydrocarbyl |
| II. 2851 | O | O | ((CH$_2$)O)$_2$ | Heterocyclic ring | Hydrogen |
| II. 2852 | O | O | ((CH$_2$)O)$_2$ | Heterocyclic ring | Hydrocarbyl |
| II. 2853 | O | O | ((CH$_2$)O)$_2$ | Heterocyclic ring | Substituted hydrocarbyl |
| II. 2854 | O | O | ((CH$_2$)O)$_3$ | Aromatic ring | Hydrogen |
| II. 2855 | O | O | ((CH$_2$)O)$_3$ | Aromatic ring | Hydrocarbyl |
| II. 2856 | O | O | ((CH$_2$)O)$_3$ | Aromatic ring | Substituted hydrocarbyl |
| II. 2857 | O | O | ((CH$_2$)O)$_3$ | Cylic ring | Hydrogen |
| II. 2858 | O | O | ((CH$_2$)O)$_3$ | Cylic ring | Hydrocarbyl |
| II. 2859 | O | O | ((CH$_2$)O)$_3$ | Cylic ring | Substituted hydrocarbyl |
| II. 2860 | O | O | ((CH$_2$)O)$_3$ | Heterocyclic ring | Hydrogen |
| II. 2861 | O | O | ((CH$_2$)O)$_3$ | Heterocyclic ring | Hydrocarbyl |
| II. 2862 | O | O | ((CH$_2$)O)$_3$ | Heterocyclic ring | Substituted hydrocarbyl |
| II. 2863 | O | O | ((CH$_2$)$_2$O) | Aromatic ring | Hydrogen |
| II. 2864 | O | O | ((CH$_2$)$_2$O) | Aromatic ring | Hydrocarbyl |
| II. 2865 | O | O | ((CH$_2$)$_2$O) | Aromatic ring | Substituted hydrocarbyl |
| II. 2866 | O | O | ((CH$_2$)$_2$O) | Cylic ring | Hydrogen |
| II. 2867 | O | O | ((CH$_2$)$_2$O) | Cylic ring | Hydrocarbyl |
| II. 2868 | O | O | ((CH$_2$)$_2$O) | Cylic ring | Substituted hydrocarbyl |
| II. 2869 | O | O | ((CH$_2$)$_2$O) | Heterocyclic ring | Hydrogen |
| II. 2870 | O | O | ((CH$_2$)$_2$O) | Heterocyclic ring | Hydrocarbyl |
| II. 2871 | O | O | ((CH$_2$)$_2$O) | Heterocyclic ring | Substituted hydrocarbyl |
| II. 2872 | O | O | ((CH$_2$)$_2$O)$_2$ | Aromatic ring | Hydrogen |
| II. 2873 | O | O | ((CH$_2$)$_2$O)$_2$ | Aromatic ring | Hydrocarbyl |
| II. 2874 | O | O | ((CH$_2$)$_2$O)$_2$ | Aromatic ring | Substituted hydrocarbyl |
| II. 2875 | O | O | ((CH$_2$)$_2$O)$_2$ | Cylic ring | Hydrogen |
| II. 2876 | O | O | ((CH$_2$)$_2$O)$_2$ | Cylic ring | Hydrocarbyl |
| II. 2877 | O | O | ((CH$_2$)$_2$O)$_2$ | Cylic ring | Substituted hydrocarbyl |
| II. 2878 | O | O | ((CH$_2$)$_2$O)$_2$ | Heterocyclic ring | Hydrogen |
| II. 2879 | O | O | ((CH$_2$)$_2$O)$_2$ | Heterocyclic ring | Hydrocarbyl |
| II. 2880 | O | O | ((CH$_2$)$_2$O)$_2$ | Heterocyclic ring | Substituted hydrocarbyl |
| II. 2881 | O | O | ((CH$_2$)$_2$O)$_3$ | Aromatic ring | Hydrogen |
| II. 2882 | O | O | ((CH$_2$)$_2$O)$_3$ | Aromatic ring | Hydrocarbyl |
| II. 2883 | O | O | ((CH$_2$)$_2$O)$_3$ | Aromatic ring | Substituted hydrocarbyl |
| II. 2884 | O | O | ((CH$_2$)$_2$O)$_3$ | Cylic ring | Hydrogen |
| II. 2885 | O | O | ((CH$_2$)$_2$O)$_3$ | Cylic ring | Hydrocarbyl |
| II. 2886 | O | O | ((CH$_2$)$_2$O)$_3$ | Cylic ring | Substituted hydrocarbyl |
| II. 2887 | O | O | ((CH$_2$)$_2$O)$_3$ | Heterocyclic ring | Hydrogen |
| II. 2888 | O | O | ((CH$_2$)$_2$O)$_3$ | Heterocyclic ring | Hydrocarbyl |
| II. 2889 | O | O | ((CH$_2$)$_2$O)$_3$ | Heterocyclic ring | Substituted hydrocarbyl |
| II. 2890 | O | O | ((CH$_2$)$_3$O) | Aromatic ring | Hydrogen |
| II. 2891 | O | O | ((CH$_2$)$_3$O) | Aromatic ring | Hydrocarbyl |
| II. 2892 | O | O | ((CH$_2$)$_3$O) | Aromatic ring | Substituted hydrocarbyl |
| II. 2893 | O | O | ((CH$_2$)$_3$O) | Cylic ring | Hydrogen |
| II. 2894 | O | O | ((CH$_2$)$_3$O) | Cylic ring | Hydrocarbyl |
| II. 2895 | O | O | ((CH$_2$)$_3$O) | Cylic ring | Substituted hydrocarbyl |
| II. 2896 | O | O | ((CH$_2$)$_3$O) | Heterocyclic ring | Hydrogen |
| II. 2897 | O | O | ((CH$_2$)$_3$O) | Heterocyclic ring | Hydrocarbyl |
| II. 2898 | O | O | ((CH$_2$)$_3$O) | Heterocyclic ring | Substituted hydrocarbyl |
| II. 2899 | O | O | ((CH$_2$)$_3$O)$_2$ | Aromatic ring | Hydrogen |
| II. 2900 | O | O | ((CH$_2$)$_3$O)$_2$ | Aromatic ring | Hydrocarbyl |
| II. 2901 | O | O | ((CH$_2$)$_3$O)$_2$ | Aromatic ring | Substituted hydrocarbyl |
| II. 2902 | O | O | ((CH$_2$)$_3$O)$_2$ | Cylic ring | Hydrogen |
| II. 2903 | O | O | ((CH$_2$)$_3$O)$_2$ | Cylic ring | Hydrocarbyl |
| II. 2904 | O | O | ((CH$_2$)$_3$O)$_2$ | Cylic ring | Substituted hydrocarbyl |
| II. 2905 | O | O | ((CH$_2$)$_3$O)$_2$ | Heterocyclic ring | Hydrogen |
| II. 2906 | O | O | ((CH$_2$)$_3$O)$_2$ | Heterocyclic ring | Hydrocarbyl |

TABLE 2-continued

Selected compounds from Formula (II)

| | R1 | R2 | R4 | R5 | R6 |
|---|---|---|---|---|---|
| II. 2907 | O | O | ((CH$_2$)$_3$O)$_2$ | Heterocyclic ring | Substituted hydrocarbyl |
| II. 2908 | O | O | ((CH$_2$)$_3$O)$_3$ | Aromatic ring | Hydrogen |
| II. 2909 | O | O | ((CH$_2$)$_3$O)$_3$ | Aromatic ring | Hydrocarbyl |
| II. 2910 | O | O | ((CH$_2$)$_3$O)$_3$ | Aromatic ring | Substituted hydrocarbyl |
| II. 2911 | O | O | ((CH$_2$)$_3$O)$_3$ | Cylic ring | Hydrogen |
| II. 2912 | O | O | ((CH$_2$)$_3$O)$_3$ | Cylic ring | Hydrocarbyl |
| II. 2913 | O | O | ((CH$_2$)$_3$O)$_3$ | Cylic ring | Substituted hydrocarbyl |
| II. 2914 | O | O | ((CH$_2$)$_3$O)$_3$ | Heterocyclic ring | Hydrogen |
| II. 2915 | O | O | ((CH$_2$)$_3$O)$_3$ | Heterocyclic ring | Hydrocarbyl |
| II. 2916 | O | O | ((CH$_2$)$_3$O)$_3$ | Heterocyclic ring | Substituted hydrocarbyl |
| II. 2917 | O | O | ((CH$_2$)O(CH$_2$)) | Aromatic ring | Hydrogen |
| II. 2918 | O | O | ((CH$_2$)O(CH$_2$)) | Aromatic ring | Hydrocarbyl |
| II. 2919 | O | O | ((CH$_2$)O(CH$_2$)) | Aromatic ring | Substituted hydrocarbyl |
| II. 2920 | O | O | ((CH$_2$)O(CH$_2$)) | Cylic ring | Hydrogen |
| II. 2921 | O | O | ((CH$_2$)O(CH$_2$)) | Cylic ring | Hydrocarbyl |
| II. 2922 | O | O | ((CH$_2$)O(CH$_2$)) | Cylic ring | Substituted hydrocarbyl |
| II. 2923 | O | O | ((CH$_2$)O(CH$_2$)) | Heterocyclic ring | Hydrogen |
| II. 2924 | O | O | ((CH$_2$)O(CH$_2$)) | Heterocyclic ring | Hydrocarbyl |
| II. 2925 | O | O | ((CH$_2$)O(CH$_2$)) | Heterocyclic ring | Substituted hydrocarbyl |
| II. 2926 | O | O | ((CH$_2$)O(CH$_2$))$_2$ | Aromatic ring | Hydrogen |
| II. 2927 | O | O | ((CH$_2$)O(CH$_2$))$_2$ | Aromatic ring | Hydrocarbyl |
| II. 2928 | O | O | ((CH$_2$)O(CH$_2$))$_2$ | Aromatic ring | Substituted hydrocarbyl |
| II. 2929 | O | O | ((CH$_2$)O(CH$_2$))$_2$ | Cylic ring | Hydrogen |
| II. 2930 | O | O | ((CH$_2$)O(CH$_2$))$_2$ | Cylic ring | Hydrocarbyl |
| II. 2931 | O | O | ((CH$_2$)O(CH$_2$))$_2$ | Cylic ring | Substituted hydrocarbyl |
| II. 2932 | O | O | ((CH$_2$)O(CH$_2$))$_2$ | Heterocyclic ring | Hydrogen |
| II. 2933 | O | O | ((CH$_2$)O(CH$_2$))$_2$ | Heterocyclic ring | Hydrocarbyl |
| II. 2934 | O | O | ((CH$_2$)O(CH$_2$))$_2$ | Heterocyclic ring | Substituted hydrocarbyl |
| II. 2935 | O | O | ((CH$_2$)O(CH$_2$))$_3$ | Aromatic ring | Hydrogen |
| II. 2936 | O | O | ((CH$_2$)O(CH$_2$))$_3$ | Aromatic ring | Hydrocarbyl |
| II. 2937 | O | O | ((CH$_2$)O(CH$_2$))$_3$ | Aromatic ring | Substituted hydrocarbyl |
| II. 2938 | O | O | ((CH$_2$)O(CH$_2$))$_3$ | Cylic ring | Hydrogen |
| II. 2939 | O | O | ((CH$_2$)O(CH$_2$))$_3$ | Cylic ring | Hydrocarbyl |
| II. 2940 | O | O | ((CH$_2$)O(CH$_2$))$_3$ | Cylic ring | Substituted hydrocarbyl |
| II. 2941 | O | O | ((CH$_2$)O(CH$_2$))$_3$ | Heterocyclic ring | Hydrogen |
| II. 2942 | O | O | ((CH$_2$)O(CH$_2$))$_3$ | Heterocyclic ring | Hydrocarbyl |
| II. 2943 | O | O | ((CH$_2$)O(CH$_2$))$_3$ | Heterocyclic ring | Substituted hydrocarbyl |
| II. 2944 | O | O | ((CH$_2$)O(CH$_2$)$_2$) | Aromatic ring | Hydrogen |
| II. 2945 | O | O | ((CH$_2$)O(CH$_2$)$_2$) | Aromatic ring | Hydrocarbyl |
| II. 2946 | O | O | ((CH$_2$)O(CH$_2$)$_2$) | Aromatic ring | Substituted hydrocarbyl |
| II. 2947 | O | O | ((CH$_2$)O(CH$_2$)$_2$) | Cylic ring | Hydrogen |
| II. 2948 | O | O | ((CH$_2$)O(CH$_2$)$_2$) | Cylic ring | Hydrocarbyl |
| II. 2949 | O | O | ((CH$_2$)O(CH$_2$)$_2$) | Cylic ring | Substituted hydrocarbyl |
| II. 2950 | O | O | ((CH$_2$)O(CH$_2$)$_2$) | Heterocyclic ring | Hydrogen |
| II. 2951 | O | O | ((CH$_2$)O(CH$_2$)$_2$) | Heterocyclic ring | Hydrocarbyl |
| II. 2952 | O | O | ((CH$_2$)O(CH$_2$)$_2$) | Heterocyclic ring | Substituted hydrocarbyl |
| II. 2953 | O | O | ((CH$_2$)O(CH$_2$)$_2$)$_2$ | Aromatic ring | Hydrogen |
| II. 2954 | O | O | ((CH$_2$)O(CH$_2$)$_2$)$_2$ | Aromatic ring | Hydrocarbyl |
| II. 2955 | O | O | ((CH$_2$)O(CH$_2$)$_2$)$_2$ | Aromatic ring | Substituted hydrocarbyl |
| II. 2956 | O | O | ((CH$_2$)O(CH$_2$)$_2$)$_2$ | Cylic ring | Hydrogen |
| II. 2957 | O | O | ((CH$_2$)O(CH$_2$)$_2$)$_2$ | Cylic ring | Hydrocarbyl |
| II. 2958 | O | O | ((CH$_2$)O(CH$_2$)$_2$)$_2$ | Cylic ring | Substituted hydrocarbyl |
| II. 2959 | O | O | ((CH$_2$)O(CH$_2$)$_2$)$_2$ | Heterocyclic ring | Hydrogen |
| II. 2960 | O | O | ((CH$_2$)O(CH$_2$)$_2$)$_2$ | Heterocyclic ring | Hydrocarbyl |
| II. 2961 | O | O | ((CH$_2$)O(CH$_2$)$_2$)$_2$ | Heterocyclic ring | Substituted hydrocarbyl |
| II. 2962 | O | O | ((CH$_2$)O(CH$_2$)$_2$)$_3$ | Aromatic ring | Hydrogen |
| II. 2963 | O | O | ((CH$_2$)O(CH$_2$)$_2$)$_3$ | Aromatic ring | Hydrocarbyl |
| II. 2964 | O | O | ((CH$_2$)O(CH$_2$)$_2$)$_3$ | Aromatic ring | Substituted hydrocarbyl |
| II. 2965 | O | O | ((CH$_2$)O(CH$_2$)$_2$)$_3$ | Cylic ring | Hydrogen |
| II. 2966 | O | O | ((CH$_2$)O(CH$_2$)$_2$)$_3$ | Cylic ring | Hydrocarbyl |
| II. 2967 | O | O | ((CH$_2$)O(CH$_2$)$_2$)$_3$ | Cylic ring | Substituted hydrocarbyl |
| II. 2968 | O | O | ((CH$_2$)O(CH$_2$)$_2$)$_3$ | Heterocyclic ring | Hydrogen |
| II. 2969 | O | O | ((CH$_2$)O(CH$_2$)$_2$)$_3$ | Heterocyclic ring | Hydrocarbyl |
| II. 2970 | O | O | ((CH$_2$)O(CH$_2$)$_2$)$_3$ | Heterocyclic ring | Substituted hydrocarbyl |
| II. 2971 | O | O | ((CH$_2$)O(CH$_2$)$_3$) | Aromatic ring | Hydrogen |
| II. 2972 | O | O | ((CH$_2$)O(CH$_2$)$_3$) | Aromatic ring | Hydrocarbyl |
| II. 2973 | O | O | ((CH$_2$)O(CH$_2$)$_3$) | Aromatic ring | Substituted hydrocarbyl |
| II. 2974 | O | O | ((CH$_2$)O(CH$_2$)$_3$) | Cylic ring | Hydrogen |
| II. 2975 | O | O | ((CH$_2$)O(CH$_2$)$_3$) | Cylic ring | Hydrocarbyl |
| II. 2976 | O | O | ((CH$_2$)O(CH$_2$)$_3$) | Cylic ring | Substituted hydrocarbyl |
| II. 2977 | O | O | ((CH$_2$)O(CH$_2$)$_3$) | Heterocyclic ring | Hydrogen |
| II. 2978 | O | O | ((CH$_2$)O(CH$_2$)$_3$) | Heterocyclic ring | Hydrocarbyl |
| II. 2979 | O | O | ((CH$_2$)O(CH$_2$)$_3$) | Heterocyclic ring | Substituted hydrocarbyl |
| II. 2980 | O | O | ((CH$_2$)O(CH$_2$)$_3$)$_2$ | Aromatic ring | Hydrogen |
| II. 2981 | O | O | ((CH$_2$)O(CH$_2$)$_3$)$_2$ | Aromatic ring | Hydrocarbyl |
| II. 2982 | O | O | ((CH$_2$)O(CH$_2$)$_3$)$_2$ | Aromatic ring | Substituted hydrocarbyl |

TABLE 2-continued

Selected compounds from Formula (II)

| | R1 | R2 | R4 | R5 | R6 |
|---|---|---|---|---|---|
| II. 2983 | O | O | $((CH_2)O(CH_2)_3)_2$ | Cylic ring | Hydrogen |
| II. 2984 | O | O | $((CH_2)O(CH_2)_3)_2$ | Cylic ring | Hydrocarbyl |
| II. 2985 | O | O | $((CH_2)O(CH_2)_3)_2$ | Cylic ring | Substituted hydrocarbyl |
| II. 2986 | O | O | $((CH_2)O(CH_2)_3)_2$ | Heterocyclic ring | Hydrogen |
| II. 2987 | O | O | $((CH_2)O(CH_2)_3)_2$ | Heterocyclic ring | Hydrocarbyl |
| II. 2988 | O | O | $((CH_2)O(CH_2)_3)_2$ | Heterocyclic ring | Substituted hydrocarbyl |
| II. 2989 | O | O | $((CH_2)O(CH_2)_3)_3$ | Aromatic ring | Hydrogen |
| II. 2990 | O | O | $((CH_2)O(CH_2)_3)_3$ | Aromatic ring | Hydrocarbyl |
| II. 2991 | O | O | $((CH_2)O(CH_2)_3)_3$ | Aromatic ring | Substituted hydrocarbyl |
| II. 2992 | O | O | $((CH_2)O(CH_2)_3)_3$ | Cylic ring | Hydrogen |
| II. 2993 | O | O | $((CH_2)O(CH_2)_3)_3$ | Cylic ring | Hydrocarbyl |
| II. 2994 | O | O | $((CH_2)O(CH_2)_3)_3$ | Cylic ring | Substituted hydrocarbyl |
| II. 2995 | O | O | $((CH_2)O(CH_2)_3)_3$ | Heterocyclic ring | Hydrogen |
| II. 2996 | O | O | $((CH_2)O(CH_2)_3)_3$ | Heterocyclic ring | Hydrocarbyl |
| II. 2997 | O | O | $((CH_2)O(CH_2)_3)_3$ | Heterocyclic ring | Substituted hydrocarbyl |
| II. 2998 | O | O | $((CH_2)_2O(CH_2))$ | Aromatic ring | Hydrogen |
| II. 2999 | O | O | $((CH_2)_2O(CH_2))$ | Aromatic ring | Hydrocarbyl |
| II. 3000 | O | O | $((CH_2)_2O(CH_2))$ | Aromatic ring | Substituted hydrocarbyl |
| II. 3001 | O | O | $((CH_2)_2O(CH_2))$ | Cylic ring | Hydrogen |
| II. 3002 | O | O | $((CH_2)_2O(CH_2))$ | Cylic ring | Hydrocarbyl |
| II. 3003 | O | O | $((CH_2)_2O(CH_2))$ | Cylic ring | Substituted hydrocarbyl |
| II. 3004 | O | O | $((CH_2)_2O(CH_2))$ | Heterocyclic ring | Hydrogen |
| II. 3005 | O | O | $((CH_2)_2O(CH_2))$ | Heterocyclic ring | Hydrocarbyl |
| II. 3006 | O | O | $((CH_2)_2O(CH_2))$ | Heterocyclic ring | Substituted hydrocarbyl |
| II. 3007 | O | O | $((CH_2)_2O(CH_2))_2$ | Aromatic ring | Hydrogen |
| II. 3008 | O | O | $((CH_2)_2O(CH_2))_2$ | Aromatic ring | Hydrocarbyl |
| II. 3009 | O | O | $((CH_2)_2O(CH_2))_2$ | Aromatic ring | Substituted hydrocarbyl |
| II. 3010 | O | O | $((CH_2)_2O(CH_2))_2$ | Cylic ring | Hydrogen |
| II. 3011 | O | O | $((CH_2)_2O(CH_2))_2$ | Cylic ring | Hydrocarbyl |
| II. 3012 | O | O | $((CH_2)_2O(CH_2))_2$ | Cylic ring | Substituted hydrocarbyl |
| II. 3013 | O | O | $((CH_2)_2O(CH_2))_2$ | Heterocyclic ring | Hydrogen |
| II. 3014 | O | O | $((CH_2)_2O(CH_2))_2$ | Heterocyclic ring | Hydrocarbyl |
| II. 3015 | O | O | $((CH_2)_2O(CH_2))_2$ | Heterocyclic ring | Substituted hydrocarbyl |
| II. 3016 | O | O | $((CH_2)_2O(CH_2))_3$ | Aromatic ring | Hydrogen |
| II. 3017 | O | O | $((CH_2)_2O(CH_2))_3$ | Aromatic ring | Hydrocarbyl |
| II. 3018 | O | O | $((CH_2)_2O(CH_2))_3$ | Aromatic ring | Substituted hydrocarbyl |
| II. 3019 | O | O | $((CH_2)_2O(CH_2))_3$ | Cylic ring | Hydrogen |
| II. 3020 | O | O | $((CH_2)_2O(CH_2))_3$ | Cylic ring | Hydrocarbyl |
| II. 3021 | O | O | $((CH_2)_2O(CH_2))_3$ | Cylic ring | Substituted hydrocarbyl |
| II. 3022 | O | O | $((CH_2)_2O(CH_2))_3$ | Heterocyclic ring | Hydrogen |
| II. 3023 | O | O | $((CH_2)_2O(CH_2))_3$ | Heterocyclic ring | Hydrocarbyl |
| II. 3024 | O | O | $((CH_2)_2O(CH_2))_3$ | Heterocyclic ring | Substituted hydrocarbyl |
| II. 3025 | O | O | $((CH_2)_2O(CH_2)_2)$ | Aromatic ring | Hydrogen |
| II. 3026 | O | O | $((CH_2)_2O(CH_2)_2)$ | Aromatic ring | Hydrocarbyl |
| II. 3027 | O | O | $((CH_2)_2O(CH_2)_2)$ | Aromatic ring | Substituted hydrocarbyl |
| II. 3028 | O | O | $((CH_2)_2O(CH_2)_2)$ | Cylic ring | Hydrogen |
| II. 3029 | O | O | $((CH_2)_2O(CH_2)_2)$ | Cylic ring | Hydrocarbyl |
| II. 3030 | O | O | $((CH_2)_2O(CH_2)_2)$ | Cylic ring | Substituted hydrocarbyl |
| II. 3031 | O | O | $((CH_2)_2O(CH_2)_2)$ | Heterocyclic ring | Hydrogen |
| II. 3032 | O | O | $((CH_2)_2O(CH_2)_2)$ | Heterocyclic ring | Hydrocarbyl |
| II. 3033 | O | O | $((CH_2)_2O(CH_2)_2)$ | Heterocyclic ring | Substituted hydrocarbyl |
| II. 3034 | O | O | $((CH_2)_2O(CH_2)_2)_2$ | Aromatic ring | Hydrogen |
| II. 3035 | O | O | $((CH_2)_2O(CH_2)_2)_2$ | Aromatic ring | Hydrocarbyl |
| II. 3036 | O | O | $((CH_2)_2O(CH_2)_2)_2$ | Aromatic ring | Substituted hydrocarbyl |
| II. 3037 | O | O | $((CH_2)_2O(CH_2)_2)_2$ | Cylic ring | Hydrogen |
| II. 3038 | O | O | $((CH_2)_2O(CH_2)_2)_2$ | Cylic ring | Hydrocarbyl |
| II. 3039 | O | O | $((CH_2)_2O(CH_2)_2)_2$ | Cylic ring | Substituted hydrocarbyl |
| II. 3040 | O | O | $((CH_2)_2O(CH_2)_2)_2$ | Heterocyclic ring | Hydrogen |
| II. 3041 | O | O | $((CH_2)_2O(CH_2)_2)_2$ | Heterocyclic ring | Hydrocarbyl |
| II. 3042 | O | O | $((CH_2)_2O(CH_2)_2)_2$ | Heterocyclic ring | Substituted hydrocarbyl |
| II. 3043 | O | O | $((CH_2)_2O(CH_2)_2)_3$ | Aromatic ring | Hydrogen |
| II. 3044 | O | O | $((CH_2)_2O(CH_2)_2)_3$ | Aromatic ring | Hydrocarbyl |
| II. 3045 | O | O | $((CH_2)_2O(CH_2)_2)_3$ | Aromatic ring | Substituted hydrocarbyl |
| II. 3046 | O | O | $((CH_2)_2O(CH_2)_2)_3$ | Cylic ring | Hydrogen |
| II. 3047 | O | O | $((CH_2)_2O(CH_2)_2)_3$ | Cylic ring | Hydrocarbyl |
| II. 3048 | O | O | $((CH_2)_2O(CH_2)_2)_3$ | Cylic ring | Substituted hydrocarbyl |
| II. 3049 | O | O | $((CH_2)_2O(CH_2)_2)_3$ | Heterocyclic ring | Hydrogen |
| II. 3050 | O | O | $((CH_2)_2O(CH_2)_2)_3$ | Heterocyclic ring | Hydrocarbyl |
| II. 3051 | O | O | $((CH_2)_2O(CH_2)_2)_3$ | Heterocyclic ring | Substituted hydrocarbyl |
| II. 3052 | O | O | $((CH_2)_2O(CH_2)_3)$ | Aromatic ring | Hydrogen |
| II. 3053 | O | O | $((CH_2)_2O(CH_2)_3)$ | Aromatic ring | Hydrocarbyl |
| II. 3054 | O | O | $((CH_2)_2O(CH_2)_3)$ | Aromatic ring | Substituted hydrocarbyl |
| II. 3055 | O | O | $((CH_2)_2O(CH_2)_3)$ | Cylic ring | Hydrogen |
| II. 3056 | O | O | $((CH_2)_2O(CH_2)_3)$ | Cylic ring | Hydrocarbyl |
| II. 3057 | O | O | $((CH_2)_2O(CH_2)_3)$ | Cylic ring | Substituted hydrocarbyl |
| II. 3058 | O | O | $((CH_2)_2O(CH_2)_3)$ | Heterocyclic ring | Hydrogen |

TABLE 2-continued

Selected compounds from Formula (II)

| | R1 | R2 | R4 | R5 | R6 |
|---|---|---|---|---|---|
| II. 3059 | O | O | $((CH_2)_2O(CH_2)_3)$ | Heterocyclic ring | Hydrocarbyl |
| II. 3060 | O | O | $((CH_2)_2O(CH_2)_3)$ | Heterocyclic ring | Substituted hydrocarbyl |
| II. 3061 | O | O | $((CH_2)_2O(CH_2)_3)_2$ | Aromatic ring | Hydrogen |
| II. 3062 | O | O | $((CH_2)_2O(CH_2)_3)_2$ | Aromatic ring | Hydrocarbyl |
| II. 3063 | O | O | $((CH_2)_2O(CH_2)_3)_2$ | Aromatic ring | Substituted hydrocarbyl |
| II. 3064 | O | O | $((CH_2)_2O(CH_2)_3)_2$ | Cylic ring | Hydrogen |
| II. 3065 | O | O | $((CH_2)_2O(CH_2)_3)_2$ | Cylic ring | Hydrocarbyl |
| II. 3066 | O | O | $((CH_2)_2O(CH_2)_3)_2$ | Cylic ring | Substituted hydrocarbyl |
| II. 3067 | O | O | $((CH_2)_2O(CH_2)_3)_2$ | Heterocyclic ring | Hydrogen |
| II. 3068 | O | O | $((CH_2)_2O(CH_2)_3)_2$ | Heterocyclic ring | Hydrocarbyl |
| II. 3069 | O | O | $((CH_2)_2O(CH_2)_3)_2$ | Heterocyclic ring | Substituted hydrocarbyl |
| II. 3070 | O | O | $((CH_2)_2O(CH_2)_3)_3$ | Aromatic ring | Hydrogen |
| II. 3071 | O | O | $((CH_2)_2O(CH_2)_3)_3$ | Aromatic ring | Hydrocarbyl |
| II. 3072 | O | O | $((CH_2)_2O(CH_2)_3)_3$ | Aromatic ring | Substituted hydrocarbyl |
| II. 3073 | O | O | $((CH_2)_2O(CH_2)_3)_3$ | Cylic ring | Hydrogen |
| II. 3074 | O | O | $((CH_2)_2O(CH_2)_3)_3$ | Cylic ring | Hydrocarbyl |
| II. 3075 | O | O | $((CH_2)_2O(CH_2)_3)_3$ | Cylic ring | Substituted hydrocarbyl |
| II. 3076 | O | O | $((CH_2)_2O(CH_2)_3)_3$ | Heterocyclic ring | Hydrogen |
| II. 3077 | O | O | $((CH_2)_2O(CH_2)_3)_3$ | Heterocyclic ring | Hydrocarbyl |
| II. 3078 | O | O | $((CH_2)_2O(CH_2)_3)_3$ | Heterocyclic ring | Substituted hydrocarbyl |
| II. 3079 | O | O | $((CH_2)_3O(CH_2))$ | Aromatic ring | Hydrogen |
| II. 3080 | O | O | $((CH_2)_3O(CH_2))$ | Aromatic ring | Hydrocarbyl |
| II. 3081 | O | O | $((CH_2)_3O(CH_2))$ | Aromatic ring | Substituted hydrocarbyl |
| II. 3082 | O | O | $((CH_2)_3O(CH_2))$ | Cylic ring | Hydrogen |
| II. 3083 | O | O | $((CH_2)_3O(CH_2))$ | Cylic ring | Hydrocarbyl |
| II. 3084 | O | O | $((CH_2)_3O(CH_2))$ | Cylic ring | Substituted hydrocarbyl |
| II. 3085 | O | O | $((CH_2)_3O(CH_2))$ | Heterocyclic ring | Hydrogen |
| II. 3086 | O | O | $((CH_2)_3O(CH_2))$ | Heterocyclic ring | Hydrocarbyl |
| II. 3087 | O | O | $((CH_2)_3O(CH_2))$ | Heterocyclic ring | Substituted hydrocarbyl |
| II. 3088 | O | O | $((CH_2)_3O(CH_2))_2$ | Aromatic ring | Hydrogen |
| II. 3089 | O | O | $((CH_2)_3O(CH_2))_2$ | Aromatic ring | Hydrocarbyl |
| II. 3090 | O | O | $((CH_2)_3O(CH_2))_2$ | Aromatic ring | Substituted hydrocarbyl |
| II. 3091 | O | O | $((CH_2)_3O(CH_2))_2$ | Cylic ring | Hydrogen |
| II. 3092 | O | O | $((CH_2)_3O(CH_2))_2$ | Cylic ring | Hydrocarbyl |
| II. 3093 | O | O | $((CH_2)_3O(CH_2))_2$ | Cylic ring | Substituted hydrocarbyl |
| II. 3094 | O | O | $((CH_2)_3O(CH_2))_2$ | Heterocyclic ring | Hydrogen |
| II. 3095 | O | O | $((CH_2)_3O(CH_2))_2$ | Heterocyclic ring | Hydrocarbyl |
| II. 3096 | O | O | $((CH_2)_3O(CH_2))_2$ | Heterocyclic ring | Substituted hydrocarbyl |
| II. 3097 | O | O | $((CH_2)_3O(CH_2))_3$ | Aromatic ring | Hydrogen |
| II. 3098 | O | O | $((CH_2)_3O(CH_2))_3$ | Aromatic ring | Hydrocarbyl |
| II. 3099 | O | O | $((CH_2)_3O(CH_2))_3$ | Aromatic ring | Substituted hydrocarbyl |
| II. 3100 | O | O | $((CH_2)_3O(CH_2))_3$ | Cylic ring | Hydrogen |
| II. 3101 | O | O | $((CH_2)_3O(CH_2))_3$ | Cylic ring | Hydrocarbyl |
| II. 3102 | O | O | $((CH_2)_3O(CH_2))_3$ | Cylic ring | Substituted hydrocarbyl |
| II. 3103 | O | O | $((CH_2)_3O(CH_2))_3$ | Heterocyclic ring | Hydrogen |
| II. 3104 | O | O | $((CH_2)_3O(CH_2))_3$ | Heterocyclic ring | Hydrocarbyl |
| II. 3105 | O | O | $((CH_2)_3O(CH_2))_3$ | Heterocyclic ring | Substituted hydrocarbyl |
| II. 3106 | O | O | $((CH_2)_3O(CH_2)_2)$ | Aromatic ring | Hydrogen |
| II. 3107 | O | O | $((CH_2)_3O(CH_2)_2)$ | Aromatic ring | Hydrocarbyl |
| II. 3108 | O | O | $((CH_2)_3O(CH_2)_2)$ | Aromatic ring | Substituted hydrocarbyl |
| II. 3109 | O | O | $((CH_2)_3O(CH_2)_2)$ | Cylic ring | Hydrogen |
| II. 3110 | O | O | $((CH_2)_3O(CH_2)_2)$ | Cylic ring | Hydrocarbyl |
| II. 3111 | O | O | $((CH_2)_3O(CH_2)_2)$ | Cylic ring | Substituted hydrocarbyl |
| II. 3112 | O | O | $((CH_2)_3O(CH_2)_2)$ | Heterocyclic ring | Hydrogen |
| II. 3113 | O | O | $((CH_2)_3O(CH_2)_2)$ | Heterocyclic ring | Hydrocarbyl |
| II. 3114 | O | O | $((CH_2)_3O(CH_2)_2)$ | Heterocyclic ring | Substituted hydrocarbyl |
| II. 3115 | O | O | $((CH_2)_3O(CH_2)_2)_2$ | Aromatic ring | Hydrogen |
| II. 3116 | O | O | $((CH_2)_3O(CH_2)_2)_2$ | Aromatic ring | Hydrocarbyl |
| II. 3117 | O | O | $((CH_2)_3O(CH_2)_2)_2$ | Aromatic ring | Substituted hydrocarbyl |
| II. 3118 | O | O | $((CH_2)_3O(CH_2)_2)_2$ | Cylic ring | Hydrogen |
| II. 3119 | O | O | $((CH_2)_3O(CH_2)_2)_2$ | Cylic ring | Hydrocarbyl |
| II. 3120 | O | O | $((CH_2)_3O(CH_2)_2)_2$ | Cylic ring | Substituted hydrocarbyl |
| II. 3121 | O | O | $((CH_2)_3O(CH_2)_2)_2$ | Heterocyclic ring | Hydrogen |
| II. 3122 | O | O | $((CH_2)_3O(CH_2)_2)_2$ | Heterocyclic ring | Hydrocarbyl |
| II. 3123 | O | O | $((CH_2)_3O(CH_2)_2)_2$ | Heterocyclic ring | Substituted hydrocarbyl |
| II. 3124 | O | O | $((CH_2)_3O(CH_2)_2)_3$ | Aromatic ring | Hydrogen |
| II. 3125 | O | O | $((CH_2)_3O(CH_2)_2)_3$ | Aromatic ring | Hydrocarbyl |
| II. 3126 | O | O | $((CH_2)_3O(CH_2)_2)_3$ | Aromatic ring | Substituted hydrocarbyl |
| II. 3127 | O | O | $((CH_2)_3O(CH_2)_2)_3$ | Cylic ring | Hydrogen |
| II. 3128 | O | O | $((CH_2)_3O(CH_2)_2)_3$ | Cylic ring | Hydrocarbyl |
| II. 3129 | O | O | $((CH_2)_3O(CH_2)_2)_3$ | Cylic ring | Substituted hydrocarbyl |
| II. 3130 | O | O | $((CH_2)_3O(CH_2)_2)_3$ | Heterocyclic ring | Hydrogen |
| II. 3131 | O | O | $((CH_2)_3O(CH_2)_2)_3$ | Heterocyclic ring | Hydrocarbyl |
| II. 3132 | O | O | $((CH_2)_3O(CH_2)_2)_3$ | Heterocyclic ring | Substituted hydrocarbyl |
| II. 3133 | O | O | $((CH_2)_3O(CH_2)_3)$ | Aromatic ring | Hydrogen |
| II. 3134 | O | O | $((CH_2)_3O(CH_2)_3)$ | Aromatic ring | Hydrocarbyl |

TABLE 2-continued

Selected compounds from Formula (II)

| | R1 | R2 | R4 | R5 | R6 |
|---|---|---|---|---|---|
| II. 3135 | O | O | $((CH_2)_3O(CH_2)_3)$ | Aromatic ring | Substituted hydrocarbyl |
| II. 3136 | O | O | $((CH_2)_3O(CH_2)_3)$ | Cylic ring | Hydrogen |
| II. 3137 | O | O | $((CH_2)_3O(CH_2)_3)$ | Cylic ring | Hydrocarbyl |
| II. 3138 | O | O | $((CH_2)_3O(CH_2)_3)$ | Cylic ring | Substituted hydrocarbyl |
| II. 3139 | O | O | $((CH_2)_3O(CH_2)_3)$ | Heterocyclic ring | Hydrogen |
| II. 3140 | O | O | $((CH_2)_3O(CH_2)_3)$ | Heterocyclic ring | Hydrocarbyl |
| II. 3141 | O | O | $((CH_2)_3O(CH_2)_3)$ | Heterocyclic ring | Substituted hydrocarbyl |
| II. 3142 | O | O | $((CH_2)_3O(CH_2)_3)_2$ | Aromatic ring | Hydrogen |
| II. 3143 | O | O | $((CH_2)_3O(CH_2)_3)_2$ | Aromatic ring | Hydrocarbyl |
| II. 3144 | O | O | $((CH_2)_3O(CH_2)_3)_2$ | Aromatic ring | Substituted hydrocarbyl |
| II. 3145 | O | O | $((CH_2)_3O(CH_2)_3)_2$ | Cylic ring | Hydrogen |
| II. 3146 | O | O | $((CH_2)_3O(CH_2)_3)_2$ | Cylic ring | Hydrocarbyl |
| II. 3147 | O | O | $((CH_2)_3O(CH_2)_3)_2$ | Cylic ring | Substituted hydrocarbyl |
| II. 3148 | O | O | $((CH_2)_3O(CH_2)_3)_2$ | Heterocyclic ring | Hydrogen |
| II. 3149 | O | O | $((CH_2)_3O(CH_2)_3)_2$ | Heterocyclic ring | Hydrocarbyl |
| II. 3150 | O | O | $((CH_2)_3O(CH_2)_3)_2$ | Heterocyclic ring | Substituted hydrocarbyl |
| II. 3151 | O | O | $((CH_2)_3O(CH_2)_3)_3$ | Aromatic ring | Hydrogen |
| II. 3152 | O | O | $((CH_2)_3O(CH_2)_3)_3$ | Aromatic ring | Hydrocarbyl |
| II. 3153 | O | O | $((CH_2)_3O(CH_2)_3)_3$ | Aromatic ring | Substituted hydrocarbyl |
| II. 3154 | O | O | $((CH_2)_3O(CH_2)_3)_3$ | Cylic ring | Hydrogen |
| II. 3155 | O | O | $((CH_2)_3O(CH_2)_3)_3$ | Cylic ring | Hydrocarbyl |
| II. 3156 | O | O | $((CH_2)_3O(CH_2)_3)_3$ | Cylic ring | Substituted hydrocarbyl |
| II. 3157 | O | O | $((CH_2)_3O(CH_2)_3)_3$ | Heterocyclic ring | Hydrogen |
| II. 3158 | O | O | $((CH_2)_3O(CH_2)_3)_3$ | Heterocyclic ring | Hydrocarbyl |
| II. 3159 | O | O | $((CH_2)_3O(CH_2)_3)_3$ | Heterocyclic ring | Substituted hydrocarbyl |

In yet another embodiment, the present invention encompasses a compound of formula (III):

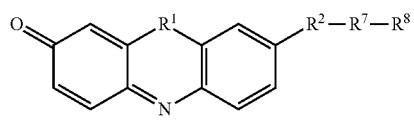

wherein:
$R^1$ is chosen from N, S, or O;
$R^2$ is chosen from N, S, or O;
$R^7$ is chosen from the group consisting of $((CH_2)_dO)_e$, and $((CH_2)_fO(CH_2)_g)_h$, wherein d, e, f, g, and h are integers from 1 to 3; and
$R^8$ is chosen from the group consisting of hydrogen, a hydrocarbyl, and substituted hydrocarbyl.

In certain embodiments, a compound of the invention may be a compound of formula (III) wherein $R^1$ is O. In other embodiments, a compound of the invention may be a compound of formula (III) wherein $R^1$ is N. In still other embodiments, a compound of the invention may be a compound of formula (III) wherein $R^1$ is S.

In particular embodiments, a compound of the invention may be a compound listed in Table 3.

TABLE 3

Selected compounds of Formula (III)

| Compound | R1 | R2 | R7 | R8 |
|---|---|---|---|---|
| III.1 | N | N | $((CH_2)O)$ | Hydrogen |
| III.2 | N | N | $((CH_2)O)$ | Hydrocarbyl |
| III.3 | N | N | $((CH_2)O)$ | Substituted hydrocarbyl |
| III.4 | N | N | $((CH_2)O)_2$ | Hydrogen |
| III.5 | N | N | $((CH_2)O)_2$ | Hydrocarbyl |
| III.6 | N | N | $((CH_2)O)_2$ | Substituted hydrocarbyl |
| III.7 | N | N | $((CH_2)O)_3$ | Hydrogen |
| III.8 | N | N | $((CH_2)O)_3$ | Hydrocarbyl |

TABLE 3-continued

Selected compounds of Formula (III)

| Compound | R1 | R2 | R7 | R8 |
|---|---|---|---|---|
| III.9 | N | N | $((CH_2)O)_3$ | Substituted hydrocarbyl |
| III.10 | N | N | $((CH_2)_2O)$ | Hydrogen |
| III.11 | N | N | $((CH_2)_2O)$ | Hydrocarbyl |
| III.12 | N | N | $((CH_2)_2O)$ | Substituted hydrocarbyl |
| III.13 | N | N | $((CH_2)_2O)_2$ | Hydrogen |
| III.14 | N | N | $((CH_2)_2O)_2$ | Hydrocarbyl |
| III.15 | N | N | $((CH_2)_2O)_2$ | Substituted hydrocarbyl |
| III.16 | N | N | $((CH_2)_2O)_3$ | Hydrogen |
| III.17 | N | N | $((CH_2)_2O)_3$ | Hydrocarbyl |
| III.18 | N | N | $((CH_2)_2O)_3$ | Substituted hydrocarbyl |
| III.19 | N | N | $((CH_2)_3O)$ | Hydrogen |
| III.20 | N | N | $((CH_2)_3O)$ | Hydrocarbyl |
| III.21 | N | N | $((CH_2)_3O)$ | Substituted hydrocarbyl |
| III.22 | N | N | $((CH_2)_3O)_2$ | Hydrogen |
| III.23 | N | N | $((CH_2)_3O)_2$ | Hydrocarbyl |
| III.24 | N | N | $((CH_2)_3O)_2$ | Substituted hydrocarbyl |
| III.25 | N | N | $((CH_2)_3O)_3$ | Hydrogen |
| III.26 | N | N | $((CH_2)_3O)_3$ | Hydrocarbyl |
| III.27 | N | N | $((CH_2)_3O)_3$ | Substituted hydrocarbyl |
| III.28 | N | N | $((CH_2)O(CH_2))$ | Hydrogen |
| III.29 | N | N | $((CH_2)O(CH_2))$ | Hydrocarbyl |
| III.30 | N | N | $((CH_2)O(CH_2))$ | Substituted hydrocarbyl |
| III.31 | N | N | $((CH_2)O(CH_2))_2$ | Hydrogen |
| III.32 | N | N | $((CH_2)O(CH_2))_2$ | Hydrocarbyl |
| III.33 | N | N | $((CH_2)O(CH_2))_2$ | Substituted hydrocarbyl |
| III.34 | N | N | $((CH_2)O(CH_2))_3$ | Hydrogen |
| III.35 | N | N | $((CH_2)O(CH_2))_3$ | Hydrocarbyl |
| III.36 | N | N | $((CH_2)O(CH_2))_3$ | Substituted hydrocarbyl |
| III.37 | N | N | $((CH_2)O(CH_2)_2)$ | Hydrogen |
| III.38 | N | N | $((CH_2)O(CH_2)_2)$ | Hydrocarbyl |
| III.39 | N | N | $((CH_2)O(CH_2)_2)$ | Substituted hydrocarbyl |
| III.40 | N | N | $((CH_2)O(CH_2)_2)_2$ | Hydrogen |
| III.41 | N | N | $((CH_2)O(CH_2)_2)_2$ | Hydrocarbyl |
| III.42 | N | N | $((CH_2)O(CH_2)_2)_2$ | Substituted hydrocarbyl |
| III.43 | N | N | $((CH_2)O(CH_2)_2)_3$ | Hydrogen |
| III.44 | N | N | $((CH_2)O(CH_2)_2)_3$ | Hydrocarbyl |
| III.45 | N | N | $((CH_2)O(CH_2)_2)_3$ | Substituted hydrocarbyl |
| III.46 | N | N | $((CH_2)O(CH_2)_3)$ | Hydrogen |
| III.47 | N | N | $((CH_2)O(CH_2)_3)$ | Hydrocarbyl |
| III.48 | N | N | $((CH_2)O(CH_2)_3)$ | Substituted hydrocarbyl |
| III.49 | N | N | $((CH_2)O(CH_2)_3)_2$ | Hydrogen |

TABLE 3-continued

Selected compounds of Formula (III)

| Compound | R1 | R2 | R7 | R8 |
|---|---|---|---|---|
| III.50 | N | N | $((CH_2)O(CH_2)_3)_2$ | Hydrocarbyl |
| III.51 | N | N | $((CH_2)O(CH_2)_3)_2$ | Substituted hydrocarbyl |
| III.52 | N | N | $((CH_2)O(CH_2)_3)_3$ | Hydrogen |
| III.53 | N | N | $((CH_2)O(CH_2)_3)_3$ | Hydrocarbyl |
| III.54 | N | N | $((CH_2)O(CH_2)_3)_3$ | Substituted hydrocarbyl |
| III.55 | N | N | $((CH_2)_2O(CH_2))$ | Hydrogen |
| III.56 | N | N | $((CH_2)_2O(CH_2))$ | Hydrocarbyl |
| III.57 | N | N | $((CH_2)_2O(CH_2))$ | Substituted hydrocarbyl |
| III.58 | N | N | $((CH_2)_2O(CH_2))_2$ | Hydrogen |
| III.59 | N | N | $((CH_2)_2O(CH_2))_2$ | Hydrocarbyl |
| III.60 | N | N | $((CH_2)_2O(CH_2))_2$ | Substituted hydrocarbyl |
| III.61 | N | N | $((CH_2)_2O(CH_2))_3$ | Hydrogen |
| III.62 | N | N | $((CH_2)_2O(CH_2))_3$ | Hydrocarbyl |
| III.63 | N | N | $((CH_2)_2O(CH_2))_3$ | Substituted hydrocarbyl |
| III.64 | N | N | $((CH_2)_2O(CH_2)_2)$ | Hydrogen |
| III.65 | N | N | $((CH_2)_2O(CH_2)_2)$ | Hydrocarbyl |
| III.66 | N | N | $((CH_2)_2O(CH_2)_2)$ | Substituted hydrocarbyl |
| III.67 | N | N | $((CH_2)_2O(CH_2)_2)_2$ | Hydrogen |
| III.68 | N | N | $((CH_2)_2O(CH_2)_2)_2$ | Hydrocarbyl |
| III.69 | N | N | $((CH_2)_2O(CH_2)_2)_2$ | Substituted hydrocarbyl |
| III.70 | N | N | $((CH_2)_2O(CH_2)_2)_3$ | Hydrogen |
| III.71 | N | N | $((CH_2)_2O(CH_2)_2)_3$ | Hydrocarbyl |
| III.72 | N | N | $((CH_2)_2O(CH_2)_2)_3$ | Substituted hydrocarbyl |
| III.73 | N | N | $((CH_2)_2O(CH_2)_3)$ | Hydrogen |
| III.74 | N | N | $((CH_2)_2O(CH_2)_3)$ | Hydrocarbyl |
| III.75 | N | N | $((CH_2)_2O(CH_2)_3)$ | Substituted hydrocarbyl |
| III.76 | N | N | $((CH_2)_2O(CH_2)_3)_2$ | Hydrogen |
| III.77 | N | N | $((CH_2)_2O(CH_2)_3)_2$ | Hydrocarbyl |
| III.78 | N | N | $((CH_2)_2O(CH_2)_3)_2$ | Substituted hydrocarbyl |
| III.79 | N | N | $((CH_2)_2O(CH_2)_3)_3$ | Hydrogen |
| III.80 | N | N | $((CH_2)_2O(CH_2)_3)_3$ | Hydrocarbyl |
| III.81 | N | N | $((CH_2)_2O(CH_2)_3)_3$ | Substituted hydrocarbyl |
| III.82 | N | N | $((CH_2)_3O(CH_2))$ | Hydrogen |
| III.83 | N | N | $((CH_2)_3O(CH_2))$ | Hydrocarbyl |
| III.84 | N | N | $((CH_2)_3O(CH_2))$ | Substituted hydrocarbyl |
| III.85 | N | N | $((CH_2)_3O(CH_2))_2$ | Hydrogen |
| III.86 | N | N | $((CH_2)_3O(CH_2))_2$ | Hydrocarbyl |
| III.87 | N | N | $((CH_2)_3O(CH_2))_2$ | Substituted hydrocarbyl |
| III.88 | N | N | $((CH_2)_3O(CH_2))_3$ | Hydrogen |
| III.89 | N | N | $((CH_2)_3O(CH_2))_3$ | Hydrocarbyl |
| III.90 | N | N | $((CH_2)_3O(CH_2))_3$ | Substituted hydrocarbyl |
| III.91 | N | N | $((CH_2)_3O(CH_2)_2)$ | Hydrogen |
| III.92 | N | N | $((CH_2)_3O(CH_2)_2)$ | Hydrocarbyl |
| III.93 | N | N | $((CH_2)_3O(CH_2)_2)$ | Substituted hydrocarbyl |
| III.94 | N | N | $((CH_2)_3O(CH_2)_2)_2$ | Hydrogen |
| III.95 | N | N | $((CH_2)_3O(CH_2)_2)_2$ | Hydrocarbyl |
| III.96 | N | N | $((CH_2)_3O(CH_2)_2)_2$ | Substituted hydrocarbyl |
| III.97 | N | N | $((CH_2)_3O(CH_2)_2)_3$ | Hydrogen |
| III.98 | N | N | $((CH_2)_3O(CH_2)_2)_3$ | Hydrocarbyl |
| III.99 | N | N | $((CH_2)_3O(CH_2)_2)_3$ | Substituted hydrocarbyl |
| III.100 | N | N | $((CH_2)_3O(CH_2)_3)$ | Hydrogen |
| III.101 | N | N | $((CH_2)_3O(CH_2)_3)$ | Hydrocarbyl |
| III.102 | N | N | $((CH_2)_3O(CH_2)_3)$ | Substituted hydrocarbyl |
| III.103 | N | N | $((CH_2)_3O(CH_2)_3)_2$ | Hydrogen |
| III.104 | N | N | $((CH_2)_3O(CH_2)_3)_2$ | Hydrocarbyl |
| III.105 | N | N | $((CH_2)_3O(CH_2)_3)_2$ | Substituted hydrocarbyl |
| III.106 | N | N | $((CH_2)_3O(CH_2)_3)_3$ | Hydrogen |
| III.107 | N | N | $((CH_2)_3O(CH_2)_3)_3$ | Hydrocarbyl |
| III.108 | N | N | $((CH_2)_3O(CH_2)_3)_3$ | Substituted hydrocarbyl |
| III.109 | N | S | $((CH_2)O)$ | Hydrogen |
| III.110 | N | S | $((CH_2)O)$ | Hydrocarbyl |
| III.111 | N | S | $((CH_2)O)$ | Substituted hydrocarbyl |
| III.112 | N | S | $((CH_2)O)_2$ | Hydrogen |
| III.113 | N | S | $((CH_2)O)_2$ | Hydrocarbyl |
| III.114 | N | S | $((CH_2)O)_2$ | Substituted hydrocarbyl |
| III.115 | N | S | $((CH_2)O)_3$ | Hydrogen |
| III.116 | N | S | $((CH_2)O)_3$ | Hydrocarbyl |
| III.117 | N | S | $((CH_2)O)_3$ | Substituted hydrocarbyl |
| III.118 | N | S | $((CH_2)_2O)$ | Hydrogen |
| III.119 | N | S | $((CH_2)_2O)$ | Hydrocarbyl |
| III.120 | N | S | $((CH_2)_2O)$ | Substituted hydrocarbyl |
| III.121 | N | S | $((CH_2)_2O)_2$ | Hydrogen |
| III.122 | N | S | $((CH_2)_2O)_2$ | Hydrocarbyl |
| III.123 | N | S | $((CH_2)_2O)_2$ | Substituted hydrocarbyl |
| III.124 | N | S | $((CH_2)_2O)_3$ | Hydrogen |
| III.125 | N | S | $((CH_2)_2O)_3$ | Hydrocarbyl |
| III.126 | N | S | $((CH_2)_2O)_3$ | Substituted hydrocarbyl |
| III.127 | N | S | $((CH_2)_3O)$ | Hydrogen |
| III.128 | N | S | $((CH_2)_3O)$ | Hydrocarbyl |
| III.129 | N | S | $((CH_2)_3O)$ | Substituted hydrocarbyl |
| III.130 | N | S | $((CH_2)_3O)_2$ | Hydrogen |
| III.131 | N | S | $((CH_2)_3O)_2$ | Hydrocarbyl |
| III.132 | N | S | $((CH_2)_3O)_2$ | Substituted hydrocarbyl |
| III.133 | N | S | $((CH_2)_3O)_3$ | Hydrogen |
| III.134 | N | S | $((CH_2)_3O)_3$ | Hydrocarbyl |
| III.135 | N | S | $((CH_2)_3O)_3$ | Substituted hydrocarbyl |
| III.136 | N | S | $((CH_2)O(CH_2))$ | Hydrogen |
| III.137 | N | S | $((CH_2)O(CH_2))$ | Hydrocarbyl |
| III.138 | N | S | $((CH_2)O(CH_2))$ | Substituted hydrocarbyl |
| III.139 | N | S | $((CH_2)O(CH_2))_2$ | Hydrogen |
| III.140 | N | S | $((CH_2)O(CH_2))_2$ | Hydrocarbyl |
| III.141 | N | S | $((CH_2)O(CH_2))_2$ | Substituted hydrocarbyl |
| III.142 | N | S | $((CH_2)O(CH_2))_3$ | Hydrogen |
| III.143 | N | S | $((CH_2)O(CH_2))_3$ | Hydrocarbyl |
| III.144 | N | S | $((CH_2)O(CH_2))_3$ | Substituted hydrocarbyl |
| III.145 | N | S | $((CH_2)O(CH_2)_2)$ | Hydrogen |
| III.146 | N | S | $((CH_2)O(CH_2)_2)$ | Hydrocarbyl |
| III.147 | N | S | $((CH_2)O(CH_2)_2)$ | Substituted hydrocarbyl |
| III.148 | N | S | $((CH_2)O(CH_2)_2)_2$ | Hydrogen |
| III.149 | N | S | $((CH_2)O(CH_2)_2)_2$ | Hydrocarbyl |
| III.150 | N | S | $((CH_2)O(CH_2)_2)_2$ | Substituted hydrocarbyl |
| III.151 | N | S | $((CH_2)O(CH_2)_2)_3$ | Hydrogen |
| III.152 | N | S | $((CH_2)O(CH_2)_2)_3$ | Hydrocarbyl |
| III.153 | N | S | $((CH_2)O(CH_2)_2)_3$ | Substituted hydrocarbyl |
| III.154 | N | S | $((CH_2)O(CH_2)_3)$ | Hydrogen |
| III.155 | N | S | $((CH_2)O(CH_2)_3)$ | Hydrocarbyl |
| III.156 | N | S | $((CH_2)O(CH_2)_3)$ | Substituted hydrocarbyl |
| III.157 | N | S | $((CH_2)O(CH_2)_3)_2$ | Hydrogen |
| III.158 | N | S | $((CH_2)O(CH_2)_3)_2$ | Hydrocarbyl |
| III.159 | N | S | $((CH_2)O(CH_2)_3)_2$ | Substituted hydrocarbyl |
| III.160 | N | S | $((CH_2)O(CH_2)_3)_3$ | Hydrogen |
| III.161 | N | S | $((CH_2)O(CH_2)_3)_3$ | Hydrocarbyl |
| III.162 | N | S | $((CH_2)O(CH_2)_3)_3$ | Substituted hydrocarbyl |
| III.163 | N | S | $((CH_2)_2O(CH_2))$ | Hydrogen |
| III.164 | N | S | $((CH_2)_2O(CH_2))$ | Hydrocarbyl |
| III.165 | N | S | $((CH_2)_2O(CH_2))$ | Substituted hydrocarbyl |
| III.166 | N | S | $((CH_2)_2O(CH_2))_2$ | Hydrogen |
| III.167 | N | S | $((CH_2)_2O(CH_2))_2$ | Hydrocarbyl |
| III.168 | N | S | $((CH_2)_2O(CH_2))_2$ | Substituted hydrocarbyl |
| III.169 | N | S | $((CH_2)_2O(CH_2))_3$ | Hydrogen |
| III.170 | N | S | $((CH_2)_2O(CH_2))_3$ | Hydrocarbyl |
| III.171 | N | S | $((CH_2)_2O(CH_2))_3$ | Substituted hydrocarbyl |
| III.172 | N | S | $((CH_2)_2O(CH_2)_2)$ | Hydrogen |
| III.173 | N | S | $((CH_2)_2O(CH_2)_2)$ | Hydrocarbyl |
| III.174 | N | S | $((CH_2)_2O(CH_2)_2)$ | Substituted hydrocarbyl |
| III.175 | N | S | $((CH_2)_2O(CH_2)_2)_2$ | Hydrogen |
| III.176 | N | S | $((CH_2)_2O(CH_2)_2)_2$ | Hydrocarbyl |
| III.177 | N | S | $((CH_2)_2O(CH_2)_2)_2$ | Substituted hydrocarbyl |
| III.178 | N | S | $((CH_2)_2O(CH_2)_2)_3$ | Hydrogen |
| III.179 | N | S | $((CH_2)_2O(CH_2)_2)_3$ | Hydrocarbyl |
| III.180 | N | S | $((CH_2)_2O(CH_2)_2)_3$ | Substituted hydrocarbyl |
| III.181 | N | S | $((CH_2)_2O(CH_2)_3)$ | Hydrogen |
| III.182 | N | S | $((CH_2)_2O(CH_2)_3)$ | Hydrocarbyl |
| III.183 | N | S | $((CH_2)_2O(CH_2)_3)$ | Substituted hydrocarbyl |
| III.184 | N | S | $((CH_2)_2O(CH_2)_3)_2$ | Hydrogen |
| III.185 | N | S | $((CH_2)_2O(CH_2)_3)_2$ | Hydrocarbyl |
| III.186 | N | S | $((CH_2)_2O(CH_2)_3)_2$ | Substituted hydrocarbyl |
| III.187 | N | S | $((CH_2)_2O(CH_2)_3)_3$ | Hydrogen |
| III.188 | N | S | $((CH_2)_2O(CH_2)_3)_3$ | Hydrocarbyl |
| III.189 | N | S | $((CH_2)_2O(CH_2)_3)_3$ | Substituted hydrocarbyl |
| III.190 | N | S | $((CH_2)_3O(CH_2))$ | Hydrogen |
| III.191 | N | S | $((CH_2)_3O(CH_2))$ | Hydrocarbyl |
| III.192 | N | S | $((CH_2)_3O(CH_2))$ | Substituted hydrocarbyl |
| III.193 | N | S | $((CH_2)_3O(CH_2))_2$ | Hydrogen |
| III.194 | N | S | $((CH_2)_3O(CH_2))_2$ | Hydrocarbyl |
| III.195 | N | S | $((CH_2)_3O(CH_2))_2$ | Substituted hydrocarbyl |
| III.196 | N | S | $((CH_2)_3O(CH_2))_3$ | Hydrogen |
| III.197 | N | S | $((CH_2)_3O(CH_2))_3$ | Hydrocarbyl |
| III.198 | N | S | $((CH_2)_3O(CH_2))_3$ | Substituted hydrocarbyl |
| III.199 | N | S | $((CH_2)_3O(CH_2)_2)$ | Hydrogen |
| III.200 | N | S | $((CH_2)_3O(CH_2)_2)$ | Hydrocarbyl |
| III.201 | N | S | $((CH_2)_3O(CH_2)_2)$ | Substituted hydrocarbyl |

TABLE 3-continued

Selected compounds of Formula (III)

| Compound | R1 | R2 | R7 | R8 |
|---|---|---|---|---|
| III.202 | N | S | $((CH_2)_3O(CH_2)_2)_2$ | Hydrogen |
| III.203 | N | S | $((CH_2)_3O(CH_2)_2)_2$ | Hydrocarbyl |
| III.204 | N | S | $((CH_2)_3O(CH_2)_2)_2$ | Substituted hydrocarbyl |
| III.205 | N | S | $((CH_2)_3O(CH_2)_2)_3$ | Hydrogen |
| III.206 | N | S | $((CH_2)_3O(CH_2)_2)_3$ | Hydrocarbyl |
| III.207 | N | S | $((CH_2)_3O(CH_2)_2)_3$ | Substituted hydrocarbyl |
| III.208 | N | S | $((CH_2)_3O(CH_2)_3)$ | Hydrogen |
| III.209 | N | S | $((CH_2)_3O(CH_2)_3)$ | Hydrocarbyl |
| III.210 | N | S | $((CH_2)_3O(CH_2)_3)$ | Substituted hydrocarbyl |
| III.211 | N | S | $((CH_2)_3O(CH_2)_3)_2$ | Hydrogen |
| III.212 | N | S | $((CH_2)_3O(CH_2)_3)_2$ | Hydrocarbyl |
| III.213 | N | S | $((CH_2)_3O(CH_2)_3)_2$ | Substituted hydrocarbyl |
| III.214 | N | S | $((CH_2)_3O(CH_2)_3)_3$ | Hydrogen |
| III.215 | N | S | $((CH_2)_3O(CH_2)_3)_3$ | Hydrocarbyl |
| III.216 | N | S | $((CH_2)_3O(CH_2)_3)_3$ | Substituted hydrocarbyl |
| III.217 | N | O | $((CH_2)O)$ | Hydrogen |
| III.218 | N | O | $((CH_2)O)$ | Hydrocarbyl |
| III.219 | N | O | $((CH_2)O)$ | Substituted hydrocarbyl |
| III.220 | N | O | $((CH_2)O)_2$ | Hydrogen |
| III.221 | N | O | $((CH_2)O)_2$ | Hydrocarbyl |
| III.222 | N | O | $((CH_2)O)_2$ | Substituted hydrocarbyl |
| III.223 | N | O | $((CH_2)O)_3$ | Hydrogen |
| III.224 | N | O | $((CH_2)O)_3$ | Hydrocarbyl |
| III.225 | N | O | $((CH_2)O)_3$ | Substituted hydrocarbyl |
| III.226 | N | O | $((CH_2)_2O)$ | Hydrogen |
| III.227 | N | O | $((CH_2)_2O)$ | Hydrocarbyl |
| III.228 | N | O | $((CH_2)_2O)$ | Substituted hydrocarbyl |
| III.229 | N | O | $((CH_2)_2O)_2$ | Hydrogen |
| III.230 | N | O | $((CH_2)_2O)_2$ | Hydrocarbyl |
| III.231 | N | O | $((CH_2)_2O)_2$ | Substituted hydrocarbyl |
| III.232 | N | O | $((CH_2)_2O)_3$ | Hydrogen |
| III.233 | N | O | $((CH_2)_2O)_3$ | Hydrocarbyl |
| III.234 | N | O | $((CH_2)_2O)_3$ | Substituted hydrocarbyl |
| III.235 | N | O | $((CH_2)_3O)$ | Hydrogen |
| III.236 | N | O | $((CH_2)_3O)$ | Hydrocarbyl |
| III.237 | N | O | $((CH_2)_3O)$ | Substituted hydrocarbyl |
| III.238 | N | O | $((CH_2)_3O)_2$ | Hydrogen |
| III.239 | N | O | $((CH_2)_3O)_2$ | Hydrocarbyl |
| III.240 | N | O | $((CH_2)_3O)_2$ | Substituted hydrocarbyl |
| III.241 | N | O | $((CH_2)_3O)_3$ | Hydrogen |
| III.242 | N | O | $((CH_2)_3O)_3$ | Hydrocarbyl |
| III.243 | N | O | $((CH_2)_3O)_3$ | Substituted hydrocarbyl |
| III.244 | N | O | $((CH_2)O(CH_2))$ | Hydrogen |
| III.245 | N | O | $((CH_2)O(CH_2))$ | Hydrocarbyl |
| III.246 | N | O | $((CH_2)O(CH_2))$ | Substituted hydrocarbyl |
| III.247 | N | O | $((CH_2)O(CH_2))_2$ | Hydrogen |
| III.248 | N | O | $((CH_2)O(CH_2))_2$ | Hydrocarbyl |
| III.249 | N | O | $((CH_2)O(CH_2))_2$ | Substituted hydrocarbyl |
| III.250 | N | O | $((CH_2)O(CH_2))_3$ | Hydrogen |
| III.251 | N | O | $((CH_2)O(CH_2))_3$ | Hydrocarbyl |
| III.252 | N | O | $((CH_2)O(CH_2))_3$ | Substituted hydrocarbyl |
| III.253 | N | O | $((CH_2)O(CH_2)_2)$ | Hydrogen |
| III.254 | N | O | $((CH_2)O(CH_2)_2)$ | Hydrocarbyl |
| III.255 | N | O | $((CH_2)O(CH_2)_2)$ | Substituted hydrocarbyl |
| III.256 | N | O | $((CH_2)O(CH_2)_2)_2$ | Hydrogen |
| III.257 | N | O | $((CH_2)O(CH_2)_2)_2$ | Hydrocarbyl |
| III.258 | N | O | $((CH_2)O(CH_2)_2)_2$ | Substituted hydrocarbyl |
| III.259 | N | O | $((CH_2)O(CH_2)_2)_3$ | Hydrogen |
| III.260 | N | O | $((CH_2)O(CH_2)_2)_3$ | Hydrocarbyl |
| III.261 | N | O | $((CH_2)O(CH_2)_2)_3$ | Substituted hydrocarbyl |
| III.262 | N | O | $((CH_2)O(CH_2)_3)$ | Hydrogen |
| III.263 | N | O | $((CH_2)O(CH_2)_3)$ | Hydrocarbyl |
| III.264 | N | O | $((CH_2)O(CH_2)_3)$ | Substituted hydrocarbyl |
| III.265 | N | O | $((CH_2)O(CH_2)_3)_2$ | Hydrogen |
| III.266 | N | O | $((CH_2)O(CH_2)_3)_2$ | Hydrocarbyl |
| III.267 | N | O | $((CH_2)O(CH_2)_3)_2$ | Substituted hydrocarbyl |
| III.268 | N | O | $((CH_2)O(CH_2)_3)_3$ | Hydrogen |
| III.269 | N | O | $((CH_2)O(CH_2)_3)_3$ | Hydrocarbyl |
| III.270 | N | O | $((CH_2)O(CH_2)_3)_3$ | Substituted hydrocarbyl |
| III.271 | N | O | $((CH_2)_2O(CH_2))$ | Hydrogen |
| III.272 | N | O | $((CH_2)_2O(CH_2))$ | Hydrocarbyl |
| III.273 | N | O | $((CH_2)_2O(CH_2))$ | Substituted hydrocarbyl |
| III.274 | N | O | $((CH_2)_2O(CH_2))_2$ | Hydrogen |
| III.275 | N | O | $((CH_2)_2O(CH_2))_2$ | Hydrocarbyl |
| III.276 | N | O | $((CH_2)_2O(CH_2))_2$ | Substituted hydrocarbyl |
| III.277 | N | O | $((CH_2)_2O(CH_2))_3$ | Hydrogen |
| III.278 | N | O | $((CH_2)_2O(CH_2))_3$ | Hydrocarbyl |
| III.279 | N | O | $((CH_2)_2O(CH_2))_3$ | Substituted hydrocarbyl |
| III.280 | N | O | $((CH_2)_2O(CH_2)_2)$ | Hydrogen |
| III.281 | N | O | $((CH_2)_2O(CH_2)_2)$ | Hydrocarbyl |
| III.282 | N | O | $((CH_2)_2O(CH_2)_2)$ | Substituted hydrocarbyl |
| III.283 | N | O | $((CH_2)_2O(CH_2)_2)_2$ | Hydrogen |
| III.284 | N | O | $((CH_2)_2O(CH_2)_2)_2$ | Hydrocarbyl |
| III.285 | N | O | $((CH_2)_2O(CH_2)_2)_2$ | Substituted hydrocarbyl |
| III.286 | N | O | $((CH_2)_2O(CH_2)_2)_3$ | Hydrogen |
| III.287 | N | O | $((CH_2)_2O(CH_2)_2)_3$ | Hydrocarbyl |
| III.288 | N | O | $((CH_2)_2O(CH_2)_2)_3$ | Substituted hydrocarbyl |
| III.289 | N | O | $((CH_2)_2O(CH_2)_3)$ | Hydrogen |
| III.290 | N | O | $((CH_2)_2O(CH_2)_3)$ | Hydrocarbyl |
| III.291 | N | O | $((CH_2)_2O(CH_2)_3)$ | Substituted hydrocarbyl |
| III.292 | N | O | $((CH_2)_2O(CH_2)_3)_2$ | Hydrogen |
| III.293 | N | O | $((CH_2)_2O(CH_2)_3)_2$ | Hydrocarbyl |
| III.294 | N | O | $((CH_2)_2O(CH_2)_3)_2$ | Substituted hydrocarbyl |
| III.295 | N | O | $((CH_2)_2O(CH_2)_3)_3$ | Hydrogen |
| III.296 | N | O | $((CH_2)_2O(CH_2)_3)_3$ | Hydrocarbyl |
| III.297 | N | O | $((CH_2)_2O(CH_2)_3)_3$ | Substituted hydrocarbyl |
| III.298 | N | O | $((CH_2)_3O(CH_2))$ | Hydrogen |
| III.299 | N | O | $((CH_2)_3O(CH_2))$ | Hydrocarbyl |
| III.300 | N | O | $((CH_2)_3O(CH_2))$ | Substituted hydrocarbyl |
| III.301 | N | O | $((CH_2)_3O(CH_2))_2$ | Hydrogen |
| III.302 | N | O | $((CH_2)_3O(CH_2))_2$ | Hydrocarbyl |
| III.303 | N | O | $((CH_2)_3O(CH_2))_2$ | Substituted hydrocarbyl |
| III.304 | N | O | $((CH_2)_3O(CH_2))_3$ | Hydrogen |
| III.305 | N | O | $((CH_2)_3O(CH_2))_3$ | Hydrocarbyl |
| III.306 | N | O | $((CH_2)_3O(CH_2))_3$ | Substituted hydrocarbyl |
| III.307 | N | O | $((CH_2)_3O(CH_2)_2)$ | Hydrogen |
| III.308 | N | O | $((CH_2)_3O(CH_2)_2)$ | Hydrocarbyl |
| III.309 | N | O | $((CH_2)_3O(CH_2)_2)$ | Substituted hydrocarbyl |
| III.310 | N | O | $((CH_2)_3O(CH_2)_2)_2$ | Hydrogen |
| III.311 | N | O | $((CH_2)_3O(CH_2)_2)_2$ | Hydrocarbyl |
| III.312 | N | O | $((CH_2)_3O(CH_2)_2)_2$ | Substituted hydrocarbyl |
| III.313 | N | O | $((CH_2)_3O(CH_2)_2)_3$ | Hydrogen |
| III.314 | N | O | $((CH_2)_3O(CH_2)_2)_3$ | Hydrocarbyl |
| III.315 | N | O | $((CH_2)_3O(CH_2)_2)_3$ | Substituted hydrocarbyl |
| III.316 | N | O | $((CH_2)_3O(CH_2)_3)$ | Hydrogen |
| III.317 | N | O | $((CH_2)_3O(CH_2)_3)$ | Hydrocarbyl |
| III.318 | N | O | $((CH_2)_3O(CH_2)_3)$ | Substituted hydrocarbyl |
| III.319 | N | O | $((CH_2)_3O(CH_2)_3)_2$ | Hydrogen |
| III.320 | N | O | $((CH_2)_3O(CH_2)_3)_2$ | Hydrocarbyl |
| III.321 | N | O | $((CH_2)_3O(CH_2)_3)_2$ | Substituted hydrocarbyl |
| III.322 | N | O | $((CH_2)_3O(CH_2)_3)_3$ | Hydrogen |
| III.323 | N | O | $((CH_2)_3O(CH_2)_3)_3$ | Hydrocarbyl |
| III.324 | N | O | $((CH_2)_3O(CH_2)_3)_3$ | Substituted hydrocarbyl |
| III.325 | S | N | $((CH_2)O)$ | Hydrogen |
| III.326 | S | N | $((CH_2)O)$ | Hydrocarbyl |
| III.327 | S | N | $((CH_2)O)$ | Substituted hydrocarbyl |
| III.328 | S | N | $((CH_2)O)_2$ | Hydrogen |
| III.329 | S | N | $((CH_2)O)_2$ | Hydrocarbyl |
| III.330 | S | N | $((CH_2)O)_2$ | Substituted hydrocarbyl |
| III.331 | S | N | $((CH_2)O)_3$ | Hydrogen |
| III.332 | S | N | $((CH_2)O)_3$ | Hydrocarbyl |
| III.333 | S | N | $((CH_2)O)_3$ | Substituted hydrocarbyl |
| III.334 | S | N | $((CH_2)_2O)$ | Hydrogen |
| III.335 | S | N | $((CH_2)_2O)$ | Hydrocarbyl |
| III.336 | S | N | $((CH_2)_2O)$ | Substituted hydrocarbyl |
| III.337 | S | N | $((CH_2)_2O)_2$ | Hydrogen |
| III.338 | S | N | $((CH_2)_2O)_2$ | Hydrocarbyl |
| III.339 | S | N | $((CH_2)_2O)_2$ | Substituted hydrocarbyl |
| III.340 | S | N | $((CH_2)_2O)_3$ | Hydrogen |
| III.341 | S | N | $((CH_2)_2O)_3$ | Hydrocarbyl |
| III.342 | S | N | $((CH_2)_2O)_3$ | Substituted hydrocarbyl |
| III.343 | S | N | $((CH_2)_3O)$ | Hydrogen |
| III.344 | S | N | $((CH_2)_3O)$ | Hydrocarbyl |
| III.345 | S | N | $((CH_2)_3O)$ | Substituted hydrocarbyl |
| III.346 | S | N | $((CH_2)_3O)_2$ | Hydrogen |
| III.347 | S | N | $((CH_2)_3O)_2$ | Hydrocarbyl |
| III.348 | S | N | $((CH_2)_3O)_2$ | Substituted hydrocarbyl |
| III.349 | S | N | $((CH_2)_3O)_3$ | Hydrogen |
| III.350 | S | N | $((CH_2)_3O)_3$ | Hydrocarbyl |
| III.351 | S | N | $((CH_2)_3O)_3$ | Substituted hydrocarbyl |
| III.352 | S | N | $((CH_2)O(CH_2))$ | Hydrogen |
| III.353 | S | N | $((CH_2)O(CH_2))$ | Hydrocarbyl |

TABLE 3-continued

Selected compounds of Formula (III)

| Compound | R1 | R2 | R7 | R8 |
|---|---|---|---|---|
| III.354 | S | N | $((CH_2)O(CH_2))$ | Substituted hydrocarbyl |
| III.355 | S | N | $((CH_2)O(CH_2))_2$ | Hydrogen |
| III.356 | S | N | $((CH_2)O(CH_2))_2$ | Hydrocarbyl |
| III.357 | S | N | $((CH_2)O(CH_2))_2$ | Substituted hydrocarbyl |
| III.358 | S | N | $((CH_2)O(CH_2))_3$ | Hydrogen |
| III.359 | S | N | $((CH_2)O(CH_2))_3$ | Hydrocarbyl |
| III.360 | S | N | $((CH_2)O(CH_2))_3$ | Substituted hydrocarbyl |
| III.361 | S | N | $((CH_2)O(CH_2)_2)$ | Hydrogen |
| III.362 | S | N | $((CH_2)O(CH_2)_2)$ | Hydrocarbyl |
| III.363 | S | N | $((CH_2)O(CH_2)_2)$ | Substituted hydrocarbyl |
| III.364 | S | N | $((CH_2)O(CH_2)_2)_2$ | Hydrogen |
| III.365 | S | N | $((CH_2)O(CH_2)_2)_2$ | Hydrocarbyl |
| III.366 | S | N | $((CH_2)O(CH_2)_2)_2$ | Substituted hydrocarbyl |
| III.367 | S | N | $((CH_2)O(CH_2)_2)_3$ | Hydrogen |
| III.368 | S | N | $((CH_2)O(CH_2)_2)_3$ | Hydrocarbyl |
| III.369 | S | N | $((CH_2)O(CH_2)_2)_3$ | Substituted hydrocarbyl |
| III.370 | S | N | $((CH_2)O(CH_2)_3)$ | Hydrogen |
| III.371 | S | N | $((CH_2)O(CH_2)_3)$ | Hydrocarbyl |
| III.372 | S | N | $((CH_2)O(CH_2)_3)$ | Substituted hydrocarbyl |
| III.373 | S | N | $((CH_2)O(CH_2)_3)_2$ | Hydrogen |
| III.374 | S | N | $((CH_2)O(CH_2)_3)_2$ | Hydrocarbyl |
| III.375 | S | N | $((CH_2)O(CH_2)_3)_2$ | Substituted hydrocarbyl |
| III.376 | S | N | $((CH_2)O(CH_2)_3)_3$ | Hydrogen |
| III.377 | S | N | $((CH_2)O(CH_2)_3)_3$ | Hydrocarbyl |
| III.378 | S | N | $((CH_2)O(CH_2)_3)_3$ | Substituted hydrocarbyl |
| III.379 | S | N | $((CH_2)_2O(CH_2))$ | Hydrogen |
| III.380 | S | N | $((CH_2)_2O(CH_2))$ | Hydrocarbyl |
| III.381 | S | N | $((CH_2)_2O(CH_2))$ | Substituted hydrocarbyl |
| III.382 | S | N | $((CH_2)_2O(CH_2))_2$ | Hydrogen |
| III.383 | S | N | $((CH_2)_2O(CH_2))_2$ | Hydrocarbyl |
| III.384 | S | N | $((CH_2)_2O(CH_2))_2$ | Substituted hydrocarbyl |
| III.385 | S | N | $((CH_2)_2O(CH_2))_3$ | Hydrogen |
| III.386 | S | N | $((CH_2)_2O(CH_2))_3$ | Hydrocarbyl |
| III.387 | S | N | $((CH_2)_2O(CH_2))_3$ | Substituted hydrocarbyl |
| III.388 | S | N | $((CH_2)_2O(CH_2)_2)$ | Hydrogen |
| III.389 | S | N | $((CH_2)_2O(CH_2)_2)$ | Hydrocarbyl |
| III.390 | S | N | $((CH_2)_2O(CH_2)_2)$ | Substituted hydrocarbyl |
| III.391 | S | N | $((CH_2)_2O(CH_2)_2)_2$ | Hydrogen |
| III.392 | S | N | $((CH_2)_2O(CH_2)_2)_2$ | Hydrocarbyl |
| III.393 | S | N | $((CH_2)_2O(CH_2)_2)_2$ | Substituted hydrocarbyl |
| III.394 | S | N | $((CH_2)_2O(CH_2)_2)_3$ | Hydrogen |
| III.395 | S | N | $((CH_2)_2O(CH_2)_2)_3$ | Hydrocarbyl |
| III.396 | S | N | $((CH_2)_2O(CH_2)_2)_3$ | Substituted hydrocarbyl |
| III.397 | S | N | $((CH_2)_2O(CH_2)_3)$ | Hydrogen |
| III.398 | S | N | $((CH_2)_2O(CH_2)_3)$ | Hydrocarbyl |
| III.399 | S | N | $((CH_2)_2O(CH_2)_3)$ | Substituted hydrocarbyl |
| III.400 | S | N | $((CH_2)_2O(CH_2)_3)_2$ | Hydrogen |
| III.401 | S | N | $((CH_2)_2O(CH_2)_3)_2$ | Hydrocarbyl |
| III.402 | S | N | $((CH_2)_2O(CH_2)_3)_2$ | Substituted hydrocarbyl |
| III.403 | S | N | $((CH_2)_2O(CH_2)_3)_3$ | Hydrogen |
| III.404 | S | N | $((CH_2)_2O(CH_2)_3)_3$ | Hydrocarbyl |
| III.405 | S | N | $((CH_2)_2O(CH_2)_3)_3$ | Substituted hydrocarbyl |
| III.406 | S | N | $((CH_2)_3O(CH_2))$ | Hydrogen |
| III.407 | S | N | $((CH_2)_3O(CH_2))$ | Hydrocarbyl |
| III.408 | S | N | $((CH_2)_3O(CH_2))$ | Substituted hydrocarbyl |
| III.409 | S | N | $((CH_2)_3O(CH_2))_2$ | Hydrogen |
| III.410 | S | N | $((CH_2)_3O(CH_2))_2$ | Hydrocarbyl |
| III.411 | S | N | $((CH_2)_3O(CH_2))_2$ | Substituted hydrocarbyl |
| III.412 | S | N | $((CH_2)_3O(CH_2))_3$ | Hydrogen |
| III.413 | S | N | $((CH_2)_3O(CH_2))_3$ | Hydrocarbyl |
| III.414 | S | N | $((CH_2)_3O(CH_2))_3$ | Substituted hydrocarbyl |
| III.415 | S | N | $((CH_2)_3O(CH_2)_2)$ | Hydrogen |
| III.416 | S | N | $((CH_2)_3O(CH_2)_2)$ | Hydrocarbyl |
| III.417 | S | N | $((CH_2)_3O(CH_2)_2)$ | Substituted hydrocarbyl |
| III.418 | S | N | $((CH_2)_3O(CH_2)_2)_2$ | Hydrogen |
| III.419 | S | N | $((CH_2)_3O(CH_2)_2)_2$ | Hydrocarbyl |
| III.420 | S | N | $((CH_2)_3O(CH_2)_2)_2$ | Substituted hydrocarbyl |
| III.421 | S | N | $((CH_2)_3O(CH_2)_2)_3$ | Hydrogen |
| III.422 | S | N | $((CH_2)_3O(CH_2)_2)_3$ | Hydrocarbyl |
| III.423 | S | N | $((CH_2)_3O(CH_2)_2)_3$ | Substituted hydrocarbyl |
| III.424 | S | N | $((CH_2)_3O(CH_2)_3)$ | Hydrogen |
| III.425 | S | N | $((CH_2)_3O(CH_2)_3)$ | Hydrocarbyl |
| III.426 | S | N | $((CH_2)_3O(CH_2)_3)$ | Substituted hydrocarbyl |
| III.427 | S | N | $((CH_2)_3O(CH_2)_3)_2$ | Hydrogen |
| III.428 | S | N | $((CH_2)_3O(CH_2)_3)_2$ | Hydrocarbyl |
| III.429 | S | N | $((CH_2)_3O(CH_2)_3)_2$ | Substituted hydrocarbyl |
| III.430 | S | N | $((CH_2)_3O(CH_2)_3)_3$ | Hydrogen |
| III.431 | S | N | $((CH_2)_3O(CH_2)_3)_3$ | Hydrocarbyl |
| III.432 | S | N | $((CH_2)_3O(CH_2)_3)_3$ | Substituted hydrocarbyl |
| III.433 | S | S | $((CH_2)O)$ | Hydrogen |
| III.434 | S | S | $((CH_2)O)$ | Hydrocarbyl |
| III.435 | S | S | $((CH_2)O)$ | Substituted hydrocarbyl |
| III.436 | S | S | $((CH_2)O)_2$ | Hydrogen |
| III.437 | S | S | $((CH_2)O)_2$ | Hydrocarbyl |
| III.438 | S | S | $((CH_2)O)_2$ | Substituted hydrocarbyl |
| III.439 | S | S | $((CH_2)O)_3$ | Hydrogen |
| III.440 | S | S | $((CH_2)O)_3$ | Hydrocarbyl |
| III.441 | S | S | $((CH_2)O)_3$ | Substituted hydrocarbyl |
| III.442 | S | S | $((CH_2)_2O)$ | Hydrogen |
| III.443 | S | S | $((CH_2)_2O)$ | Hydrocarbyl |
| III.444 | S | S | $((CH_2)_2O)$ | Substituted hydrocarbyl |
| III.445 | S | S | $((CH_2)_2O)_2$ | Hydrogen |
| III.446 | S | S | $((CH_2)_2O)_2$ | Hydrocarbyl |
| III.447 | S | S | $((CH_2)_2O)_2$ | Substituted hydrocarbyl |
| III.448 | S | S | $((CH_2)_2O)_3$ | Hydrogen |
| III.449 | S | S | $((CH_2)_2O)_3$ | Hydrocarbyl |
| III.450 | S | S | $((CH_2)_2O)_3$ | Substituted hydrocarbyl |
| III.451 | S | S | $((CH_2)_3O)$ | Hydrogen |
| III.452 | S | S | $((CH_2)_3O)$ | Hydrocarbyl |
| III.453 | S | S | $((CH_2)_3O)$ | Substituted hydrocarbyl |
| III.454 | S | S | $((CH_2)_3O)_2$ | Hydrogen |
| III.455 | S | S | $((CH_2)_3O)_2$ | Hydrocarbyl |
| III.456 | S | S | $((CH_2)_3O)_2$ | Substituted hydrocarbyl |
| III.457 | S | S | $((CH_2)_3O)_3$ | Hydrogen |
| III.458 | S | S | $((CH_2)_3O)_3$ | Hydrocarbyl |
| III.459 | S | S | $((CH_2)_3O)_3$ | Substituted hydrocarbyl |
| III.460 | S | S | $((CH_2)O(CH_2))$ | Hydrogen |
| III.461 | S | S | $((CH_2)O(CH_2))$ | Hydrocarbyl |
| III.462 | S | S | $((CH_2)O(CH_2))$ | Substituted hydrocarbyl |
| III.463 | S | S | $((CH_2)O(CH_2))_2$ | Hydrogen |
| III.464 | S | S | $((CH_2)O(CH_2))_2$ | Hydrocarbyl |
| III.465 | S | S | $((CH_2)O(CH_2))_2$ | Substituted hydrocarbyl |
| III.466 | S | S | $((CH_2)O(CH_2))_3$ | Hydrogen |
| III.467 | S | S | $((CH_2)O(CH_2))_3$ | Hydrocarbyl |
| III.468 | S | S | $((CH_2)O(CH_2))_3$ | Substituted hydrocarbyl |
| III.469 | S | S | $((CH_2)O(CH_2)_2)$ | Hydrogen |
| III.470 | S | S | $((CH_2)O(CH_2)_2)$ | Hydrocarbyl |
| III.471 | S | S | $((CH_2)O(CH_2)_2)$ | Substituted hydrocarbyl |
| III.472 | S | S | $((CH_2)O(CH_2)_2)_2$ | Hydrogen |
| III.473 | S | S | $((CH_2)O(CH_2)_2)_2$ | Hydrocarbyl |
| III.474 | S | S | $((CH_2)O(CH_2)_2)_2$ | Substituted hydrocarbyl |
| III.475 | S | S | $((CH_2)O(CH_2)_2)_3$ | Hydrogen |
| III.476 | S | S | $((CH_2)O(CH_2)_2)_3$ | Hydrocarbyl |
| III.477 | S | S | $((CH_2)O(CH_2)_2)_3$ | Substituted hydrocarbyl |
| III.478 | S | S | $((CH_2)O(CH_2)_3)$ | Hydrogen |
| III.479 | S | S | $((CH_2)O(CH_2)_3)$ | Hydrocarbyl |
| III.480 | S | S | $((CH_2)O(CH_2)_3)$ | Substituted hydrocarbyl |
| III.481 | S | S | $((CH_2)O(CH_2)_3)_2$ | Hydrogen |
| III.482 | S | S | $((CH_2)O(CH_2)_3)_2$ | Hydrocarbyl |
| III.483 | S | S | $((CH_2)O(CH_2)_3)_2$ | Substituted hydrocarbyl |
| III.484 | S | S | $((CH_2)O(CH_2)_3)_3$ | Hydrogen |
| III.485 | S | S | $((CH_2)O(CH_2)_3)_3$ | Hydrocarbyl |
| III.486 | S | S | $((CH_2)O(CH_2)_3)_3$ | Substituted hydrocarbyl |
| III.487 | S | S | $((CH_2)_2O(CH_2))$ | Hydrogen |
| III.488 | S | S | $((CH_2)_2O(CH_2))$ | Hydrocarbyl |
| III.489 | S | S | $((CH_2)_2O(CH_2))$ | Substituted hydrocarbyl |
| III.490 | S | S | $((CH_2)_2O(CH_2))_2$ | Hydrogen |
| III.491 | S | S | $((CH_2)_2O(CH_2))_2$ | Hydrocarbyl |
| III.492 | S | S | $((CH_2)_2O(CH_2))_2$ | Substituted hydrocarbyl |
| III.493 | S | S | $((CH_2)_2O(CH_2))_3$ | Hydrogen |
| III.494 | S | S | $((CH_2)_2O(CH_2))_3$ | Hydrocarbyl |
| III.495 | S | S | $((CH_2)_2O(CH_2))_3$ | Substituted hydrocarbyl |
| III.496 | S | S | $((CH_2)_2O(CH_2)_2)$ | Hydrogen |
| III.497 | S | S | $((CH_2)_2O(CH_2)_2)$ | Hydrocarbyl |
| III.498 | S | S | $((CH_2)_2O(CH_2)_2)$ | Substituted hydrocarbyl |
| III.499 | S | S | $((CH_2)_2O(CH_2)_2)_2$ | Hydrogen |
| III.500 | S | S | $((CH_2)_2O(CH_2)_2)_2$ | Hydrocarbyl |
| III.501 | S | S | $((CH_2)_2O(CH_2)_2)_2$ | Substituted hydrocarbyl |
| III.502 | S | S | $((CH_2)_2O(CH_2)_2)_3$ | Hydrogen |
| III.503 | S | S | $((CH_2)_2O(CH_2)_2)_3$ | Hydrocarbyl |
| III.504 | S | S | $((CH_2)_2O(CH_2)_2)_3$ | Substituted hydrocarbyl |
| III.505 | S | S | $((CH_2)_2O(CH_2)_3)$ | Hydrogen |

TABLE 3-continued

Selected compounds of Formula (III)

| Compound | R1 | R2 | R7 | R8 |
|---|---|---|---|---|
| III.506 | S | S | $((CH_2)_2O(CH_2)_3)$ | Hydrocarbyl |
| III.507 | S | S | $((CH_2)_2O(CH_2)_3)$ | Substituted hydrocarbyl |
| III.508 | S | S | $((CH_2)_2O(CH_2)_3)_2$ | Hydrogen |
| III.509 | S | S | $((CH_2)_2O(CH_2)_3)_2$ | Hydrocarbyl |
| III.510 | S | S | $((CH_2)_2O(CH_2)_3)_2$ | Substituted hydrocarbyl |
| III.511 | S | S | $((CH_2)_2O(CH_2)_3)_3$ | Hydrogen |
| III.512 | S | S | $((CH_2)_2O(CH_2)_3)_3$ | Hydrocarbyl |
| III.513 | S | S | $((CH_2)_2O(CH_2)_3)_3$ | Substituted hydrocarbyl |
| III.514 | S | S | $((CH_2)_3O(CH_2))$ | Hydrogen |
| III.515 | S | S | $((CH_2)_3O(CH_2))$ | Hydrocarbyl |
| III.516 | S | S | $((CH_2)_3O(CH_2))$ | Substituted hydrocarbyl |
| III.517 | S | S | $((CH_2)_3O(CH_2))_2$ | Hydrogen |
| III.518 | S | S | $((CH_2)_3O(CH_2))_2$ | Hydrocarbyl |
| III.519 | S | S | $((CH_2)_3O(CH_2))_2$ | Substituted hydrocarbyl |
| III.520 | S | S | $((CH_2)_3O(CH_2))_3$ | Hydrogen |
| III.521 | S | S | $((CH_2)_3O(CH_2))_3$ | Hydrocarbyl |
| III.522 | S | S | $((CH_2)_3O(CH_2))_3$ | Substituted hydrocarbyl |
| III.523 | S | S | $((CH_2)_3O(CH_2)_2)$ | Hydrogen |
| III.524 | S | S | $((CH_2)_3O(CH_2)_2)$ | Hydrocarbyl |
| III.525 | S | S | $((CH_2)_3O(CH_2)_2)$ | Substituted hydrocarbyl |
| III.526 | S | S | $((CH_2)_3O(CH_2)_2)_2$ | Hydrogen |
| III.527 | S | S | $((CH_2)_3O(CH_2)_2)_2$ | Hydrocarbyl |
| III.528 | S | S | $((CH_2)_3O(CH_2)_2)_2$ | Substituted hydrocarbyl |
| III.529 | S | S | $((CH_2)_3O(CH_2)_2)_3$ | Hydrogen |
| III.530 | S | S | $((CH_2)_3O(CH_2)_2)_3$ | Hydrocarbyl |
| III.531 | S | S | $((CH_2)_3O(CH_2)_2)_3$ | Substituted hydrocarbyl |
| III.532 | S | S | $((CH_2)_3O(CH_2)_3)$ | Hydrogen |
| III.533 | S | S | $((CH_2)_3O(CH_2)_3)$ | Hydrocarbyl |
| III.534 | S | S | $((CH_2)_3O(CH_2)_3)$ | Substituted hydrocarbyl |
| III.535 | S | S | $((CH_2)_3O(CH_2)_3)_2$ | Hydrogen |
| III.536 | S | S | $((CH_2)_3O(CH_2)_3)_2$ | Hydrocarbyl |
| III.537 | S | S | $((CH_2)_3O(CH_2)_3)_2$ | Substituted hydrocarbyl |
| III.538 | S | S | $((CH_2)_3O(CH_2)_3)_3$ | Hydrogen |
| III.539 | S | S | $((CH_2)_3O(CH_2)_3)_3$ | Hydrocarbyl |
| III.540 | S | S | $((CH_2)_3O(CH_2)_3)_3$ | Substituted hydrocarbyl |
| III.541 | S | O | $((CH_2)O)$ | Hydrogen |
| III.542 | S | O | $((CH_2)O)$ | Hydrocarbyl |
| III.543 | S | O | $((CH_2)O)$ | Substituted hydrocarbyl |
| III.544 | S | O | $((CH_2)O)_2$ | Hydrogen |
| III.545 | S | O | $((CH_2)O)_2$ | Hydrocarbyl |
| III.546 | S | O | $((CH_2)O)_2$ | Substituted hydrocarbyl |
| III.547 | S | O | $((CH_2)O)_3$ | Hydrogen |
| III.548 | S | O | $((CH_2)O)_3$ | Hydrocarbyl |
| III.549 | S | O | $((CH_2)O)_3$ | Substituted hydrocarbyl |
| III.550 | S | O | $((CH_2)_2O)$ | Hydrogen |
| III.551 | S | O | $((CH_2)_2O)$ | Hydrocarbyl |
| III.552 | S | O | $((CH_2)_2O)$ | Substituted hydrocarbyl |
| III.553 | S | O | $((CH_2)_2O)_2$ | Hydrogen |
| III.554 | S | O | $((CH_2)_2O)_2$ | Hydrocarbyl |
| III.555 | S | O | $((CH_2)_2O)_2$ | Substituted hydrocarbyl |
| III.556 | S | O | $((CH_2)_2O)_3$ | Hydrogen |
| III.557 | S | O | $((CH_2)_2O)_3$ | Hydrocarbyl |
| III.558 | S | O | $((CH_2)_2O)_3$ | Substituted hydrocarbyl |
| III.559 | S | O | $((CH_2)_3O)$ | Hydrogen |
| III.560 | S | O | $((CH_2)_3O)$ | Hydrocarbyl |
| III.561 | S | O | $((CH_2)_3O)$ | Substituted hydrocarbyl |
| III.562 | S | O | $((CH_2)_3O)_2$ | Hydrogen |
| III.563 | S | O | $((CH_2)_3O)_2$ | Hydrocarbyl |
| III.564 | S | O | $((CH_2)_3O)_2$ | Substituted hydrocarbyl |
| III.565 | S | O | $((CH_2)_3O)_3$ | Hydrogen |
| III.566 | S | O | $((CH_2)_3O)_3$ | Hydrocarbyl |
| III.567 | S | O | $((CH_2)_3O)_3$ | Substituted hydrocarbyl |
| III.568 | S | O | $((CH_2)O(CH_2))$ | Hydrogen |
| III.569 | S | O | $((CH_2)O(CH_2))$ | Hydrocarbyl |
| III.570 | S | O | $((CH_2)O(CH_2))$ | Substituted hydrocarbyl |
| III.571 | S | O | $((CH_2)O(CH_2))_2$ | Hydrogen |
| III.572 | S | O | $((CH_2)O(CH_2))_2$ | Hydrocarbyl |
| III.573 | S | O | $((CH_2)O(CH_2))_2$ | Substituted hydrocarbyl |
| III.574 | S | O | $((CH_2)O(CH_2))_3$ | Hydrogen |
| III.575 | S | O | $((CH_2)O(CH_2))_3$ | Hydrocarbyl |
| III.576 | S | O | $((CH_2)O(CH_2))_3$ | Substituted hydrocarbyl |
| III.577 | S | O | $((CH_2)O(CH_2)_2)$ | Hydrogen |
| III.578 | S | O | $((CH_2)O(CH_2)_2)$ | Hydrocarbyl |
| III.579 | S | O | $((CH_2)O(CH_2)_2)$ | Substituted hydrocarbyl |
| III.580 | S | O | $((CH_2)O(CH_2)_2)_2$ | Hydrogen |
| III.581 | S | O | $((CH_2)O(CH_2)_2)_2$ | Hydrocarbyl |
| III.582 | S | O | $((CH_2)O(CH_2)_2)_2$ | Substituted hydrocarbyl |
| III.583 | S | O | $((CH_2)O(CH_2)_2)_3$ | Hydrogen |
| III.584 | S | O | $((CH_2)O(CH_2)_2)_3$ | Hydrocarbyl |
| III.585 | S | O | $((CH_2)O(CH_2)_2)_3$ | Substituted hydrocarbyl |
| III.586 | S | O | $((CH_2)O(CH_2)_3)$ | Hydrogen |
| III.587 | S | O | $((CH_2)O(CH_2)_3)$ | Hydrocarbyl |
| III.588 | S | O | $((CH_2)O(CH_2)_3)$ | Substituted hydrocarbyl |
| III.589 | S | O | $((CH_2)O(CH_2)_3)_2$ | Hydrogen |
| III.590 | S | O | $((CH_2)O(CH_2)_3)_2$ | Hydrocarbyl |
| III.591 | S | O | $((CH_2)O(CH_2)_3)_2$ | Substituted hydrocarbyl |
| III.592 | S | O | $((CH_2)O(CH_2)_3)_3$ | Hydrogen |
| III.593 | S | O | $((CH_2)O(CH_2)_3)_3$ | Hydrocarbyl |
| III.594 | S | O | $((CH_2)O(CH_2)_3)_3$ | Substituted hydrocarbyl |
| III.595 | S | O | $((CH_2)_2O(CH_2))$ | Hydrogen |
| III.596 | S | O | $((CH_2)_2O(CH_2))$ | Hydrocarbyl |
| III.597 | S | O | $((CH_2)_2O(CH_2))$ | Substituted hydrocarbyl |
| III.598 | S | O | $((CH_2)_2O(CH_2))_2$ | Hydrogen |
| III.599 | S | O | $((CH_2)_2O(CH_2))_2$ | Hydrocarbyl |
| III.600 | S | O | $((CH_2)_2O(CH_2))_2$ | Substituted hydrocarbyl |
| III.601 | S | O | $((CH_2)_2O(CH_2))_3$ | Hydrogen |
| III.602 | S | O | $((CH_2)_2O(CH_2))_3$ | Hydrocarbyl |
| III.603 | S | O | $((CH_2)_2O(CH_2))_3$ | Substituted hydrocarbyl |
| III.604 | S | O | $((CH_2)_2O(CH_2)_2)$ | Hydrogen |
| III.605 | S | O | $((CH_2)_2O(CH_2)_2)$ | Hydrocarbyl |
| III.606 | S | O | $((CH_2)_2O(CH_2)_2)$ | Substituted hydrocarbyl |
| III.607 | S | O | $((CH_2)_2O(CH_2)_2)_2$ | Hydrogen |
| III.608 | S | O | $((CH_2)_2O(CH_2)_2)_2$ | Hydrocarbyl |
| III.609 | S | O | $((CH_2)_2O(CH_2)_2)_2$ | Substituted hydrocarbyl |
| III.610 | S | O | $((CH_2)_2O(CH_2)_2)_3$ | Hydrogen |
| III.611 | S | O | $((CH_2)_2O(CH_2)_2)_3$ | Hydrocarbyl |
| III.612 | S | O | $((CH_2)_2O(CH_2)_2)_3$ | Substituted hydrocarbyl |
| III.613 | S | O | $((CH_2)_2O(CH_2)_3)$ | Hydrogen |
| III.614 | S | O | $((CH_2)_2O(CH_2)_3)$ | Hydrocarbyl |
| III.615 | S | O | $((CH_2)_2O(CH_2)_3)$ | Substituted hydrocarbyl |
| III.616 | S | O | $((CH_2)_2O(CH_2)_3)_2$ | Hydrogen |
| III.617 | S | O | $((CH_2)_2O(CH_2)_3)_2$ | Hydrocarbyl |
| III.618 | S | O | $((CH_2)_2O(CH_2)_3)_2$ | Substituted hydrocarbyl |
| III.619 | S | O | $((CH_2)_2O(CH_2)_3)_3$ | Hydrogen |
| III.620 | S | O | $((CH_2)_2O(CH_2)_3)_3$ | Hydrocarbyl |
| III.621 | S | O | $((CH_2)_2O(CH_2)_3)_3$ | Substituted hydrocarbyl |
| III.622 | S | O | $((CH_2)_3O(CH_2))$ | Hydrogen |
| III.623 | S | O | $((CH_2)_3O(CH_2))$ | Hydrocarbyl |
| III.624 | S | O | $((CH_2)_3O(CH_2))$ | Substituted hydrocarbyl |
| III.625 | S | O | $((CH_2)_3O(CH_2))_2$ | Hydrogen |
| III.626 | S | O | $((CH_2)_3O(CH_2))_2$ | Hydrocarbyl |
| III.627 | S | O | $((CH_2)_3O(CH_2))_2$ | Substituted hydrocarbyl |
| III.628 | S | O | $((CH_2)_3O(CH_2))_3$ | Hydrogen |
| III.629 | S | O | $((CH_2)_3O(CH_2))_3$ | Hydrocarbyl |
| III.630 | S | O | $((CH_2)_3O(CH_2))_3$ | Substituted hydrocarbyl |
| III.631 | S | O | $((CH_2)_3O(CH_2)_2)$ | Hydrogen |
| III.632 | S | O | $((CH_2)_3O(CH_2)_2)$ | Hydrocarbyl |
| III.633 | S | O | $((CH_2)_3O(CH_2)_2)$ | Substituted hydrocarbyl |
| III.634 | S | O | $((CH_2)_3O(CH_2)_2)_2$ | Hydrogen |
| III.635 | S | O | $((CH_2)_3O(CH_2)_2)_2$ | Hydrocarbyl |
| III.636 | S | O | $((CH_2)_3O(CH_2)_2)_2$ | Substituted hydrocarbyl |
| III.637 | S | O | $((CH_2)_3O(CH_2)_2)_3$ | Hydrogen |
| III.638 | S | O | $((CH_2)_3O(CH_2)_2)_3$ | Hydrocarbyl |
| III.639 | S | O | $((CH_2)_3O(CH_2)_2)_3$ | Substituted hydrocarbyl |
| III.640 | S | O | $((CH_2)_3O(CH_2)_3)$ | Hydrogen |
| III.641 | S | O | $((CH_2)_3O(CH_2)_3)$ | Hydrocarbyl |
| III.642 | S | O | $((CH_2)_3O(CH_2)_3)$ | Substituted hydrocarbyl |
| III.643 | S | O | $((CH_2)_3O(CH_2)_3)_2$ | Hydrogen |
| III.644 | S | O | $((CH_2)_3O(CH_2)_3)_2$ | Hydrocarbyl |
| III.645 | S | O | $((CH_2)_3O(CH_2)_3)_2$ | Substituted hydrocarbyl |
| III.646 | S | O | $((CH_2)_3O(CH_2)_3)_3$ | Hydrogen |
| III.647 | S | O | $((CH_2)_3O(CH_2)_3)_3$ | Hydrocarbyl |
| III.648 | S | O | $((CH_2)_3O(CH_2)_3)_3$ | Substituted hydrocarbyl |
| III.649 | O | N | $((CH_2)O)$ | Hydrogen |
| III.650 | O | N | $((CH_2)O)$ | Hydrocarbyl |
| III.651 | O | N | $((CH_2)O)$ | Substituted hydrocarbyl |
| III.652 | O | N | $((CH_2)O)_2$ | Hydrogen |
| III.653 | O | N | $((CH_2)O)_2$ | Hydrocarbyl |
| III.654 | O | N | $((CH_2)O)_2$ | Substituted hydrocarbyl |
| III.655 | O | N | $((CH_2)O)_3$ | Hydrogen |
| III.656 | O | N | $((CH_2)O)_3$ | Hydrocarbyl |
| III.657 | O | N | $((CH_2)O)_3$ | Substituted hydrocarbyl |

TABLE 3-continued

Selected compounds of Formula (III)

| Compound | R1 | R2 | R7 | R8 |
|---|---|---|---|---|
| III.658 | O | N | $((CH_2)_2O)$ | Hydrogen |
| III.659 | O | N | $((CH_2)_2O)$ | Hydrocarbyl |
| III.660 | O | N | $((CH_2)_2O)$ | Substituted hydrocarbyl |
| III.661 | O | N | $((CH_2)_2O)_2$ | Hydrogen |
| III.662 | O | N | $((CH_2)_2O)_2$ | Hydrocarbyl |
| III.663 | O | N | $((CH_2)_2O)_2$ | Substituted hydrocarbyl |
| III.664 | O | N | $((CH_2)_2O)_3$ | Hydrogen |
| III.665 | O | N | $((CH_2)_2O)_3$ | Hydrocarbyl |
| III.666 | O | N | $((CH_2)_2O)_3$ | Substituted hydrocarbyl |
| III.667 | O | N | $((CH_2)_3O)$ | Hydrogen |
| III.668 | O | N | $((CH_2)_3O)$ | Hydrocarbyl |
| III.669 | O | N | $((CH_2)_3O)$ | Substituted hydrocarbyl |
| III.670 | O | N | $((CH_2)_3O)_2$ | Hydrogen |
| III.671 | O | N | $((CH_2)_3O)_2$ | Hydrocarbyl |
| III.672 | O | N | $((CH_2)_3O)_2$ | Substituted hydrocarbyl |
| III.673 | O | N | $((CH_2)_3O)_3$ | Hydrogen |
| III.674 | O | N | $((CH_2)_3O)_3$ | Hydrocarbyl |
| III.675 | O | N | $((CH_2)_3O)_3$ | Substituted hydrocarbyl |
| III.676 | O | N | $((CH_2)O(CH_2))$ | Hydrogen |
| III.677 | O | N | $((CH_2)O(CH_2))$ | Hydrocarbyl |
| III.678 | O | N | $((CH_2)O(CH_2))$ | Substituted hydrocarbyl |
| III.679 | O | N | $((CH_2)O(CH_2))_2$ | Hydrogen |
| III.680 | O | N | $((CH_2)O(CH_2))_2$ | Hydrocarbyl |
| III.681 | O | N | $((CH_2)O(CH_2))_2$ | Substituted hydrocarbyl |
| III.682 | O | N | $((CH_2)O(CH_2))_3$ | Hydrogen |
| III.683 | O | N | $((CH_2)O(CH_2))_3$ | Hydrocarbyl |
| III.684 | O | N | $((CH_2)O(CH_2))_3$ | Substituted hydrocarbyl |
| III.685 | O | N | $((CH_2)O(CH_2)_2)$ | Hydrogen |
| III.686 | O | N | $((CH_2)O(CH_2)_2)$ | Hydrocarbyl |
| III.687 | O | N | $((CH_2)O(CH_2)_2)$ | Substituted hydrocarbyl |
| III.688 | O | N | $((CH_2)O(CH_2)_2)_2$ | Hydrogen |
| III.689 | O | N | $((CH_2)O(CH_2)_2)_2$ | Hydrocarbyl |
| III.690 | O | N | $((CH_2)O(CH_2)_2)_2$ | Substituted hydrocarbyl |
| III.691 | O | N | $((CH_2)O(CH_2)_2)_3$ | Hydrogen |
| III.692 | O | N | $((CH_2)O(CH_2)_2)_3$ | Hydrocarbyl |
| III.693 | O | N | $((CH_2)O(CH_2)_2)_3$ | Substituted hydrocarbyl |
| III.694 | O | N | $((CH_2)O(CH_2)_3)$ | Hydrogen |
| III.695 | O | N | $((CH_2)O(CH_2)_3)$ | Hydrocarbyl |
| III.696 | O | N | $((CH_2)O(CH_2)_3)$ | Substituted hydrocarbyl |
| III.697 | O | N | $((CH_2)O(CH_2)_3)_2$ | Hydrogen |
| III.698 | O | N | $((CH_2)O(CH_2)_3)_2$ | Hydrocarbyl |
| III.699 | O | N | $((CH_2)O(CH_2)_3)_2$ | Substituted hydrocarbyl |
| III.700 | O | N | $((CH_2)O(CH_2)_3)_3$ | Hydrogen |
| III.701 | O | N | $((CH_2)O(CH_2)_3)_3$ | Hydrocarbyl |
| III.702 | O | N | $((CH_2)O(CH_2)_3)_3$ | Substituted hydrocarbyl |
| III.703 | O | N | $((CH_2)_2O(CH_2))$ | Hydrogen |
| III.704 | O | N | $((CH_2)_2O(CH_2))$ | Hydrocarbyl |
| III.705 | O | N | $((CH_2)_2O(CH_2))$ | Substituted hydrocarbyl |
| III.706 | O | N | $((CH_2)_2O(CH_2))_2$ | Hydrogen |
| III.707 | O | N | $((CH_2)_2O(CH_2))_2$ | Hydrocarbyl |
| III.708 | O | N | $((CH_2)_2O(CH_2))_2$ | Substituted hydrocarbyl |
| III.709 | O | N | $((CH_2)_2O(CH_2))_3$ | Hydrogen |
| III.710 | O | N | $((CH_2)_2O(CH_2))_3$ | Hydrocarbyl |
| III.711 | O | N | $((CH_2)_2O(CH_2))_3$ | Substituted hydrocarbyl |
| III.712 | O | N | $((CH_2)_2O(CH_2)_2)$ | Hydrogen |
| III.713 | O | N | $((CH_2)_2O(CH_2)_2)$ | Hydrocarbyl |
| III.714 | O | N | $((CH_2)_2O(CH_2)_2)$ | Substituted hydrocarbyl |
| III.715 | O | N | $((CH_2)_2O(CH_2)_2)_2$ | Hydrogen |
| III.716 | O | N | $((CH_2)_2O(CH_2)_2)_2$ | Hydrocarbyl |
| III.717 | O | N | $((CH_2)_2O(CH_2)_2)_2$ | Substituted hydrocarbyl |
| III.718 | O | N | $((CH_2)_2O(CH_2)_2)_3$ | Hydrogen |
| III.719 | O | N | $((CH_2)_2O(CH_2)_2)_3$ | Hydrocarbyl |
| III.720 | O | N | $((CH_2)_2O(CH_2)_2)_3$ | Substituted hydrocarbyl |
| III.721 | O | N | $((CH_2)_2O(CH_2)_3)$ | Hydrogen |
| III.722 | O | N | $((CH_2)_2O(CH_2)_3)$ | Hydrocarbyl |
| III.723 | O | N | $((CH_2)_2O(CH_2)_3)$ | Substituted hydrocarbyl |
| III.724 | O | N | $((CH_2)_2O(CH_2)_3)_2$ | Hydrogen |
| III.725 | O | N | $((CH_2)_2O(CH_2)_3)_2$ | Hydrocarbyl |
| III.726 | O | N | $((CH_2)_2O(CH_2)_3)_2$ | Substituted hydrocarbyl |
| III.727 | O | N | $((CH_2)_2O(CH_2)_3)_3$ | Hydrogen |
| III.728 | O | N | $((CH_2)_2O(CH_2)_3)_3$ | Hydrocarbyl |
| III.729 | O | N | $((CH_2)_2O(CH_2)_3)_3$ | Substituted hydrocarbyl |
| III.730 | O | N | $((CH_2)_3O(CH_2))$ | Hydrogen |
| III.731 | O | N | $((CH_2)_3O(CH_2))$ | Hydrocarbyl |
| III.732 | O | N | $((CH_2)_3O(CH_2))$ | Substituted hydrocarbyl |
| III.733 | O | N | $((CH_2)_3O(CH_2))_2$ | Hydrogen |
| III.734 | O | N | $((CH_2)_3O(CH_2))_2$ | Hydrocarbyl |
| III.735 | O | N | $((CH_2)_3O(CH_2))_2$ | Substituted hydrocarbyl |
| III.736 | O | N | $((CH_2)_3O(CH_2))_3$ | Hydrogen |
| III.737 | O | N | $((CH_2)_3O(CH_2))_3$ | Hydrocarbyl |
| III.738 | O | N | $((CH_2)_3O(CH_2))_3$ | Substituted hydrocarbyl |
| III.739 | O | N | $((CH_2)_3O(CH_2)_2)$ | Hydrogen |
| III.740 | O | N | $((CH_2)_3O(CH_2)_2)$ | Hydrocarbyl |
| III.741 | O | N | $((CH_2)_3O(CH_2)_2)$ | Substituted hydrocarbyl |
| III.742 | O | N | $((CH_2)_3O(CH_2)_2)_2$ | Hydrogen |
| III.743 | O | N | $((CH_2)_3O(CH_2)_2)_2$ | Hydrocarbyl |
| III.744 | O | N | $((CH_2)_3O(CH_2)_2)_2$ | Substituted hydrocarbyl |
| III.745 | O | N | $((CH_2)_3O(CH_2)_2)_3$ | Hydrogen |
| III.746 | O | N | $((CH_2)_3O(CH_2)_2)_3$ | Hydrocarbyl |
| III.747 | O | N | $((CH_2)_3O(CH_2)_2)_3$ | Substituted hydrocarbyl |
| III.748 | O | N | $((CH_2)_3O(CH_2)_3)$ | Hydrogen |
| III.749 | O | N | $((CH_2)_3O(CH_2)_3)$ | Hydrocarbyl |
| III.750 | O | N | $((CH_2)_3O(CH_2)_3)$ | Substituted hydrocarbyl |
| III.751 | O | N | $((CH_2)_3O(CH_2)_3)_2$ | Hydrogen |
| III.752 | O | N | $((CH_2)_3O(CH_2)_3)_2$ | Hydrocarbyl |
| III.753 | O | N | $((CH_2)_3O(CH_2)_3)_2$ | Substituted hydrocarbyl |
| III.754 | O | N | $((CH_2)_3O(CH_2)_3)_3$ | Hydrogen |
| III.755 | O | N | $((CH_2)_3O(CH_2)_3)_3$ | Hydrocarbyl |
| III.756 | O | N | $((CH_2)_3O(CH_2)_3)_3$ | Substituted hydrocarbyl |
| III.757 | O | S | $((CH_2)O)$ | Hydrogen |
| III.758 | O | S | $((CH_2)O)$ | Hydrocarbyl |
| III.759 | O | S | $((CH_2)O)$ | Substituted hydrocarbyl |
| III.760 | O | S | $((CH_2)O)_2$ | Hydrogen |
| III.761 | O | S | $((CH_2)O)_2$ | Hydrocarbyl |
| III.762 | O | S | $((CH_2)O)_2$ | Substituted hydrocarbyl |
| III.763 | O | S | $((CH_2)O)_3$ | Hydrogen |
| III.764 | O | S | $((CH_2)O)_3$ | Hydrocarbyl |
| III.765 | O | S | $((CH_2)O)_3$ | Substituted hydrocarbyl |
| III.766 | O | S | $((CH_2)_2O)$ | Hydrogen |
| III.767 | O | S | $((CH_2)_2O)$ | Hydrocarbyl |
| III.768 | O | S | $((CH_2)_2O)$ | Substituted hydrocarbyl |
| III.769 | O | S | $((CH_2)_2O)_2$ | Hydrogen |
| III.770 | O | S | $((CH_2)_2O)_2$ | Hydrocarbyl |
| III.771 | O | S | $((CH_2)_2O)_2$ | Substituted hydrocarbyl |
| III.772 | O | S | $((CH_2)_2O)_3$ | Hydrogen |
| III.773 | O | S | $((CH_2)_2O)_3$ | Hydrocarbyl |
| III.774 | O | S | $((CH_2)_2O)_3$ | Substituted hydrocarbyl |
| III.775 | O | S | $((CH_2)_3O)$ | Hydrogen |
| III.776 | O | S | $((CH_2)_3O)$ | Hydrocarbyl |
| III.777 | O | S | $((CH_2)_3O)$ | Substituted hydrocarbyl |
| III.778 | O | S | $((CH_2)_3O)_2$ | Hydrogen |
| III.779 | O | S | $((CH_2)_3O)_2$ | Hydrocarbyl |
| III.780 | O | S | $((CH_2)_3O)_2$ | Substituted hydrocarbyl |
| III.781 | O | S | $((CH_2)_3O)_3$ | Hydrogen |
| III.782 | O | S | $((CH_2)_3O)_3$ | Hydrocarbyl |
| III.783 | O | S | $((CH_2)_3O)_3$ | Substituted hydrocarbyl |
| III.784 | O | S | $((CH_2)O(CH_2))$ | Hydrogen |
| III.785 | O | S | $((CH_2)O(CH_2))$ | Hydrocarbyl |
| III.786 | O | S | $((CH_2)O(CH_2))$ | Substituted hydrocarbyl |
| III.787 | O | S | $((CH_2)O(CH_2))_2$ | Hydrogen |
| III.788 | O | S | $((CH_2)O(CH_2))_2$ | Hydrocarbyl |
| III.789 | O | S | $((CH_2)O(CH_2))_2$ | Substituted hydrocarbyl |
| III.790 | O | S | $((CH_2)O(CH_2))_3$ | Hydrogen |
| III.791 | O | S | $((CH_2)O(CH_2))_3$ | Hydrocarbyl |
| III.792 | O | S | $((CH_2)O(CH_2))_3$ | Substituted hydrocarbyl |
| III.793 | O | S | $((CH_2)O(CH_2)_2)$ | Hydrogen |
| III.794 | O | S | $((CH_2)O(CH_2)_2)$ | Hydrocarbyl |
| III.795 | O | S | $((CH_2)O(CH_2)_2)$ | Substituted hydrocarbyl |
| III.796 | O | S | $((CH_2)O(CH_2)_2)_2$ | Hydrogen |
| III.797 | O | S | $((CH_2)O(CH_2)_2)_2$ | Hydrocarbyl |
| III.798 | O | S | $((CH_2)O(CH_2)_2)_2$ | Substituted hydrocarbyl |
| III.799 | O | S | $((CH_2)O(CH_2)_2)_3$ | Hydrogen |
| III.800 | O | S | $((CH_2)O(CH_2)_2)_3$ | Hydrocarbyl |
| III.801 | O | S | $((CH_2)O(CH_2)_2)_3$ | Substituted hydrocarbyl |
| III.802 | O | S | $((CH_2)O(CH_2)_3)$ | Hydrogen |
| III.803 | O | S | $((CH_2)O(CH_2)_3)$ | Hydrocarbyl |
| III.804 | O | S | $((CH_2)O(CH_2)_3)$ | Substituted hydrocarbyl |
| III.805 | O | S | $((CH_2)O(CH_2)_3)_2$ | Hydrogen |
| III.806 | O | S | $((CH_2)O(CH_2)_3)_2$ | Hydrocarbyl |
| III.807 | O | S | $((CH_2)O(CH_2)_3)_2$ | Substituted hydrocarbyl |
| III.808 | O | S | $((CH_2)O(CH_2)_3)_3$ | Hydrogen |
| III.809 | O | S | $((CH_2)O(CH_2)_3)_3$ | Hydrocarbyl |

TABLE 3-continued

Selected compounds of Formula (III)

| Compound | R1 | R2 | R7 | R8 |
|---|---|---|---|---|
| III.810 | O | S | $((CH_2)O(CH_2)_3)_3$ | Substituted hydrocarbyl |
| III.811 | O | S | $((CH_2)_2O(CH_2))$ | Hydrogen |
| III.812 | O | S | $((CH_2)_2O(CH_2))$ | Hydrocarbyl |
| III.813 | O | S | $((CH_2)_2O(CH_2))$ | Substituted hydrocarbyl |
| III.814 | O | S | $((CH_2)_2O(CH_2))_2$ | Hydrogen |
| III.815 | O | S | $((CH_2)_2O(CH_2))_2$ | Hydrocarbyl |
| III.816 | O | S | $((CH_2)_2O(CH_2))_2$ | Substituted hydrocarbyl |
| III.817 | O | S | $((CH_2)_2O(CH_2))_3$ | Hydrogen |
| III.818 | O | S | $((CH_2)_2O(CH_2))_3$ | Hydrocarbyl |
| III.819 | O | S | $((CH_2)_2O(CH_2))_3$ | Substituted hydrocarbyl |
| III.820 | O | S | $((CH_2)_2O(CH_2)_2)$ | Hydrogen |
| III.821 | O | S | $((CH_2)_2O(CH_2)_2)$ | Hydrocarbyl |
| III.822 | O | S | $((CH_2)_2O(CH_2)_2)$ | Substituted hydrocarbyl |
| III.823 | O | S | $((CH_2)_2O(CH_2)_2)_2$ | Hydrogen |
| III.824 | O | S | $((CH_2)_2O(CH_2)_2)_2$ | Hydrocarbyl |
| III.825 | O | S | $((CH_2)_2O(CH_2)_2)_2$ | Substituted hydrocarbyl |
| III.826 | O | S | $((CH_2)_2O(CH_2)_2)_3$ | Hydrogen |
| III.827 | O | S | $((CH_2)_2O(CH_2)_2)_3$ | Hydrocarbyl |
| III.828 | O | S | $((CH_2)_2O(CH_2)_2)_3$ | Substituted hydrocarbyl |
| III.829 | O | S | $((CH_2)_2O(CH_2)_3)$ | Hydrogen |
| III.830 | O | S | $((CH_2)_2O(CH_2)_3)$ | Hydrocarbyl |
| III.831 | O | S | $((CH_2)_2O(CH_2)_3)$ | Substituted hydrocarbyl |
| III.832 | O | S | $((CH_2)_2O(CH_2)_3)_2$ | Hydrogen |
| III.833 | O | S | $((CH_2)_2O(CH_2)_3)_2$ | Hydrocarbyl |
| III.834 | O | S | $((CH_2)_2O(CH_2)_3)_2$ | Substituted hydrocarbyl |
| III.835 | O | S | $((CH_2)_2O(CH_2)_3)_3$ | Hydrogen |
| III.836 | O | S | $((CH_2)_2O(CH_2)_3)_3$ | Hydrocarbyl |
| III.837 | O | S | $((CH_2)_2O(CH_2)_3)_3$ | Substituted hydrocarbyl |
| III.838 | O | S | $((CH_2)_3O(CH_2))$ | Hydrogen |
| III.839 | O | S | $((CH_2)_3O(CH_2))$ | Hydrocarbyl |
| III.840 | O | S | $((CH_2)_3O(CH_2))$ | Substituted hydrocarbyl |
| III.841 | O | S | $((CH_2)_3O(CH_2))_2$ | Hydrogen |
| III.842 | O | S | $((CH_2)_3O(CH_2))_2$ | Hydrocarbyl |
| III.843 | O | S | $((CH_2)_3O(CH_2))_2$ | Substituted hydrocarbyl |
| III.844 | O | S | $((CH_2)_3O(CH_2))_3$ | Hydrogen |
| III.845 | O | S | $((CH_2)_3O(CH_2))_3$ | Hydrocarbyl |
| III.846 | O | S | $((CH_2)_3O(CH_2))_3$ | Substituted hydrocarbyl |
| III.847 | O | S | $((CH_2)_3O(CH_2)_2)$ | Hydrogen |
| III.848 | O | S | $((CH_2)_3O(CH_2)_2)$ | Hydrocarbyl |
| III.849 | O | S | $((CH_2)_3O(CH_2)_2)$ | Substituted hydrocarbyl |
| III.850 | O | S | $((CH_2)_3O(CH_2)_2)_2$ | Hydrogen |
| III.851 | O | S | $((CH_2)_3O(CH_2)_2)_2$ | Hydrocarbyl |
| III.852 | O | S | $((CH_2)_3O(CH_2)_2)_2$ | Substituted hydrocarbyl |
| III.853 | O | S | $((CH_2)_3O(CH_2)_2)_3$ | Hydrogen |
| III.854 | O | S | $((CH_2)_3O(CH_2)_2)_3$ | Hydrocarbyl |
| III.855 | O | S | $((CH_2)_3O(CH_2)_2)_3$ | Substituted hydrocarbyl |
| III.856 | O | S | $((CH_2)_3O(CH_2)_3)$ | Hydrogen |
| III.857 | O | S | $((CH_2)_3O(CH_2)_3)$ | Hydrocarbyl |
| III.858 | O | S | $((CH_2)_3O(CH_2)_3)$ | Substituted hydrocarbyl |
| III.859 | O | S | $((CH_2)_3O(CH_2)_3)_2$ | Hydrogen |
| III.860 | O | S | $((CH_2)_3O(CH_2)_3)_2$ | Hydrocarbyl |
| III.861 | O | S | $((CH_2)_3O(CH_2)_3)_2$ | Substituted hydrocarbyl |
| III.862 | O | S | $((CH_2)_3O(CH_2)_3)_3$ | Hydrogen |
| III.863 | O | S | $((CH_2)_3O(CH_2)_3)_3$ | Hydrocarbyl |
| III.864 | O | S | $((CH_2)_3O(CH_2)_3)_3$ | Substituted hydrocarbyl |
| III.865 | O | O | $((CH_2)O)$ | Hydrogen |
| III.866 | O | O | $((CH_2)O)$ | Hydrocarbyl |
| III.867 | O | O | $((CH_2)O)$ | Substituted hydrocarbyl |
| III.868 | O | O | $((CH_2)O)_2$ | Hydrogen |
| III.869 | O | O | $((CH_2)O)_2$ | Hydrocarbyl |
| III.870 | O | O | $((CH_2)O)_2$ | Substituted hydrocarbyl |
| III.871 | O | O | $((CH_2)O)_3$ | Hydrogen |
| III.872 | O | O | $((CH_2)O)_3$ | Hydrocarbyl |
| III.873 | O | O | $((CH_2)O)_3$ | Substituted hydrocarbyl |
| III.874 | O | O | $((CH_2)_2O)$ | Hydrogen |
| III.875 | O | O | $((CH_2)_2O)$ | Hydrocarbyl |
| III.876 | O | O | $((CH_2)_2O)$ | Substituted hydrocarbyl |
| III.877 | O | O | $((CH_2)_2O)_2$ | Hydrogen |
| III.878 | O | O | $((CH_2)_2O)_2$ | Hydrocarbyl |
| III.879 | O | O | $((CH_2)_2O)_2$ | Substituted hydrocarbyl |
| III.880 | O | O | $((CH_2)_2O)_3$ | Hydrogen |
| III.881 | O | O | $((CH_2)_2O)_3$ | Hydrocarbyl |
| III.882 | O | O | $((CH_2)_2O)_3$ | Substituted hydrocarbyl |
| III.883 | O | O | $((CH_2)_3O)$ | Hydrogen |
| III.884 | O | O | $((CH_2)_3O)$ | Hydrocarbyl |
| III.885 | O | O | $((CH_2)_3O)$ | Substituted hydrocarbyl |
| III.886 | O | O | $((CH_2)_3O)_2$ | Hydrogen |
| III.887 | O | O | $((CH_2)_3O)_2$ | Hydrocarbyl |
| III.888 | O | O | $((CH_2)_3O)_2$ | Substituted hydrocarbyl |
| III.889 | O | O | $((CH_2)_3O)_3$ | Hydrogen |
| III.890 | O | O | $((CH_2)_3O)_3$ | Hydrocarbyl |
| III.891 | O | O | $((CH_2)_3O)_3$ | Substituted hydrocarbyl |
| III.892 | O | O | $((CH_2)O(CH_2))$ | Hydrogen |
| III.893 | O | O | $((CH_2)O(CH_2))$ | Hydrocarbyl |
| III.894 | O | O | $((CH_2)O(CH_2))$ | Substituted hydrocarbyl |
| III.895 | O | O | $((CH_2)O(CH_2))_2$ | Hydrogen |
| III.896 | O | O | $((CH_2)O(CH_2))_2$ | Hydrocarbyl |
| III.897 | O | O | $((CH_2)O(CH_2))_2$ | Substituted hydrocarbyl |
| III.898 | O | O | $((CH_2)O(CH_2))_3$ | Hydrogen |
| III.899 | O | O | $((CH_2)O(CH_2))_3$ | Hydrocarbyl |
| III.900 | O | O | $((CH_2)O(CH_2))_3$ | Substituted hydrocarbyl |
| III.901 | O | O | $((CH_2)O(CH_2)_2)$ | Hydrogen |
| III.902 | O | O | $((CH_2)O(CH_2)_2)$ | Hydrocarbyl |
| III.903 | O | O | $((CH_2)O(CH_2)_2)$ | Substituted hydrocarbyl |
| III.904 | O | O | $((CH_2)O(CH_2)_2)_2$ | Hydrogen |
| III.905 | O | O | $((CH_2)O(CH_2)_2)_2$ | Hydrocarbyl |
| III.906 | O | O | $((CH_2)O(CH_2)_2)_2$ | Substituted hydrocarbyl |
| III.907 | O | O | $((CH_2)O(CH_2)_2)_3$ | Hydrogen |
| III.908 | O | O | $((CH_2)O(CH_2)_2)_3$ | Hydrocarbyl |
| III.909 | O | O | $((CH_2)O(CH_2)_2)_3$ | Substituted hydrocarbyl |
| III.910 | O | O | $((CH_2)O(CH_2)_3)$ | Hydrogen |
| III.911 | O | O | $((CH_2)O(CH_2)_3)$ | Hydrocarbyl |
| III.912 | O | O | $((CH_2)O(CH_2)_3)$ | Substituted hydrocarbyl |
| III.913 | O | O | $((CH_2)O(CH_2)_3)_2$ | Hydrogen |
| III.914 | O | O | $((CH_2)O(CH_2)_3)_2$ | Hydrocarbyl |
| III.915 | O | O | $((CH_2)O(CH_2)_3)_2$ | Substituted hydrocarbyl |
| III.916 | O | O | $((CH_2)O(CH_2)_3)_3$ | Hydrogen |
| III.917 | O | O | $((CH_2)O(CH_2)_3)_3$ | Hydrocarbyl |
| III.918 | O | O | $((CH_2)O(CH_2)_3)_3$ | Substituted hydrocarbyl |
| III.919 | O | O | $((CH_2)_2O(CH_2))$ | Hydrogen |
| III.920 | O | O | $((CH_2)_2O(CH_2))$ | Hydrocarbyl |
| III.921 | O | O | $((CH_2)_2O(CH_2))$ | Substituted hydrocarbyl |
| III.922 | O | O | $((CH_2)_2O(CH_2))_2$ | Hydrogen |
| III.923 | O | O | $((CH_2)_2O(CH_2))_2$ | Hydrocarbyl |
| III.924 | O | O | $((CH_2)_2O(CH_2))_2$ | Substituted hydrocarbyl |
| III.925 | O | O | $((CH_2)_2O(CH_2))_3$ | Hydrogen |
| III.926 | O | O | $((CH_2)_2O(CH_2))_3$ | Hydrocarbyl |
| III.927 | O | O | $((CH_2)_2O(CH_2))_3$ | Substituted hydrocarbyl |
| III.928 | O | O | $((CH_2)_2O(CH_2)_2)$ | Hydrogen |
| III.929 | O | O | $((CH_2)_2O(CH_2)_2)$ | Hydrocarbyl |
| III.930 | O | O | $((CH_2)_2O(CH_2)_2)$ | Substituted hydrocarbyl |
| III.931 | O | O | $((CH_2)_2O(CH_2)_2)_2$ | Hydrogen |
| III.932 | O | O | $((CH_2)_2O(CH_2)_2)_2$ | Hydrocarbyl |
| III.933 | O | O | $((CH_2)_2O(CH_2)_2)_2$ | Substituted hydrocarbyl |
| III.934 | O | O | $((CH_2)_2O(CH_2)_2)_3$ | Hydrogen |
| III.935 | O | O | $((CH_2)_2O(CH_2)_2)_3$ | Hydrocarbyl |
| III.936 | O | O | $((CH_2)_2O(CH_2)_2)_3$ | Substituted hydrocarbyl |
| III.937 | O | O | $((CH_2)_2O(CH_2)_3)$ | Hydrogen |
| III.938 | O | O | $((CH_2)_2O(CH_2)_3)$ | Hydrocarbyl |
| III.939 | O | O | $((CH_2)_2O(CH_2)_3)$ | Substituted hydrocarbyl |
| III.940 | O | O | $((CH_2)_2O(CH_2)_3)_2$ | Hydrogen |
| III.941 | O | O | $((CH_2)_2O(CH_2)_3)_2$ | Hydrocarbyl |
| III.942 | O | O | $((CH_2)_2O(CH_2)_3)_2$ | Substituted hydrocarbyl |
| III.943 | O | O | $((CH_2)_2O(CH_2)_3)_3$ | Hydrogen |
| III.944 | O | O | $((CH_2)_2O(CH_2)_3)_3$ | Hydrocarbyl |
| III.945 | O | O | $((CH_2)_2O(CH_2)_3)_3$ | Substituted hydrocarbyl |
| III.946 | O | O | $((CH_2)_3O(CH_2))$ | Hydrogen |
| III.947 | O | O | $((CH_2)_3O(CH_2))$ | Hydrocarbyl |
| III.948 | O | O | $((CH_2)_3O(CH_2))$ | Substituted hydrocarbyl |
| III.949 | O | O | $((CH_2)_3O(CH_2))_2$ | Hydrogen |
| III.950 | O | O | $((CH_2)_3O(CH_2))_2$ | Hydrocarbyl |
| III.951 | O | O | $((CH_2)_3O(CH_2))_2$ | Substituted hydrocarbyl |
| III.952 | O | O | $((CH_2)_3O(CH_2))_3$ | Hydrogen |
| III.953 | O | O | $((CH_2)_3O(CH_2))_3$ | Hydrocarbyl |
| III.954 | O | O | $((CH_2)_3O(CH_2))_3$ | Substituted hydrocarbyl |
| III.955 | O | O | $((CH_2)_3O(CH_2)_2)$ | Hydrogen |
| III.956 | O | O | $((CH_2)_3O(CH_2)_2)$ | Hydrocarbyl |
| III.957 | O | O | $((CH_2)_3O(CH_2)_2)$ | Substituted hydrocarbyl |
| III.958 | O | O | $((CH_2)_3O(CH_2)_2)_2$ | Hydrogen |
| III.959 | O | O | $((CH_2)_3O(CH_2)_2)_2$ | Hydrocarbyl |
| III.960 | O | O | $((CH_2)_3O(CH_2)_2)_2$ | Substituted hydrocarbyl |
| III.961 | O | O | $((CH_2)_3O(CH_2)_2)_3$ | Hydrogen |

TABLE 3-continued

Selected compounds of Formula (III)

| Compound | R1 | R2 | R7 | R8 |
|---|---|---|---|---|
| III.962 | O | O | $((CH_2)_3O(CH_2)_2)_3$ | Hydrocarbyl |
| III.963 | O | O | $((CH_2)_3O(CH_2)_2)_3$ | Substituted hydrocarbyl |
| III.964 | O | O | $((CH_2)_3O(CH_2)_3)$ | Hydrogen |
| III.965 | O | O | $((CH_2)_3O(CH_2)_3)$ | Hydrocarbyl |
| III.966 | O | O | $((CH_2)_3O(CH_2)_3)$ | Substituted hydrocarbyl |
| III.967 | O | O | $((CH_2)_3O(CH_2)_3)_2$ | Hydrogen |
| III.968 | O | O | $((CH_2)_3O(CH_2)_3)_2$ | Hydrocarbyl |
| III.969 | O | O | $((CH_2)_3O(CH_2)_3)_2$ | Substituted hydrocarbyl |
| III.970 | O | O | $((CH_2)_3O(CH_2)_3)_3$ | Hydrogen |
| III.971 | O | O | $((CH_2)_3O(CH_2)_3)_3$ | Hydrocarbyl |
| III.972 | O | O | $((CH_2)_3O(CH_2)_3)_3$ | Substituted hydrocarbyl |

In still yet another embodiment, the present invention encompasses a compound of formula (IV):

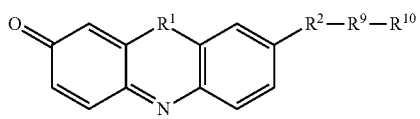

wherein:
$R^1$ is chosen from N, S, or O;
$R^2$ is chosen from N, S, or O;
$R^9$ is $(CH_2)_j$, wherein j is an integer from 1 to 10, and
$R^{10}$ is chosen from a halogen, an alkenyl group, an alkynyl group, and a substituted hydrocarbyl.

Additionally, in some embodiments of formula (IV), $R^{10}$ is hydrogen when h is in integer greater than 5. In certain embodiments, a compound of the invention may be a compound of formula (IV) wherein $R^1$ is O. In other embodiments, a compound of the invention may be a compound of formula (IV) wherein $R^1$ is N. In still other embodiments, a compound of the invention may be a compound of formula (IV) wherein $R^1$ is S.

In particular embodiments, a compound of the invention may be a compound listed in Table 4.

TABLE 4

Selected compounds of Formula (IV)

| Compound | R1 | R2 | R9 | R10 |
|---|---|---|---|---|
| IV.1 | N | N | $(CH_2)$ | Halogen |
| IV.2 | N | N | $(CH_2)$ | Alkenyl |
| IV.3 | N | N | $(CH_2)$ | Alkynyl |
| IV.4 | N | N | $(CH_2)$ | Substituted hydrocarbyl |
| IV.5 | N | N | $(CH_2)_2$ | Halogen |
| IV.6 | N | N | $(CH_2)_2$ | Alkenyl |
| IV.7 | N | N | $(CH_2)_2$ | Alkynyl |
| IV.8 | N | N | $(CH_2)_2$ | Substituted hydrocarbyl |
| IV.9 | N | N | $(CH_2)_3$ | Halogen |
| IV.10 | N | N | $(CH_2)_3$ | Alkenyl |
| IV.11 | N | N | $(CH_2)_3$ | Alkynyl |
| IV.12 | N | N | $(CH_2)_3$ | Substituted hydrocarbyl |
| IV.13 | N | N | $(CH_2)_4$ | Halogen |
| IV.14 | N | N | $(CH_2)_4$ | Alkenyl |
| IV.15 | N | N | $(CH_2)_4$ | Alkynyl |
| IV.16 | N | N | $(CH_2)_4$ | Substituted hydrocarbyl |
| IV.17 | N | N | $(CH_2)_5$ | Halogen |
| IV.18 | N | N | $(CH_2)_5$ | Alkenyl |
| IV.19 | N | N | $(CH_2)_5$ | Alkynyl |
| IV.20 | N | N | $(CH_2)_5$ | Substituted hydrocarbyl |
| IV.21 | N | N | $(CH_2)_6$ | Halogen |
| IV.22 | N | N | $(CH_2)_6$ | Alkenyl |
| IV.23 | N | N | $(CH_2)_6$ | Alkynyl |
| IV.24 | N | N | $(CH_2)_6$ | Substituted hydrocarbyl |
| IV.25 | N | N | $(CH_2)_6$ | Hydrogen |
| IV.26 | N | N | $(CH_2)_7$ | Halogen |
| IV.27 | N | N | $(CH_2)_7$ | Alkenyl |
| IV.28 | N | N | $(CH_2)_7$ | Alkynyl |
| IV.29 | N | N | $(CH_2)_7$ | Substituted hydrocarbyl |
| IV.30 | N | N | $(CH_2)_7$ | Hydrogen |
| IV.31 | N | N | $(CH_2)_8$ | Halogen |
| IV.32 | N | N | $(CH_2)_8$ | Alkenyl |
| IV.33 | N | N | $(CH_2)_8$ | Alkynyl |
| IV.34 | N | N | $(CH_2)_8$ | Substituted hydrocarbyl |
| IV.35 | N | N | $(CH_2)_8$ | Hydrogen |
| IV.36 | N | N | $(CH_2)_9$ | Halogen |
| IV.37 | N | N | $(CH_2)_9$ | Alkenyl |
| IV.38 | N | N | $(CH_2)_9$ | Alkynyl |
| IV.39 | N | N | $(CH_2)_9$ | Substituted hydrocarbyl |
| IV.40 | N | N | $(CH_2)_9$ | Hydrogen |
| IV.41 | N | N | $(CH_2)_{10}$ | Halogen |
| IV.42 | N | N | $(CH_2)_{10}$ | Alkenyl |
| IV.43 | N | N | $(CH_2)_{10}$ | Alkynyl |
| IV.44 | N | N | $(CH_2)_{10}$ | Substituted hydrocarbyl |
| IV.45 | N | N | $(CH_2)_{10}$ | Hydrogen |
| IV.46 | N | S | $(CH_2)$ | Halogen |
| IV.47 | N | S | $(CH_2)$ | Alkenyl |
| IV.48 | N | S | $(CH_2)$ | Alkynyl |
| IV.49 | N | S | $(CH_2)$ | Substituted hydrocarbyl |
| IV.50 | N | S | $(CH_2)_2$ | Halogen |
| IV.51 | N | S | $(CH_2)_2$ | Alkenyl |
| IV.52 | N | S | $(CH_2)_2$ | Alkynyl |
| IV.53 | N | S | $(CH_2)_2$ | Substituted hydrocarbyl |
| IV.54 | N | S | $(CH_2)_3$ | Halogen |
| IV.55 | N | S | $(CH_2)_3$ | Alkenyl |
| IV.56 | N | S | $(CH_2)_3$ | Alkynyl |
| IV.57 | N | S | $(CH_2)_3$ | Substituted hydrocarbyl |
| IV.58 | N | S | $(CH_2)_4$ | Halogen |
| IV.59 | N | S | $(CH_2)_4$ | Alkenyl |
| IV.60 | N | S | $(CH_2)_4$ | Alkynyl |
| IV.61 | N | S | $(CH_2)_4$ | Substituted hydrocarbyl |
| IV.62 | N | S | $(CH_2)_5$ | Halogen |
| IV.63 | N | S | $(CH_2)_5$ | Alkenyl |
| IV.64 | N | S | $(CH_2)_5$ | Alkynyl |
| IV.65 | N | S | $(CH_2)_5$ | Substituted hydrocarbyl |
| IV.66 | N | S | $(CH_2)_6$ | Halogen |
| IV.67 | N | S | $(CH_2)_6$ | Alkenyl |
| IV.68 | N | S | $(CH_2)_6$ | Alkynyl |
| IV.69 | N | S | $(CH_2)_6$ | Substituted hydrocarbyl |
| IV.70 | N | S | $(CH_2)_6$ | Hydrogen |
| IV.71 | N | S | $(CH_2)_7$ | Halogen |
| IV.72 | N | S | $(CH_2)_7$ | Alkenyl |
| IV.73 | N | S | $(CH_2)_7$ | Alkynyl |
| IV.74 | N | S | $(CH_2)_7$ | Substituted hydrocarbyl |
| IV.75 | N | S | $(CH_2)_7$ | Hydrogen |
| IV.76 | N | S | $(CH_2)_8$ | Halogen |
| IV.77 | N | S | $(CH_2)_8$ | Alkenyl |
| IV.78 | N | S | $(CH_2)_8$ | Alkynyl |
| IV.79 | N | S | $(CH_2)_8$ | Substituted hydrocarbyl |
| IV.80 | N | S | $(CH_2)_8$ | Hydrogen |
| IV.81 | N | S | $(CH_2)_9$ | Halogen |
| IV.82 | N | S | $(CH_2)_9$ | Alkenyl |
| IV.83 | N | S | $(CH_2)_9$ | Alkynyl |
| IV.84 | N | S | $(CH_2)_9$ | Substituted hydrocarbyl |
| IV.85 | N | S | $(CH_2)_9$ | Hydrogen |
| IV.86 | N | S | $(CH_2)_{10}$ | Halogen |
| IV.87 | N | S | $(CH_2)_{10}$ | Alkenyl |
| IV.88 | N | S | $(CH_2)_{10}$ | Alkynyl |
| IV.89 | N | S | $(CH_2)_{10}$ | Substituted hydrocarbyl |
| IV.90 | N | S | $(CH_2)_{10}$ | Hydrogen |
| IV.91 | N | O | $(CH_2)$ | Halogen |
| IV.92 | N | O | $(CH_2)$ | Alkenyl |
| IV.93 | N | O | $(CH_2)$ | Alkynyl |
| IV.94 | N | O | $(CH_2)$ | Substituted hydrocarbyl |
| IV.95 | N | O | $(CH_2)_2$ | Halogen |
| IV.96 | N | O | $(CH_2)_2$ | Alkenyl |
| IV.97 | N | O | $(CH_2)_2$ | Alkynyl |
| IV.98 | N | O | $(CH_2)_2$ | Substituted hydrocarbyl |
| IV.99 | N | O | $(CH_2)_3$ | Halogen |
| IV.100 | N | O | $(CH_2)_3$ | Alkenyl |

TABLE 4-continued

Selected compounds of Formula (IV)

| Compound | R1 | R2 | R9 | R10 |
|---|---|---|---|---|
| IV.101 | N | O | $(CH_2)_3$ | Alkynyl |
| IV.102 | N | O | $(CH_2)_3$ | Substituted hydrocarbyl |
| IV.103 | N | O | $(CH_2)_4$ | Halogen |
| IV.104 | N | O | $(CH_2)_4$ | Alkenyl |
| IV.105 | N | O | $(CH_2)_4$ | Alkynyl |
| IV.106 | N | O | $(CH_2)_4$ | Substituted hydrocarbyl |
| IV.107 | N | O | $(CH_2)_5$ | Halogen |
| IV.108 | N | O | $(CH_2)_5$ | Alkenyl |
| IV.109 | N | O | $(CH_2)_5$ | Alkynyl |
| IV.110 | N | O | $(CH_2)_5$ | Substituted hydrocarbyl |
| IV.111 | N | O | $(CH_2)_6$ | Halogen |
| IV.112 | N | O | $(CH_2)_6$ | Alkenyl |
| IV.113 | N | O | $(CH_2)_6$ | Alkynyl |
| IV.114 | N | O | $(CH_2)_6$ | Substituted hydrocarbyl |
| IV.115 | N | O | $(CH_2)_6$ | Hydrogen |
| IV.116 | N | O | $(CH_2)_7$ | Halogen |
| IV.117 | N | O | $(CH_2)_7$ | Alkenyl |
| IV.118 | N | O | $(CH_2)_7$ | Alkynyl |
| IV.119 | N | O | $(CH_2)_7$ | Substituted hydrocarbyl |
| IV.120 | N | O | $(CH_2)_7$ | Hydrogen |
| IV.121 | N | O | $(CH_2)_8$ | Halogen |
| IV.122 | N | O | $(CH_2)_8$ | Alkenyl |
| IV.123 | N | O | $(CH_2)_8$ | Alkynyl |
| IV.124 | N | O | $(CH_2)_8$ | Substituted hydrocarbyl |
| IV.125 | N | O | $(CH_2)_8$ | Hydrogen |
| IV.126 | N | O | $(CH_2)_9$ | Halogen |
| IV.127 | N | O | $(CH_2)_9$ | Alkenyl |
| IV.128 | N | O | $(CH_2)_9$ | Alkynyl |
| IV.129 | N | O | $(CH_2)_9$ | Substituted hydrocarbyl |
| IV.130 | N | O | $(CH_2)_9$ | Hydrogen |
| IV.131 | N | O | $(CH_2)_{10}$ | Halogen |
| IV.132 | N | O | $(CH_2)_{10}$ | Alkenyl |
| IV.133 | N | O | $(CH_2)_{10}$ | Alkynyl |
| IV.134 | N | O | $(CH_2)_{10}$ | Substituted hydrocarbyl |
| IV.135 | N | O | $(CH_2)_{10}$ | Hydrogen |
| IV.136 | S | N | $(CH_2)$ | Halogen |
| IV.137 | S | N | $(CH_2)$ | Alkenyl |
| IV.138 | S | N | $(CH_2)$ | Alkynyl |
| IV.139 | S | N | $(CH_2)$ | Substituted hydrocarbyl |
| IV.140 | S | N | $(CH_2)_2$ | Halogen |
| IV.141 | S | N | $(CH_2)_2$ | Alkenyl |
| IV.142 | S | N | $(CH_2)_2$ | Alkynyl |
| IV.143 | S | N | $(CH_2)_2$ | Substituted hydrocarbyl |
| IV.144 | S | N | $(CH_2)_3$ | Halogen |
| IV.145 | S | N | $(CH_2)_3$ | Alkenyl |
| IV.146 | S | N | $(CH_2)_3$ | Alkynyl |
| IV.147 | S | N | $(CH_2)_3$ | Substituted hydrocarbyl |
| IV.148 | S | N | $(CH_2)_4$ | Halogen |
| IV.149 | S | N | $(CH_2)_4$ | Alkenyl |
| IV.150 | S | N | $(CH_2)_4$ | Alkynyl |
| IV.151 | S | N | $(CH_2)_4$ | Substituted hydrocarbyl |
| IV.152 | S | N | $(CH_2)_5$ | Halogen |
| IV.153 | S | N | $(CH_2)_5$ | Alkenyl |
| IV.154 | S | N | $(CH_2)_5$ | Alkynyl |
| IV.155 | S | N | $(CH_2)_5$ | Substituted hydrocarbyl |
| IV.156 | S | N | $(CH_2)_6$ | Halogen |
| IV.157 | S | N | $(CH_2)_6$ | Alkenyl |
| IV.158 | S | N | $(CH_2)_6$ | Alkynyl |
| IV.159 | S | N | $(CH_2)_6$ | Substituted hydrocarbyl |
| IV.160 | S | N | $(CH_2)_6$ | Hydrogen |
| IV.161 | S | N | $(CH_2)_7$ | Halogen |
| IV.162 | S | N | $(CH_2)_7$ | Alkenyl |
| IV.163 | S | N | $(CH_2)_7$ | Alkynyl |
| IV.164 | S | N | $(CH_2)_7$ | Substituted hydrocarbyl |
| IV.165 | S | N | $(CH_2)_7$ | Hydrogen |
| IV.166 | S | N | $(CH_2)_8$ | Halogen |
| IV.167 | S | N | $(CH_2)_8$ | Alkenyl |
| IV.168 | S | N | $(CH_2)_8$ | Alkynyl |
| IV.169 | S | N | $(CH_2)_8$ | Substituted hydrocarbyl |
| IV.170 | S | N | $(CH_2)_8$ | Hydrogen |
| IV.171 | S | N | $(CH_2)_9$ | Halogen |
| IV.172 | S | N | $(CH_2)_9$ | Alkenyl |
| IV.173 | S | N | $(CH_2)_9$ | Alkynyl |
| IV.174 | S | N | $(CH_2)_9$ | Substituted hydrocarbyl |
| IV.175 | S | N | $(CH_2)_9$ | Hydrogen |
| IV.176 | S | N | $(CH_2)_{10}$ | Halogen |
| IV.177 | S | N | $(CH_2)_{10}$ | Alkenyl |
| IV.178 | S | N | $(CH_2)_{10}$ | Alkynyl |
| IV.179 | S | N | $(CH_2)_{10}$ | Substituted hydrocarbyl |
| IV.180 | S | N | $(CH_2)_{10}$ | Hydrogen |
| IV.181 | S | S | $(CH_2)$ | Halogen |
| IV.182 | S | S | $(CH_2)$ | Alkenyl |
| IV.183 | S | S | $(CH_2)$ | Alkynyl |
| IV.184 | S | S | $(CH_2)$ | Substituted hydrocarbyl |
| IV.185 | S | S | $(CH_2)_2$ | Halogen |
| IV.186 | S | S | $(CH_2)_2$ | Alkenyl |
| IV.187 | S | S | $(CH_2)_2$ | Alkynyl |
| IV.188 | S | S | $(CH_2)_2$ | Substituted hydrocarbyl |
| IV.189 | S | S | $(CH_2)_3$ | Halogen |
| IV.190 | S | S | $(CH_2)_3$ | Alkenyl |
| IV.191 | S | S | $(CH_2)_3$ | Alkynyl |
| IV.192 | S | S | $(CH_2)_3$ | Substituted hydrocarbyl |
| IV.193 | S | S | $(CH_2)_4$ | Halogen |
| IV.194 | S | S | $(CH_2)_4$ | Alkenyl |
| IV.195 | S | S | $(CH_2)_4$ | Alkynyl |
| IV.196 | S | S | $(CH_2)_4$ | Substituted hydrocarbyl |
| IV.197 | S | S | $(CH_2)_5$ | Halogen |
| IV.198 | S | S | $(CH_2)_5$ | Alkenyl |
| IV.199 | S | S | $(CH_2)_5$ | Alkynyl |
| IV.200 | S | S | $(CH_2)_5$ | Substituted hydrocarbyl |
| IV.201 | S | S | $(CH_2)_6$ | Halogen |
| IV.202 | S | S | $(CH_2)_6$ | Alkenyl |
| IV.203 | S | S | $(CH_2)_6$ | Alkynyl |
| IV.204 | S | S | $(CH_2)_6$ | Substituted hydrocarbyl |
| IV.205 | S | S | $(CH_2)_6$ | Hydrogen |
| IV.206 | S | S | $(CH_2)_7$ | Halogen |
| IV.207 | S | S | $(CH_2)_7$ | Alkenyl |
| IV.208 | S | S | $(CH_2)_7$ | Alkynyl |
| IV.209 | S | S | $(CH_2)_7$ | Substituted hydrocarbyl |
| IV.210 | S | S | $(CH_2)_7$ | Hydrogen |
| IV.211 | S | S | $(CH_2)_8$ | Halogen |
| IV.212 | S | S | $(CH_2)_8$ | Alkenyl |
| IV.213 | S | S | $(CH_2)_8$ | Alkynyl |
| IV.214 | S | S | $(CH_2)_8$ | Substituted hydrocarbyl |
| IV.215 | S | S | $(CH_2)_8$ | Hydrogen |
| IV.216 | S | S | $(CH_2)_9$ | Halogen |
| IV.217 | S | S | $(CH_2)_9$ | Alkenyl |
| IV.218 | S | S | $(CH_2)_9$ | Alkynyl |
| IV.219 | S | S | $(CH_2)_9$ | Substituted hydrocarbyl |
| IV.220 | S | S | $(CH_2)_9$ | Hydrogen |
| IV.221 | S | S | $(CH_2)_{10}$ | Halogen |
| IV.222 | S | S | $(CH_2)_{10}$ | Alkenyl |
| IV.223 | S | S | $(CH_2)_{10}$ | Alkynyl |
| IV.224 | S | S | $(CH_2)_{10}$ | Substituted hydrocarbyl |
| IV.225 | S | S | $(CH_2)_{10}$ | Hydrogen |
| IV.226 | S | O | $(CH_2)$ | Halogen |
| IV.227 | S | O | $(CH_2)$ | Alkenyl |
| IV.228 | S | O | $(CH_2)$ | Alkynyl |
| IV.229 | S | O | $(CH_2)$ | Substituted hydrocarbyl |
| IV.230 | S | O | $(CH_2)_2$ | Halogen |
| IV.231 | S | O | $(CH_2)_2$ | Alkenyl |
| IV.232 | S | O | $(CH_2)_2$ | Alkynyl |
| IV.233 | S | O | $(CH_2)_2$ | Substituted hydrocarbyl |
| IV.234 | S | O | $(CH_2)_3$ | Halogen |
| IV.235 | S | O | $(CH_2)_3$ | Alkenyl |
| IV.236 | S | O | $(CH_2)_3$ | Alkynyl |
| IV.237 | S | O | $(CH_2)_3$ | Substituted hydrocarbyl |
| IV.238 | S | O | $(CH_2)_4$ | Halogen |
| IV.239 | S | O | $(CH_2)_4$ | Alkenyl |
| IV.240 | S | O | $(CH_2)_4$ | Alkynyl |
| IV.241 | S | O | $(CH_2)_4$ | Substituted hydrocarbyl |
| IV.242 | S | O | $(CH_2)_5$ | Halogen |
| IV.243 | S | O | $(CH_2)_5$ | Alkenyl |
| IV.244 | S | O | $(CH_2)_5$ | Alkynyl |
| IV.245 | S | O | $(CH_2)_5$ | Substituted hydrocarbyl |
| IV.246 | S | O | $(CH_2)_6$ | Halogen |
| IV.247 | S | O | $(CH_2)_6$ | Alkenyl |
| IV.248 | S | O | $(CH_2)_6$ | Alkynyl |
| IV.249 | S | O | $(CH_2)_6$ | Substituted hydrocarbyl |
| IV.250 | S | O | $(CH_2)_6$ | Hydrogen |
| IV.251 | S | O | $(CH_2)_7$ | Halogen |
| IV.252 | S | O | $(CH_2)_7$ | Alkenyl |

TABLE 4-continued

Selected compounds of Formula (IV)

| Compound | R1 | R2 | R9 | R10 |
|---|---|---|---|---|
| IV.253 | S | O | $(CH_2)_7$ | Alkynyl |
| IV.254 | S | O | $(CH_2)_7$ | Substituted hydrocarbyl |
| IV.255 | S | O | $(CH_2)_7$ | Hydrogen |
| IV.256 | S | O | $(CH_2)_8$ | Halogen |
| IV.257 | S | O | $(CH_2)_8$ | Alkenyl |
| IV.258 | S | O | $(CH_2)_8$ | Alkynyl |
| IV.259 | S | O | $(CH_2)_8$ | Substituted hydrocarbyl |
| IV.260 | S | O | $(CH_2)_8$ | Hydrogen |
| IV.261 | S | O | $(CH_2)_9$ | Halogen |
| IV.262 | S | O | $(CH_2)_9$ | Alkenyl |
| IV.263 | S | O | $(CH_2)_9$ | Alkynyl |
| IV.264 | S | O | $(CH_2)_9$ | Substituted hydrocarbyl |
| IV.265 | S | O | $(CH_2)_9$ | Hydrogen |
| IV.266 | S | O | $(CH_2)_{10}$ | Halogen |
| IV.267 | S | O | $(CH_2)_{10}$ | Alkenyl |
| IV.268 | S | O | $(CH_2)_{10}$ | Alkynyl |
| IV.269 | S | O | $(CH_2)_{10}$ | Substituted hydrocarbyl |
| IV.270 | S | O | $(CH_2)_{10}$ | Hydrogen |
| IV.271 | O | N | $(CH_2)$ | Halogen |
| IV.272 | O | N | $(CH_2)$ | Alkenyl |
| IV.273 | O | N | $(CH_2)$ | Alkynyl |
| IV.274 | O | N | $(CH_2)$ | Substituted hydrocarbyl |
| IV.275 | O | N | $(CH_2)_2$ | Halogen |
| IV.276 | O | N | $(CH_2)_2$ | Alkenyl |
| IV.277 | O | N | $(CH_2)_2$ | Alkynyl |
| IV.278 | O | N | $(CH_2)_2$ | Substituted hydrocarbyl |
| IV.279 | O | N | $(CH_2)_3$ | Halogen |
| IV.280 | O | N | $(CH_2)_3$ | Alkenyl |
| IV.281 | O | N | $(CH_2)_3$ | Alkynyl |
| IV.282 | O | N | $(CH_2)_3$ | Substituted hydrocarbyl |
| IV.283 | O | N | $(CH_2)_4$ | Halogen |
| IV.284 | O | N | $(CH_2)_4$ | Alkenyl |
| IV.285 | O | N | $(CH_2)_4$ | Alkynyl |
| IV.286 | O | N | $(CH_2)_4$ | Substituted hydrocarbyl |
| IV.287 | O | N | $(CH_2)_5$ | Halogen |
| IV.288 | O | N | $(CH_2)_5$ | Alkenyl |
| IV.289 | O | N | $(CH_2)_5$ | Alkynyl |
| IV.290 | O | N | $(CH_2)_5$ | Substituted hydrocarbyl |
| IV.291 | O | N | $(CH_2)_6$ | Halogen |
| IV.292 | O | N | $(CH_2)_6$ | Alkenyl |
| IV.293 | O | N | $(CH_2)_6$ | Alkynyl |
| IV.294 | O | N | $(CH_2)_6$ | Substituted hydrocarbyl |
| IV.295 | O | N | $(CH_2)_6$ | Hydrogen |
| IV.296 | O | N | $(CH_2)_7$ | Halogen |
| IV.297 | O | N | $(CH_2)_7$ | Alkenyl |
| IV.298 | O | N | $(CH_2)_7$ | Alkynyl |
| IV.299 | O | N | $(CH_2)_7$ | Substituted hydrocarbyl |
| IV.300 | O | N | $(CH_2)_7$ | Hydrogen |
| IV.301 | O | N | $(CH_2)_8$ | Halogen |
| IV.302 | O | N | $(CH_2)_8$ | Alkenyl |
| IV.303 | O | N | $(CH_2)_8$ | Alkynyl |
| IV.304 | O | N | $(CH_2)_8$ | Substituted hydrocarbyl |
| IV.305 | O | N | $(CH_2)_8$ | Hydrogen |
| IV.306 | O | N | $(CH_2)_9$ | Halogen |
| IV.307 | O | N | $(CH_2)_9$ | Alkenyl |
| IV.308 | O | N | $(CH_2)_9$ | Alkynyl |
| IV.309 | O | N | $(CH_2)_9$ | Substituted hydrocarbyl |
| IV.310 | O | N | $(CH_2)_9$ | Hydrogen |
| IV.311 | O | N | $(CH_2)_{10}$ | Halogen |
| IV.312 | O | N | $(CH_2)_{10}$ | Alkenyl |
| IV.313 | O | N | $(CH_2)_{10}$ | Alkynyl |
| IV.314 | O | N | $(CH_2)_{10}$ | Substituted hydrocarbyl |
| IV.315 | O | N | $(CH_2)_{10}$ | Hydrogen |
| IV.316 | O | S | $(CH_2)$ | Halogen |
| IV.317 | O | S | $(CH_2)$ | Alkenyl |
| IV.318 | O | S | $(CH_2)$ | Alkynyl |
| IV.319 | O | S | $(CH_2)$ | Substituted hydrocarbyl |
| IV.320 | O | S | $(CH_2)_2$ | Halogen |
| IV.321 | O | S | $(CH_2)_2$ | Alkenyl |
| IV.322 | O | S | $(CH_2)_2$ | Alkynyl |
| IV.323 | O | S | $(CH_2)_2$ | Substituted hydrocarbyl |
| IV.324 | O | S | $(CH_2)_3$ | Halogen |
| IV.325 | O | S | $(CH_2)_3$ | Alkenyl |
| IV.326 | O | S | $(CH_2)_3$ | Alkynyl |
| IV.327 | O | S | $(CH_2)_3$ | Substituted hydrocarbyl |
| IV.328 | O | S | $(CH_2)_4$ | Halogen |
| IV.329 | O | S | $(CH_2)_4$ | Alkenyl |
| IV.330 | O | S | $(CH_2)_4$ | Alkynyl |
| IV.331 | O | S | $(CH_2)_4$ | Substituted hydrocarbyl |
| IV.332 | O | S | $(CH_2)_5$ | Halogen |
| IV.333 | O | S | $(CH_2)_5$ | Alkenyl |
| IV.334 | O | S | $(CH_2)_5$ | Alkynyl |
| IV.335 | O | S | $(CH_2)_5$ | Substituted hydrocarbyl |
| IV.336 | O | S | $(CH_2)_6$ | Halogen |
| IV.337 | O | S | $(CH_2)_6$ | Alkenyl |
| IV.338 | O | S | $(CH_2)_6$ | Alkynyl |
| IV.339 | O | S | $(CH_2)_6$ | Substituted hydrocarbyl |
| IV.340 | O | S | $(CH_2)_6$ | Hydrogen |
| IV.341 | O | S | $(CH_2)_7$ | Halogen |
| IV.342 | O | S | $(CH_2)_7$ | Alkenyl |
| IV.343 | O | S | $(CH_2)_7$ | Alkynyl |
| IV.344 | O | S | $(CH_2)_7$ | Substituted hydrocarbyl |
| IV.345 | O | S | $(CH_2)_7$ | Hydrogen |
| IV.346 | O | S | $(CH_2)_8$ | Halogen |
| IV.347 | O | S | $(CH_2)_8$ | Alkenyl |
| IV.348 | O | S | $(CH_2)_8$ | Alkynyl |
| IV.349 | O | S | $(CH_2)_8$ | Substituted hydrocarbyl |
| IV.350 | O | S | $(CH_2)_8$ | Hydrogen |
| IV.351 | O | S | $(CH_2)_9$ | Halogen |
| IV.352 | O | S | $(CH_2)_9$ | Alkenyl |
| IV.353 | O | S | $(CH_2)_9$ | Alkynyl |
| IV.354 | O | S | $(CH_2)_9$ | Substituted hydrocarbyl |
| IV.355 | O | S | $(CH_2)_9$ | Hydrogen |
| IV.356 | O | S | $(CH_2)_{10}$ | Halogen |
| IV.357 | O | S | $(CH_2)_{10}$ | Alkenyl |
| IV.358 | O | S | $(CH_2)_{10}$ | Alkynyl |
| IV.359 | O | S | $(CH_2)_{10}$ | Substituted hydrocarbyl |
| IV.360 | O | S | $(CH_2)_{10}$ | Hydrogen |
| IV.361 | O | O | $(CH_2)$ | Halogen |
| IV.362 | O | O | $(CH_2)$ | Alkenyl |
| IV.363 | O | O | $(CH_2)$ | Alkynyl |
| IV.364 | O | O | $(CH_2)$ | Substituted hydrocarbyl |
| IV.365 | O | O | $(CH_2)_2$ | Halogen |
| IV.366 | O | O | $(CH_2)_2$ | Alkenyl |
| IV.367 | O | O | $(CH_2)_2$ | Alkynyl |
| IV.368 | O | O | $(CH_2)_2$ | Substituted hydrocarbyl |
| IV.369 | O | O | $(CH_2)_3$ | Halogen |
| IV.370 | O | O | $(CH_2)_3$ | Alkenyl |
| IV.371 | O | O | $(CH_2)_3$ | Alkynyl |
| IV.372 | O | O | $(CH_2)_3$ | Substituted hydrocarbyl |
| IV.373 | O | O | $(CH_2)_4$ | Halogen |
| IV.374 | O | O | $(CH_2)_4$ | Alkenyl |
| IV.375 | O | O | $(CH_2)_4$ | Alkynyl |
| IV.376 | O | O | $(CH_2)_4$ | Substituted hydrocarbyl |
| IV.377 | O | O | $(CH_2)_5$ | Halogen |
| IV.378 | O | O | $(CH_2)_5$ | Alkenyl |
| IV.379 | O | O | $(CH_2)_5$ | Alkynyl |
| IV.380 | O | O | $(CH_2)_5$ | Substituted hydrocarbyl |
| IV.381 | O | O | $(CH_2)_6$ | Halogen |
| IV.382 | O | O | $(CH_2)_6$ | Alkenyl |
| IV.383 | O | O | $(CH_2)_6$ | Alkynyl |
| IV.384 | O | O | $(CH_2)_6$ | Substituted hydrocarbyl |
| IV.385 | O | O | $(CH_2)_6$ | Hydrogen |
| IV.386 | O | O | $(CH_2)_7$ | Halogen |
| IV.387 | O | O | $(CH_2)_7$ | Alkenyl |
| IV.388 | O | O | $(CH_2)_7$ | Alkynyl |
| IV.389 | O | O | $(CH_2)_7$ | Substituted hydrocarbyl |
| IV.390 | O | O | $(CH_2)_7$ | Hydrogen |
| IV.391 | O | O | $(CH_2)_8$ | Halogen |
| IV.392 | O | O | $(CH_2)_8$ | Alkenyl |
| IV.393 | O | O | $(CH_2)_8$ | Alkynyl |
| IV.394 | O | O | $(CH_2)_8$ | Substituted hydrocarbyl |
| IV.395 | O | O | $(CH_2)_8$ | Hydrogen |
| IV.396 | O | O | $(CH_2)_9$ | Halogen |
| IV.397 | O | O | $(CH_2)_9$ | Alkenyl |
| IV.398 | O | O | $(CH_2)_9$ | Alkynyl |
| IV.399 | O | O | $(CH_2)_9$ | Substituted hydrocarbyl |
| IV.400 | O | O | $(CH_2)_9$ | Hydrogen |
| IV.401 | O | O | $(CH_2)_{10}$ | Halogen |
| IV.402 | O | O | $(CH_2)_{10}$ | Alkenyl |
| IV.403 | O | O | $(CH_2)_{10}$ | Alkynyl |

TABLE 4-continued

Selected compounds of Formula (IV)

| Compound | R1 | R2 | R9 | R10 |
|---|---|---|---|---|
| IV.404 | O | O | $(CH_2)_{10}$ | Substituted hydrocarbyl |
| IV.405 | O | O | $(CH_2)_{10}$ | Hydrogen |

Compounds of formulas (I), (II), (III), or (IV), or listed in Tables 1-4 may be further modified to comprise an imaging moiety. As used herein, an "imaging moiety" refers to a chemical moiety capable of generating a detectable signal. For instance, imaging agents may generate a detectable signal for microscopy, e.g. fluorescent microscopy, confocal microscopy, or electron microscopy, magnetic resonance imaging, tomography, such as gamma (SPECT/CT, planar) and positron emission tomography (PET/CT), radiography, or ultrasound. Imaging agents may be detectable in situ, in vivo, ex vivo, and in vitro. In one embodiment, an imaging moiety may be selected from tritium, $C^{11}$, $N^{13}$, $O^{15}$, or $F^{18}$.

In other embodiments, a compound described herein may further comprise a therapeutic moiety. As used herein, a "therapeutic moiety" refers to a chemical moiety capable of ameliorating one or more clinical consequences of CAA. For instance, a therapeutic moiety may be capable of ameliorating lobar hemorrhage, dementia, or ischemic brain injury.

In certain embodiments of the invention, a compound described above may comprise a salt or chelate. Non-limiting examples of suitable salts or chelates include those that are non-toxic to living cells.

Methods of making a compound of the invention described in this section are known in the art. For instance, see the Examples. Additionally, see Journal of the American Chemical Society (2003), 125, 11146-11147, and Chemical Communications 2007, (44), 4647-4649, each of which is hereby incorporated by reference in its entirety.

II. Methods

Another aspect of the invention encompasses methods of use of a compound that selectively recognizes cerebral vessel amyloid deposits, as opposed to parenchyma amyloid deposits, as described in section I. above.

In one embodiment, the invention encompasses a method for selectively detecting cerebral vessel amyloid deposits, as opposed to parenchyma amyloid deposits. Generally speaking, the method comprises, in part, contacting a tissue sample with a compound of the invention. Suitable tissue samples may include samples that are suspected of comprising amyloid deposits, at risk of comprising amyloid deposits, or are known to comprise amyloid deposits. Tissue samples may be derived from any organism capable of having amyloid deposits. Non-limiting examples may include mammals, such as rodents, non-human primates, and humans. Typically, the compound comprises an imaging agent, as described in section I above. The method further comprises detecting the imaging agent. Detection of the compound comprising the imaging agent is indicative of the presence of cerebral vessel amyloid deposits in the tissue.

In another embodiment, the invention encompasses a method for diagnosing CAA in subject. Generally speaking, the method comprises, in part, administering a compound of the invention to a subject. Suitable subjects may include subjects that are suspected of having amyloid deposits, at risk of having amyloid deposits, or are known to have amyloid deposits. Exemplary subjects are those without clinical symptoms of CAA. For instance, an exemplary subject is a subject without cerebral hemorrhage. Non-limiting examples of suitable subjects may include mammals, such as rodents, non-human primates, and humans. Typically, the compound administered to the subject comprises an imaging agent, as described in section I above. The method further comprises detecting the imaging agent. If the compound comprising the imaging agent is detected within the subject, then the subject is diagnosed with CAA.

In yet another embodiment, the invention encompasses a method for quantifying the severity of CAA. In this regard, the amount of compound detected in a subject is proportional to the severity of CAA.

Still another embodiment of the invention encompasses a method for monitoring the progression of CAA over time. The method typically comprises administering a compound of the invention to a subject and detecting the compound as described above, at a first time point, and administering a compound of the invention to a subject and detecting the compound as described above, at least one additional time point. The different in quantity of the compound detected is an indication of the progression of CAA over time. For example, an increase in the quantity of the compound between two time points is an indication that the CAA is progressing, while a decrease in the quantity of the compound detected between two time points is an indication that the CAA is resolving. The two time points may be hours, days, weeks, or months apart. In some embodiments, the two time points may even be years apart.

In still yet another embodiment, the invention encompasses a method for monitoring the response of CAA to a therapy. Generally speaking the method comprises administering a compound of the invention to a subject and detecting the compound at a first time point, administering a therapy to the subject, and then administering a compound of the invention to a subject and detecting the compound at least one other time point after the therapy has been administered. The difference in the quantity of the compound detected is an indication of the response of the subject to the therapy. For example, an increase in the quantity of the compound after therapy is an indication that the CAA is progressing (e.g. the subject is not responding to the therapy), while a decrease in the quantity of the compound detected after therapy is an indication that the CAA is resolving (e.g. the subject is responding to the therapy). The compound may be administered and detected hours, days, weeks, or months after the therapy was given. In some embodiments, the two time points may even be years apart.

The following examples are included to demonstrate preferred embodiments of the invention. It should be appreciated by those of skill in the art that the techniques disclosed in the examples that follow represent techniques discovered by the inventors to function well in the practice of the invention. Those of skill in the art should, however, in light of the present disclosure, appreciate that may changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

EXAMPLES

The following examples illustrate various iterations of the invention.

Example 1

Since the mid-1990s, many groups have sought to develop probes for PET and SPECT imaging of amyloid deposits in AD patients via chemical modification of amyloid-binding dyes such as Congo red, chrysamine G, and thioflavin. To date, three amyloid tracers labeled with positron-emitting radioligands ([$^{11}$C]PIB, [$^{11}$C]SB-13, and [$^{18}$F]FDDNP) have shown promise. Unfortunately, these tracers have been unable to define whether the observed amyloid represents neuritic plaques vs. CAA due to the low resolution of PET imaging and the almost equal affinity of these tracers for parenchymal vs. cerebrovascular amyloid. During our laboratory's exploration into the effects of CAA on neurovascular function, we observed that a fluorescent phenoxazine derivative, resorufin, preferentially bound CAA over neuritic plaques in aged Tg2576 mice (a common mouse model of AD and CAA). Moreover, phenoxazine analogs including ethyl-resorufin, phenyl-resorufin, and methoxyphenyl-resorufin demonstrated favorable properties for non-invasive amyloid-imaging probes, including moderate lipophilicity which is essential for rapid tracer uptake into the brain, selective binding affinity for CAA deposits at a low nanomolar range, and a functional group feasible for labeling with positron-emitting radioligands.

CAA may be defined by amyloid deposition within walls of leptomeningeal and cortical arterioles. Among the several types of amyloid proteins causing CAA, amyloid β (β) is by far the most common. Aβ is a 39-43-amino acid peptide (including A$β_{40}$ and A$β_{42}$) that is produced from the amyloid precursor protein (APP) via sequential proteolytic cleavage processed by β- and γ-secretases (Sisodia, 1999; Selkoe, 2001; Zhang and Xu, 2007). Aβ monomers are a soluble form of Aβ that are produced throughout life. In certain individuals, soluble Aβ monomers aggregate to form insoluble amyloid fibrils. This pathological form of Aβ is the major constituent of CAA. It is also the primary component of senile plaques—one of the pathological hallmarks of Alzheimer's Disease (AD). Aβ deposits within cerebral vessels are significantly different from Aβ deposits in brain parenchyma in regards to composition and pathogenesis. For example, while A$β_{42}$ is thought to be an important seed for CAA formation (Kim et al., 2007), the higher the level of A$β_{40}$ and the A$β_{40}$/A$β_{42}$ ratio, the greater the % of CAA vs. parenchymal plaques. Similarly, when APP transgenic mice with the HCHWA-D mutation (the mutation associated with Dutch type of familial CAA) are bred to mice over-expressing a presenilin-1 (PS1) Mutation that increases A$β_{42}$ production and decreases the A$β_{40}$/A$β_{42}$ ratio, the pathology shifts from CAA to parenchymal deposits (Herzig et al., 2004). Yet not until our preliminary work with phenoxazine has a difference in specificity between parenchymal vs. cerebrovascular plaques been noted with an amyloid imaging dye (see below).

CAA is primarily a disease of the elderly. When assessed by post-mortem neuropathological examination, it affects about one-third of individuals aged 60 years or older. An even higher incidence of CAA is found in patients with AD—also an age-dependent condition. In fact, up to 90% of AD patients have histological evidence of amyloid deposits within cerebral vessels (Nicoll et al., 2004; Maia et al., 2007). Regarding the clinical consequences of CAA, there is compelling evidence that CAA causes "lobar" cerebral hemorrhage (Vinters, 1987; Greenberg, 2002). In addition, several population-based autopsy studies indicate that CAA is also an independent risk factor for ischemic stroke and dementia (Okazaki et al., 1979; Greenberg et al., 1993; Mann et al., 1996; Itoh and Yamada, 1997; Vermeer et al., 2003).

Though amyloid PET imaging tracers have shown great promise in the setting of AD, the lack of specificity of these dyes for parenchymal vs. cerebrovascular Aβ deposits makes utilization of these tracers for the diagnosis and quantitation of CAA extremely difficult, if not impossible. The development of a selective CAA PET imaging tracer is therefore desperately needed.

Figure 3:
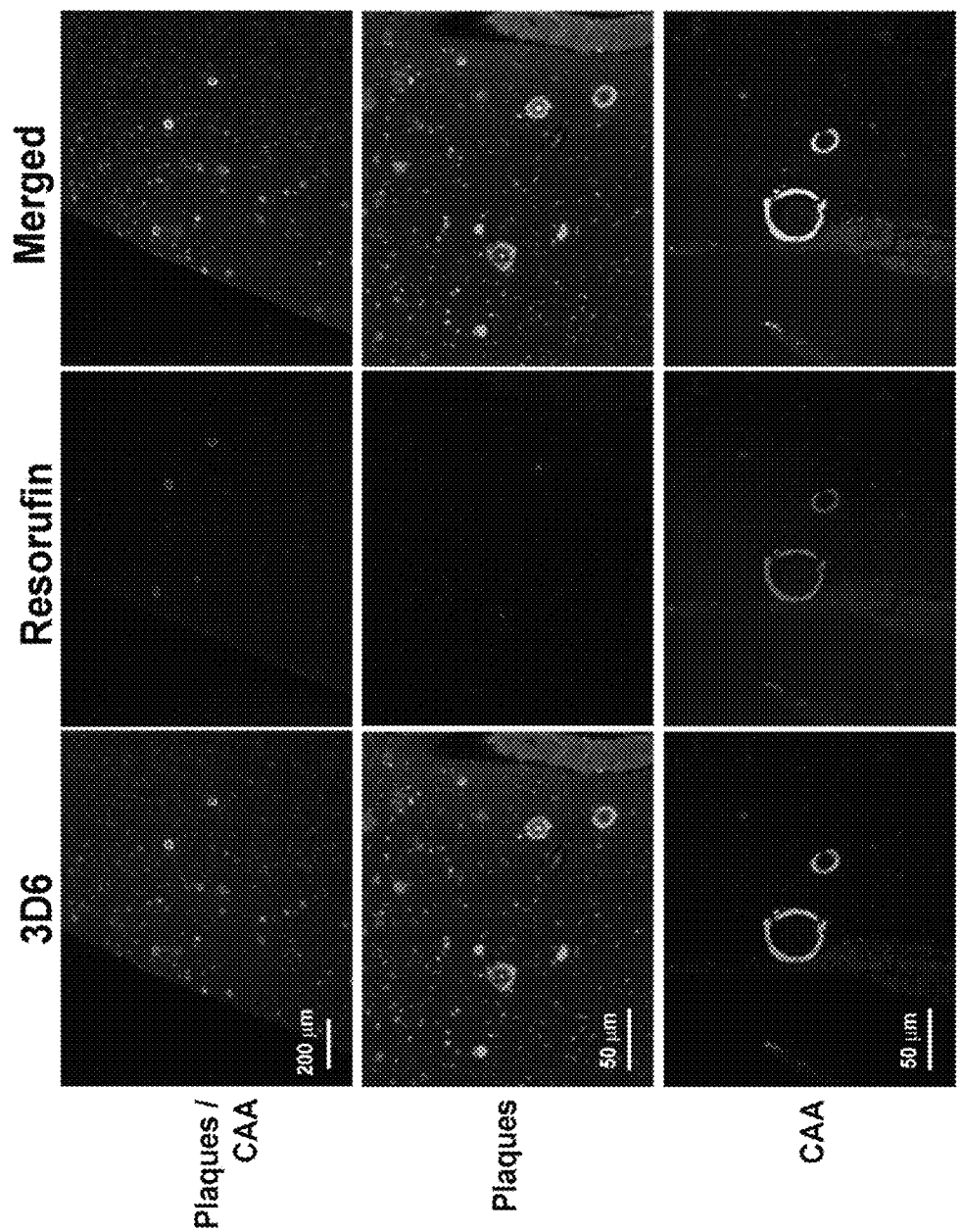
FIG. 3 depicts images showing the preferential binding of resorufin to CAA vs. neuritic plaques in human AD brains. Paraffin-embedded cortical brain sections of a human AD patient were subjected to immunofluorescent labeling with anti-Aβ antibody (3D6, green) followed by staining with resorufin (red). Note that resorufin selectively labeled 3D6-immunoreactive amyloid deposits in arterioles but less likely neuritic plaques.

Tg2576 mice are a well characterized mouse model of AD and CAA. They develop congophilic Aβ aggregates within neuritic plaques and leptomeningeal and cortical penetrating arteries at 11 months of age (Hsiao et al., 1996; Kawarabayashi et al., 2001; Fryer et al., 2005; Han et al., 2008). Consistent with previous reports (Hsiao et al., 1996; Kawarabayashi et al., 2001; Fryer et al., 2005; Han et al., 2008), we found that the congophilic dye methoxy-X34 visualized both CAA and neuritic plaques in aged Tg2576 mice. Resorufin, on the other hand, was found to bind CAA>>>neuritic plaques (FIG. 1). We calculated the binding affinity ($K_D$) of resorufin to be 458±68 nM for CAA, while its binding to neuritic plaques was negligible even when the in situ binding assay was performed at a concentration of 160 μM (FIG. 2). In contrast, a Congo red derivative methoxy-X34 had almost an equal affinity for both CAA and neuritic plaques (FIG. 2). Moreover, alkyl or aryl modification of resorufin at the 7-OH position increases the binding affinity for CAA (while maintaining its selectivity). Moderate lipophilicity (log$P_{oct}$ in range of 1-3) is an essential element of brain tracers, as this ensures high brain uptake and rapid clearance from the brain (Henriksen et al., 2008). We found that modification at the 7-OH position of resorufin led to increased lipophilicity (log-$P_{oct}$: 1.9-2.2) suggesting the feasibility of these molecules for in vivo amyloid imaging (FIG. 2). To test whether resorufin preferentially binds CAA in humans, paraffin-embedded cortical sections from an autopsied AD patient were labeled with the anti-Aβ antibody 3D6 and resorufin (FIG. 3). Consistent with our findings in Tg2576 mice, resorufin-positive staining was prominent in 3D6-positive cerebral arterioles but was rarely seen in 3D6-positive neuritic plaques (FIG. 3). Double labeling with resorufin and methoxy-X34 further confirmed the preferential binding of resorufin to CAA over neuritic plaques (data not shown).

REFERENCES FOR EXAMPLE 1

Fryer J D, Simmons K, Parsadanian M, Bales K R, Paul S M, Sullivan P M, Holtzman D M (2005) Human apolipoprotein E4 alters the amyloid-beta 40:42 ratio and promotes the formation of cerebral amyloid angiopathy in an amyloid precursor protein transgenic model. J Neurosci 25:2803-2810.

Greenberg S M (2002) Cerebral amyloid angiopathy and vessel dysfunction. Cerebrovasc Dis 13 Suppl 2:42-47.

Greenberg S M, Vonsattel J P, Stakes J W, Gruber M, Finklestein S P (1993) The clinical spectrum of cerebral amyloid angiopathy: presentations without lobar hemorrhage. Neurology 43:2073-2079.

Han B H, Zhou M L, Abousaleh F, Brendza R P, Dietrich H H, Koenigsknecht-Talboo J, Cirrito J R, Milner E, Holtzman D M, Zipfel G J (2008) Cerebrovascular dysfunction in amyloid precursor protein transgenic mice: contribution of soluble and insoluble amyloid-beta peptide, partial restoration via gamma-secretase inhibition. J Neurosci 28:13542-13550.

Henriksen G, Yousefi B H, Drzezga A, Wester H J (2008) Development and evaluation of compounds for imaging of beta-amyloid plaque by means of positron emission tomography. European journal of nuclear medicine and molecular imaging 35 Suppl 1:S75-81.

Herzig M C, Winkler D T, Burgermeister P, Pfeifer M, Kohler E, Schmidt S D, Danner S, Abramowski D, Sturchler-Pierrat C, Burki K, van Duinen S G, Maat-Schieman M L, Staufenbiel M, Mathews P M, Jucker M (2004) Abeta is targeted to the vasculature in a mouse model of hereditary cerebral hemorrhage with amyloidosis. Nat Neurosci 7:954-960.

Hsiao K, Chapman P, Nilsen S, Eckman C, Harigaya Y, Younkin S, Yang F, Cole G (1996) Correlative memory deficits, Abeta elevation, and amyloid plaques in transgenic mice. Science 274:99-102.

Itoh Y, Yamada M (1997) Cerebral amyloid angiopathy in the elderly: the clinicopathological features, pathogenesis, and risk factors. J Med Dent Sci 44:11-19.

Kawarabayashi T, Younkin L H, Saido T C, Shoji M, Ashe K H, Younkin S G (2001) Age-dependent changes in brain, CSF, and plasma amyloid (beta) protein in the Tg2576 transgenic mouse model of Alzheimer's disease. J Neurosci 21:372-381.

Kim J, Onstead L, Randle S, Price R, Smithson L, Zwizinski C, Dickson D W, Golde T, McGowan E (2007) Abeta40 inhibits amyloid deposition in vivo. J Neurosci 27:627-633.

Klunk W E et al. (2004) Imaging brain amyloid in Alzheimer's disease with Pittsburgh Compound-B. Ann Neurol 55:306-319.

Lee V M (2002) Amyloid binding ligands as Alzheimer's disease therapies. Neurobiol Aging 23:1039-1042.

Maia L F, Mackenzie I R, Feldman H H (2007) Clinical phenotypes of Cerebral Amyloid Angiopathy. J Neurol Sci 257:23-30.

Mann D M, Iwatsubo T, Ihara Y, Cairns N J, Lantos P L, Bogdanovic N, Lannfelt L, Winblad B, Maat-Schieman M L, Rossor M N (1996) Predominant deposition of amyloid-beta 42(43) in plaques in cases of Alzheimer's disease and hereditary cerebral hemorrhage associated with mutations in the amyloid precursor protein gene. Am J Pathol 148:1257-1266.

Mathis C A, Wang Y, Holt D P, Huang G F, Debnath M L, Klunk W E (2003) Synthesis and evaluation of 11C-labeled 6-substituted 2-arylbenzothiazoles as amyloid imaging agents. Journal of medicinal chemistry 46:2740-2754.

Nicoll J A, Yamada M, Frackowiak J, Mazur-Kolecka B, Weller R O (2004) Cerebral amyloid angiopathy plays a direct role in the pathogenesis of Alzheimer's disease. Pro-CAA position statement. Neurobiol Aging 25:589-597; discussion 603-584.

Nordberg A (2007) Amyloid imaging in Alzheimer's disease. Current opinion in neurology 20:398-402.

Nordberg A (2008) Amyloid plaque imaging in vivo: current achievement and future prospects. European journal of nuclear medicine and molecular imaging 35 Suppl 1:S46-50.

Okazaki H, Reagan T J, Campbell R J (1979) Clinicopathologic studies of primary cerebral amyloid angiopathy. Mayo Clin Proc 54:22-31.

Selkoe D J (2001) Alzheimer's disease: genes, proteins, and therapy. Physiol Rev 81:741-766.

Sisodia S S (1999) Alzheimer's disease: perspectives for the new millennium. J Clin Invest 104:1169-1170.

Suhara T, Higuchi M, Miyoshi M (2008) Neuroimaging in dementia: in vivo amyloid imaging. The Tohoku journal of experimental medicine 215:119-124.

Vermeer S E, Prins N D, den Heijer T, Hofman A, Koudstaal P J, Breteler M M (2003) Silent brain infarcts and the risk of dementia and cognitive decline. N Engl J Med 348:1215-1222.

Vinters H V (1987) Cerebral amyloid angiopathy. A critical review. Stroke 18:311-324.

Zhang Y W, Xu H (2007) Molecular and Cellular Mechanisms for Alzheimer's Disease: Understanding APP Metabolism. Curr Mol Med 7:687-696.

Example 2

Resorufin Selectively Visualizes Cerebrovascular Aβ Deposits in Live Tg2576 Mice.

Figure 4:
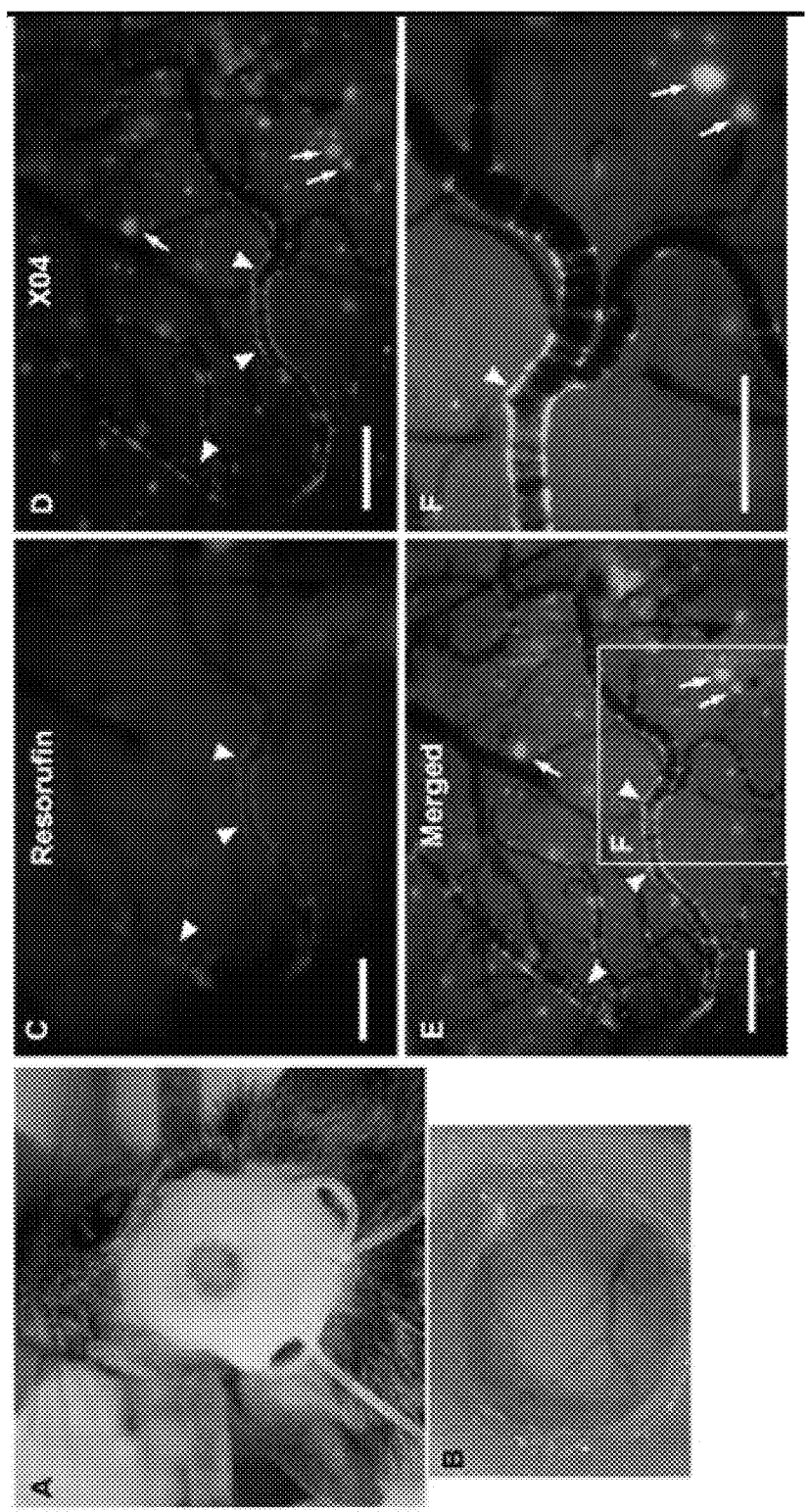
FIG. 4 depicts in vivo live imaging of CAA amyloid deposits through closed cranial window. A,B. Closed cranial window was prepared on the right parietal bone of 16-month-old Tg2576 mice. Leptomeningeal arterioles (B) were subjected to live imaging using a fluorescent microscope. C-F. Both resorufin and methoxy-X04 were infused for 5 min into the brain through a closed cranial window in Tg2576 mice. After wash for 10 min with artificial cerebrospinal fluid solution, fluorescent images of resorufin (red) and methoxy-X04 (blue) were taken (N=6). Resorufin selectively labeled amyloid deposits in arterioles (arrows) whereas methoxy-X04 staining was noted in both arterioles and senile plaques (arrowheads). Scale bars: in C-E: 250 µm, in E: 100 µm.

We examined whether resorufin preferentially visualizes CAA deposits in vivo utilizing a closed cranial window preparation with live imaging fluorescent microscopy as we described previously (19). Topical application of resorufin (2 μM) onto the surface of the brain through the cranial window resulted in marked fluorescent labeling within the walls of leptomeningeal arteries (but not in neuritic plaques) in the brains of 16-month old Tg2576 mice (FIG. 4C). In contrast, methoxy-X04 labeled Aβ aggregates were present in both cerebral arteries and parenchymal neuritic plaques (FIG. 4D). Higher magnification images showed that both resorufin and methoxy-X04 were co-localized to the vascular smooth muscle cell layer forming bands around the circumference of the vessel—a characteristic feature of CAA Aβ deposits (FIG. 4F). Neither resorufin—nor methoxy-X04-positive staining was present in age-matched normal mice or young Tg2576 mice (data not shown).

Figure 5:
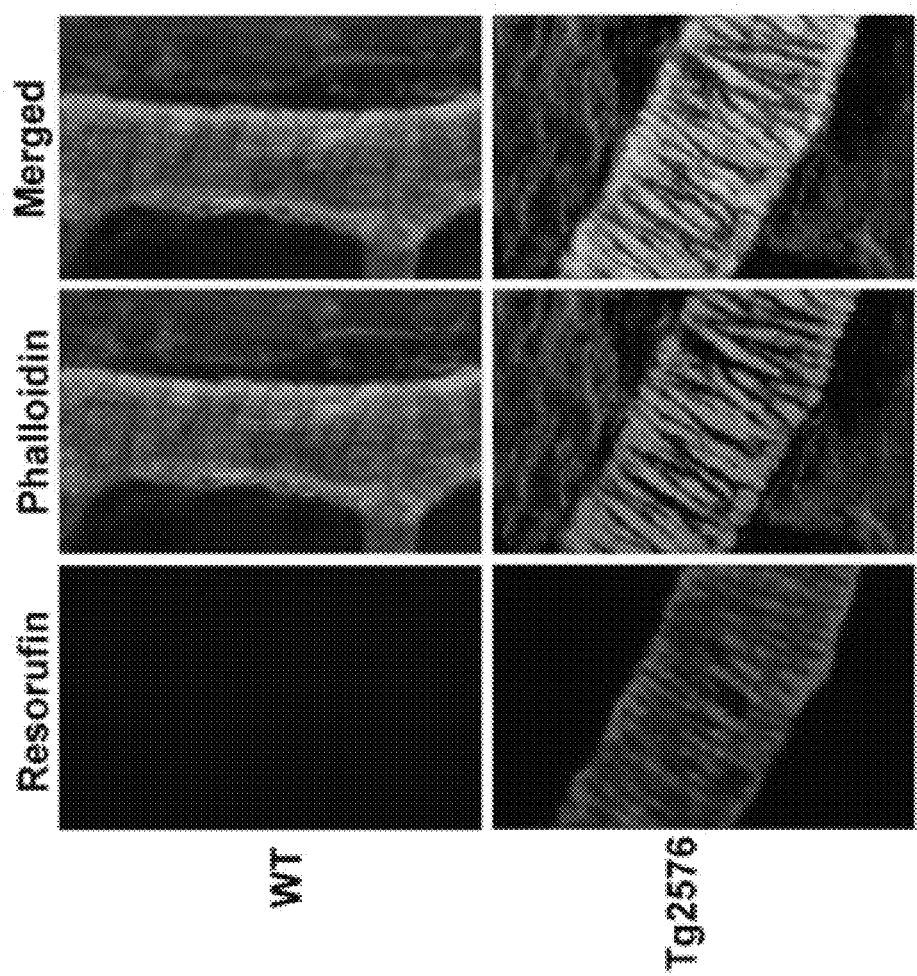
FIG. 5 depicts a multi-photon imaging reveals the disruption of vascular smooth muscle cells in CAA-affected vessels. Amyloid deposition and vascular smooth muscle cells (VSMCs) in the leptomeningeal vessels were stained with resorufin (red) and phalloidin-Alexa 488 (green), and imaged with multi-photon microscope. In 16-month-old wild type mice, VSMCs are arranged closely in parallel to each other in the leptomeningeal vessels (upper panels), whereas severe disruption of VSMC arrangement in vessel segments having CAA deposits was noted in age-matched Tg2576 mice (lower panels).

Multi-Photon Microscopy:

To explore whether resorufin-positive amyloid deposits influence the vascular smooth muscle cell (VSMC) architecture, whole brains prepared from 16-month-old Tg2576 transgenic and littermate control mice were stained with resorufin and a VSMC marker, phalloidin as we described previously (19). When imaged by multi-photon microscopy, VSMCs were arranged closely in parallel in all examined pial arterioles of control mice, but these vessels were not found to stain with resorufin (FIG. 5, upper panels). In aged Tg2576 mice, however, resorufin-positive Aβ deposits in cerebral vessels were frequently noted. In those vessels with substantial resorufin-positive deposits, VSMC arrangement was found to be substantially disrupted (FIG. 5, lower panels). The intensity of resorufin staining was greater in pial arterioles than in penetrating arterioles or capillaries.

Example 3

Overview:

In our preliminary study, we found that resorufin preferentially binds cerebrovascular Aβ deposits over neuritic plaques in brains of aged Tg2576 mice. We also found that alkylation at the 7-position of resorufin enhances its binding affinity for cerebrovascular Aβ deposits and increases its lipophilicity, indicating favorable properties for CAA-selective amyloid imaging tracers. In this example, we will synthesize novel resorufin derivatives and perform in vitro and in situ assays to select amyloid tracer candidates that would be suitable for non-invasive imaging of cerebrovascular Aβ deposits. We will determine the binding affinity of resorufin derivatives for synthetic Aβ340 fibrils as well as cerebral vessel homogenates from aged Tg2576 mice. The octanol-water partition coefficient ($logP_{oct}$) for each derivative will also be determined. We will then select resorufin derivatives having enhanced binding affinity for cerebrovascular Aβ deposits (Ki<10 nM) and moderate lipophilicity ($logP_{oct}$=1-3) in order to further explore the feasibility of using these agents for noninvasive imaging of cerebrovascular Aβ in live Tg2576 mice.

Synthesis of Non-Radioactive 19F- or $^{11}$C-Containing Analogs of Resorufin as Potential PET Radiotracers for CAA Imaging.

Figure 6:
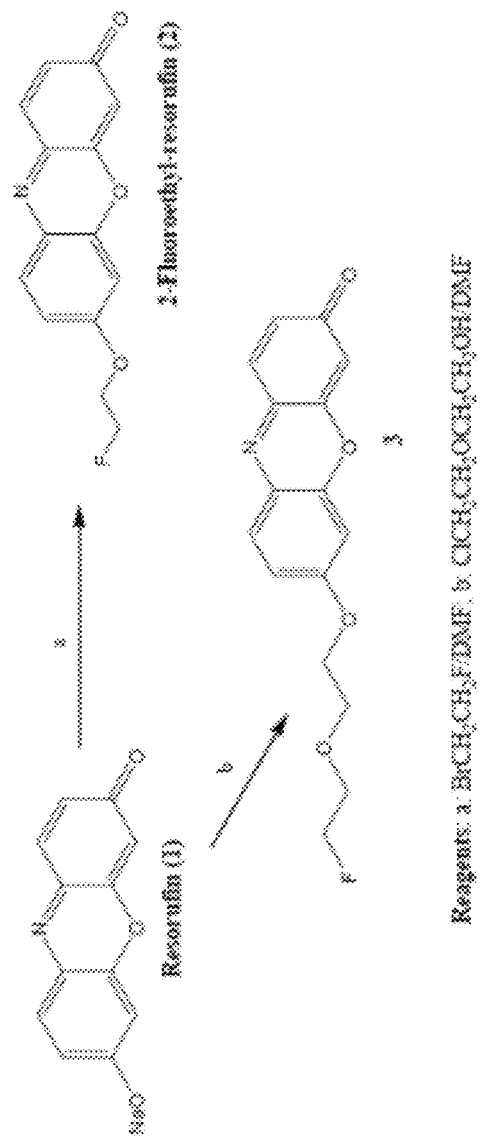
FIG. 6 depicts the synthesis of analogs 2 and 3.
Figure 7:
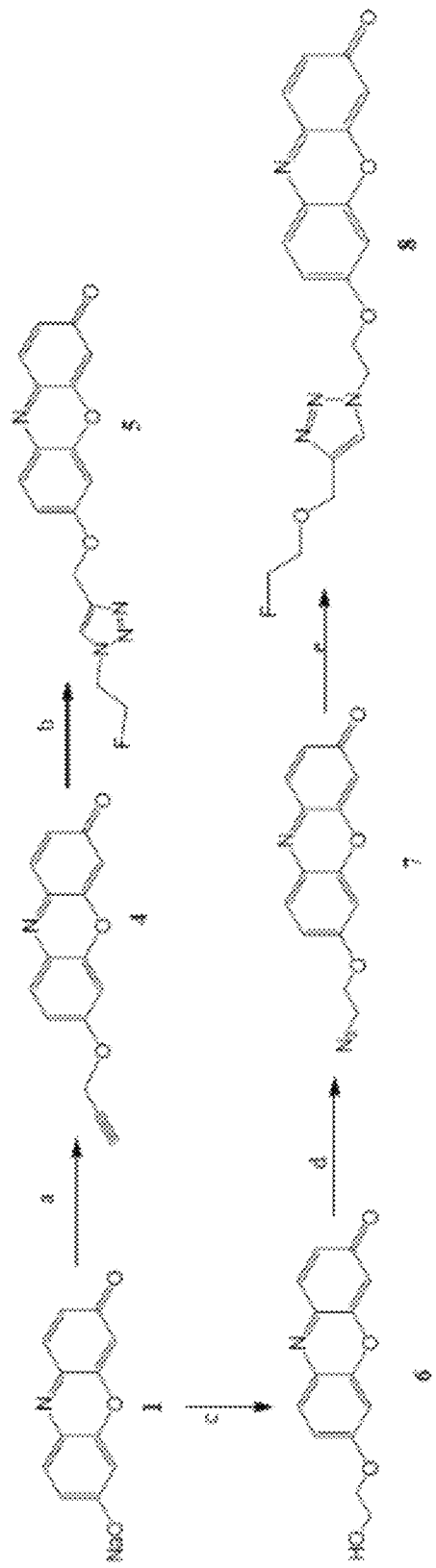
FIG. 7 depicts the synthesis of the click and reverse click analogs of resorufin.

The analogs will be designed in a manner in which the corresponding [$^{18}$F]- or [$^{11}$C]-labeled radiotracers can be prepared via standard PET radiochemistry techniques. The corresponding precursors for radiolabeling will also be synthesized. Based on the preliminary structure-activity relationships shown in Table 5, alkylation of the phenol of resorufin with a methyl group results in a moderate improvement in affinity for cerebrovascular Aβ deposits. Addition of a methylene group to give the corresponding ethyl analog resulted in a further improvement in potency for inhibiting resorufin to cerebrovascular Aβ deposits. These data suggest that the phenol position of resorufin is in a region of "bulk tolerance" with respect to binding to cerebrovascular Aβ deposits, and that addition of either larger alkyl groups of a fluoropegylated group should lead to compounds having the desired affinity of <10 nM for cerebrovascular Aβ deposits. The synthesis of the target compounds is shown in FIGS. 6 and 7. O-alkylation of the phenolate of resorufin with 2-bromofluoroethane or 1-chloro-2-(2-fluoroethothxy)ethane will give the correspondine 2-Fluoroethyl (2) and 2'-fluoroethoxyethyl (3) analogs of resorufin. Similarly, the corresponding "click" and "reverse click" analogs will be synthesized using the sequence of reactions outlined in FIG. 7.

We will determine the binding affinity (Ki) of resorufin analogs for cerebrovascular Aβ deposits by in vitro competitive radioligand binding assays utilizing [$^{3}$H]ethoxyresorufin. (See Table 6 below.) Our preliminary studies demonstrate that 7-ethoxyresorufin shows higher binding affinity (Ki=247 nM) for cerebrovascular Aβ deposits than resorufin. We will utilize [$^{3}$H]-labeled ethoxyresorufin as a radioligand to determine the binding affinity of resorufin derivatives. First, we will perform ligand binding assays in vessel homogenates prepared from 15-month-old Tg2576 mice. Cerebral vessel homogenates from these mice will contain extensive amounts of endogenous vascular Aβ deposits based on our previous experience with same age Tg2576 mice where CAA was found to affect almost all segments of leptomeningeal and cortical arterioles (19). We will also determine the binding affinity of resorufin derivatives to synthetic Aβ fibrils. Because Aβ40 is the major constituent of amyloid deposits in cerebral vessels and Aβ42 is dominantly present in neuritic plaques, we expect resorufin analogs to have higher affinity to Aβ40 fibrils and CAA-like (Aβ40 dominant) fibrils over Aβ42 fibrils and neuritic plaque-like (Aβ42 dominant) fibrils. To test this, we will perform radioligand binding assays with [$^{3}$H]ethoxyresorufin in the presence of various forms of fibrillar Aβ. If selective binding of [$^{3}$H]ethoxyresorufin to certain Aβ fibrils is realized, we will perform competitive radioligand binding assays using this specific Aβ fibril. To obtain endogenous cerebrovascular Aβ aggregates, brain vessels will be dissected from 15-month-old Tg2576 mice and age-matched wild type mice (N=10 per group), and homogenated in phosphate-buffered saline (PBS). PBS-insoluble Aβ aggregates will be then soulblized in a buffer containing 5 M guanidine and neutralized in a binding assay buffer. Different species of synthetic Aβ fibrils will be prepared from soluble monomeric Aβ peptides (92). The dissociation constant (KD) of [$^{3}$H]ethoxyresorufin will be determined by a saturation binding assay. After incubation of [$^{3}$H]ethoxyresorufin at various concentrations ($10^{-9}$-$10^{-6}$ M) with fixed amount of Aβ aggregates (10 µg/reaction), the bound and free ligand will be separated by filtration through a membrane-type filter. Non-specific binding will be determined in the presence of 1000-fold excess amount of un-labeled ethoxyresorufin or vessel homogenates from wild type mice. To determine the binding inhibition constant (Ki) of resorufin analogs, competitive binding assays will be performed by incubation of 1 nM [$^{3}$H]ethoxyresorufin in the presence of 5-6 different concentrations of competitors ($10^{-9}$-$10^{-6}$ M). Specific binding will be calculated. The maximum binding capacity (Bmax) and binding inhibition constant (Ki) will be calculated using a GraphPad Prism 5 software. Experiments will be repeated at least three times with duplicated samples. Data will be presented as the mean±SD.

Determining which Resorufin Analogs Preferentially Bind CAA Over Neuritic Plaques In Situ in Brain Tissues of 15-Month-Old Tg2576 Mice.

The Ki values for CAA vs. neuritic plaques will be calculated utilizing the fluorescent amyloid-ligand methoxy-X34 and fluorescent microscopic method. Once the binding affinity of resorufin derivatives is determined by in vitro radioligand binding assays, we will further determine whether these compounds preferentially bind cerebrovascular Aβ deposits over neuritic plaques utilizing in situ competitive binding assays using methoxy-X34 as the fluorescent ligand that binds Aβ deposits in both cerebral vessels and neuritic plaques. To determine the Ki values, fixed brain tissues prepared from 15-month-old Tg2576 mice (N=5) will be incubated for 30 min with 1 µM methoxy-X34 in the presence of a serial dilution of test compounds ($10^{-9}$-$10^{-6}$ M, 6 concentrations/compound). Tissue sections (3 sections per reaction) will be then mounted and coverslipped. Photographs of methoxy-X34 binding images will be taken using a Nikon fluorescent microscope. The fluorescent intensity on cerebral amyloid deposits and neuritic plaques will be separately quantified using Image J software. Finally, Ki values will be calculated by plotting % bound vs. log concentrations of competitors followed by non-linear regression using the GraphPad Prism software. The maximum binding will be obtained from the methoxy-X34 intensity in the absence of competitors, while non-specific binding will be detected by the fluorescent intensity in brain tissues incubated without methoxy-X34.

Determining the Lipophilicity of Resorufin Analogs by Octanol-Water Partition Coefficient (logP$_{oct}$) Assay to Predict which Analogs Will Demonstrate Rapid Brain Uptake.

The logP$_{oct}$ value is widely used in quantitative structure-activity relationship (QSAR) studies and rational drug design as a measure of molecular hydrophobicity. Hydrophobicity affects drug absorption, bioavailability, hydrophobic drug-receptor interactions, metabolism of molecules, and their toxicity. In regard to brain PET imaging tracers, it is well documented that brain imaging tracers require moderate lipophilicity with a logP$_{oct}$ value ranging 1-3 to ensure a high initial brain uptake and rapid clearance from normal brain (59). In our preliminary study, we observed that the acidic resorufin (logP$_{oct}$=0.427) visualized cerebrovascular Aβ deposits in live Tg2576 mice when it was administered topically to the surface of the brain. In contrast, when i.v. injected, resorufin failed to bind vascular Aβ deposits, presumably due to its inability to cross the BBB. These data strongly suggest that the lipophilicity should be considered as a determining factor for selecting amyloid PET imaging ligand candidates. In our preliminary study, we also found that substitution of hydrogen at the 7-position of resorufin with an alkyl group markedly increased the logP$_{oct}$ values as well as the binding affinity for cerebrovascular Aβ deposits. Therefore, it is logical to derivative resorufin at the 7-position to develop resorufin analogs that optimize lipophilicity and preserve (or even enhance) cerebrovascular Aβ binding properties. To determine logP$_{oct}$ of resorufin derivatives, a test compound will be dissolved in n-octanol and an equal volume of water will be added in a 1.5-ml microcentrifuge tube. The mixture will be incubated with agitation for 30 min until ionic and non-ionic forms of test compound reach equilibrium. Two layers will be separated by centrifugation. Test compound's concentrations in octanol and water layers will be determined by UV/VIS spectrophotometry. The $\log P_{oct}$ value will be calculated from log(concentration in n-octanol fraction/concentration in water fraction). Experiments will be repeated at least 3 times with triplicated samples.

TABLE 5

CAA Binding Activities of Resorufin Analogs

| No | Compound | Structure | M.W. | Preparation Stock (10 mM) | Preparation Actual stock | Preparation ul (per 1 mg) | Fluorescent Intensity at 10 uM in H2O | Fluorescent Intensity Relative | Lipophilicity Poct | $B_{max}$ on CAA | $B_{max}$ on CAA | Binding affinity in situ $K_D$ (nM) on Plaques |
|---|---|---|---|---|---|---|---|---|---|---|---|---|
| 1 | Resorufin | 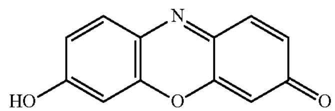 [SMILES: O=c1ccc2nc3ccc(O)cc3oc-2c1] | 213.2 | 2.132 mg in 1 ml H2O | 10 mM in H2O | 469.0 | 60000 | 1 | 0.387 | 1523/ 885 | $^a$874 | >>4000 |
| 2 | Methoxy-resorufin | 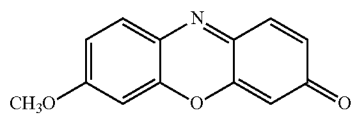 | 227.2 | 2.227 mg in 1 ml DMSO | 5 mM in DMSO | 449.0 | 31009 | 0.52 | 1.945 | | N/D | N/D |
| 3 | Ethoxy-resorufin | 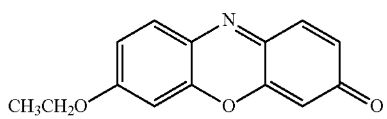 | 241.2 | 2.412 mg in 1 ml DMSO | 10 mM in DMSO | 414.6 | 39041 | 0.65 | 2.353 | 107 | 247 | >>4000 |
| 4 | Pentoxy-resorufin | 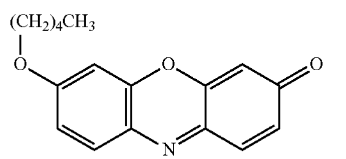 | 283.3 | 2.833 mg in 1 ml DMSO | 5 mM in DMSO | 283.3 | 6475 | 0.11 | 2.339 | | N/D | N/D |
| 5 | Benzyloxy-resorufin | 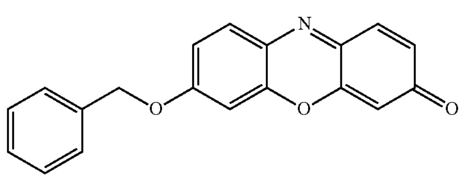 [SMILES: O=c1ccc2nc3ccc(OCc4ccccc4)cc3oc-2c1] | 303.3 | 3.033 mg in 1 ml DMSO | 2.5 mM in DMSO | 303.3 | 4993 | 0.08 | 2.213 | 410 | 473 | >>4000 |
| 6 | Resorufin acetate | 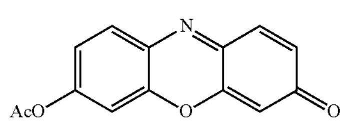 [SMILES: CC(=O)Oc1ccc2nc3ccc(=O)cc-3oc2c1] | 252.2 | 2.522 mg in 1 ml DMSO | 10 mM in DMSO | 396.5 | 8170 | 0.14 | 2.786 | | N/D | N/D |

TABLE 5-continued

CAA Binding Activities of Resorufin Analogs

| No | Compound | Structure | M.W. | Preparation Stock (10 mM) | Preparation Actual stock | Preparation ul (per 1 mg) | Fluorescent Intensity at 10 uM in H2O | Fluorescent Intensity Relative | Lipophilicity Poct | Binding affinity in situ $B_{max}$ on CAA | Binding affinity in situ $B_{max}$ on CAA | Binding affinity in situ $K_D$ (nM) on Plaques |
|----|----------|-----------|------|---------------------------|--------------------------|----------------------------|---------------------------------------|-------------------------------|---------------------|---------|---------|---------|
| 7 | WC5.1 | 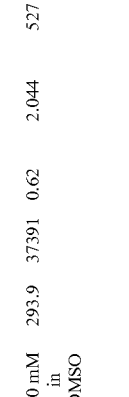 | 259.2 | 2.592 mg in 1 ml DMSO | 10 mM in DMSO | 442.6 | 17395 | 0.29 | 2.407 | 485 | 173 | >>4000 |
| 8 | WC5-2 | 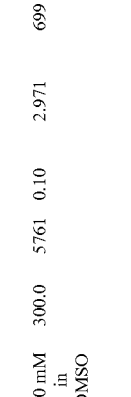 | 251.2 | 2.512 mg in 1 ml DMSO | 10 mM in DMSO | 444.2 | 12471 | 0.21 | 2.774 | 869 | 235 | >>4000 |
| 9 | WC5-3 | 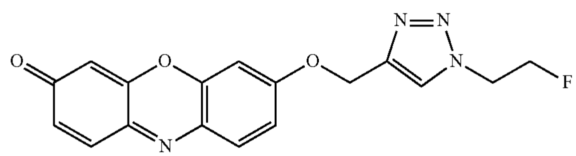 [SMILES: O=c1ccc2nc3ccc(OCc4cn(CCF)nn4)cc3oc-2c1] | 340.3 | 340.3 mg in 1 ml DMSO | 10 mM in DMSO | 293.9 | 37391 | 0.62 | 2.044 | 527 | 1040 | >>4000 |
| 10 | WC-5-4 | 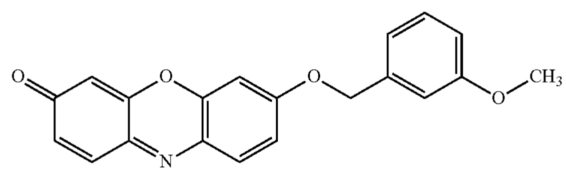 [SMILES: COc1cccc(COc2ccc3nc4ccc(=O)cc-4oc3c2)c1] | 333.3 | 3.333 mg in 1 ml DMSO | 10 mM in DMSO | 300.0 | 5761 | 0.10 | 2.971 | 699 | 283 | >>4000 |
| 11 | WC-5-5 | 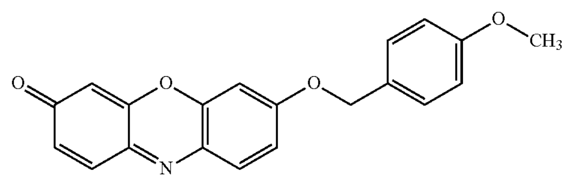 [SMILES: COc1ccc(COc2ccc3nc4ccc(=O)cc-4oc3c2)cc1] | 333.3 | 3.333 mg in 1 ml DMSO | 10 mM in DMSO | 300.0 | 4849 | 0.08 | 1.907 | 135 | 186 | >>4000 |
| 12 | WC-5-7 | 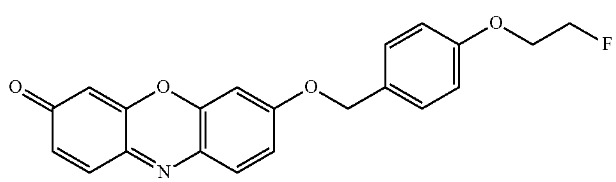 [SMILES: O=c1ccc2nc3ccc(OCc4ccc(OCCF)cc4)cc3oc-2c1] | 365.4 | 3.654 mg in 1 ml DMSO | 10 mM in DMSO | 273.7 | 4166 | 0.07 | 3.419 | 1304 | 316 | >>4000 |

TABLE 5-continued

CAA Binding Activities of Resorufin Analogs

| No | Compound | Structure | M.W. | Preparation Stock (10 mM) | Preparation Actual stock | Fluorescent Intensity at 10 uM in H₂O ul (per 1 mg) | Fluorescent Intensity at 10 uM in H₂O Relative | Lipophilicity Poct | Binding affinity in situ $B_{max}$ on CAA | Binding affinity in situ $B_{max}$ on Plaques | Binding affinity in situ $K_D$ (nM) on CAA | Binding affinity in situ $K_D$ (nM) on Plaques |
|---|---|---|---|---|---|---|---|---|---|---|---|---|
| 13 | WC-5-8 | | 299.3 | 299.3 mg in 1 ml DMSO | 10 mM in DMSO | 467.8 | | 2.086 | | | N/A | N/A |
| 14 | WC-5-9 | | 320.1 | 3.2 mg in 1 ml DMSO | 10 mM in DMSO | 560.7 | | 2.203 | | | N/A | N/A |
| 15 | WC-5-22 | | 318.3 | 3.183 mg in 1 ml DMSO | 10 mM in DMSO | 502.7 | | | | >10,000 | | >10,000 |
| 16 | WC-5-26 | | 380.8 | 3.808 mg in 1 ml DMSO | 10 mM in DMSO | 393.9 | | | | >10,000 | | >10,000 |

TABLE 5-continued

CAA Binding Activities of Resorufin Analogs

| No | Compound | Structure | M.W. | Preparation Stock (10 mM) | Preparation Actual stock | Fluorescent Intensity at 10 uM in H₂O ul (per 1 mg) | Fluorescent Intensity at 10 uM in H₂O Relative | Lipophilicity Poct | Binding affinity in situ $B_{max}$ on CAA | Binding affinity in situ $B_{max}$ on Plaques | $K_D$ (nM) on CAA | $K_D$ (nM) on Plaques |
|---|---|---|---|---|---|---|---|---|---|---|---|---|
| 17 | WC-5-31 | 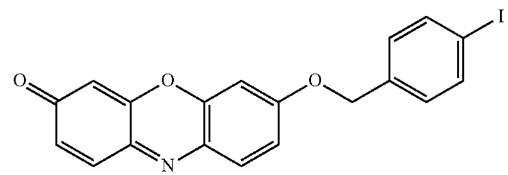 [SMILES: O=c1ccc2nc3ccc(OCc4ccc(I)cc4)cc3oc-2c1] | 429.2 | 4.29 mg in 1 ml DMSO | 10 mM in DMSO | 535.9 | | >4.89?? | N/A | N/A | N/A | N/A |
| 18 | WC-5-42 | 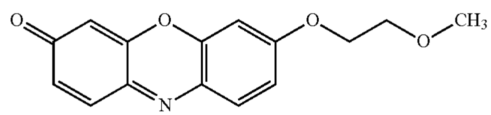 [SMILES: COCCOc1ccc2nc3ccc(=O)cc-3oc2c1] | 271.3 | 2.71 mg in 1 ml DMSO | 10 mM in DMSO | | | | N/A | N/A | N/A | N/A |
| 19 | WC-5-43 | 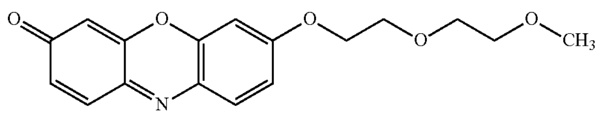 [SMILES: COCCOCCOc1ccc2nc3ccc(=O)cc-3oc2c1] | 315.3 | 3.15 mg in 1 ml DMSO | 10 mM in DMSO | | | | N/D | N/D | N/D | N/D |
| 20 | WC-5-45 | 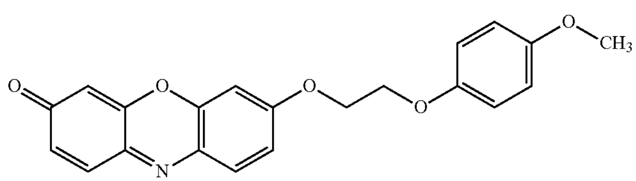 [SMILES: COc1ccc(OCCOc2ccc3nc4ccc(=O)cc-4oc3c2)cc1] | 363.4 | 3.63 mg in 1 ml DMSO | 10 mM in DMSO | | | | | N/A | N/A | N/A |
| 21 | WC-5-47 | 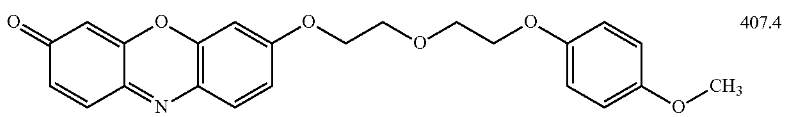 | 407.4 | 4.07 mg in 1 ml DMSO | 10 mM in DMSO | | | | | N/A | N/A | N/A |

TABLE 5-continued

CAA Binding Activities of Resorufin Analogs

| No | Compound | Structure | M.W. | Preparation Stock (10 mM) | Preparation Actual stock | Fluorescent Intensity at 10 uM in $H_2O$ ul (per 1 mg) | Fluorescent Intensity Relative | Lipophilicity Poct | Binding affinity in situ $B_{max}$ on CAA | Binding affinity in situ $B_{max}$ on CAA | Binding affinity in situ $K_D$ (nM) on Plaques |
|---|---|---|---|---|---|---|---|---|---|---|---|
| 22 | Methoxy-X34 | (structure with $O^{11}CH_3$, COOH groups) | 416 | | | | | [b]0.19 | | 325 | 219 |
| 23 | Methoxy-X04 | (structure with $O^{11}CH_3$, OH groups) | 344 | | | | | [b]2.6 | | N/D | N/D |

[a]average from three experiments (670, 971, 981 nM)
[b]data from the previous report (Klunk, et al., J. Neuropathol. Exp. Neurol. 61:797-805, 2002).
N/D: not determined;
N/A: not available.

TABLE 6

Binding affinities for CAA performed on isolated vessels determined by fluorescent binding.

| Compounds | Binding affinity (nM) | |
|---|---|---|
| | $K_D$ | $K_i$ |
| Resorufin | 225 | |
| Methoxy-resorufin | | 4675 |
| Ethoxy-resorufin | | 262 |
| WC-5-1 | 828 | 4613 |
| WC-5-2 | 800 | |
| WC-5-3 | 2380 | |
| WC-5-4 | 537 | |
| WC-5-5 | | 218 |
| WC-5-8 | | 860 |
| WC-5-9 | 927 | |
| WC-5-31 | >10000 | |
| WC-5-42 | | 347 |
| WC-5-43 | | 407 |
| WC-5-45 | | 421 |
| WC-5-47 | | >10000 |

Example 4

Overview:

Resorufin analogs having high binding affinity (KD: <10 nM) and moderate lipophilicity ($logP_{oct}$=1-3) will be examined in this example for suitability as CAA-selective PET imaging ligands. First, select resorufin analogs will be radiolabeled with [$^{18}$F] or [$^{11}$C] using displacement of a single leaving group. Thereafter, initial brain uptake, clearance, and retention of each radioactive resorufin analog will be determined in normal mice. Finally, in situ and ex vivo autoradiography methods will be utilized to determine whether [$^{18}$F]- or [$^{11}$C]-labeled resorufin analogs preferentially visualize cerebrovascular Aβ deposits in aged Tg2576 mice having AD and CAA pathology.

Figure 8:
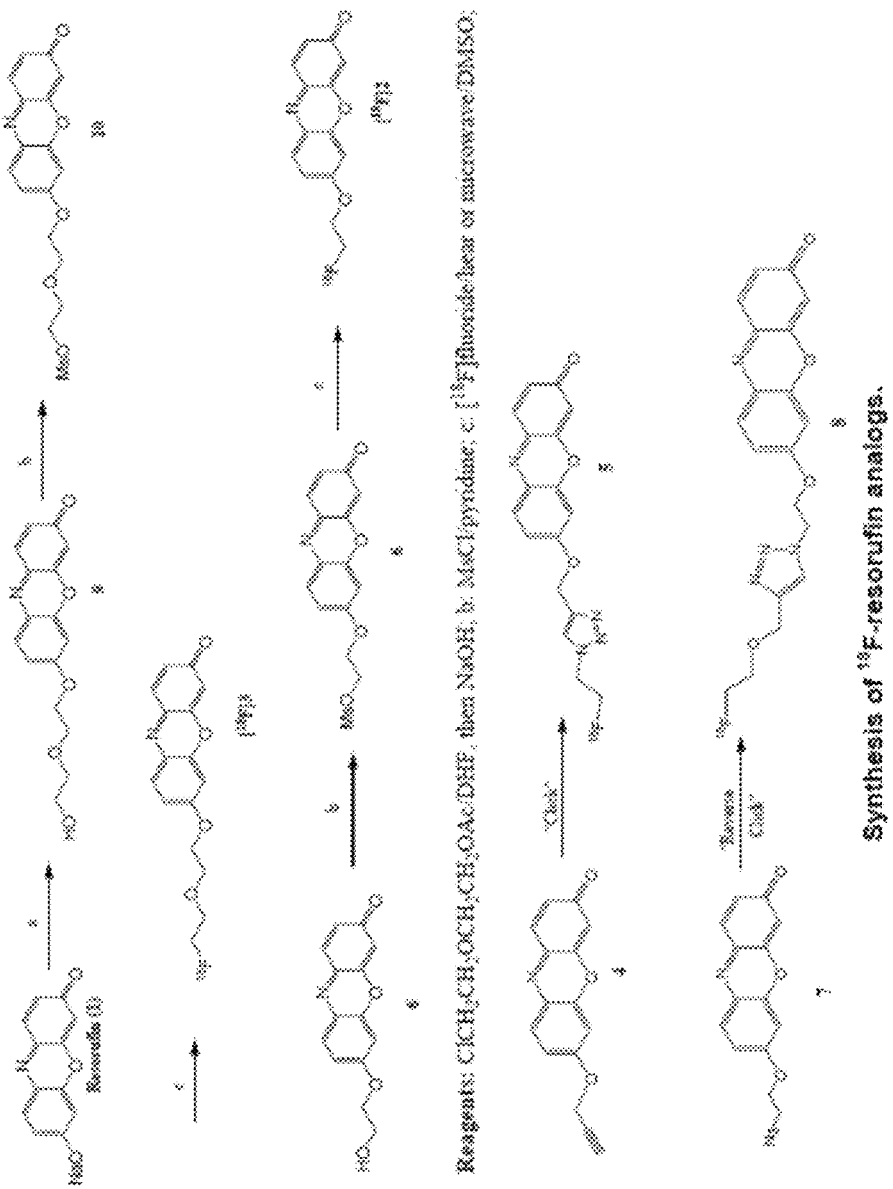
FIG. 8 depicts the synthesis of $^{18}$F-resorufin analogs.
Figure 9:
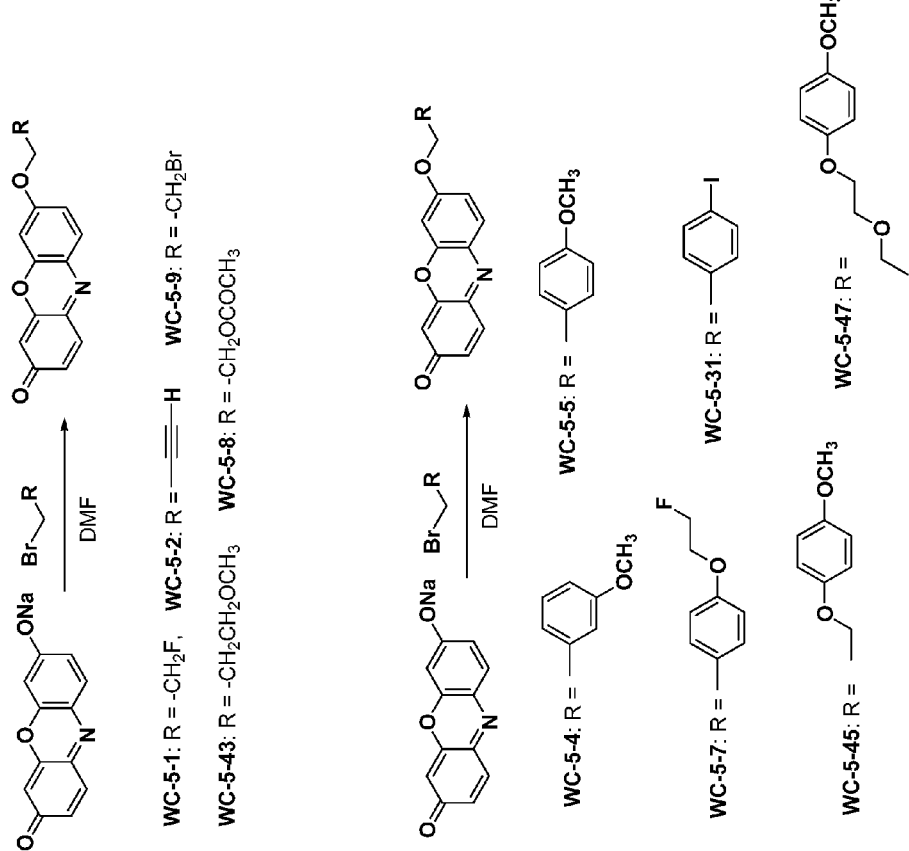
FIG. 9 depicts several compounds of the invention.
Figure 9:
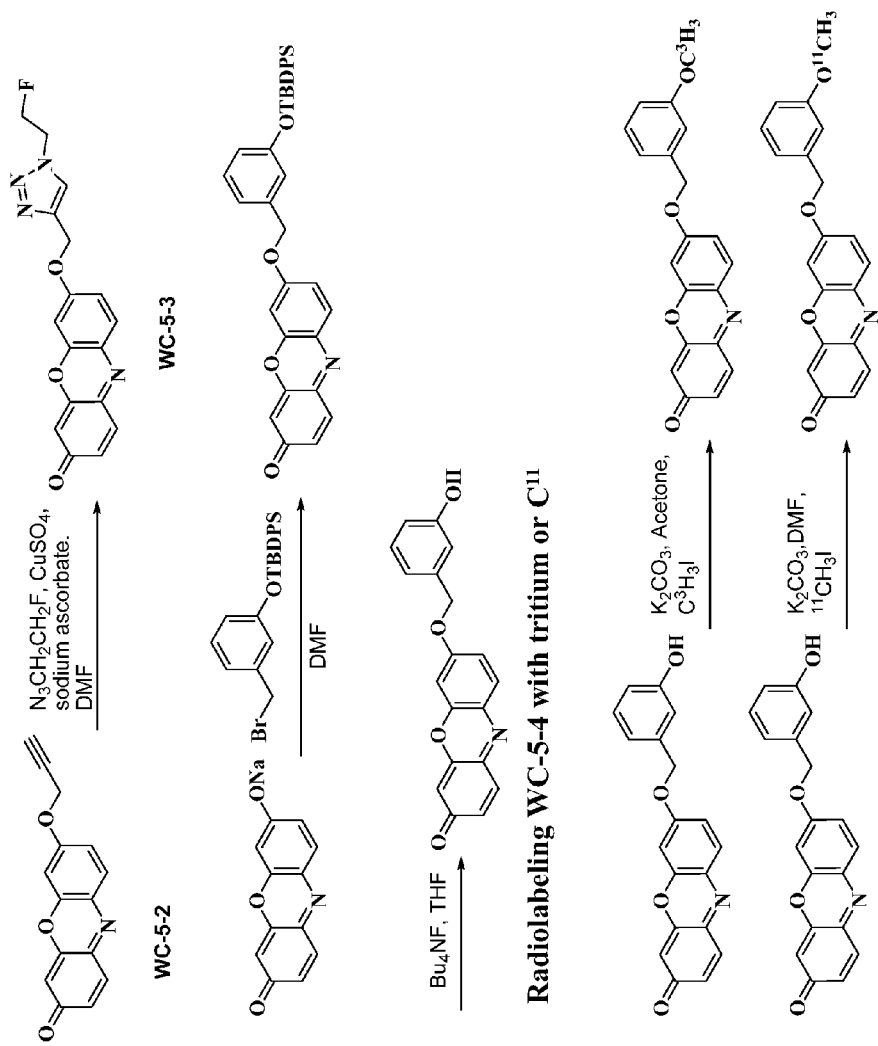
Figure 9:
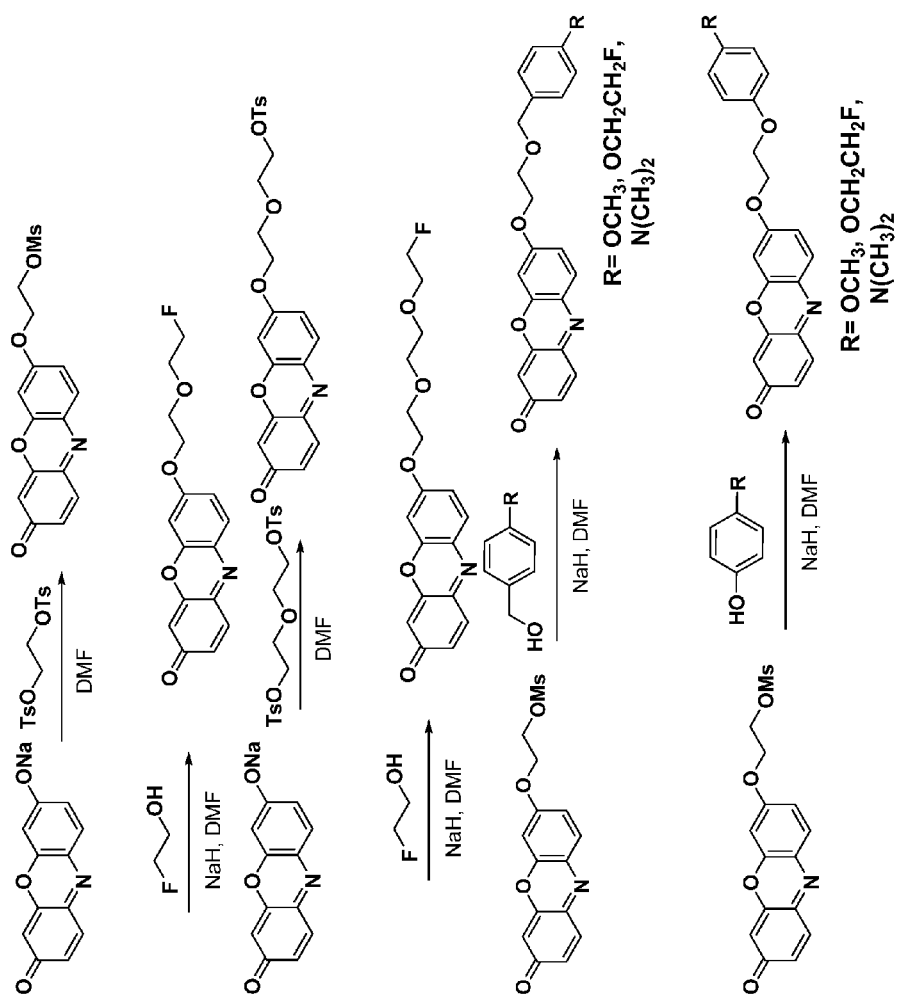
Figure 9:
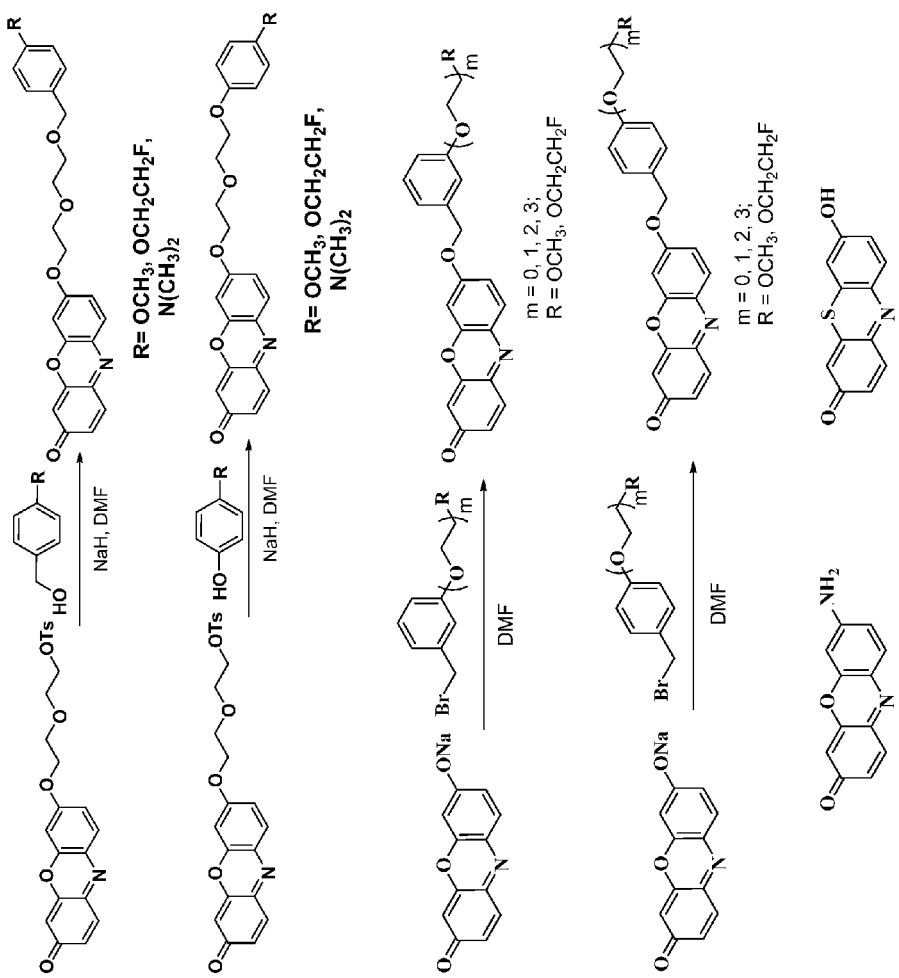
Figure 9:
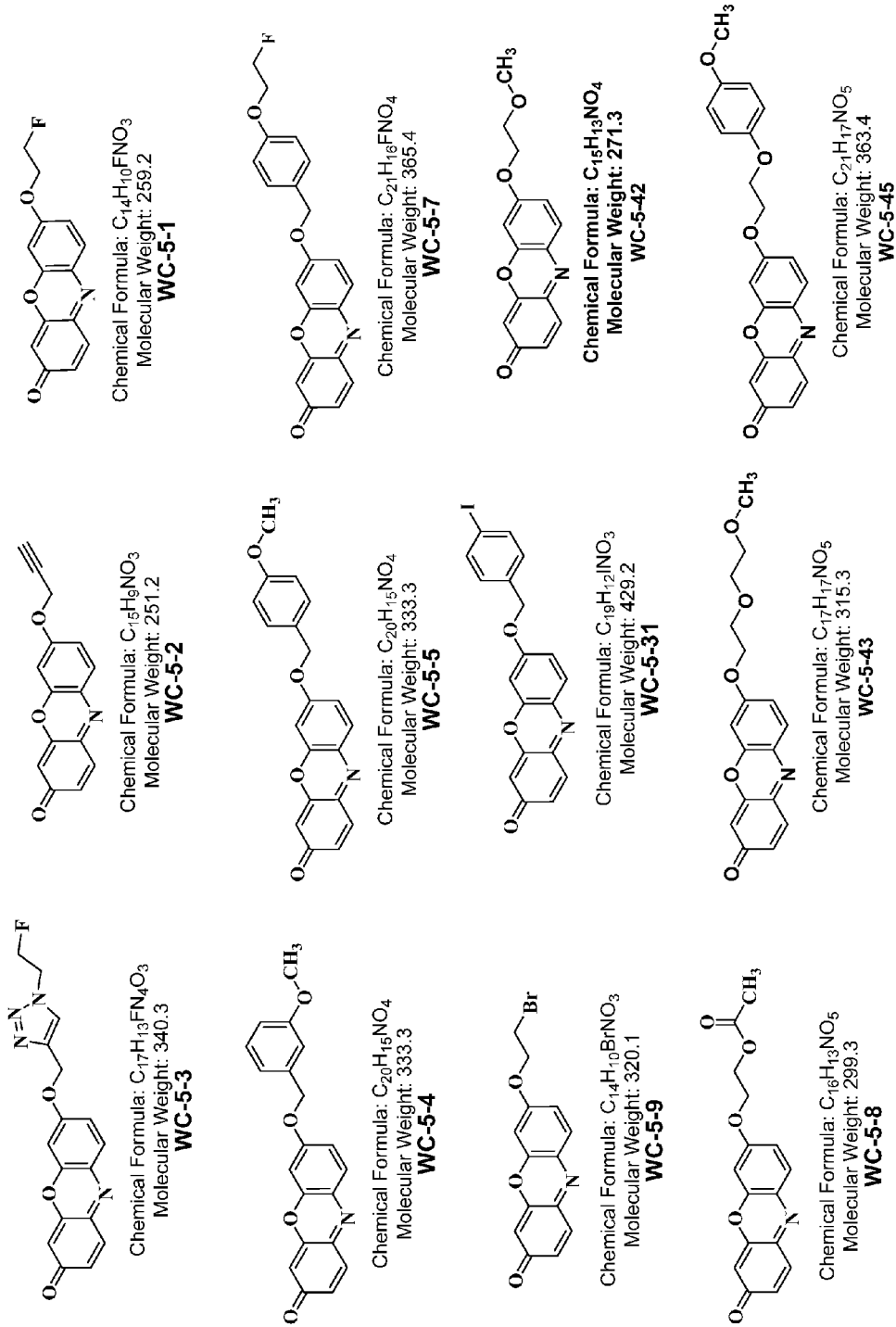
Figure 9:
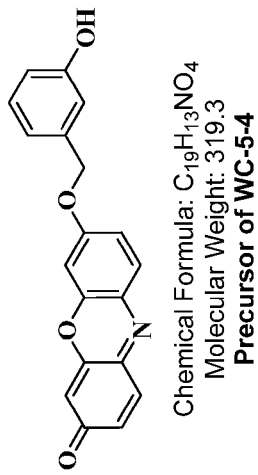
Figure 9:
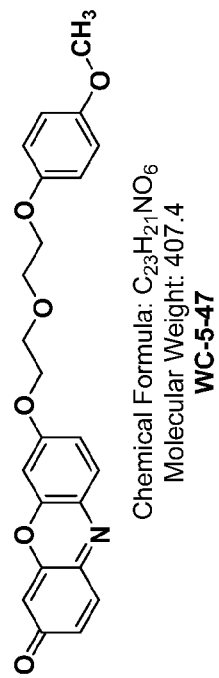

Synthesis of [$^{18}$F]- or [$^{11}$C]-labeled compounds will be accomplished using displacement of a suitable leaving group by [$^{18}$F] or [$^{11}$C]. —[$^{18}$F]- or [$^{11}$C]-labeled analogs of resorufin will be designed because of the optimal half-life of [$^{18}$F] (t ½=110 min) or [$^{11}$C] (t ½=20 min) for image acquisition and the improved methods for incorporating [$^{18}$F] or [$^{11}$C] into small molecules that have been introduced over the past 5 years. The radiosynthesis of the [$^{18}$F]- or [$^{11}$C]-resorufin analogs will involve standard radiochemistry procedures as outlined in FIG. 8.

Examining the Initial Brain Distribution and Clearance of [$^{18}$F]- or [$^{11}$C]-Labeled Resorufin Analogs in Normal Mice.

The radiolabeled compounds will be intravenously injected, and brain and plasma samples will be collected 2 or 30 min after injection to determine the % brain uptake and clearance rate. In addition to high affinity for Aβ aggregates at subnanomolar ranges, amyloid PET imaging tracers are required to pass through the BBB to substantial levels immediately after systemic administration. Useful brain PET imaging tracers typically have the initial brain distribution in the range of 100%-500% "injected does index (IDI)" at 2 to 5 min following injection (61, 93, 94). The initial brain uptake of a tracer is affected by many factors such as molecular size, lipophilicity, ionic charge, non-specific binding to plasma proteins. Though moderate lipophilicity ($logP_{oct}$=1-3) with a small molecular size (molecular weight: <400) of a compound is prerequisite for brain entry, the initial brain distribution needs to be experimentally determined to anticipate to what extent a tracer reaches the brain immediately after injection. The initial brain uptake is typically determined by the percent of radioactivity dose normalized by brain weight (% ID/g) within 2-5 min post i.v. injection (63, 93, 94). Klunk et al (61) has demonstrated that organ distribution in terms of % IDI, which is calculated from % organ dose divided by % organ weight, is useful to compare organ distribution between different species with different brain:body ratios. Thus, this method allows for the extrapolation of the brain uptake data obtained from small experimental animals to humans. In addition to the high initial uptake to the brain, unbound tracers should be rapidly washed out from the brain to minimize non-specific background in PET imaging. For example, a pharmacokinetic study in normal mice showed that [$^{11}$C]PIB entered the brain at a high level (3.2% ID/g) at 2 min after injection, followed by a fast washout (0.21% ID/g at 60 min) (95), indicating that 93% [$^{11}$C]PIB in the brain is cleared within 60 min. In another study with [$^{11}$C]methoxy-X04 in normal rats (96), this compound ($logP_{oct}$=2.6) demonstrated a high initial brain distribution within 2 min after injection followed by rapid clearance with an estimated half life (t½) of ~45 min. To determine the pharmacokinetic profile of resorufin derivatives, normal C57Bl6 mice will be i.v. injected with each [$^{18}$F]- or [$^{11}$C]-labeled resorufin derivative (25-50 µCi; N=5 per group). Two and thirty minutes later, mice will be anesthetized and blood will be sampled by cardiac puncture. Brains will be rapidly removed and dissected into two parts (cerebellum and remaining whole brain). The radioactivity in brain and blood samples will be counted. Brain distribution of [$^{18}$F]- or [$^{11}$C]-labeled compounds will be calculated as % IDI (see above). Clearance rate in the brain and plasma will be estimated by comparing % IDI between 2 min and 30 min after injection.

Performing In Situ and Ex Vivo Autoradiography to Determine if Retention of [$^{18}$F]- or [$^{11}$C]-Labeled Resorufin Analogs in the Brain Correlates with CAA Deposition in Aged Tg2576 Mice vs. Littermate Controls.

We will compare autoradiography to fluorescent amyloid imaging with resorufin (CAA-selective) and methoxy-X34 (both CAA- and neuritic plaque-reactive). In our preliminary studies, we have demonstrated that resorufin is able to visualize cerebrovascular Aβ deposits with minimal cross-reactivity with neuritic plaques in live Tg2576 mice. Due to the intrinsic fluorescent property of resorufin, use of this dye allows for visualization of Aβ deposits in live animals via fluorescent imaging methods. However, because resorufin derivatives with chemical modification at the 7-position do not fluoresce, fluorescence-based imaging methods are not applicable to evaluate the effectiveness of resorufin derivatives for cerebrovascular Aβ imaging in live animals. Therefore, we will validate the feasibility of selected resorufin derivatives for non-invasive imaging of cerebrovascular Aβ deposits utilizing in situ as well as ex vivo autoradiography methods. First, we will perform in situ autoradiography in fixed brain tissues to explore whether [$^{18}$F]- or [$^{11}$C]-labeled resorufin derivatives preferentially binds cerebrovascular Aβ deposits. Fifteen-month-old Tg2576 mice and age-matched wild type mice will be perfused with saline and whole brain will be post-fixed in 4% paraformaldehyde solution. Seven to eight coronal sections (40 µm/section), will be rinsed with phosphate-buffered saline. Sections will be incubated with [$^{18}$F]- or [$^{11}$C]-labeled tracers for 30 min. Sections will be then co-stained with resorufin and methoxy-X34, followed by wash with PBS and 40% ethanol. Brain sections will be mounted on slide glass and subjected to autoradiography using a digital beta imaging system. Fluorescent images of resorufin (CAA deposits) and methoxy-X34 (both CAA deposits and neuritic plaques) will be digitally recorded using a fluorescent microscope. Three images will be merged to determine whether autoradiographic [$^{18}$F] signals are correlative to CAA deposits (in the cortical area) defined by resorufin staining. If selective binding of [$^{18}$F]- or [$^{11}$C]-labeled tracers is demonstrated by in situ autoradiography, we will perform ex vivo autoradiography to determine whether high retention of [$^{18}$F]- or [$^{11}$C]-labeled tracers occurs in old Tg2576 mice compared with age-matched wild type mice, and correlates with cerebrovascular Aβ load confirmed by costaining with resorufin and methoxy-X34. [$^{18}$F]- or [$^{11}$C]-labeled tracers will be i.v. injected (10-20 µCi) to old Tg2576 mice or age-matched wild type mice (N=5 per group). Fifteen to thirty min later, whole brain will be removed and sliced using a 1-mm mouse brain matrix. Brain slices will be mounted on slide glass and radioactivity will be scanned with the Packard InstantImager. Non-specific binding will be determined by injecting [$^{18}$F]- or [$^{11}$C]-labeled tracers along with 1000-fold molar excess of unlabeled tracers. After autoradiography, brain slices will be postfixed, stained with resorufin and methoxy-X34, and subjected to fluorescent microscopic assessment of cerebrovascular Aβ deposits. Three images will be merged to determine whether autoradiographic [$^{18}$F] or [$^{11}$C] signals correlate to CAA deposits defined by resorufin staining.

Methods for Examples 3 and 4

Experimental Animals:
Mice will be housed in standard cages, given access to food and water ad. lib, and exposed to 12 hour light-12 hour dark cycle. All experiments have been approved by the animal studies committee at Washington University. Detailed attention will be devoted to minimizing pain and distress experienced by the animals. Tg2576 mice were generous gift from Dr. K. Ashe (University of Minnesota, Minneapolis, Minn.). APP/PS1 mice were gifted by Dr. Jin-Moo Lee (collaborator). Genotyping will be performed by PCR using genomic DNA extracted from the toe. C57Bl6 mice will be purchased from the Jackson laboratory.

In Situ Binding Assay:
Tg2576 mice or littermate controls at 15 months of age will be perfused with phosphatebuffered saline (PBS) for 5 min. Brains will be removed, fixed in 4% paraformaldehyde, and preserved in 30% glucose-PBS solution at 4° C. Brains will be coronally sectioned using a microtome and kept in cryoprotectant solution at −20° C. To label amyloid deposits, brain sections (3 sections per reaction) will be permeabilized with PBS containing 0.25% Triton X-100 for 20 min at room temperature, followed by incubation with 1 µM methoxy-X34 in the presence or absence of competitors at various concentrations (10-9-10-6 M). Sections will be subjected to fluorescent microscopy using a Nikon Eclipse C600 microscope. The fluorescent intensity of methoxy-X34 in vessels and neuritic plaques will be quantified using the ImageJ software. The binding affinity (Ki) will be calculated using the GraphPad Prism software.

Preparation of Endogenous Cerebrovascular Aβ Fibrils:
The isolation of cerebral vessels for biochemical analysis will be performed as described (78, 98). Briefly, brain will be removed and placed in ice-cold vessel buffer containing 1% dextran (M.W.: ~64,000). After the cerebellum is removed, the brain will be homogenized in fivefold excess of vessel buffer. An equal volume of 26% dextran will be added, and the tissue will be centrifuged at 6200×g for 30 min at 4° C. The resulting vessels form a pellet, whereas the parenchymal "vessel-free" material forms a solid, compact disc at the top of the solution. The parenchymal pellet will be resuspended in vessel buffer and passed over a 40-µm nylon mesh to capture vessels. Vessel and parenchymal material will be lysed in 5 M guanidine, 50 mM Tris, pH 8, with protease inhibitor cocktail (Roche) for 3 hr. Vessel homogenates will be neutralize in binding buffer (10 mM sodium phosphate, pH 7.4, 1 mM EDTA) using a desalting column (Pierce).

Preparation of Synthetic Aβ Fibrils:
Synthetic amyloid fibrils will be generated as described previously (91, 92, 99) in collaboration with Dr. Lee (collaborator). Synthetic Aβ40 and Aβ42 peptides will be purchased from American Peptides. Aβ40 fibrils will be obtained by incubation of 1 mg/ml Aβ40 in 50 mM HEPES with 50 mM NaCl at 37° C. for 5 days (99). For Aβ42 fibrils (91, 92), monomeric Aβ42 peptide will be dissolved in trifluoroacetic acid and dried. The peptide will be washed with hexafluoropropanol and redissolved in dimethylsulfoxide to 5 mM, then diluted in 10 mM HCl to 100 µM to form freshly soluble Aβ42. The solution will be incubated at 37° C. for 1 month to form fibrillar Aβ40.

Radioligand Binding Assays:
Saturation binding assays and competition assays will be performed as described with modification (73, 100-102). Briefly, [3H]ethoxyresorufin (specific activity: 15-30 Ci/mmol [0.555-1.11 Tbq/mmol]) will be custom synthesized by American Radiolabeled Chemicals. For saturation binding assays, a fixed concentration of Aβ fibrils (25 pg of synthetic fibrils; 10 ng of vessel homogenates) in binding buffer (10 mM sodium phosphate, pH 7.4, 1 mM EDTA) will be incubated with various concentrations (0.1-200 nM) of [3H]ethoxyresorufin in a final volume of 500 µl at room temperature for 30 min. Non-specific binding will be determined in the presence of 100 µM cold (unlabeled) ethoxyresorufin. The bound and free fractions will be separated by filtration through MultiScreenHTS-FB plates (Millipore). The filters will be washed with 1 ml binding buffer containing 10% ethanol. The filters containing bound radioligand will be mixed with scintillation cocktail (Fisher Scientific) and the radioactivity will be determined using a scintillation counter (1600 TR Liquid Scintillation analyzer, Packard). The disscociation constant (KD) and the maximal number of binding sites (Bmax) will be calculated using a GraphPad Prism 5 software (GraphPad Software, Inc). For competitive binding assay, binding assays will be preformed with a fixed concentration of Aβ fibrils (25 pg of synthetic fibrils; 10 ng of vessel homogenates), 1 nM [3H]ethoxyresorufin and varying concentrations of competitors. 5-6 concentrations of competitors will be assayed with triplicated samples. IC50 and Ki values will be calculated using a GraphPad Prism 5 software.

Brain Distribution and Clearance Experiments:
Pharmacokinetic studies will be performed as previously described with modifications (61, 103). To determine the initial brain uptake of [$^{18}$F]- or [$^{11}$C]-labeled resorufin derivatives, male C57Bl6 mice (25±2 g, n=5 per group) will be i.v. injected via a tail vein with 25-50 µCi of [$^{18}$F]- or [$^{11}$C]-labeled tracersdissolved in 0.1 ml isotonic saline solution. Mice will be anesthetized by chloral hydrate 2 and 30 min after injection. Arterial blood samples will be collected via cardiac puncture. The brain will be rapidly removed and dissected into cerebellum and remaining whole brain fractions. Brain and blood samples will be counted using a Beckman Gamma 8000 well counter with standard dilution of the injectate. The counts will be decay-corrected with the [$^{18}$F] or [$^{11}$C] standards prepared from the injection solution. The samples will be weighed to calculate the percent injected dose, and these values will be normalized to body weight to obtain the percent injected dose index (=% injected dose in brain/brain weight (g)/total body weight (g)).

In Vitro Autoradiography:

In vitro autoradiography will be performed as described (103) with modification. Fixed brain sections prepared from 15-month-old Tg2576 mice will be incubated with [$^{18}$F]- or [$^{11}$C]-labeled tracers (10,000,000-15,000,000 cpm in 1 ml binding buffer) for 30 min. Sections will be then co-stained with 1 μM resorufin and 10 μM methoxy-X34 for 10 min at room temperature. Sections will be washed three times with PBS and 40% ethanol. Sections will be dried and covered with film, and counted using the Packard InstantImager. Brains sections will be then coverslipped with Vectorshield mounting media (Vector) and subjected to fluorescent microscopic imaging of resorufin- (CAA deposits) and methoxy-X34- (both CAA deposits and neuritic plaques) reactivity using the Nikon Eclipse C600 fluorescent microscope with the MetaMorph software.

Ex Vivo Autoradiography:

Tg2576 and littermate controls (male, 15 months of age, N=5 per group) will be anesthetize with isoflurane and [$^{18}$F]- or [$^{11}$C]-labeled tracers (25-50 μCi) will be i.v. injected via a tail vein. To determine non-specific binding, a 1000-fold excess amount of unlabeled tracers will be co-injected with [$^{18}$F]- or [$^{11}$C]-labeled tracers. Fifteen to thirty min later, whole brain will be removed and sliced using a 1-mm mouse brain matrix. Brain slices will be mounted on slide glass and radioactivity will be scanned with the Packard InstantImager. After autoradiography, brain slices will be post-fixed in 4% paraformaldehyde for 30 min followed by washing three times with PBS and 0.25% Triton-X100-containing PBS. Brain tissues will be incubated for 30 min with 1 μM resorufin and 10 μM methoxy-X34, and subjected to fluorescent microscopic assessment of cerebrovascular Aβ deposits. Three images will be merged to determine whether autoradiographic [$^{18}$F] or [$^{11}$C] signals are correlative to CAA deposits defined by resorufin staining.

Statistical Analysis:

We will first test for normality using Shapiro-Willis W test. If data are distributed normally, t-tests will be used when comparing 2 groups and ANOVA will be used when comparing >2 groups. If data are not distributed normally, the Mann-Whitney U test will be used when comparing 2 groups and Kruskal-Wallis nonparametric ANOVA will be used when comparing >2 groups.

REFERENCES FOR EXAMPLES 2-4

1. Maia L F, Mackenzie I R, Feldman H H. Clinical phenotypes of Cerebral Amyloid Angiopathy. J Neurol Sci 2007: 257; 23-30.
2. Soffer D. Cerebral amyloid angiopathy—a disease or age-related condition. Isr Med Assoc J 2006:8; 803-6.
3. Thal D R, Ghebremedhin E, Orantes M, Wiestler O D. Vascular pathology in Alzheimer diseas: correlation of cerebral amyloid angiopathy and arteriosclerosis/lipohyalinosis with cognitive decline. J Neuropathol Exp Neurol 2003:62; 1287-301.
4. Vinters H V. Cerebral amyloid angiopathy. A critical review. Stroke 1987:18; 311-24.
5. Rensink A A, de Waal R M, Kremer B, Verbeek M M. Pathogenesis of cerebral amyloid angiopathy. Brain Res Brain Res Rev 2003:43; 207-23.
6. McCarron M O, Nicoll J A. Cerebral amyloid angiopathy and thrombolysis-related intracerebral haemorrhage. Lancet Neurol 2004:3; 484-92.
7. Mandybur T I. The incidence of cerebral amyloid angiopathy in Alzheimer's disease. Neurology 1975:25; 120-6.
8. Glenner G G. Amyloidosis. Its role in Alzheimer's disease and other diseases. Ann Pathol 1981:1; 105-8.
9. Esiri M M, Nagy Z, Smith M Z, Barnetson L, Smith A D. Cerebrovascular disease and threshold for dementia in the early stages of Alzheimer's disease. Lancet 1999:354; 919-20.
10. Jellinger K A. Alzheimer disease and cerebrovascular pathology: an update. J Neural Transm 2002:109; 813-36.
11. Hebert L E, Scherr P A, Bienias J L, Bennett D A, Evans D A. Alzheimer disease in the US population: prevalence estimates using the 2000 census. Arch Neurol 2003:60; 1119-22.
12. Bloom B S, de Pouvourville N, Straus W L. Cost of illness of Alzheimer's diseas: how useful are current estimates? Gerontologist 2003:43; 158-64.
13. Golde T E, Eckman C B, Younkin S G. Biochemical detection of Abeta isoforms: implications for pathogenesis, diagnosis, and treatment of Alzheimer's disease. Biochim Biophys Acta 2000:1502; 172-87.
14. Selkoe D J. Alzheimer's diseas: genes, proteins, and therapy. Physiol Rev 2001:81; 741-66. 15. McGeer P L, McGeer E G. The inflammatory response system of brain: implications for therapy of Alzheimer and other neurodegenerative diseases. Brain Res Brain Res Rev 1995:21; 195-218.
16. Selkoe D J. Alzheimer's diseas: genotypes, phenotypes, and treatments. Science 1997:275; 630-1.
17. Greenberg S M. Cerebral amyloid angiopathy and vessel dysfunction. Cerebrovasc Dis 2002:13 Suppl 2; 42-7.
18. Mandybur T I. Cerebral amyloid angiopathy: the vascular pathology and complications. J Neuropathol Exp Neurol 1986:45; 79-90.
19. Han B H, Zhou M L, Abousaleh F, Brendza R P, Dietrich H H, Koenigsknecht-Talboo J, Cirrito J R, Milner E, Holtzman D M, Zipfel G J. Cerebrovascular dysfunction in amyloid precursor protein transgenic mic: contribution of soluble and insoluble amyloid-beta peptide, partial restoration via gamma-secretase inhibition. J Neurosci 2008: 28; 13542-50.
20. Christie R, Yamada M, Moskowitz M, Hyman B. Structural and functional disruption of vascular smooth muscle cells in a transgenic mouse model of amyloid angiopathy. Am J Pathol 2001:158; 1065-71.
21. Shin H K, Jones P B, Garcia-Alloza M, Borrelli L, Greenberg S M, Bacskai B J, Frosch M P, Hyman B T, Moskowitz M A, Ayata C. Age-dependent cerebrovascular dysfunction in a transgenic mouse model of cerebral amyloid angiopathy. Brain 2007:130; 2310-9.
22. Park L, Zhou P, Pitstick R, Capone C, Anrather J, Norris E H, Younkin L, Younkin S, Carlson G, McEwen B S, Iadecola C. Nox2-derived radicals contribute to neurovascular and behavioral dysfunction in mice overexpressing the amyloid precursor protein. Proc Natl Acad Sci USA 2008:105; 1347-52.
23. Revesz T, Holton J L, Doshi B, Anderton B H, Scaravilli F, Plant G T. Cytoskeletal pathology in familial cerebral amyloid angiopathy (British type) with non-neuritic amyloid plaque formation. Acta Neuropathol (Berl) 1999:97; 170-6.
24. Greenberg S M. Cerebral amyloid angiopathy: prospects for clinical diagnosis and treatment. Neurology 1998:51; 690-4.
25. Yamada M. Cerebral amyloid angiopathy: an overview. Neuropathology 2000:20; 8-22.
26. Ishii N, Nishihara Y, Horie A. Amyloid angiopathy and lobar cerebral haemorrhage. J Neurol Neurosurg Psychiatry 1984:47; 1203-10.

27. Itoh Y, Yamada M, Hayakawa M, Otomo E, Miyatake T. Cerebral amyloid angiopathy: a significant cause of cerebellar as well as lobar cerebral hemorrhage in the elderly. J Neurol Sci 1993:116; 135-41.
28. O'Donnell H C, Rosand J, Knudsen K A, Furie K L, Segal A Z, Chiu R I, Ikeda D, Greenberg S M. Apolipoprotein E genotype and the risk of recurrent lobar intracerebral hemorrhage. N Engl J Med 2000:342; 240-5.
29. Petridis A K, Barth H, Buhl R, Hugo H H, Mehdorn H M. Outcome of cerebral amyloid angiopathic brain haemorrhage. Acta Neurochir (Wien) 2008:150; 889-95.
30. Greenberg S M, Eng J A, Ning M, Smith E E, Rosand J. Hemorrhage burden predicts recurrent intracerebral hemorrhage after lobar hemorrhage. Stroke 2004:35; 1415-20.
31. Pfeifer L A, White L R, Ross G W, Petrovitch H, Launer L J. Cerebral amyloid angiopathy and cognitive function: the HAAS autopsy study. Neurology 2002:58; 1629-34.
32. Zekry D, Duyckaerts C, Belmin J, Geoffre C, Moulias R, Hauw J J. Cerebral amyloid angiopathy in the elderly: vessel walls changes and relationship with dementia. Acta Neuropathol (Berl) 2003:106; 367-73.
33. Greenberg S M, Gurol M E, Rosand J, Smith E E. Amyloid angiopathy-related vascular cognitive impairment. Stroke 2004:35; 2616-9.
34. Pathological correlates of late-onset dementia in a multicentre, community-based population in England and Wales. Neuropathology Group of the Medical Research Council Cognitive Function and Ageing Study (MRC CFAS). Lancet 2001:357; 169-75.
35. Olichney J M, Hansen L A, Hofstetter C R, Lee J H, Katzman R, Thal U. Association between severe cerebral amyloid angiopathy and cerebrovascular lesions in Alzheimer disease is not a spurious one attributable to apolipoprotein E4. Arch Neurol 2000:57; 869-74.
36. Olichney J M, Hansen L A, Hofstetter C R, Grundman M, Katzman R, Thal U. Cerebral infarction in Alzheimer's disease is associated with severe amyloid angiopathy and hypertension. Arch Neurol 1995:52; 702-8.
37. Olichney J M, Hansen L A, Lee J H, Hofstetter C R, Katzman R, Thal L J. Relationship between severe amyloid angiopathy, apolipoprotein E genotype, and vascular lesions in Alzheimer's disease. Ann N Y Acad Sci 2000: 903; 138-43.
38. Okazaki H, Reagan T J, Campbell R J. Clinicopathologic studies of primary cerebral amyloid angiopathy. Mayo Clin Proc 1979:54; 22-31.
39. Premkumar D R, Cohen D L, Hedera P, Friedland R P, Kalaria R N. Apolipoprotein E-epsilon4 alleles in cerebral amyloid angiopathy and cerebrovascular pathology associated with Alzheimer's disease. Am J Pathol 1996:148; 2083-95.
40. Greenberg S M. Cerebral amyloid angiopathy and dementia: two amyloids are worse than one. Neurology 2002:58; 1587-8.
41. Cadavid D, Mena H, Koeller K, Frommelt R A. Cerebral beta amyloid angiopathy is a risk factor for cerebral ischemic infarction. A case control study in human brain biopsies. J Neuropathol Exp Neurol 2000:59; 768-73.
42. Kimberly W T, Gilson A, Rost N S, Rosand J, Viswanathan A, Smith E E, Greenberg S M. Silent ischemic infarcts are associated with hemorrhage burden in cerebral amyloid angiopathy. Neurology 2009:72; 1230-5.
43. Knudsen K A, Rosand J, Karluk D, Greenberg S M. Clinical diagnosis of cerebral amyloid angiopathy: validation of the Boston criteria. Neurology 2001:56; 537-9.
44. Levy E, Carman M D, Fernandez-Madrid I J, Power M D, Lieberburg I, van Duinen S G, Bots G T, Luyendijk W, Frangione B. Mutation of the Alzheimer's disease amyloid gene in hereditary cerebral hemorrhage, Dutch type. Science 1990:248; 1124-6.
45. Davis J, Van Nostrand W E. Enhanced pathologic properties of Dutch-type mutant amyloid beta-protein. Proc Natl Acad Sci USA 1996:93; 2996-3000.
46. Grabowski T J, Cho H S, Vonsattel J P, Rebeck G W, Greenberg S M. Novel amyloid precursor protein mutation in an Iowa family with dementia and severe cerebral amyloid angiopathy. Ann Neurol 2001:49; 697-705.
47. Van Nostrand W E, Melchor J P, Cho H S, Greenberg S M, Rebeck G W. Pathogenic effects of D23N Iowa mutant amyloid beta-protein. J Biol Chem 2001:276; 32860-6.
48. Nilsberth C, Westlind-Danielsson A, Eckman C B, Condron M M, Axelman K, Forsell C, Stenh C, Luthman J, Teplow D B, Younkin S G, Naslund J, Lannfelt L. The 'Arctic' APP mutation (E693G) causes Alzheimer's disease by enhanced Abeta protofibril formation. Nat Neurosci 2001:4; 887-93. 49. Greenberg S M, Rebeck G W, Vonsattel J P, Gomez-Isla T, Hyman B T. Apolipoprotein E epsilon 4 and cerebral hemorrhage associated with amyloid angiopathy. Ann Neurol 1995:38; 254-9.
50. Horsburgh K, Fitzpatrick M, Nilsen M, Nicoll J A. Marked alterations in the cellular localisation and levels of apolipoprotein E following acute subdural haematoma in rat. Brain Res 1997:763; 103-10.
51. Corder E H, Saunders A M, Strittmatter W J, Schmechel D E, Gaskell P C, Small G W, Roses A D, Haines J L, Pericak-Vance M A. Gene dose of apolipoprotein E type 4 allele and the risk of Alzheimer's disease in late onset families. Science 1993:261; 921-3.
52. Alonzo N C, Hyman B T, Rebeck G W, Greenberg S M. Progression of cerebral amyloid angiopathy: accumulation of amyloid-beta40 in affected vessels. J Neuropathol Exp Neurol 1998:57; 353-9.
53. Fryer J D, Simmons K, Parsadanian M, Bales K R, Paul S M, Sullivan P M, Holtzman D M. Human apolipoprotein E4 alters the amyloid-beta 40:42 ratio and promotes the formation of cerebral amyloid angiopathy in an amyloid precursor protein transgenic model. J Neurosci 2005:25; 2803-10.
54. Vidal R, Calero M, Piccardo P, Farlow M R, Unverzagt F W, Mendez E, Jimenez-Huete A, Beavis R, Gallo G, Gomez-Tortosa E, Ghiso J, Hyman B T, Frangione B, Ghetti B. Senile dementia associated with amyloid beta protein angiopathy and tau perivascular pathology but not neuritic plaques in patients homozygous for the APOE-epsilon4 allele. Acta Neuropathol (Bed) 2000:100; 1-12.
55. Kim J, Onstead L, Randle S, Price R, Smithson L, Zwizinski C, Dickson D W, Golde T, McGowan E. Abeta40 inhibits amyloid deposition in vivo. J Neurosci 2007:27; 627-33.
56. Herzig M C, Winkler D T, Burgermeister P, Pfeifer M, Kohler E, Schmidt S D, Danner S, Abramowski D, Sturchler-Pierrat C, Burki K, van Duinen S G, Maat-Schieman M L, Staufenbiel M, Mathews P M, Jucker M. Abeta is targeted to the vasculature in a mouse model of hereditary cerebral hemorrhage with amyloidosis. Nat Neurosci 2004:7; 954-60.
57. Chao C P, Kotsenas A L, Broderick D F. Cerebral amyloid angiopathy: CT and MR imaging findings. Radiographics 2006:26; 1517-31.
58. Greenberg S M, Briggs M E, Hyman B T, Kokoris G J, Takis C, Kanter D S, Kase C S, Pessin M S. Apolipoprotein E epsilon 4 is associated with the presence and earlier onset of hemorrhage in cerebral amyloid angiopathy. Stroke 1996:27; 1333-7.
59. Henriksen G, Yousefi B H, Drzezga A, Wester H J. Development and evaluation of compounds for imaging of beta-amyloid plaque by means of positron emission tomography. European journal of nuclear medicine and molecular imaging 2008:35 Suppl 1; S75-81.
60. Nordberg A. PET imaging of amyloid in Alzheimer's disease. Lancet Neurol 2004:3; 519-27. 61. Klunk W E, Bacskai B J, Mathis C A, Kajdasz S T, McLellan M E, Frosch M P, Debnath M L, Holt D P, Wang Y, Hyman B T. Imaging Abeta plaques in living transgenic mice with multiphoton microscopy and methoxy-X04, a systemically administered Congo red derivative. J Neuropathol Exp Neurol 2002:61; 797-805.
62. Mathis C A, Wang Y, Holt D P, Huang G F, Debnath M L, Klunk W E. Synthesis and evaluation of 11C labeled 6-substituted 2-arylbenzothiazoles as amyloid imaging agents. Journal of medicinal chemistry 2003:46; 2740-54.
63. Klunk W E, Engler H, Nordberg A, Wang Y, Blomqvist G, Holt D P, Bergstrom M, Savitcheva I, Huang G F, Estrada S, Ausen B, Debnath M L, Barletta J, Price J C, Sandell J, Lopresti B J, Wall A, Koivisto P, Antoni G, Mathis C A, Langstrom B. Imaging brain amyloid in Alzheimer's disease with Pittsburgh Compound-B. Ann Neurol 2004:55; 306-19.
64. Archer H A, Edison P, Brooks D J, Barnes J, Frost C, Yeatman T, Fox N C, Rossor M N. Amyloid load and cerebral atrophy in Alzheimer's diseas: an 11C-PIB positron emission tomography study. Ann Neurol 2006:60; 145-7.
65. Kemppainen N M, Aalto S, Wilson I A, Nagren K, Helin S, Bruck A, Oikonen V, Kailajarvi M, Scheinin M, Viitanen M, Parkkola R, Rinne J O. Voxel-based analysis of PET amyloid ligand [11C]PIB uptake in Alzheimer disease. Neurology 2006:67; 1575-80.66. Mintun M A, Larossa G N, Sheline Y I, Dence C S, Lee S Y, Mach R H, Klunk W E, Mathis C A, DeKosky S T, Morris J C. [11C]PIB in a nondemented population: potential antecedent marker of Alzheimer disease. Neurology 2006:67; 446-52.
67. Engler H, Forsberg A, Almkvist O, Blomquist G, Larsson E, Savitcheva I, Wall A, Ringheim A, Langstrom B, Nordberg A. Two-year follow-up of amyloid deposition in patients with Alzheimer's disease. Brain 2006:129; 2856-66.
68. Kemppainen N M, Aalto S, Wilson I A, Nagren K, Helin S, Bruck A, Oikonen V, Kailajarvi M, Scheinin M, Viitanen M, Parkkola R, Rinne J O. PET amyloid ligand [11C]PIB uptake is increased in mild cognitive impairment. Neurology 2007:68; 1603-6.
69. Price J C, Klunk W E, Lopresti B J, Lu X, Hoge J A, Ziolko S K, Holt D P, Meltzer C C, DeKosky S T, Mathis C A. Kinetic modeling of amyloid binding in humans using PET imaging and Pittsburgh Compound-B. J Cereb Blood Flow Metab 2005:25; 1528-47.
70. Forsberg A, Engler H, Almkvist O, Blomquist G, Hagman G, Wall A, Ringheim A, Langstrom B, Nordberg A. PET imaging of amyloid deposition in patients with mild cognitive impairment. Neurobiol Aging 2008:29; 1456-65.
71. Ono M, Wilson A, Nobrega J, Westaway D, Verhoeff P, Zhuang Z P, Kung M P, Kung H F. 11C-labeled stilbene derivatives as Abeta-aggregate-specific PET imaging agents for Alzheimer's disease. Nuclear medicine and biology 2003:30; 565-71.
72. Verhoeff N P, Wilson A A, Takeshita S, Trop L, Hussey D, Singh K, Kung H F, Kung M P, Houle S. In-vivo imaging of Alzheimer disease beta-amyloid with [11C]SB-13 PET. Am J Geriatr Psychiatry 2004:12; 584-95.
73. Agdeppa E D, Kepe V, Liu J, Flores-Torres S, Satyamurthy N, Petric A, Cole G M, Small G W, Huang S C, Barrio J R. Binding characteristics of radiofluorinated 6-dialkylamino-2-naphthylethylidene derivatives as positron emission tomography imaging probes for beta-amyloid plaques in Alzheimer's disease. J Neurosci 2001:21; RC189.
74. Shoghi-Jadid K, Small G W, Agdeppa E D, Kepe V, Ercoli L M, Siddarth P, Read S, Satyamurthy N, Petric A, Huang S C, Barrio J R. Localization of neurofibrillary tangles and beta-amyloid plaques in the brains of living patients with Alzheimer disease. Am J Geriatr Psychiatry 2002:10; 24-35.
75. Small G W, Kepe V, Ercoli L M, Siddarth P, Bookheimer S Y, Miller K J, Lavretsky H, Burggren A C, Cole G M, Vinters H V, Thompson P M, Huang S C, Satyamurthy N, Phelps M E, Barrio J R. PET of brain amyloid and tau in mild cognitive impairment. N Engl J Med 2006:355; 2652-63.
76. Lee J M, Yin K, Hsin I, Chen S, Fryer J D, Holtzman D M, Hsu C Y, Xu J. Matrix metalloproteinase-9 in cerebral-amyloid-angiopathy-related hemorrhage. J Neurol Sci 2005:229-230; 249-54.
77. Lee J M, Yin K J, Hsin I, Chen S, Fryer J D, Holtzman D M, Hsu C Y, Xu J. Matrix metalloproteinase-9 and spontaneous hemorrhage in an animal model of cerebral amyloid angiopathy. Ann Neurol 2003:54; 379-82.
78. Fryer J D, Taylor J W, DeMattos R B, Bales K R, Paul S M, Parsadanian M, Holtzman D M. Apolipoprotein E markedly facilitates age-dependent cerebral amyloid angiopathy and spontaneous hemorrhage in amyloid precursor protein transgenic mice. J Neurosci 2003:23; 7889-96.
79. Christie R, Kimchi E, Kajdasz S, Bacskai B, Hyman B T. Multiphoton microscopy and amyloid angiopathy. Amyloid 2001:8 Suppl 1; 48-50.
80. Kimchi E Y, Kajdasz S, Bacskai B J, Hyman B T. Analysis of cerebral amyloid angiopathy in a transgenic mouse model of Alzheimer disease using in vivo multiphoton microscopy. J Neuropathol Exp Neurol 2001:60; 274-9.
81. Hsiao K, Chapman P, Nilsen S, Eckman C, Harigaya Y, Younkin S, Yang F, Cole G. Correlative memory deficits, Abeta elevation, and amyloid plaques in transgenic mice. Science 1996:274; 99-102.
82. Games D, Adams D, Alessandrini R, Barbour R, Berthelette P, Blackwell C, Carr T, Clemens J, Donaldson T, Gillespie F, et al. Alzheimer-type neuropathology in transgenic mice overexpressing V717F beta-amyloid precursor protein. Nature 1995:373; 523-7.
83. Johnson-Wood K, Lee M, Motter R, Hu K, Gordon G, Barbour R, Khan K, Gordon M, Tan H, Games D, Lieberburg I, Schenk D, Seubert P, McConlogue L. Amyloid precursor protein processing and A beta42 deposition in a transgenic mouse model of Alzheimer disease. Proc Natl Acad Sci USA 1997:94; 1550-5.
84. Racke M M, Boone L I, Hepburn D L, Parsadainian M, Bryan M T, Ness D K, Piroozi K S, Jordan W H, Brown D D, Hoffman W P, D. M. H, Bales K R, Gitter B D, May P C, Paul S M, DeMattos R B. Exacerbation of cerebral amyloid angiopathy-associated microhemorrhage in amyloid precursor protein transgenic mice by immunotherapy is dependent on antibody recognition of deposited forms of amyloid beta. J Neurosci 2005:25; 629-36.
85. Iwatsubo T, Saido T C, Mann D M, Lee V M, Trojanowski J Q. Full-length amyloid-beta (1-42(43)) and amino-terminally modified and truncated amyloid-beta 42(43) deposit in diffuse plaques. Am J Pathol 1996:149; 1823-30.

86. Borchelt D R, Ratovitski T, van Lare J, Lee M K, Gonzales V, Jenkins N A, Copeland N G, Price D L, Sisodia S S. Accelerated amyloid deposition in the brains of transgenic mice coexpressing mutant presenilin 1 and amyloid precursor proteins. Neuron 1997:19; 939-45.
87. Borchelt D R, Thinakaran G, Eckman C B, Lee M K, Davenport F, Ratovitsky T, Prada C M, Kim G, Seekins S, Yager D, Slunt H H, Wang R, Seeger M, Levey A I, Gandy S E, Copeland N G, Jenkins N A, Price D L, Younkin S G, Sisodia S S. Familial Alzheimer's disease-linked presenilin 1 variants elevate Abeta1-42/1-40 ratio in vitro and in vivo. Neuron 1996:17; 1005-13.
88. Jankowsky J L, Slunt H H, Gonzales V, Jenkins N A, Copeland N G, Borchelt D R. APP processing and amyloid deposition in mice haplo-insufficient for presenilin 1. Neurobiol Aging 2004:25; 885-92.
89. Kawarabayashi T, Younkin L H, Saido T C, Shoji M, Ashe K H, Younkin S G. Age-dependent changes in brain, CSF, and plasma amyloid (beta) protein in the Tg2576 transgenic mouse model of Alzheimer's disease. J Neurosci 2001:21; 372-81.
90. Quik M, Police S, He L, Di Monte D A, Langston J W. Expression of D(3) receptor messenger RNA and binding sites in monkey striatum and substantia nigra after nigrostriatal degeneration: effect of levodopa treatment. Neuroscience 2000:98; 263-73.
91. Stine W B, Jr., Dahlgren K N, Krafft G A, LaDu M J. In vitro characterization of conditions for amyloid-beta peptide oligomerization and fibrillogenesis. J Biol Chem 2003:278; 11612-22.
92. Zhang R, Hu X, Khant H, Ludtke S J, Chiu W, Schmid M F, Frieden C, Lee J M. Interprotofilament interactions between Alzheimer's Abeta1-42 peptides in amyloid fibrils revealed by cryoEM. Proc Natl Acad Sci USA 2009:106; 4653-8.
93. Lemaire C, Cantineau R, Guillaume M, Plenevaux A, Christiaens L. Fluorine-18-altanserin: a radioligand for the study of serotonin receptors with PET: radiolabeling and in vivo biologic behavior in rats. J Nucl Med 1991:32; 2266-72.
94. Hume S P, Myers R, Bloomfield P M, Opacka-Juffry J, Cremer J E, Ahier R G, Luthra S K, Brooks D J, Lammertsma A A. Quantitation of carbon-11-labeled raclopride in rat striatum using positron emission tomography. Synapse (New York, N.Y. 1992:12; 47-54.
95. Serdons K, Verduyckt T, Vanderghinste D, Cleynhens J, Borghgraef P, Vermaelen P, Terwinghe C, Van Leuven F, Van Laere K, Kung H, Bormans G, Verbruggen A. Synthesis of 18F-labelled 2-(4'-fluorophenyl)-1,3-benzothiazole and evaluation as amyloid imaging agent in comparison with [11C]PIB. Bioorganic & medicinal chemistry letters 2009:19; 602-5.
96. Klunk W E. Biopsy support for the validity of Pittsburgh compound B positron emission tomography with a twist. Arch Neurol 2008:65; 1281-3.
97. Wyss-Coray T, Masliah E, Mallory M, McConlogue L, Johnson-Wood K, Lin C, Mucke L. Amyloidogenic role of cytokine TGF-beta1 in transgenic mice and in Alzheimer's disease. Nature 1997:389; 603-6.
98. Fryer J D, Holtzman D M. The bad seed in Alzheimer's disease. Neuron 2005:47; 167-8.
99. Habicht G, Haupt C, Friedrich R P, Hortschansky P, Sachse C, Meinhardt J, Wieligmann K, Gellermann G P, Brodhun M, Gotz J, Halbhuber K J, Rocken C, Horn U, Fandrich M. Directed selection of a conformational antibody domain that prevents mature amyloid fibril formation by stabilizing Abeta protofibrils. Proc Natl Acad Sci USA 2007:104; 19232-7.
100. Lockhart A, Ye L, Judd D B, Merritt A T, Lowe P N, Morgenstern J L, Hong G, Gee A D, Brown J. Evidence for the presence of three distinct binding sites for the thioflavin T class of Alzheimer's disease PET imaging agents on beta-amyloid peptide fibrils. J Biol Chem 2005:280; 7677-84.
101. Kung M P, Hou C, Zhuang Z P, Skovronsky D, Kung H F. Binding of two potential imaging agents targeting amyloid plaques in postmortem brain tissues of patients with Alzheimer's disease. Brain Res 2004:1025; 98-105.
102. Xu J, Chu W, Tu Z, JoneS L A, Luedtke R R, Perlmutter J S, Mintun M A, Mach R H. [(3)H]-4-(Dimethylamino)-N-[4-(4-(2-methoxyphenyl)piperazin-1-yl)butyl]benzamide, a selective radioligand for dopamine D(3) receptors. I. In vitro characterization. Synapse (New York, N.Y. 2009: 63; 717-28.
103. Tu Z, Efange S M, Xu J, Li S, Jones L A, Parsons S M, Mach R H. Synthesis and in Vitro and in Vivo Evaluation of (18)F-Labeled Positron Emission Tomography (PET) Ligands for Imaging the Vesicular Acetylcholine Transporter. Journal of medicinal chemistry 2009e.

What is claimed is:
1. A compound of formula (IV):

wherein:
$R^1$ is O;
$R^2$ is chosen from N, S, or O;
$R^9$ is $(CH_2)_g$, wherein g is an integer from 1 to 10, and $R^{10}$ is chosen from a halogen, an alkenyl group, and an alkynyl group.

2. The compound of claim 1, wherein $R^{10}$ is a halogen.
3. The compound of claim 1, wherein $R^{10}$ is an alkenyl group.
4. The compound of claim 1, wherein $R^{10}$ is an alkynyl group.
5. The compound of claim 1, wherein $R^1$ is O, $R^2$ is O, $R^9$ is $(CH_2)_g$, wherein g is an integer from 1 to 4, and $R^{10}$ is a halogen.
6. The compound of claim 1, wherein $R^1$ is O, $R^2$ is O, $R^9$ is $(CH_2)_2$, and $R^{10}$ is halogen.
7. The compound of claim 1, wherein $R^1$ is O, $R^2$ is O, $R^9$ is $(CH_2)_2$, and $R^{10}$ is F.
8. The compound of claim 1, wherein $R^1$ is O, $R^2$ is O, $R^9$ is $(CH_2)_g$, wherein g is an integer from 1 to 10, and $R^{10}$ is halogen.
9. The compound of claim 1, wherein $R^1$ is O, $R^2$ is O, $R^9$ is $(CH_2)_g$, wherein g is an integer from 1 to 10, and $R^{10}$ is F.

* * * * *